United States Patent
Yang et al.

(10) Patent No.: US 10,184,126 B2
(45) Date of Patent: Jan. 22, 2019

(54) LIGHT-SWITCHABLE GENE EXPRESSION SYSTEM AND THE METHODS FOR CONTROLLING GENE EXPRESSION IN PROKARYOTIC BACTERIUM

(71) Applicant: EAST CHINA UNIVERSITY OF SCIENCE AND TECHNOLOGY, Shanghai (CN)

(72) Inventors: Yi Yang, Shanghai (CN); Xianjun Chen, Shanghai (CN); Zhengcai Ma, Shanghai (CN); Renmei Liu, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 14/419,106

(22) PCT Filed: Aug. 1, 2013

(86) PCT No.: PCT/CN2013/080580
§ 371 (c)(1),
(2) Date: Jul. 13, 2015

(87) PCT Pub. No.: WO2014/019527
PCT Pub. Date: Feb. 6, 2014

(65) Prior Publication Data
US 2016/0040173 A1    Feb. 11, 2016

(30) Foreign Application Priority Data
Aug. 2, 2012 (CN) .......................... 2012 1 0274040

(51) Int. Cl.
| | |
|---|---|
| C12N 15/62 | (2006.01) |
| C12N 15/70 | (2006.01) |
| C12N 15/74 | (2006.01) |
| C12N 15/63 | (2006.01) |
| C12N 15/75 | (2006.01) |
| C12P 21/02 | (2006.01) |
| C12N 9/02 | (2006.01) |
| C12N 13/00 | (2006.01) |

(52) U.S. Cl.
CPC ......... *C12N 15/635* (2013.01); *C12N 9/0051* (2013.01); *C12N 13/00* (2013.01); *C12N 15/70* (2013.01); *C12N 15/74* (2013.01); *C12N 15/75* (2013.01); *C12P 21/02* (2013.01)

(58) Field of Classification Search
None
See application file for complete search history.

(56) References Cited

U.S. PATENT DOCUMENTS

2003/0082809 A1* 5/2003 Quail ................. C12N 15/8217
435/446
2013/0345294 A1* 12/2013 Yang ...................... C12N 15/63
514/44 R

FOREIGN PATENT DOCUMENTS

| CN | 1609216 | 4/2005 |
| CN | 102643852 A | 8/2012 |
| CN | 103031327 A | 4/2013 |
| WO | WO 0140492 A2 | 6/2001 |

OTHER PUBLICATIONS

Martinez-Garcia et al. Direct Targeting of Light Signals to a Promoter Element-Bound Transcription Factor. May 5, 2000. Science. vol. 288, pp. 859-863.*
Zoltowski et al. Light activation of the LOV protein Vivid generates a rapidly exchanging dimer. Jul. 8, 2008. Biochemistry. vol. 47, No. 27, pp. 7012-1019.*
pcDNAII. printed on Dec. 18, 2017, Invitrogen, 1 page.*

* cited by examiner

*Primary Examiner* — Channing S Mahatan
(74) *Attorney, Agent, or Firm* — Global IP Services; Tianhua Gu

(57) ABSTRACT

Provided is an optically controlled gene expression system of prokaryotic bacterium, comprising: a) a photosensitive recombinant transcription factor encoding gene, the photosensitive recombinant transcription factor is one fusion protein comprising a first polypeptide as the DNA bonding domain and a second polypeptide as the photosensitive domain; b) a target transcription unit comprising promoter or promoter-reaction element or reaction element-promoter containing at least one reaction element recognized/bound by the first polypeptide and the nucleic acid sequence to be transcribed. Also provided is a prokaryotic expression vector comprising said optically controlled gene expression system, and a method for regulating gene expression in a prokaryotic host cell by using the optically controlled gene expression system. Also provided is a reagent kit containing different components of the optically controlled gene expression system. The optically controlled gene expression system of prokaryotic bacterium has a quick, effective and powerful induction, is safer than other inducers, is of little or no toxicity, and can control gene expression both spatially and temporally, and can regulate many life processes of prokaryotic bacterium.

12 Claims, 12 Drawing Sheets
Specification includes a Sequence Listing.

Co-transformation plasmids:
1: pALV-L0+pB-ColE-cI-P$_{\lambda O12}$-CheZ
2: pCDFDuet1+pB-ColE-cI-P$_{\lambda O12}$-CheZ
3: pCDFDuet1+pRSETb

Fig. 36

SEQUENCE LISTING

<160> NUMBER OF SEQ ID NOS: 327

<210> SEQ ID NO 1
<211> LENGTH: 261
<212> TYPE: DNA
<213> ORGANISM: Escherichia coli

<400> SEQUENCE: 1
atgaaagcgt taacggccag gcaacaagag gtgtttgatc tcatccgtga tcacatcagc        60
cagacaggta tgccgccgac gcgtgcggaa atcgcgcagc gtttgggggtt ccgttcccca      120 aacgcggctg aagaacatct gaaggcgctg gcacgcaaag gcgttattga aattgtttcc      180
ggcgcatcac gcgggattcg tctgttgcag gaagaggaag aagggttgcc gctggtaggt      240
cgtgtggctg ccggtgaacc g                                                261

<210> SEQ ID NO 2
<211> LENGTH: 87
<212> TYPE: PRT
<213> ORGANISM: Escherichia coli

<400> SEQUENCE: 2

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro
            85

<210> SEQ ID NO 3
<211> LENGTH: 306
<212> TYPE: DNA
<213> ORGANISM: bacteriophage lambda

<400> SEQUENCE: 3
atgtctacca agaagaaacc tttaactcaa gaacaattgg aggatgctag aaggttgaag       60
gccatctacg aaaagaaaaa gaatgagtta gggctatctc aggaaagtgt ggccgacaag     120
atgggaatgg gccaatcagg tgttggtgct tgttcaacg ggataaacgc attaaatgcc      180
tacaatgctg ccttactggc aaagatattg aaggtatctg tagaagagtt ctcaccttct     240
attgctcgtg aaatctatga aatgtatgag gcggttagca tgcagccgtc tttgaggtca     300
gaatat                                                                306

<210> SEQ ID NO 4
<211> LENGTH: 102
<212> TYPE: PRT
<213> ORGANISM: bacteriophage lambda

<400> SEQUENCE: 4

Met Ser Thr Lys Lys Lys Pro Leu Thr Gln Glu Gln Leu Glu Asp Ala
1               5                   10                  15

Arg Arg Leu Lys Ala Ile Tyr Glu Lys Lys Lys Asn Glu Leu Gly Leu
            20                  25                  30

Ser Gln Glu Ser Val Ala Asp Lys Met Gly Met Gly Gln Ser Gly Val
         35                  40                  45

Gly Ala Leu Phe Asn Gly Ile Asn Ala Leu Asn Ala Tyr Asn Ala Ala
     50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                 85                  90                  95

Ser Leu Arg Ser Glu Tyr
            100

<210> SEQ ID NO 5
<211> LENGTH: 186
<212> TYPE: DNA
<213> ORGANISM: Artificial Sequence
<220> FEATURE:
<223> OTHER INFORMATION: Synthetic

<400> SEQUENCE: 5
atgaaaccag taacgttata cgatgtcgca gagtatgccg gtgtctctta tcagaccgtt     60
tcccgcgtgg tgaaccaggc cagccacgtt tctgcgaaaa cgcgggaaaa agtggaagcg    120
gcgatggcgg agctgaatta cattcccaac cgcgtggcac aacaactggc gggcaaacag    180
tcgttg                                                               186

<210> SEQ ID NO 6
<211> LENGTH: 62
<212> TYPE: PRT
<213> ORGANISM: Artificial Sequence
<220> FEATURE:
<223> OTHER INFORMATION: Synthetic

<400> SEQUENCE: 6

Met Lys Pro Val Thr Leu Tyr Asp Val Ala Glu Tyr Ala Gly Val Ser
1               5                  10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
         35                  40                  45

Pro Asn Arg Val Ala Gln Gln Leu Ala Gly Lys Gln Ser Leu
     50                  55                  60

<210> SEQ ID NO 7
<211> LENGTH: 195
<212> TYPE: DNA
<213> ORGANISM: Artificial Sequence
<220> FEATURE:
<223> OTHER INFORMATION: Synthetic

<400> SEQUENCE: 7
atgaagctac tgtcttctat cgaacaagca tgcgatattt gccgacttaa aaagctcaag     60
tgctccaaag aaaaaccgaa gtgcgccaag tgtctgaaga caactgggga gtgtcgctac    120
tctcccaaaa ccaaaaggtc tccgctgact agggcacatc tgacagaagt ggaatcaagg    180
ctagaaagac tggaa                                                    195

<210> SEQ ID NO 8
<211> LENGTH: 65
<212> TYPE: PRT
<213> ORGANISM: Artificial Sequence
<220> FEATURE:
<223> OTHER INFORMATION: Synthetic

<400> SEQUENCE: 8

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu
65

<210> SEQ ID NO 9
<211> LENGTH: 189
<212> TYPE: DNA
<213> ORGANISM: Artificial Sequence
<220> FEATURE:
<223> OTHER INFORMATION: Synthetic

<400> SEQUENCE: 9
atgtctaggc tagataagag caaagtcatc aattccgcgt tggaattact taacgaagta      60
ggtattgagg gtttgactac gagaaaacta gcgcaaaaat tgggtgtgga acaaccaaca    120
ctatactggc acgttaagaa taaacgtgca ttattagacg cattagccat cgagatgctg    180
gatagacac                                                            189

<210> SEQ ID NO 10
<211> LENGTH: 63
<212> TYPE: PRT
<213> ORGANISM: Artificial Sequence
<220> FEATURE:
<223> OTHER INFORMATION: Synthetic

<400> SEQUENCE: 10

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His
    50                  55                  60

<210> SEQ ID NO 11
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(12)
<223> OTHER INFORMATION: n is a, c, g, or t

<400> SEQUENCE: 11
ctgtnnnnnn nnacag                                                     16

<210> SEQ ID NO 12
<211> LENGTH: 64

```
<212> TYPE: DNA
<213> ORGANISM: Artificial Sequence
<220> FEATURE:
<223> OTHER INFORMATION: Synthetic

<400> SEQUENCE: 12
tatcaccgca agggataaat atctaacacc gtgcgtgttg actattttac ctctggcggt    60
gata                                                                 64

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gaattgtgag cgctcacaat t                                              21

<210> SEQ ID NO 14
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 14
cggrnnrcyn ynycnccg                                                  19

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
tccctatcag tgatagaga                                                 19

<210> SEQ ID NO 16
<211> LENGTH: 450
<212> TYPE: DNA
<213> ORGANISM: Artificial Sequence
<220> FEATURE:
<223> OTHER INFORMATION: Synthetic

<400> SEQUENCE: 16
catacgctct acgctcccgg cggttatgac attatgggct atctgattca gattatgaac    60
```

```
aggccaaacc cccaagtaga actgggacct gttgacacgt cagttgctct gattctgtgc    120
gacctgaagc aaaaagacac gccaattgtg tacgcctcgg aagcttttct ctatatgaca    180
ggatacagca atgcggaggt cttggggaga aactgccgtt ttcttcagtc acccgacgga    240
atggtcaagc cgaaatcgac aaggaagtac gtcgactcca acacgatcaa tacgatgagg    300
aaagcgattg ataggaacgc cgaggtgcag gttgaggtgg tcaattttaa gaagaacggc    360
caacggtttg tcaacttctt gacgatgatt ccggtgcgag atgaaacagg ggaataccgg    420
tacagcatgg gtttccagtg cgaaacggaa                                    450
```

<210> SEQ ID NO 17
<211> LENGTH: 150
<212> TYPE: PRT
<213> ORGANISM: Artificial Sequence
<220> FEATURE:
<223> OTHER INFORMATION: Synthetic

<400> SEQUENCE: 17

```
His Thr Leu Tyr Ala Pro Gly Gly Tyr Asp Ile Met Gly Tyr Leu Ile
1               5                   10                  15

Gln Ile Met Asn Arg Pro Asn Pro Gln Val Glu Leu Gly Pro Val Asp
            20                  25                  30

Thr Ser Val Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150
```

<210> SEQ ID NO 18
<211> LENGTH: 450
<212> TYPE: DNA
<213> ORGANISM: Artificial Sequence
<220> FEATURE:
<223> OTHER INFORMATION: Synthetic

<400> SEQUENCE: 18

```
catacgctct acgctcccgg cggttatgac attatgggct atctgattca gattatgaag     60
aggccaaacc cccaagtaga actgggacct gttgacacgt catgcgctct gattctgtgc    120
gacctgaagc aaaaagacac gccaattgtg tacgcctcgg aagcttttct ctatatgaca    180
ggatacagca atgcggaggt cttggggaga aactgccgtt ttcttcagtc acccgacgga    240
atggtcaagc cgaaatcgac aaggaagtac gtcgactcca acacgatcaa tacgatgagg    300
aaagcgattg ataggaacgc cgaggtgcag gttgaggtgg tcaattttaa gaagaacggc    360
caacggtttg tcaacttctt gacgatgatt ccggtgcgag atgaaacagg ggaataccgg    420
tacagcatgg gtttccagtg cgaaacggaa                                    450
```

<210> SEQ ID NO 19
<211> LENGTH: 150
<212> TYPE: PRT
<213> ORGANISM: Artificial Sequence
<220> FEATURE:
<223> OTHER INFORMATION: Synthetic

<400> SEQUENCE: 19

```
His Thr Leu Tyr Ala Pro Gly Gly Tyr Asp Ile Met Gly Tyr Leu Ile
1               5                   10                  15

Gln Ile Met Lys Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150
```

<210> SEQ ID NO 20
<211> LENGTH: 450
<212> TYPE: DNA
<213> ORGANISM: Artificial Sequence
<220> FEATURE:
<223> OTHER INFORMATION: Synthetic

<400> SEQUENCE: 20

```
catacgctct acgctcccgg cggttatgac attatgggct ggctgattca gattatgaac      60
aggccaaacc cccaagtaga actgggacct gttgacacgt catgcgctct gattctgtgc     120
gacctgaagc aaaaagacac gccaattgtg tacgcctcgg aagctttttct ctatatgaca    180
ggatacagca atgcggaggt cttggggaga aactgccgtt ttcttcagtc acccgacgga     240
atggtcaagc cgaaatcgac aaggaagtac gtcgactcca acacgatcaa tacgatgagg     300
aaagcgattg ataggaacgc cgaggtgcag gttgaggtgg tcaattttaa gaagaacggc     360
caacggtttg tcaacttctt gacgatgatt ccggtgcgag atgaaacagg ggaataccgg     420
tacagcatgg gtttccagtg cgaaacggaa                                      450
```

<210> SEQ ID NO 21
<211> LENGTH: 150
<212> TYPE: PRT
<213> ORGANISM: Artificial Sequence
<220> FEATURE:
<223> OTHER INFORMATION: Synthetic

<400> SEQUENCE: 21

```
His Thr Leu Tyr Ala Pro Gly Gly Tyr Asp Ile Met Gly Trp Leu Ile
1               5                   10                  15
```

Gln Ile Met Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150

<210> SEQ ID NO 22
<211> LENGTH: 450
<212> TYPE: DNA
<213> ORGANISM: Artificial Sequence
<220> FEATURE:
<223> OTHER INFORMATION: Synthetic

<400> SEQUENCE: 22
catacgctct acgctcccgg cggttatgac attatgggct atctgattca gattatgaac        60
aggccaaacc cccaagtaga actgggacct gttgacacgt catgcgctct gattctgtgc       120
gacctgaagc aaaagacac gccaattgtg tacgcctcgg aagctttct ctatatgaca        180 ggatacagca atgcggaggt cttggggaga aactgccgtt ttcttcagtc acccgacgga       240
atggtcaagc cgaaatcgac aaggaagtac gtcgactcca acacgatcaa tacgatgagg       300
aaagcgattg ataggaacgc cgaggtgcag gttgaggtgg tcaattttaa gaagaacggc       360
caacggtttg tcaacttctt gacgatgatt ccggtgcgag atgaaacagg ggaataccgg       420
tacagcatgg gtttccagtg cgaaacggaa                                         450

<210> SEQ ID NO 23
<211> LENGTH: 150
<212> TYPE: PRT
<213> ORGANISM: Artificial Sequence
<220> FEATURE:
<223> OTHER INFORMATION: Synthetic

<400> SEQUENCE: 23

His Thr Leu Tyr Ala Pro Gly Gly Tyr Asp Ile Met Gly Tyr Leu Ile
1               5                   10                  15

Gln Ile Met Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

```
Met Val Lys Pro Lys Ser Thr Arg Lys Tyr Val Asp Ser Asn Thr Ile
             85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
                115                 120                 125

Met Ile Pro Val Arg Asp Glu Thr Gly Glu Tyr Arg Tyr Ser Met Gly
        130                 135                 140

Phe Gln Cys Glu Thr Glu
145                 150

<210> SEQ ID NO 24
<211> LENGTH: 450
<212> TYPE: DNA
<213> ORGANISM: Artificial Sequence
<220> FEATURE:
<223> OTHER INFORMATION: Synthetic

<400> SEQUENCE: 24
catacgctct acgctcccgg cggttatgac attatgggct atctggcgca gattatgaac      60
aggccaaacc cccaagtaga actgggacct gttgacacgt cagttgctct gattctgtgc     120
gacctgaagc aaaaagacac gccaattgtg tacgcctcgg aagcttttct ctatatgaca     180
ggatacagca atgcggaggt cttggggaga aactgccgtt tcttcagtc acccgacgga      240 atggtcaagc cgaaatcgac aaggaagtac gtcgactcca cacgatcaa tacgatgagg      300 aaagcgattg ataggaacgc cgaggtgcag gttgaggtgg tcaattttaa gaagaacggc     360
caacggtttg tcaacttctt gacgatgatt ccggtgcgag atgaaacagg gaataccgg      420 tacagcatgg gtttccagtg cgaaacggaa                                      450

<210> SEQ ID NO 25
<211> LENGTH: 150
<212> TYPE: PRT
<213> ORGANISM: Artificial Sequence
<220> FEATURE:
<223> OTHER INFORMATION: Synthetic

<400> SEQUENCE: 25

His Thr Leu Tyr Ala Pro Gly Gly Tyr Asp Ile Met Gly Tyr Leu Ala
1               5                   10                  15

Gln Ile Met Asn Arg Pro Asn Pro Gln Val Glu Leu Gly Pro Val Asp
            20                  25                  30

Thr Ser Val Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
             85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
                115                 120                 125

Met Ile Pro Val Arg Asp Glu Thr Gly Glu Tyr Arg Tyr Ser Met Gly
        130                 135                 140

Phe Gln Cys Glu Thr Glu
145                 150
```

<210> SEQ ID NO 26
<211> LENGTH: 450
<212> TYPE: DNA
<213> ORGANISM: Artificial Sequence
<220> FEATURE:
<223> OTHER INFORMATION: Synthetic

<400> SEQUENCE: 26

```
catacgctct acgctcccgg cggttatgac attatgggct atctgtccca gattatgaac    60
aggccaaacc cccaagtaga actgggacct gttgacacgt cagttgctct gattctgtgc   120
gacctgaagc aaaaagacac gccaattgtg tacgcctcgg aagcttttct ctatatgaca   180
ggatacagca atgcggaggt cttggggaga aactgccgtt tcttcagtc acccgacgga    240
atggtcaagc cgaaatcgac aaggaagtac gtcgactcca acacgatcaa tacgatgagg   300
aaagcgattg ataggaacgc cgaggtgcag gttgaggtgg tcaattttaa gaagaacggc   360
caacggtttg tcaacttctt gacgatgatt ccggtgcgag atgaaacagg ggaataccgg   420
tacagcatgg gtttccagtg cgaaacggaa                                    450
```

<210> SEQ ID NO 27
<211> LENGTH: 150
<212> TYPE: PRT
<213> ORGANISM: Artificial Sequence
<220> FEATURE:
<223> OTHER INFORMATION: Synthetic

<400> SEQUENCE: 27

```
His Thr Leu Tyr Ala Pro Gly Gly Tyr Asp Ile Met Gly Tyr Leu Ser
1               5                   10                  15
Gln Ile Met Asn Arg Pro Asn Pro Gln Val Glu Leu Gly Pro Val Asp
            20                  25                  30
Thr Ser Val Ala Leu Ile Leu Cys Asp Leu Lys Gln Lys Asp Thr Pro
        35                  40                  45
Ile Val Tyr Ala Ser Glu Ala Phe Leu Tyr Met Thr Gly Tyr Ser Asn
    50                  55                  60
Ala Glu Val Leu Gly Arg Asn Cys Arg Phe Leu Gln Ser Pro Asp Gly
65                  70                  75                  80
Met Val Lys Pro Lys Ser Thr Arg Lys Tyr Val Asp Ser Asn Thr Ile
                85                  90                  95
Asn Thr Met Arg Lys Ala Ile Asp Arg Asn Ala Glu Val Gln Val Glu
            100                 105                 110
Val Val Asn Phe Lys Lys Asn Gly Gln Arg Phe Val Asn Phe Leu Thr
        115                 120                 125
Met Ile Pro Val Arg Asp Glu Thr Gly Glu Tyr Arg Tyr Ser Met Gly
    130                 135                 140
Phe Gln Cys Glu Thr Glu
145                 150
```

<210> SEQ ID NO 28
<211> LENGTH: 450
<212> TYPE: DNA
<213> ORGANISM: Artificial Sequence
<220> FEATURE:
<223> OTHER INFORMATION: Synthetic

<400> SEQUENCE: 28

```
catacgctct acgctcccgg cggttatgac attatgggct atctggcgca gattatgcgc    60
```

```
aggccaaacc cccaagtaga actgggacct gttgacacgt cagttgctct gattctgtgc    120
gacctgaagc aaaaagacac gccaattgtg tacgcctcgg aagctttttct ctatatgaca    180
```

```
aggccaaacc cccaagtaga actgggacct gttgacacgt cagttgctct gattctgtgc    120
gacctgaagc aaaaagacac gccaattgtg tacgcctcgg aagcttttct ctatatgaca    180
ggatacagca atgcggaggt cttggggaga aactgccgtt ttcttcagtc acccgacgga    240
atggtcaagc cgaaatcgac aaggaagtac gtcgactcca acacgatcaa tacgatgagg    300
aaagcgattg ataggaacgc cgaggtgcag gttgaggtgg tcaattttaa gaagaacggc    360
caacggtttg tcaacttctt gacgatgatt ccggtgcgag atgaaacagg gaataccgg     420 tacagcatgg gtttccagtg cgaaacggaa                                    450
```

<210> SEQ ID NO 29
<211> LENGTH: 150
<212> TYPE: PRT
<213> ORGANISM: Artificial Sequence
<220> FEATURE:
<223> OTHER INFORMATION: Synthetic

<400> SEQUENCE: 29

```
His Thr Leu Tyr Ala Pro Gly Gly Tyr Asp Ile Met Gly Tyr Leu Ala
1               5                   10                  15

Gln Ile Met Arg Arg Pro Asn Pro Gln Val Glu Leu Gly Pro Val Asp
            20                  25                  30

Thr Ser Val Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150
```

<210> SEQ ID NO 30
<211> LENGTH: 432
<212> TYPE: DNA
<213> ORGANISM: Artificial Sequence
<220> FEATURE:
<223> OTHER INFORMATION: Synthetic

<400> SEQUENCE: 30

```
ttcttggcta ctacacttga acgtattgag aagaactttg tcattactga cccaaggttg     60
ccagataatc ccattatatt cgcgtccgat agtttcttgc agttgacaga atatagccgt    120
gaagaaattt tgggaagaaa ctgcaggttt ctacaaggtc ctgaaactga tcgcgcgaca    180
gtgagaaaaa ttagagatgc catagataac caaacagagg tcactgttca gctgattaat    240
tatacaaaga gtggtaaaaa gttctggaac ctctttcact tgcagcctat gcgagatcag    300
aagggagatg tccagtactt tattggggtt cagttggatg aactgagcca tgtccgagat    360
gctgccgaga gagggagt catgctgatt aagaaaactg cagaaaatat tgatgaggcg    420
```
gcaaaagaac tt                                                              432

<210> SEQ ID NO 31
<211> LENGTH: 144
<212> TYPE: PRT
<213> ORGANISM: Artificial Sequence
<220> FEATURE:
<223> OTHER INFORMATION: Synthetic

<400> SEQUENCE: 31

Phe Leu Ala Thr Thr Leu Glu Arg Ile Glu Lys Asn Phe Val Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Asp Ala Ala Glu Arg Glu Gly Val Met
        115                 120                 125

Leu Ile Lys Lys Thr Ala Glu Asn Ile Asp Glu Ala Ala Lys Glu Leu
    130                 135                 140

<210> SEQ ID NO 32
<211> LENGTH: 339
<212> TYPE: DNA
<213> ORGANISM: Artificial Sequence
<220> FEATURE:
<223> OTHER INFORMATION: Synthetic

<400> SEQUENCE: 32
cagaattttg tgataactga tgcaagcttg ccgataatc ccatcgtcta tgcaagccga      60 ggcttttaa cgctaactgg ttattccctt gatcagattc taggtcgaaa ctgtcgtttc     120
cttcaaggcc ctgaaacaga tccacgagct gtcgataaga tccgaaatgc atcacaaaa     180 ggagtggaca catcagtgtg tcttcttaat taccgtcaag atggtacaac ctttttggaat   240 ctgttttttg ttgctggtct acgagattca aagggcaata ttgttaacta tgttggtgtg    300
cagagtaaag tttctgaaga ttacgccaag ttgctagtg                           339

<210> SEQ ID NO 33
<211> LENGTH: 113
<212> TYPE: PRT
<213> ORGANISM: Artificial Sequence
<220> FEATURE:
<223> OTHER INFORMATION: Synthetic

<400> SEQUENCE: 33

Gln Asn Phe Val Ile Thr Asp Ala Ser Leu Pro Asp Asn Pro Ile Val
1               5                   10                  15

Tyr Ala Ser Arg Gly Phe Leu Thr Leu Thr Gly Tyr Ser Leu Asp Gln
            20                  25                  30

Ile Leu Gly Arg Asn Cys Arg Phe Leu Gln Gly Pro Glu Thr Asp Pro
        35                  40                  45

Arg Ala Val Asp Lys Ile Arg Asn Ala Ile Thr Lys Gly Val Asp Thr
            50                  55                  60

Ser Val Cys Leu Leu Asn Tyr Arg Gln Asp Gly Thr Thr Phe Trp Asn
 65                  70                  75                  80

Leu Phe Phe Val Ala Gly Leu Arg Asp Ser Lys Gly Asn Ile Val Asn
                 85                  90                  95

Tyr Val Gly Val Gln Ser Lys Val Ser Glu Asp Tyr Ala Lys Leu Leu
                100                 105                 110

Val

<210> SEQ ID NO 34
<211> LENGTH: 152
<212> TYPE: DNA
<213> ORGANISM: Artificial Sequence
<220> FEATURE:
<223> OTHER INFORMATION: Synthetic

<400> SEQUENCE: 34 tgttttttg atcgttttca caaaaatgga agtccacagt cttgacaggg aaaatgcagc    60
ggcgtagctt ttatgctgta tataaaacca gtggttatat gtacagtatt tattttttaac   120 ttattgtttt aaaagtcaaa gaggatttta ta                                 152

<210> SEQ ID NO 35
<211> LENGTH: 71
<212> TYPE: DNA
<213> ORGANISM: Escherichia coli

<400> SEQUENCE: 35
atagggttga tctttgttgt cactggatgt actgtacatc catacagtaa ctcacagggg    60
ctggattgat t                                                         71

<210> SEQ ID NO 36
<211> LENGTH: 100
<212> TYPE: DNA
<213> ORGANISM: Escherichia coli

<400> SEQUENCE: 36
caatttctac aaaacacttg atactgtatg agcatacagt ataattgctt caacagaaca    60
tattgactat ccggtattac ccggcatgac aggagtaaaa                         100

<210> SEQ ID NO 37
<211> LENGTH: 100
<212> TYPE: DNA
<213> ORGANISM: Escherichia coli

<400> SEQUENCE: 37
gcctatgcag cgacaaatat tgatagcctg aatcagtatt gatctgctgg caagaacaga    60
ctactgtata taaaaacagt ataacttcag gcagattatt                         100

<210> SEQ ID NO 38
<211> LENGTH: 74
<212> TYPE: DNA
<213> ORGANISM: Artificial Sequence
<220> FEATURE:
<223> OTHER INFORMATION: Synthetic

<400> SEQUENCE: 38
tatctaacac cgtgcgtgtt gactatttta cctctggcgg tgataatggt tgcatgtact    60

```
<210> SEQ ID NO 39
<211> LENGTH: 81
<212> TYPE: DNA
<213> ORGANISM: Artificial Sequence
<220> FEATURE:
<223> OTHER INFORMATION: Synthetic

<400> SEQUENCE: 39
ttaatacgac tcactatagg gagaccacaa cggtttccct ctagaaataa ttttgtttaa    60
ctttaagaag gagatataca t                                              81

<210> SEQ ID NO 40
<211> LENGTH: 47
<212> TYPE: DNA
<213> ORGANISM: Artificial Sequence
<220> FEATURE:
<223> OTHER INFORMATION: Synthetic

<400> SEQUENCE: 40
ttatcacttg aaattggaag ggagattctt tattataaga attgtgg                  47

<210> SEQ ID NO 41
<211> LENGTH: 88
<212> TYPE: DNA
<213> ORGANISM: Artificial Sequence
<220> FEATURE:
<223> OTHER INFORMATION: Synthetic

<400> SEQUENCE: 41
cattaggcac cccgggcttt acactttatg cttccggctc gtatgttgtg tcgaccgagc    60
ggataacaat ttcacacagg aaaagctt                                       88

<210> SEQ ID NO 42
<211> LENGTH: 711
<212> TYPE: DNA
<213> ORGANISM: Artificial Sequence
<220> FEATURE:
<223> OTHER INFORMATION: Synthetic

<400> SEQUENCE: 42
atggtgagca agggcgagga ggataacatg gccatcatca aggagttcat gcgcttcaag    60
gtgcacatgg agggctccgt gaacggccac gagttcgaga tcgagggcga gggcgagggc   120
cgcccctacg agggcaccca gaccgccaag ctgaaggtga ccaagggtgg ccccctgccc   180
ttcgcctggg acatcctgtc ccctcagttc atgtacggct ccaaggccta cgtgaagcac   240
cccgccgaca tccccgacta cttgaagctg tccttcccsg agggcttcaa gtgggagcgc   300
gtgatgaact tcgaggacgg cggcgtggtg accgtgaccc aggactcctc cctgcaggac   360
ggcgagttca tctacaaggt gaagctgcgc ggcaccaact cccctccga cggccccgta   420 atgcagaaga gaccatgggg ctgggaggcc tcctccgagc ggatgtaccc cgaggacggc   480
gccctgaagg gcgagatcaa gcagaggctg aagctgaagg acggcggcca ctacgacgct   540
gaggtcaaga ccacctacaa ggccaagaag cccgtgcagc tgcccggcgc ctacaacgtc   600
aacatcaagt tggacatcac ctcccacaac gaggactaca ccatcgtgga acagtacgaa   660
cgcgccgagg ccgccactc caccggcggc atggacgagc tgtacaagta a             711

<210> SEQ ID NO 43
<211> LENGTH: 236
```

<212> TYPE: PRT
<213> ORGANISM: Artificial Sequence
<220> FEATURE:
<223> OTHER INFORMATION: Synthetic

<400> SEQUENCE: 43

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys
225                 230                 235
```

<210> SEQ ID NO 44
<211> LENGTH: 3051
<212> TYPE: DNA
<213> ORGANISM: Escherichia coli

<400> SEQUENCE: 44

```
atggtcgttt tacaacgtcg tgactgggaa aaccctggcg ttacccaact taatcgcctt      60
gcagcacatc cccctttcgc cagctggcgt aatagcgaag aggcccgcac cgatcgccct     120
tcccaacagt tgcgcagcct gaatggcgaa tggcgctttg cctggtttcc ggcaccagaa     180
gcggtgccgg aaagctggct ggagtgcgat cttcctgagg ccgatactgt cgtcgtcccc     240
tcaaactggc agatgcacgg ttacgatgcg cccatctaca ccaacgtaac ctatcccatt     300
acggtcaatc cgccgtttgt tcccacggag aatccgacgg ttgttactcg ctcacatttt     360
aatgttgatg aaagctggct acaggaaggc cagacgcgaa ttattttga tggcgttaac     420 tcggcgtttc atctgtggtg caacgggcgc tgggtcggtt acggccagga cagtcgtttg     480
ccgtctgaat ttgacctgag cgcatttttt acgcgccgga aaaacgcct cgcggtgatg     540 gtgctgcgtt ggagtgacgg cagttatctg gaagatcagg atatgtggcg gatgagcggc     600
```

```
attttccgtg acgtctcgtt gctgcataaa ccgactacac aaatcagcga tttccatgtt    660
gccactcgct ttaatgatga tttcagccgc gctgtactgg aggctgaagt tcagatgtgc    720
ggcgagttgc gtgactacct acgggtaaca gtttctttat ggcagggtga aacgcaggtc    780
gccagcggca ccgcgccttt cggcggtgaa attatcgatg agcgtggtgg ttatgccgat    840
cgcgtcacac tacgtctgaa cgtcgaaaac ccgaaactgt ggagcgccga atcccgaat    900
ctctatcgtg cggtggttga actgcacacc gccgacggca cgctgattga agcagaagcc    960
tgcgatgtcg gtttccgcga ggtgcggatt gaaaatggtc tgctgctgct gaacggcaag   1020
ccgttgctga ttcgaggcgt taaccgtcac gagcatcatc tctgcatgg tcaggtcatg    1080
gatgagcaga cgatggtgca ggatatcctg ctgatgaagc agaacaactt taacgccgtg   1140
cgctgttcgc attatccgaa ccatccgctg tggtacacgc tgtgcgaccg ctacggcctg   1200
tatgtggtgg atgaagccaa tattgaaacc cacggcatgg tgccaatgaa tcgtctgacc   1260
gatgatccgc gctggctacc ggcgatgagc gaacgcgtaa cgcgaatggt gcagcgcgat   1320
cgtaatcacc cgagtgtgat catctggtcg ctggggaatg aatcaggcca cggcgctaat   1380
cacgacgcgc tgtatcgctg atcaaatct gtcgatcctt cccgcccggt gcagtatgaa    1440
ggcggcggag ccgacaccac ggccaccgat attatttgcc cgatgtacgc gcgcgtggat   1500
gaagaccagc ccttcccggc tgtgccgaaa tggtccatca aaaatggct ttcgctacct    1560
ggagagacgc gcccgctgat cctttgcgaa tacgcccacg cgatgggtaa cagtcttggc   1620
ggtttcgcta aatactggca ggcgtttcgt cagtatcccc gtttacaggg cggcttcgtc   1680
tgggactggg tggatcagtc gctgattaaa tatgatgaaa acggcaaccc gtggtcggct   1740
tacggcggtg attttggcga tacgccgaac gatcgccagt tctgtatgaa cggtctggtc   1800
tttgccgacc gcacgccgca tccagcgctg acggaagcaa acaccagca gcagttttc    1860
cagttccgtt tatccgggca aaccatcgaa gtgaccagcg aatacctgtt ccgtcatagc   1920
gataacgagc tcctgcactg gatggtggcg ctggatggta gccgctggc aagcggtgaa   1980
gtgcctctgg atgtcgctcc acaaggtaaa cagttgattg aactgcctga actaccgcag   2040
ccggagagcg ccgggcaact ctggctcaca gtacgcgtag tgcaaccgaa cgcgaccgca   2100
tggtcagaag ccgggcacat cagcgcctgg cagcagtggc gtctggcgga aaacctcagt   2160
gtgacgctcc ccgccgcgtc ccacgccatc ccgcatctga ccaccagcga aatggatttt   2220
tgcatcgagc tgggtaataa gcgttggcaa tttaaccgcc agtcaggctt tctttcacag   2280
atgtggattg gcgataaaaa acaactgctg acgccgctgc gcgatcagtt cacccgtgca   2340
ccgctggata cgacattgg cgtaagtgaa gcgacccgca ttgaccctaa cgcctgggtc    2400
gaacgctgga aggcggcggg ccattaccag gccgaagcag cgttgttgca gtgcacggca   2460
gatacacttg ctgatgcggt gctgattacg accgctcacg cgtggcagca tcagggaaa   2520
accttatta tcagccggaa aacctaccgg attgatggta gtggtcaaat ggcgattacc   2580
gttgatgttg aagtggcgag cgatacaccg catccggcgc ggattggcct gaactgccag   2640
ctggcgcagg tagcagagcg ggtaaactgg ctcggattag gccgcaagaa aaactatccc   2700
gaccgcctta ctgccgcctg ttttgaccgc tgggatctgc cattgtcaga catgtatacc   2760
ccgtacgtct tcccgagcga aaacggtctg cgctgcggga cgcgcgaatt gaattatggc   2820
ccacaccagt ggcgcggcga cttccagttc aacatcagcc gctacagtca acagcaactg   2880
atggaaacca gccatcgcca tctgctgcac gcggaagaag gcacatggct gaatatcgac   2940
```

```
ggtttccata tggggattgg tggcgacgac tcctggagcc cgtcagtatc ggcggaattc    3000
cagctgagcg ccggtcgcta ccattaccag ttggtctggt gtcaaaaata a              3051
```

<210> SEQ ID NO 45
<211> LENGTH: 1016
<212> TYPE: PRT
<213> ORGANISM: Escherichia coli

<400> SEQUENCE: 45

```
Met Val Val Leu Gln Arg Arg Asp Trp Glu Asn Pro Gly Val Thr Gln
1               5                   10                  15

Leu Asn Arg Leu Ala Ala His Pro Pro Phe Ala Ser Trp Arg Asn Ser
            20                  25                  30

Glu Glu Ala Arg Thr Asp Arg Pro Ser Gln Gln Leu Arg Ser Leu Asn
        35                  40                  45

Gly Glu Trp Arg Phe Ala Trp Phe Pro Ala Pro Glu Ala Val Pro Glu
    50                  55                  60

Ser Trp Leu Glu Cys Asp Leu Pro Glu Ala Asp Thr Val Val Val Pro
65                  70                  75                  80

Ser Asn Trp Gln Met His Gly Tyr Asp Ala Pro Ile Tyr Thr Asn Val
                85                  90                  95

Thr Tyr Pro Ile Thr Val Asn Pro Pro Phe Val Pro Thr Glu Asn Pro
            100                 105                 110

Thr Gly Cys Tyr Ser Leu Thr Phe Asn Val Asp Glu Ser Trp Leu Gln
        115                 120                 125

Glu Gly Gln Thr Arg Ile Ile Phe Asp Gly Val Asn Ser Ala Phe His
    130                 135                 140

Leu Trp Cys Asn Gly Arg Trp Val Gly Tyr Gly Gln Asp Ser Arg Leu
145                 150                 155                 160

Pro Ser Glu Phe Asp Leu Ser Ala Phe Leu Arg Ala Gly Glu Asn Arg
                165                 170                 175

Leu Ala Val Met Val Leu Arg Trp Ser Asp Gly Ser Tyr Leu Glu Asp
            180                 185                 190

Gln Asp Met Trp Arg Met Ser Gly Ile Phe Arg Asp Val Ser Leu Leu
        195                 200                 205

His Lys Pro Thr Thr Gln Ile Ser Asp Phe His Val Ala Thr Arg Phe
    210                 215                 220

Asn Asp Asp Phe Ser Arg Ala Val Leu Glu Ala Glu Val Gln Met Cys
225                 230                 235                 240

Gly Glu Leu Arg Asp Tyr Leu Arg Val Thr Val Ser Leu Trp Gln Gly
                245                 250                 255

Glu Thr Gln Val Ala Ser Gly Thr Ala Pro Phe Gly Gly Glu Ile Ile
            260                 265                 270

Asp Glu Arg Gly Gly Tyr Ala Asp Arg Val Thr Leu Arg Leu Asn Val
        275                 280                 285

Glu Asn Pro Lys Leu Trp Ser Ala Glu Ile Pro Asn Leu Tyr Arg Ala
    290                 295                 300

Val Val Glu Leu His Thr Ala Asp Gly Thr Leu Ile Glu Ala Glu Ala
305                 310                 315                 320

Cys Asp Val Gly Phe Arg Glu Val Arg Ile Glu Asn Gly Leu Leu Leu
                325                 330                 335

Leu Asn Gly Lys Pro Leu Leu Ile Arg Gly Val Asn Arg His Glu His
            340                 345                 350

His Pro Leu His Gly Gln Val Met Asp Glu Gln Thr Met Val Gln Asp
```

-continued

```
            355                 360                 365
Ile Leu Leu Met Lys Gln Asn Asn Phe Asn Ala Val Arg Cys Ser His
    370                 375                 380
Tyr Pro Asn His Pro Leu Trp Tyr Thr Leu Cys Asp Arg Tyr Gly Leu
385                 390                 395                 400
Tyr Val Val Asp Glu Ala Asn Ile Glu Thr His Gly Met Val Pro Met
                405                 410                 415
Asn Arg Leu Thr Asp Asp Pro Arg Trp Leu Pro Ala Met Ser Glu Arg
                420                 425                 430
Val Thr Arg Met Val Gln Arg Asp Arg Asn His Pro Ser Val Ile Ile
                435                 440                 445
Trp Ser Leu Gly Asn Glu Ser Gly His Gly Ala Asn His Asp Ala Leu
            450                 455                 460
Tyr Arg Trp Ile Lys Ser Val Asp Pro Ser Arg Pro Val Gln Tyr Glu
465                 470                 475                 480
Gly Gly Gly Ala Asp Thr Thr Ala Thr Asp Ile Ile Cys Pro Met Tyr
                485                 490                 495
Ala Arg Val Asp Glu Asp Gln Pro Phe Pro Ala Val Pro Lys Trp Ser
                500                 505                 510
Ile Lys Lys Trp Leu Ser Leu Pro Gly Glu Thr Arg Pro Leu Ile Leu
            515                 520                 525
Cys Glu Tyr Ala His Ala Met Gly Asn Ser Leu Gly Gly Phe Ala Lys
            530                 535                 540
Tyr Trp Gln Ala Phe Arg Gln Tyr Pro Arg Leu Gln Gly Gly Phe Val
545                 550                 555                 560
Trp Asp Trp Val Asp Gln Ser Leu Ile Lys Tyr Asp Glu Asn Gly Asn
                565                 570                 575
Pro Trp Ser Ala Tyr Gly Gly Asp Phe Gly Asp Thr Pro Asn Asp Arg
                580                 585                 590
Gln Phe Cys Met Asn Gly Leu Val Phe Ala Asp Arg Thr Pro His Pro
            595                 600                 605
Ala Leu Thr Glu Ala Lys His Gln Gln Gln Phe Phe Gln Phe Arg Leu
            610                 615                 620
Ser Gly Gln Thr Ile Glu Val Thr Ser Glu Tyr Leu Phe Arg His Ser
625                 630                 635                 640
Asp Asn Glu Leu Leu His Trp Met Val Ala Leu Asp Gly Lys Pro Leu
                645                 650                 655
Ala Ser Gly Glu Val Pro Leu Asp Val Ala Pro Gln Gly Lys Gln Leu
                660                 665                 670
Ile Glu Leu Pro Glu Leu Pro Gln Pro Glu Ser Ala Gly Gln Leu Trp
            675                 680                 685
Leu Thr Val Arg Val Val Gln Pro Asn Ala Thr Ala Trp Ser Glu Ala
            690                 695                 700
Gly His Ile Ser Ala Trp Gln Gln Trp Arg Leu Ala Glu Asn Leu Ser
705                 710                 715                 720
Val Thr Leu Pro Ala Ala Ser His Ala Ile Pro His Leu Thr Thr Ser
                725                 730                 735
Glu Met Asp Phe Cys Ile Glu Leu Gly Asn Lys Arg Trp Gln Phe Asn
                740                 745                 750
Arg Gln Ser Gly Phe Leu Ser Gln Met Trp Ile Gly Asp Lys Lys Gln
            755                 760                 765
Leu Leu Thr Pro Leu Arg Asp Gln Phe Thr Arg Ala Pro Leu Asp Asn
            770                 775                 780
```

Asp Ile Gly Val Ser Glu Ala Thr Arg Ile Asp Pro Asn Ala Trp Val
785                 790                 795                 800

Glu Arg Trp Lys Ala Ala Gly His Tyr Gln Ala Glu Ala Ala Leu Leu
            805                 810                 815

Gln Cys Thr Ala Asp Thr Leu Ala Asp Ala Val Leu Ile Thr Thr Ala
            820                 825                 830

His Ala Trp Gln His Gln Gly Lys Thr Leu Phe Ile Ser Arg Lys Thr
            835                 840                 845

Tyr Arg Ile Asp Gly Ser Gly Gln Met Ala Ile Thr Val Asp Val Glu
850                 855                 860

Val Ala Ser Asp Thr Pro His Pro Ala Arg Ile Gly Leu Asn Cys Gln
865                 870                 875                 880

Leu Ala Gln Val Ala Glu Arg Val Asn Trp Leu Gly Leu Gly Pro Gln
            885                 890                 895

Glu Asn Tyr Pro Asp Arg Leu Thr Ala Ala Cys Phe Asp Arg Trp Asp
            900                 905                 910

Leu Pro Leu Ser Asp Met Tyr Thr Pro Tyr Val Phe Pro Ser Glu Asn
            915                 920                 925

Gly Leu Arg Cys Gly Thr Arg Glu Leu Asn Tyr Gly Pro His Gln Trp
930                 935                 940

Arg Gly Asp Phe Gln Phe Asn Ile Ser Arg Tyr Ser Gln Gln Gln Leu
945                 950                 955                 960

Met Glu Thr Ser His Arg His Leu Leu His Ala Glu Glu Gly Thr Trp
            965                 970                 975

Leu Asn Ile Asp Gly Phe His Met Gly Ile Gly Gly Asp Asp Ser Trp
            980                 985                 990

Ser Pro Ser Val Ser Ala Glu Phe Gln Leu Ser Ala Gly Arg Tyr His
            995                 1000                1005

Tyr Gln Leu Val Trp Cys Gln Lys
    1010                1015

<210> SEQ ID NO 46
<211> LENGTH: 1107
<212> TYPE: DNA
<213> ORGANISM: Saccharomyces cerevisiae

<400> SEQUENCE: 46
ttcaatgaat taaatgccat aaatgaaaac attagagatg atctttcggc gttattaaaa     60
tctgatttct tcaaatactt tcggctggat ttatacaagc aatgttcatt ttgggacgcc    120
aacgatggtc tgtgcttaaa ccgcgcttgc tctgttgatg tcgtagagga ctgggataca    180
ctgcctgagt actggcagcc tgagatcttg ggtagtttca ataatgatac aatgaaggaa    240
gcggatgata gcgatgacga atgtaagttc ttagatcaac tatgtcaaac cagtaaaaaa    300
cctgtagata tcgaagacac catcaactac tgtgatgtaa atgactttaa cggtaaaaac    360
gccgttctga ttgatttaac agcaaatccg gaacgattta caggttatgg tggtaagcaa    420
gctggtcaaa tttggtctac tatctaccaa gacaactgtt ttacaattgg cgaaactggt    480
gaatcattgg ccaaagatgc atttatagac cttgtatccg gtttccatgc ctctatcggt    540
actcacttat caaggaata tttgaacacg aaaactggta atgggagcc aatctggat    600 ttgtttatgg caagaatcgg gaactttcct gatagagtga caaacatgta tttcaattat    660
gctgttgtag ctaaggctct ctggaaaatt caaccatatt taccagaatt ttcattctgt    720
gatctagtca ataaagaaat caaaaacaaa atggataacg ttatttccca gctggacaca    780

```
aaaattttta acgaagactt agtttttgcc aacgacctaa gtttgacttt gaaggacgaa    840
ttcagatctc gcttcaagaa tgtcacgaag attatggatt gtgtgcaatg tgatagatgt    900
agattgtggg gcaaaattca aactaccggt tacgcaactg ccttgaaaat tttgtttgaa    960
atcaacgacg ctgatgaatt caccaaacaa catattgttg gtaagttaac caaatatgag   1020
ttgattgcac tattacagac tttcggtaga ttatctgaat ctattgaatc tgttaacatg   1080
ttcgaaaaaa tgtacgggaa aaggtta                                       1107
```

<210> SEQ ID NO 47
<211> LENGTH: 369
<212> TYPE: PRT
<213> ORGANISM: Saccharomyces cerevisiae

<400> SEQUENCE: 47

```
Phe Asn Glu Leu Asn Ala Ile Asn Glu Asn Ile Arg Asp Asp Leu Ser
 1               5                  10                  15

Ala Leu Leu Lys Ser Asp Phe Phe Lys Tyr Phe Arg Leu Asp Leu Tyr
            20                  25                  30

Lys Gln Cys Ser Phe Trp Asp Ala Asn Asp Gly Leu Cys Leu Asn Arg
        35                  40                  45

Ala Cys Ser Val Asp Val Val Glu Asp Trp Asp Thr Leu Pro Glu Tyr
    50                  55                  60

Trp Gln Pro Glu Ile Leu Gly Ser Phe Asn Asn Asp Thr Met Lys Glu
65                  70                  75                  80

Ala Asp Asp Ser Asp Asp Glu Cys Lys Phe Leu Asp Gln Leu Cys Gln
                85                  90                  95

Thr Ser Lys Lys Pro Val Asp Ile Glu Asp Thr Ile Asn Tyr Cys Asp
           100                 105                 110

Val Asn Asp Phe Asn Gly Lys Asn Ala Val Leu Ile Asp Leu Thr Ala
       115                 120                 125

Asn Pro Glu Arg Phe Thr Gly Tyr Gly Gly Lys Gln Ala Gly Gln Ile
   130                 135                 140

Trp Ser Thr Ile Tyr Gln Asp Asn Cys Phe Thr Ile Gly Glu Thr Gly
145                 150                 155                 160

Glu Ser Leu Ala Lys Asp Ala Phe Tyr Arg Leu Val Ser Gly Phe His
                165                 170                 175

Ala Ser Ile Gly Thr His Leu Ser Lys Glu Tyr Leu Asn Thr Lys Thr
            180                 185                 190

Gly Lys Trp Glu Pro Asn Leu Asp Leu Phe Met Ala Arg Ile Gly Asn
        195                 200                 205

Phe Pro Asp Arg Val Thr Asn Met Tyr Phe Asn Tyr Ala Val Val Ala
    210                 215                 220

Lys Ala Leu Trp Lys Ile Gln Pro Tyr Leu Pro Glu Phe Ser Phe Cys
225                 230                 235                 240

Asp Leu Val Asn Lys Glu Ile Lys Asn Lys Met Asp Asn Val Ile Ser
                245                 250                 255

Gln Leu Asp Thr Lys Ile Phe Asn Glu Asp Leu Val Phe Ala Asn Asp
            260                 265                 270

Leu Ser Leu Thr Leu Lys Asp Glu Phe Arg Ser Arg Phe Lys Asn Val
        275                 280                 285

Thr Lys Ile Met Asp Cys Val Gln Cys Asp Arg Cys Arg Leu Trp Gly
    290                 295                 300

Lys Ile Gln Thr Thr Gly Tyr Ala Thr Ala Leu Lys Ile Leu Phe Glu
```

```
                305                 310                 315                 320
Ile Asn Asp Ala Asp Glu Phe Thr Lys Gln His Ile Val Gly Lys Leu
                    325                 330                 335

Thr Lys Tyr Glu Leu Ile Ala Leu Leu Gln Thr Phe Gly Arg Leu Ser
                340                 345                 350

Glu Ser Ile Glu Ser Val Asn Met Phe Glu Lys Met Tyr Gly Lys Arg
                355                 360                 365

Leu

<210> SEQ ID NO 48
<211> LENGTH: 714
<212> TYPE: DNA
<213> ORGANISM: Artificial Sequence
<220> FEATURE:
<223> OTHER INFORMATION: Synthetic

<400> SEQUENCE: 48
atgaaagcgt taacggccag gcaacaagag gtgtttgatc tcatccgtga tcacatcagc     60
cagacaggta tgccgccgac gcgtgcggaa atcgcgcagc gtttggggtt ccgttcccca    120
aacgcggctg aagaacatct gaaggcgctg gcacgcaaag gcgttattga aattgtttcc    180
ggcgcatcac gcgggattcg tctgttgcag gaagaggaag aagggttgcc gctggtaggt    240
cgtgtggctg ccggtgaacc gcatacgctc tacgctcccg gcggttatga cattatgggc    300
tatctgattc agattatgaa caggccaaac ccccaagtag aactgggacc tgttgacacg    360
tcagttgctc tgattctgtg cgacctgaag caaaaagaca cgccaattgt gtacgcctcg    420 gaagctttc tctatatgac aggatacagc aatgcggagg tcttggggag aaactgccgt    480
tttcttcagt cacccgacgg aatggtcaag ccgaaatcga caaggaagta cgtcgactcc    540
aacacgatca atacgatgag gaaagcgatt gataggaacg ccgaggtgca ggttgaggtg    600
gtcaatttta agaagaacgg ccaacggttt gtcaacttct tgacgatgat tccggtgcga    660
gatgaaacag gggaataccg gtacagcatg ggtttccagt gcgaaacgga atga          714

<210> SEQ ID NO 49
<211> LENGTH: 237
<212> TYPE: PRT
<213> ORGANISM: Artificial Sequence
<220> FEATURE:
<223> OTHER INFORMATION: Synthetic

<400> SEQUENCE: 49

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
        50                  55                  60

Gly Ile Arg Leu Leu Gln Glu Glu Glu Gly Leu Pro Leu Val Gly
65                  70                  75                  80

Arg Val Ala Ala Gly Glu Pro His Thr Leu Tyr Ala Pro Gly Gly Tyr
                85                  90                  95

Asp Ile Met Gly Tyr Leu Ile Gln Ile Met Asn Arg Pro Asn Pro Gln
                100                 105                 110

Val Glu Leu Gly Pro Val Asp Thr Ser Val Ala Leu Ile Leu Cys Asp
```

```
                115               120                  125
Leu Lys Gln Lys Asp Thr Pro Ile Val Tyr Ala Ser Glu Ala Phe Leu
130                 135                 140

Tyr Met Thr Gly Tyr Ser Asn Ala Glu Val Leu Gly Arg Asn Cys Arg
145                 150                 155                 160

Phe Leu Gln Ser Pro Asp Gly Met Val Lys Pro Lys Ser Thr Arg Lys
                165                 170                 175

Tyr Val Asp Ser Asn Thr Ile Asn Thr Met Arg Lys Ala Ile Asp Arg
                180                 185                 190

Asn Ala Glu Val Gln Val Glu Val Val Asn Phe Lys Lys Asn Gly Gln
            195                 200                 205

Arg Phe Val Asn Phe Leu Thr Met Ile Pro Val Arg Asp Glu Thr Gly
        210                 215                 220

Glu Tyr Arg Tyr Ser Met Gly Phe Gln Cys Thr Glu
225                 230                 235

<210> SEQ ID NO 50
<211> LENGTH: 723
<212> TYPE: DNA
<213> ORGANISM: Artificial Sequence
<220> FEATURE:
<223> OTHER INFORMATION: Synthetic

<400> SEQUENCE: 50
atgaaagcgt taacggccag gcaacaagag gtgtttgatc tcatccgtga tcacatcagc      60
cagacaggta tgccgccgac gcgtgcggaa atcgcgcagc gtttgggggtt ccgttccccca    120 aacgcggctg aagaacatct gaaggcgctg gcacgcaaag gcgttattga aattgtttcc     180
ggcgcatcac gcgggattcg tctgttgcag gaagaggaag aagggttgcc gctggtaggt     240
cgtgtggctg ccggtgaacc gtgtcgtggg catacgctct acgctcccgg cggttatgac     300
attatgggct atctgattca gattatgaac aggccaaaac cccaagtaga actgggacct     360
gttgacacgt cagttgctct gattctgtgc gacctgaagc aaaaagacac gccaattgtg     420
tacgcctcgg aagctttttct ctatatgaca ggatacagca atgcggaggt cttggggaga    480
aactgccgtt tcttcagtc acccgacgga atggtcaagc cgaaatcgac aaggaagtac      540
gtcgactcca acacgatcaa tacgatgagg aaagcgattg ataggaacgc cgaggtgcag     600
gttgaggtgg tcaattttaa gaagaacggc caacggtttg tcaacttctt gacgatgatt     660
ccggtgcgag atgaaacagg ggaataccgg tacagcatgg gtttccagtg cgaaacggaa     720
tga                                                                   723

<210> SEQ ID NO 51
<211> LENGTH: 240
<212> TYPE: PRT
<213> ORGANISM: Artificial Sequence
<220> FEATURE:
<223> OTHER INFORMATION: Synthetic

<400> SEQUENCE: 51

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
```

```
            50                  55                  60
Gly Ile Arg Leu Leu Gln Glu Glu Glu Gly Leu Pro Leu Val Gly
 65                  70                  75                  80

Arg Val Ala Ala Gly Glu Pro Cys Arg Gly His Thr Leu Tyr Ala Pro
                 85                  90                  95

Gly Gly Tyr Asp Ile Met Gly Tyr Leu Ile Gln Ile Met Asn Arg Pro
            100                 105                 110

Asn Pro Gln Val Glu Leu Gly Pro Val Asp Thr Ser Val Ala Leu Ile
            115                 120                 125

Leu Cys Asp Leu Lys Gln Lys Asp Thr Pro Ile Val Tyr Ala Ser Glu
            130                 135                 140

Ala Phe Leu Tyr Met Thr Gly Tyr Ser Asn Ala Glu Val Leu Gly Arg
145                 150                 155                 160

Asn Cys Arg Phe Leu Gln Ser Pro Asp Gly Met Val Lys Pro Lys Ser
                165                 170                 175

Thr Arg Lys Tyr Val Asp Ser Asn Thr Ile Asn Thr Met Arg Lys Ala
                180                 185                 190

Ile Asp Arg Asn Ala Glu Val Gln Val Glu Val Val Asn Phe Lys Lys
            195                 200                 205

Asn Gly Gln Arg Phe Val Asn Phe Leu Thr Met Ile Pro Val Arg Asp
            210                 215                 220

Glu Thr Gly Glu Tyr Arg Tyr Ser Met Gly Phe Gln Cys Glu Thr Glu
225                 230                 235                 240

<210> SEQ ID NO 52
<211> LENGTH: 720
<212> TYPE: DNA
<213> ORGANISM: Artificial Sequence
<220> FEATURE:
<223> OTHER INFORMATION: Synthetic

<400> SEQUENCE: 52
atgaaagcgt taacggccag gcaacaagag gtgtttgatc tcatccgtga tcacatcagc      60
cagacaggta tgccgccgac gcgtgcggaa atcgcgcagc gtttgggggtt ccgttcccca    120 aacgcggctg aagaacatct gaaggcgctg gcacgcaaag gcgttattga aattgtttcc    180
ggcgcatcac gcgggattcg tctgttgcag gaagaggaag aagggttgcc gctggtaggt    240
cgtgtggctg ccggtgaacc ggtgtttcat acgctctacg ctcccggcgg ttatgacatt    300
atgggctatc tgattcagat tatgaacagg ccaaaccccc aagtagaact gggacctgtt    360
gacacgtcag ttgctctgat tctgtgcgac ctgaagcaaa aagacacgcc aattgtgtac    420
gcctcggaag cttttctcta tatgacagga tacagcaatg cggaggtctt ggggagaaac    480
tgccgttttc ttcagtcacc cgacggaatg gtcaagccga atcgacaag gaagtacgtc    540 gactccaaca cgatcaatac gatgaggaaa gcgattgata ggaacgccga ggtgcaggtt    600
gaggtggtca attttaagaa gaacggccaa cggtttgtca acttcttgac gatgattccg    660
gtgcgagatg aaacagggga ataccggtac agcatggggtt tccagtgcga aacggaatga    720

<210> SEQ ID NO 53
<211> LENGTH: 239
<212> TYPE: PRT
<213> ORGANISM: Artificial Sequence
<220> FEATURE:
<223> OTHER INFORMATION: Synthetic

<400> SEQUENCE: 53
```

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                      45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Val Phe His Thr Leu Tyr Ala Pro Gly
                85                  90                  95

Gly Tyr Asp Ile Met Gly Tyr Leu Ile Gln Ile Met Asn Arg Pro Asn
                100                 105                 110

Pro Gln Val Glu Leu Gly Pro Val Asp Thr Ser Val Ala Leu Ile Leu
            115                 120                 125

Cys Asp Leu Lys Gln Lys Asp Thr Pro Ile Val Tyr Ala Ser Glu Ala
        130                 135                 140

Phe Leu Tyr Met Thr Gly Tyr Ser Asn Ala Glu Val Leu Gly Arg Asn
145                 150                 155                 160

Cys Arg Phe Leu Gln Ser Pro Asp Gly Met Val Lys Pro Lys Ser Thr
                165                 170                 175

Arg Lys Tyr Val Asp Ser Asn Thr Ile Asn Thr Met Arg Lys Ala Ile
                180                 185                 190

Asp Arg Asn Ala Glu Val Gln Val Glu Val Val Asn Phe Lys Lys Asn
            195                 200                 205

Gly Gln Arg Phe Val Asn Phe Leu Thr Met Ile Pro Val Arg Asp Glu
    210                 215                 220

Thr Gly Glu Tyr Arg Tyr Ser Met Gly Phe Gln Cys Glu Thr Glu
225                 230                 235

<210> SEQ ID NO 54
<211> LENGTH: 720
<212> TYPE: DNA
<213> ORGANISM: Artificial Sequence
<220> FEATURE:
<223> OTHER INFORMATION: Synthetic

<400> SEQUENCE: 54
atgaaagcgt taacggccag gcaacaagag gtgtttgatc tcatccgtga tcacatcagc      60
cagacaggta tgccgccgac gcgtgcggaa atcgcgcagc gtttggggtt ccgttcccca     120
aacgcggctg aagaacatct gaaggcgctg gcacgcaaag gcgttattga aattgtttcc     180
ggcgcatcac gcgggattcg tctgttgcag gaagaggaag aagggttgcc gctggtaggt     240
cgtgtggctg ccggtgaacc gtataagcat acgctctacg ctcccggcgg ttatgacatt     300
atgggctatc tgattcagat tatgaacagg ccaaaccccc aagtagaact gggacctgtt     360
gacacgtcag ttgctctgat tctgtgcgac ctgaagcaaa agacacgcc aattgtgtac     420 gcctcggaag cttttctcta tatgacagga tacagcaatg cggaggtctt ggggagaaac     480
tgccgttttc ttcagtcacc cgacggaatg gtcaagccga atcgacaag gaagtacgtc     540 gactccaaca cgatcaatac gatgaggaaa gcgattgata ggaacgccga ggtgcaggtt     600
gaggtggtca attttaagaa gaacggccaa cggtttgtca acttcttgac gatgattccg     660
gtgcgagatg aaacagggga ataccggtac agcatggggtt tccagtgcga aacggaatga     720
```

<210> SEQ ID NO 55
<211> LENGTH: 239
<212> TYPE: PRT
<213> ORGANISM: Artificial Sequence
<220> FEATURE:
<223> OTHER INFORMATION: Synthetic

<400> SEQUENCE: 55

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu His Leu Lys
            35                  40                  45

Ala Leu Ala Arg Lys Gly Val Ile Glu Ile Val Ser Gly Ala Ser Arg
        50                  55                  60

Gly Ile Arg Leu Leu Gln Glu Glu Glu Gly Leu Pro Leu Val Gly
65                  70                  75                  80

Arg Val Ala Ala Gly Glu Pro Tyr Lys His Thr Leu Tyr Ala Pro Gly
                85                  90                  95

Gly Tyr Asp Ile Met Gly Tyr Leu Ile Gln Ile Met Asn Arg Pro Asn
            100                 105                 110

Pro Gln Val Glu Leu Gly Pro Val Asp Thr Ser Val Ala Leu Ile Leu
        115                 120                 125

Cys Asp Leu Lys Gln Lys Asp Thr Pro Ile Val Tyr Ala Ser Glu Ala
130                 135                 140

Phe Leu Tyr Met Thr Gly Tyr Ser Asn Ala Glu Val Leu Gly Arg Asn
145                 150                 155                 160

Cys Arg Phe Leu Gln Ser Pro Asp Gly Met Val Lys Pro Lys Ser Thr
                165                 170                 175

Arg Lys Tyr Val Asp Ser Asn Thr Ile Asn Thr Met Arg Lys Ala Ile
            180                 185                 190

Asp Arg Asn Ala Glu Val Gln Val Glu Val Val Asn Phe Lys Lys Asn
        195                 200                 205

Gly Gln Arg Phe Val Asn Phe Leu Thr Met Ile Pro Val Arg Asp Glu
    210                 215                 220

Thr Gly Glu Tyr Arg Tyr Ser Met Gly Phe Gln Cys Glu Thr Glu
225                 230                 235
```

<210> SEQ ID NO 56
<211> LENGTH: 720
<212> TYPE: DNA
<213> ORGANISM: Artificial Sequence
<220> FEATURE:
<223> OTHER INFORMATION: Synthetic

<400> SEQUENCE: 56

```
atgaaagcgt taacggccag gcaacaagag gtgtttgatc tcatccgtga tcacatcagc      60
cagacaggta tgccgccgac gcgtgcggaa atcgcgcagc gtttggggtt ccgttcccca     120
aacgcggctg aagaacatct gaaggcgctg gcacgcaaag gcgttattga aattgtttcc     180
ggcgcatcac gcgggattcg tctgttgcag gaagaggaag aagggttgcc gctggtaggt     240
cgtgtggctg ccggtgaacc gggatcccat acgctctacg ctcccggcgg ttatgacatt     300
atgggctatc tgattcagat tatgaacagg ccaaaccccc aagtagaact gggacctgtt     360
gacacgtcag ttgctctgat tctgtgcgac ctgaagcaaa aagacacgcc aattgtgtac     420
```

```
gcctcggaag ctttctctcta tatgacagga tacagcaatg cggaggtctt ggggagaaac    480
tgccgttttc ttcagtcacc cgacggaatg gtcaagccga aatcgacaag gaagtacgtc    540
gactccaaca cgatcaatac gatgaggaaa gcgattgata ggaacgccga ggtgcaggtt    600
gaggtggtca attttaagaa gaacggccaa cggtttgtca acttcttgac gatgattccg    660
gtgcgagatg aaacagggga ataccggtac agcatgggtt ccagtgcga aacggaatga    720
```

<210> SEQ ID NO 57
<211> LENGTH: 239
<212> TYPE: PRT
<213> ORGANISM: Artificial Sequence
<220> FEATURE:
<223> OTHER INFORMATION: Synthetic

<400> SEQUENCE: 57

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Gly Ser His Thr Leu Tyr Ala Pro Gly
                85                  90                  95

Gly Tyr Asp Ile Met Gly Tyr Leu Ile Gln Ile Met Asn Arg Pro Asn
            100                 105                 110

Pro Gln Val Glu Leu Gly Pro Val Asp Thr Ser Val Ala Leu Ile Leu
        115                 120                 125

Cys Asp Leu Lys Gln Lys Asp Thr Pro Ile Val Tyr Ala Ser Glu Ala
    130                 135                 140

Phe Leu Tyr Met Thr Gly Tyr Ser Asn Ala Glu Val Leu Gly Arg Asn
145                 150                 155                 160

Cys Arg Phe Leu Gln Ser Pro Asp Gly Met Val Lys Pro Lys Ser Thr
                165                 170                 175

Arg Lys Tyr Val Asp Ser Asn Thr Ile Asn Thr Met Lys Ala Ile
            180                 185                 190

Asp Arg Asn Ala Glu Val Gln Val Val Val Asn Phe Lys Lys Asn
        195                 200                 205

Gly Gln Arg Phe Val Asn Phe Leu Thr Met Ile Pro Val Arg Asp Glu
    210                 215                 220

Thr Gly Glu Tyr Arg Tyr Ser Met Gly Phe Gln Cys Glu Thr Glu
225                 230                 235
```

<210> SEQ ID NO 58
<211> LENGTH: 720
<212> TYPE: DNA
<213> ORGANISM: Artificial Sequence
<220> FEATURE:
<223> OTHER INFORMATION: Synthetic

<400> SEQUENCE: 58

```
atgaaagcgt taacggccag gcaacaagag gtgtttgatc tcatccgtga tcacatcagc    60
cagacaggta tgccgccgac gcgtgcggaa atcgcgcagc gtttgggggtt ccgttcccca   120
```

```
aacgcggctg aagaacatct gaaggcgctg gcacgcaaag gcgttattga aattgtttcc      180
ggcgcatcac gcgggattcg tctgttgcag gaagaggaag aagggttgcc gctggtaggt      240
cgtgtggctg ccggtgaacc ggaacctcat acgctctacg ctcccggcgg ttatgacatt      300
atgggctatc tgattcagat tatgaacagg ccaaacccccc aagtagaact gggacctgtt      360
gacacgtcag ttgctctgat tctgtgcgac ctgaagcaaa aagacacgcc aattgtgtac      420
gcctcggaag cttttctcta tatgacagga tacagcaatg cggaggtctt ggggagaaac      480
tgccgttttc ttcagtcacc cgacggaatg gtcaagccga atcgacaag gaagtacgtc       540 gactccaaca cgatcaatac gatgaggaaa gcgattgata ggaacgccga ggtgcaggtt      600
gaggtggtca attttaagaa gaacggccaa cggtttgtca acttcttgac gatgattccg      660
gtgcgagatg aaacagggga ataccggtac agcatgggtt ccagtgcga aacggaatga      720
```

<210> SEQ ID NO 59
<211> LENGTH: 239
<212> TYPE: PRT
<213> ORGANISM: Artificial Sequence
<220> FEATURE:
<223> OTHER INFORMATION: Synthetic

<400> SEQUENCE: 59

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Glu Pro His Thr Leu Tyr Ala Pro Gly
                85                  90                  95

Gly Tyr Asp Ile Met Gly Tyr Leu Ile Gln Ile Met Asn Arg Pro Asn
            100                 105                 110

Pro Gln Val Glu Leu Gly Pro Val Asp Thr Ser Val Ala Leu Ile Leu
        115                 120                 125

Cys Asp Leu Lys Gln Lys Asp Thr Pro Ile Val Tyr Ala Ser Glu Ala
    130                 135                 140

Phe Leu Tyr Met Thr Gly Tyr Ser Asn Ala Glu Val Leu Gly Arg Asn
145                 150                 155                 160

Cys Arg Phe Leu Gln Ser Pro Asp Gly Met Val Lys Pro Lys Ser Thr
                165                 170                 175

Arg Lys Tyr Val Asp Ser Asn Thr Ile Asn Thr Met Arg Lys Ala Ile
            180                 185                 190

Asp Arg Asn Ala Glu Val Gln Val Glu Val Asn Phe Lys Lys Asn
        195                 200                 205

Gly Gln Arg Phe Val Asn Phe Leu Thr Met Ile Pro Val Arg Asp Glu
    210                 215                 220

Thr Gly Glu Tyr Arg Tyr Ser Met Gly Phe Gln Cys Glu Thr Glu
225                 230                 235
```

<210> SEQ ID NO 60
<211> LENGTH: 732
<212> TYPE: DNA

<213> ORGANISM: Artificial Sequence
<220> FEATURE:
<223> OTHER INFORMATION: Synthetic

<400> SEQUENCE: 60

```
atgaaagcgt taacggccag gcaacaagag gtgtttgatc tcatccgtga tcacatcagc    60
cagacaggta tgccgccgac gcgtgcggaa atcgcgcagc gtttggggtt ccgttcccca   120
aacgcggctg aagaacatct gaaggcgctg cacgcaaag gcgttattga aattgtttcc    180
ggcgcatcac gcgggattcg tctgttgcag gaagaggaag aagggttgcc gctggtaggt   240
cgtgtggctg ccggtgaacc gctggccgag gccgctgccc atacgctcta cgctcccggc   300
ggttatgaca ttatgggcta tctgattcag attatgaaca ggccaaaccc ccaagtagaa   360
ctgggacctg ttgacacgtc agttgctctg attctgtgcg acctgaagca aaaagacacg   420
ccaattgtgt acgcctcgga agcttttctc tatatgacag atacagcaa tgcggaggtc    480
ttggggagaa actgccgttt tcttcagtca cccgacggaa tggtcaagcc gaaatcgaca   540
aggaagtacg tcgactccaa cacgatcaat acgatgagga aagcgattga taggaacgcc   600
gaggtgcagg ttgaggtggt caatttttaag aagaacggcc aacggtttgt caacttcttg   660
acgatgattc cggtgcgaga tgaaacaggg gaataccggt acagcatggg tttccagtgc   720
gaaacggaat ga                                                       732
```

<210> SEQ ID NO 61
<211> LENGTH: 243
<212> TYPE: PRT
<213> ORGANISM: Artificial Sequence
<220> FEATURE:
<223> OTHER INFORMATION: Synthetic

<400> SEQUENCE: 61

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Ala Glu Ala Ala His Thr Leu
                85                  90                  95

Tyr Ala Pro Gly Gly Tyr Asp Ile Met Gly Tyr Leu Ile Gln Ile Met
                100                 105                 110

Asn Arg Pro Asn Pro Gln Val Glu Leu Gly Pro Val Asp Thr Ser Val
            115                 120                 125

Ala Leu Ile Leu Cys Asp Leu Lys Gln Lys Asp Thr Pro Ile Val Tyr
    130                 135                 140

Ala Ser Glu Ala Phe Leu Tyr Met Thr Gly Tyr Ser Asn Ala Glu Val
145                 150                 155                 160

Leu Gly Arg Asn Cys Arg Phe Leu Gln Ser Pro Asp Gly Met Val Lys
                165                 170                 175

Pro Lys Ser Thr Arg Lys Tyr Val Asp Ser Asn Thr Ile Asn Thr Met
            180                 185                 190

Arg Lys Ala Ile Asp Arg Asn Ala Glu Val Gln Val Glu Val Val Asn
```

```
                195                 200                 205
Phe Lys Lys Asn Gly Gln Arg Phe Val Asn Phe Leu Thr Met Ile Pro
    210                 215                 220

Val Arg Asp Glu Thr Gly Glu Tyr Arg Tyr Ser Met Gly Phe Gln Cys
225                 230                 235                 240

Glu Thr Glu

<210> SEQ ID NO 62
<211> LENGTH: 738
<212> TYPE: DNA
<213> ORGANISM: Artificial Sequence
<220> FEATURE:
<223> OTHER INFORMATION: Synthetic

<400> SEQUENCE: 62
atgaaagcgt taacggccag gcaacaagag gtgtttgatc tcatccgtga tcacatcagc    60
cagacaggta tgccgccgac gcgtgcggaa atcgcgcagc gtttgggggtt ccgttccccca   120 aacgcggctg aagaacatct gaaggcgctg gcacgcaaag cgttattga aattgtttcc    180 ggcgcatcac gcgggattcg tctgttgcag gaagaggaag aagggttgcc gctggtaggt    240
cgtgtggctg ccggtgaacc gaccgagttc cccggcgtgg accagcatac gctctacgct    300
cccggcggtt atgacattat gggctatctg attcagatta tgaacaggcc aaacccccaa    360
gtagaactgg gacctgttga cacgtcagtt gctctgattc tgtgcgacct gaagcaaaaa    420
gacacgccaa ttgtgtacgc ctcggaagct tttctctata tgacaggata cagcaatgcg    480
gaggtcttgg ggagaaactg ccgttttctt cagtcacccg acggaatggt caagccgaaa    540
tcgacaagga agtacgtcga ctccaacacg atcaatacga tgaggaaagc gattgatagg    600
aacgccgagg tgcaggttga ggtggtcaat tttaagaaga acggccaacg gtttgtcaac    660
ttcttgacga tgattccggt gcgagatgaa acaggggaat accggtacag catgggtttc    720
cagtgcgaaa cggaatga                                                 738

<210> SEQ ID NO 63
<211> LENGTH: 245
<212> TYPE: PRT
<213> ORGANISM: Artificial Sequence
<220> FEATURE:
<223> OTHER INFORMATION: Synthetic

<400> SEQUENCE: 63

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu His Leu Lys
            35                  40                  45

Ala Leu Ala Arg Lys Gly Val Ile Glu Ile Val Ser Gly Ala Ser Arg
        50                  55                  60

Gly Ile Arg Leu Leu Gln Glu Glu Glu Gly Leu Pro Leu Val Gly
65                  70                  75                  80

Arg Val Ala Ala Gly Glu Pro Thr Glu Phe Pro Gly Val Asp Gln His
                85                  90                  95

Thr Leu Tyr Ala Pro Gly Gly Tyr Asp Ile Met Gly Tyr Leu Ile Gln
            100                 105                 110

Ile Met Asn Arg Pro Asn Pro Gln Val Glu Leu Gly Pro Val Asp Thr
        115                 120                 125
```

```
Ser Val Ala Leu Ile Leu Cys Asp Leu Lys Gln Lys Asp Thr Pro Ile
    130                 135                 140

Val Tyr Ala Ser Glu Ala Phe Leu Tyr Met Thr Gly Tyr Ser Asn Ala
145                 150                 155                 160

Glu Val Leu Gly Arg Asn Cys Arg Phe Leu Gln Ser Pro Asp Gly Met
                165                 170                 175

Val Lys Pro Lys Ser Thr Arg Lys Tyr Val Asp Ser Asn Thr Ile Asn
            180                 185                 190

Thr Met Arg Lys Ala Ile Asp Arg Asn Ala Glu Val Gln Val Glu Val
        195                 200                 205

Val Asn Phe Lys Lys Asn Gly Gln Arg Phe Val Asn Phe Leu Thr Met
    210                 215                 220

Ile Pro Val Arg Asp Glu Thr Gly Glu Tyr Arg Tyr Ser Met Gly Phe
225                 230                 235                 240

Gln Cys Glu Thr Glu
                245

<210> SEQ ID NO 64
<211> LENGTH: 711
<212> TYPE: DNA
<213> ORGANISM: Artificial Sequence
<220> FEATURE:
<223> OTHER INFORMATION: Synthetic

<400> SEQUENCE: 64
atgaaagcgt taacggccag gcaacaagag gtgtttgatc tcatccgtga tcacatcagc      60
cagacaggta tgccgccgac gcgtgcggaa atcgcgcagc gtttggggtt ccgttcccca     120
aacgcggctg aagaacatct gaaggcgctg gcacgcaaag gcgttattga aattgtttcc     180
ggcgcatcac gcgggattcg tctgttgcag gaagaggaag aagggttgcc gctggtaggt     240
cgtgtggctg ccggtgaacc gcatacgctc tacgctcccg gcggttatga cattatgggc     300
tatctgattc agattatgaa gaggccaaac ccccaagtag aactgggacc tgttgacacg     360
tcatgcgctc tgattctgtg cgacctgaag caaaaagaca cgccaattgt gtacgcctcg     420
gaagcttttc tctatatgac aggatacagc aatgcggagg tcttggggag aaactgccgt     480
tttcttcagt cacccgacgg aatggtcaag ccgaaatcga caaggaagta cgtcgactcc     540
aacacgatca atacgatgag gaaagcgatt gataggaacg ccgaggtgca ggttgaggtg     600
gtcaatttta agaagaacgg ccaacggttt gtcaacttct tgacgatgat tccggtgcga     660
gatgaaacag gggaataccg gtacagcatg ggtttccagt gcgaaacgga a              711

<210> SEQ ID NO 65
<211> LENGTH: 237
<212> TYPE: PRT
<213> ORGANISM: Artificial Sequence
<220> FEATURE:
<223> OTHER INFORMATION: Synthetic

<400> SEQUENCE: 65

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
```

```
                50                  55                  60
Gly Ile Arg Leu Leu Gln Glu Glu Glu Gly Leu Pro Leu Val Gly
 65                  70                  75                  80

Arg Val Ala Ala Gly Glu Pro His Thr Leu Tyr Ala Pro Gly Gly Tyr
                 85                  90                  95

Asp Ile Met Gly Tyr Leu Ile Gln Ile Met Lys Arg Pro Asn Pro Gln
                100                 105                 110

Val Glu Leu Gly Pro Val Asp Thr Ser Cys Ala Leu Ile Leu Cys Asp
            115                 120                 125

Leu Lys Gln Lys Asp Thr Pro Ile Val Tyr Ala Ser Glu Ala Phe Leu
130                 135                 140

Tyr Met Thr Gly Tyr Ser Asn Ala Glu Val Leu Gly Arg Asn Cys Arg
145                 150                 155                 160

Phe Leu Gln Ser Pro Asp Gly Met Val Lys Pro Lys Ser Thr Arg Lys
                165                 170                 175

Tyr Val Asp Ser Asn Thr Ile Asn Thr Met Arg Lys Ala Ile Asp Arg
            180                 185                 190

Asn Ala Glu Val Gln Val Glu Val Val Asn Phe Lys Lys Asn Gly Gln
        195                 200                 205

Arg Phe Val Asn Phe Leu Thr Met Ile Pro Val Arg Asp Glu Thr Gly
    210                 215                 220

Glu Tyr Arg Tyr Ser Met Gly Phe Gln Cys Glu Thr Glu
225                 230                 235

<210> SEQ ID NO 66
<211> LENGTH: 711
<212> TYPE: DNA
<213> ORGANISM: Artificial Sequence
<220> FEATURE:
<223> OTHER INFORMATION: Synthetic

<400> SEQUENCE: 66
atgaaagcgt taacggccag gcaacaagag gtgtttgatc tcatccgtga tcacatcagc      60
cagacaggta tgccgccgac gcgtgcggaa atcgcgcagc gtttgggggtt ccgttcccca    120 aacgcggctg aagaacatct gaaggcgctg gcacgcaaag gcgttattga aattgtttcc    180
ggcgcatcac gcgggattcg tctgttgcag gaagaggaag aagggttgcc gctggtaggt    240
cgtgtggctg ccggtgaacc gcatacgctc tacgctcccg gcggttatga cattatgggc    300
tggctgattc agattatgaa caggccaaac ccccaagtag aactgggacc tgttgacacg    360
tcatgcgctc tgattctgtg cgacctgaag caaaaagaca cgccaattgt gtacgcctcg    420
gaagcttttc tctatatgac aggatacagc aatgcggagg tcttggggag aaactgccgt    480
tttcttcagt cacccgacgg aatggtcaag ccgaaatcga caggaagta cgtcgactcc    540 aacacgatca atacgatgag gaaagcgatt gataggaacg ccgaggtgca ggttgaggtg    600
gtcaatttta agaagaacgg ccaacggttt gtcaacttct tgacgatgat tccggtgcga    660
gatgaaacag gggaataccg gtacagcatg ggtttccagt gcgaaacgga a             711

<210> SEQ ID NO 67
<211> LENGTH: 237
<212> TYPE: PRT
<213> ORGANISM: Artificial Sequence
<220> FEATURE:
<223> OTHER INFORMATION: Synthetic

<400> SEQUENCE: 67
```

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
50                  55                  60

Gly Ile Arg Leu Leu Gln Glu Glu Glu Gly Leu Pro Leu Val Gly
65                  70                  75                  80

Arg Val Ala Ala Gly Glu Pro His Thr Leu Tyr Ala Pro Gly Gly Tyr
                85                  90                  95

Asp Ile Met Gly Trp Leu Ile Gln Ile Met Asn Arg Pro Asn Pro Gln
            100                 105                 110

Val Glu Leu Gly Pro Val Asp Thr Ser Cys Ala Leu Ile Leu Cys Asp
        115                 120                 125

Leu Lys Gln Lys Asp Thr Pro Ile Val Tyr Ala Ser Glu Ala Phe Leu
    130                 135                 140

Tyr Met Thr Gly Tyr Ser Asn Ala Glu Val Leu Gly Arg Asn Cys Arg
145                 150                 155                 160

Phe Leu Gln Ser Pro Asp Gly Met Val Lys Pro Lys Ser Thr Arg Lys
                165                 170                 175

Tyr Val Asp Ser Asn Thr Ile Asn Thr Met Arg Lys Ala Ile Asp Arg
            180                 185                 190

Asn Ala Glu Val Gln Val Glu Val Val Asn Phe Lys Lys Asn Gly Gln
        195                 200                 205

Arg Phe Val Asn Phe Leu Thr Met Ile Pro Val Arg Asp Glu Thr Gly
    210                 215                 220

Glu Tyr Arg Tyr Ser Met Gly Phe Gln Cys Glu Thr Glu
225                 230                 235

<210> SEQ ID NO 68
<211> LENGTH: 711
<212> TYPE: DNA
<213> ORGANISM: Artificial Sequence
<220> FEATURE:
<223> OTHER INFORMATION: Synthetic

<400> SEQUENCE: 68
atgaaagcgt taacggccag gcaacaagag gtgtttgatc tcatccgtga tcacatcagc     60
cagacaggta tgccgccgac gcgtgcggaa atcgcgcagc gtttgggtt ccgttcccca    120 aacgcggctg aagaacatct gaaggcgctg gcacgcaaag gcgttattga aattgtttcc    180
ggcgcatcac gcgggattcg tctgttgcag gaagaggaag aagggttgcc gctggtaggt    240
cgtgtggctg ccggtgaacc gcatacgctc tacgctcccg gcggttatga cattatgggc    300
tatctgattc agattatgaa caggccaaac ccccaagtag aactgggacc tgttgacacg    360
tcatgcgctc tgattctgtg cgacctgaag caaaaagaca cgccaattgt gtacgcctcg    420
gaagcttttc tctatatgac aggatacagc aatgcggagg tcttggggag aaactgccgt    480
tttcttcagt cacccgacgg aatggtcaag ccgaaatcga caggaagta cgtcgactcc    540 aacacgatca atacgatgag gaaagcgatt gataggaacg ccgaggtgca ggttgaggtg    600
gtcaatttta agaagaacgg ccaacggttt gtcaacttct tgacgatgat tccggtgcga    660
gatgaaacag gggaataccg gtacagcatg ggtttccagt gcgaaacgga a             711

<210> SEQ ID NO 69
<211> LENGTH: 237
<212> TYPE: PRT
<213> ORGANISM: Artificial Sequence
<220> FEATURE:
<223> OTHER INFORMATION: Synthetic

<400> SEQUENCE: 69

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro His Thr Leu Tyr Ala Pro Gly Gly Tyr
                85                  90                  95

Asp Ile Met Gly Tyr Leu Ile Gln Ile Met Asn Arg Pro Asn Pro Gln
            100                 105                 110

Val Glu Leu Gly Pro Val Asp Thr Ser Cys Ala Leu Ile Leu Cys Asp
        115                 120                 125

Leu Lys Gln Lys Asp Thr Pro Ile Val Tyr Ala Ser Glu Ala Phe Leu
130                 135                 140

Tyr Met Thr Gly Tyr Ser Asn Ala Glu Val Leu Gly Arg Asn Cys Arg
145                 150                 155                 160

Phe Leu Gln Ser Pro Asp Gly Met Val Lys Pro Lys Ser Thr Arg Lys
                165                 170                 175

Tyr Val Asp Ser Asn Thr Ile Asn Thr Met Arg Lys Ala Ile Asp Arg
            180                 185                 190

Asn Ala Glu Val Gln Val Glu Val Val Asn Phe Lys Lys Asn Gly Gln
        195                 200                 205

Arg Phe Val Asn Phe Leu Thr Met Ile Pro Val Arg Asp Glu Thr Gly
    210                 215                 220

Glu Tyr Arg Tyr Ser Met Gly Phe Gln Cys Glu Thr Glu
225                 230                 235
```

<210> SEQ ID NO 70
<211> LENGTH: 711
<212> TYPE: DNA
<213> ORGANISM: Artificial Sequence
<220> FEATURE:
<223> OTHER INFORMATION: Synthetic

<400> SEQUENCE: 70

```
atgaaagcgt taacggccag gcaacaagag gtgtttgatc tcatccgtga tcacatcagc    60
cagacaggta tgccgccgac gcgtgcggaa atcgcgcagc gtttggggtt ccgttcccca   120
aacgcggctg aagaacatct gaaggcgctg gcacgcaaag gcgttattga aattgtttcc   180
ggcgcatcac gcgggattcg tctgttgcag gaagaggaag aagggttgcc gctggtaggt   240
cgtgtggctg ccggtgaacc gcatacgctc tacgctcccg gcggttatga cattatgggc   300
tatctggcgc agattatgaa caggccaaac ccccaagtag aactgggacc tgttgacacg   360
tcagttgctc tgattctgtg cgacctgaag caaaaagaca cgccaattgt gtacgcctcg   420
```

```
gaagctttc tctatatgac aggatacagc aatgcggagg tcttggggag aaactgccgt    480
tttcttcagt cacccgacgg aatggtcaag ccgaaatcga caaggaagta cgtcgactcc    540
aacacgatca atacgatgag gaaagcgatt gataggaacg ccgaggtgca ggttgaggtg    600 gtcaattta agaagaacgg ccaacggttt gtcaacttct tgacgatgat tccggtgcga    660
gatgaaacag gggaataccg gtacagcatg ggtttccagt gcgaaacgga a           711
```

<210> SEQ ID NO 71
<211> LENGTH: 237
<212> TYPE: PRT
<213> ORGANISM: Artificial Sequence
<220> FEATURE:
<223> OTHER INFORMATION: Synthetic

<400> SEQUENCE: 71

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro His Thr Leu Tyr Ala Pro Gly Gly Tyr
                85                  90                  95

Asp Ile Met Gly Tyr Leu Ala Gln Ile Met Asn Arg Pro Asn Pro Gln
            100                 105                 110

Val Glu Leu Gly Pro Val Asp Thr Ser Val Ala Leu Ile Leu Cys Asp
        115                 120                 125

Leu Lys Gln Lys Asp Thr Pro Ile Val Tyr Ala Ser Glu Ala Phe Leu
    130                 135                 140

Tyr Met Thr Gly Tyr Ser Asn Ala Glu Val Leu Gly Arg Asn Cys Arg
145                 150                 155                 160

Phe Leu Gln Ser Pro Asp Gly Met Val Lys Pro Lys Ser Thr Arg Lys
                165                 170                 175

Tyr Val Asp Ser Asn Thr Ile Asn Thr Met Arg Lys Ala Ile Asp Arg
            180                 185                 190

Asn Ala Glu Val Gln Val Glu Val Val Asn Phe Lys Lys Asn Gly Gln
        195                 200                 205

Arg Phe Val Asn Phe Leu Thr Met Ile Pro Val Arg Asp Glu Thr Gly
    210                 215                 220

Glu Tyr Arg Tyr Ser Met Gly Phe Gln Cys Glu Thr Glu
225                 230                 235
```

<210> SEQ ID NO 72
<211> LENGTH: 711
<212> TYPE: DNA
<213> ORGANISM: Artificial Sequence
<220> FEATURE:
<223> OTHER INFORMATION: Synthetic

<400> SEQUENCE: 72

```
atgaaagcgt taacggccag gcaacaagag gtgtttgatc tcatccgtga tcacatcagc    60
cagacaggta tgccgccgac gcgtgcggaa atcgcgcagc gtttgggggtt ccgttcccca   120
```

```
aacgcggctg aagaacatct gaaggcgctg gcacgcaaag gcgttattga aattgtttcc    180
ggcgcatcac gcgggattcg tctgttgcag gaagaggaag aagggttgcc gctggtaggt    240
cgtgtggctg ccggtgaacc gcatacgctc tacgctcccg gcggttatga cattatgggc    300
tatctgtccc agattatgaa caggccaaac ccccaagtag aactgggacc tgttgacacg    360
tcagttgctc tgattctgtg cgacctgaag caaaaagaca cgccaattgt gtacgcctcg    420
gaagcttttc tctatatgac aggatacagc aatgcgagg tcttggggag aaactgccgt     480
tttcttcagt cacccgacgg aatggtcaag ccgaaatcga caaggaagta cgtcgactcc    540
aacacgatca atacgatgag gaaagcgatt gataggaacg ccgaggtgca ggttgaggtg    600
gtcaatttta agaagaacgg ccaacggttt gtcaacttct tgacgatgat tccggtgcga    660
gatgaaacag gggaataccg gtacagcatg ggtttccagt gcgaaacgga a              711
```

<210> SEQ ID NO 73
<211> LENGTH: 237
<212> TYPE: PRT
<213> ORGANISM: Artificial Sequence
<220> FEATURE:
<223> OTHER INFORMATION: Synthetic

<400> SEQUENCE: 73

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro His Thr Leu Tyr Ala Pro Gly Gly Tyr
                85                  90                  95

Asp Ile Met Gly Tyr Leu Ser Gln Ile Met Asn Arg Pro Asn Pro Gln
            100                 105                 110

Val Glu Leu Gly Pro Val Asp Thr Ser Val Ala Leu Ile Leu Cys Asp
        115                 120                 125

Leu Lys Gln Lys Asp Thr Pro Ile Val Tyr Ala Ser Glu Ala Phe Leu
    130                 135                 140

Tyr Met Thr Gly Tyr Ser Asn Ala Glu Val Leu Gly Arg Asn Cys Arg
145                 150                 155                 160

Phe Leu Gln Ser Pro Asp Gly Met Val Lys Pro Lys Ser Thr Arg Lys
                165                 170                 175

Tyr Val Asp Ser Asn Thr Ile Asn Thr Met Arg Lys Ala Ile Asp Arg
            180                 185                 190

Asn Ala Glu Val Gln Val Glu Val Val Asn Phe Lys Lys Asn Gly Gln
        195                 200                 205

Arg Phe Val Asn Phe Leu Thr Met Ile Pro Val Arg Asp Glu Thr Gly
    210                 215                 220

Glu Tyr Arg Tyr Ser Met Gly Phe Gln Cys Glu Thr Glu
225                 230                 235
```

<210> SEQ ID NO 74
<211> LENGTH: 711
<212> TYPE: DNA

<213> ORGANISM: Artificial Sequence
<220> FEATURE:
<223> OTHER INFORMATION: Synthetic

<400> SEQUENCE: 74

```
atgaaagcgt taacggccag gcaacaagag gtgtttgatc tcatccgtga tcacatcagc      60
cagacaggta tgccgccgac gcgtgcggaa atcgcgcagc gtttggggtt ccgttcccca     120
aacgcggctg aagaacatct gaaggcgctg gcacgcaaag gcgttattga aattgtttcc     180
ggcgcatcac gcgggattcg tctgttgcag gaagaggaag aagggttgcc gctggtaggt     240
cgtgtggctg ccggtgaacc gcatacgctc tacgctcccg gcggttatga cattatgggc     300
tatctggcgc agattatgcg caggccaaac ccccaagtag aactgggacc tgttgacacg     360
tcagttgctc tgattctgtg cgacctgaag caaaaagaca cgccaattgt gtacgcctcg     420
gaagctttc tctatatgac aggatacagc aatgcggagg tcttggggag aaactgccgt     480
tttcttcagt cacccgacgg aatggtcaag ccgaaatcga caaggaagta cgtcgactcc     540
aacacgatca atacgatgag gaaagcgatt gataggaacg ccgaggtgca ggttgaggtg     600
gtcaattta agaagaacgg ccaacggttt gtcaacttct tgacgatgat tccggtgcga     660
gatgaaacag gggaataccg gtacagcatg ggtttccagt gcgaaacgga a              711
```

<210> SEQ ID NO 75
<211> LENGTH: 237
<212> TYPE: PRT
<213> ORGANISM: Artificial Sequence
<220> FEATURE:
<223> OTHER INFORMATION: Synthetic

<400> SEQUENCE: 75

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro His Thr Leu Tyr Ala Pro Gly Gly Tyr
                85                  90                  95

Asp Ile Met Gly Tyr Leu Ala Gln Ile Met Arg Arg Pro Asn Pro Gln
            100                 105                 110

Val Glu Leu Gly Pro Val Asp Thr Ser Val Ala Leu Ile Leu Cys Asp
        115                 120                 125

Leu Lys Gln Lys Asp Thr Pro Ile Val Tyr Ala Ser Glu Ala Phe Leu
    130                 135                 140

Tyr Met Thr Gly Tyr Ser Asn Ala Glu Val Leu Gly Arg Asn Cys Arg
145                 150                 155                 160

Phe Leu Gln Ser Pro Asp Gly Met Val Lys Pro Lys Ser Thr Arg Lys
                165                 170                 175

Tyr Val Asp Ser Asn Thr Ile Asn Thr Met Arg Lys Ala Ile Asp Arg
            180                 185                 190

Asn Ala Glu Val Gln Val Glu Val Val Asn Phe Lys Lys Asn Gly Gln
        195                 200                 205
```

Arg Phe Val Asn Phe Leu Thr Met Ile Pro Val Arg Asp Glu Thr Gly
    210                 215                 220

Glu Tyr Arg Tyr Ser Met Gly Phe Gln Cys Glu Thr Glu
225                 230                 235

<210> SEQ ID NO 76
<211> LENGTH: 696
<212> TYPE: DNA
<213> ORGANISM: Artificial Sequence
<220> FEATURE:
<223> OTHER INFORMATION: Synthetic

<400> SEQUENCE: 76
atgaaagcgt taacggccag gcaacaagag gtgtttgatc tcatccgtga tcacatcagc      60
cagacaggta tgccgccgac gcgtgcggaa atcgcgcagc gtttggggtt ccgttcccca     120
aacgcggctg aagaacatct gaaggcgctg gcacgcaaag gcgttattga aattgtttcc     180
ggcgcatcac gcgggattcg tctgttgcag gaagaggaag aagggttgcc gctggtaggt     240
cgtgtggctg ccggtgaacc gtccttcttg gctactacac ttgaacgtat tgagaagaac     300
tttgtcatta ctgacccaag gttgccagat aatcccatta tattcgcgtc cgatagtttc     360
ttgcagttga cagaatatag ccgtgaagaa attttgggaa gaaactgcag gtttctacaa     420
ggtcctgaaa ctgatcgcgc gacagtgaga aaattagag atgccataga taaccaaaca     480
gaggtcactg ttcagctgat taattataca agagtggtaa aaagttctg gaacctcttt     540 cacttgcagc ctatgcgaga tcagaaggga gatgtccagt actttattgg ggttcagttg     600
gatggaactg agcatgtccg agatgctgcc gagagagagg gagtcatgct gattaagaaa     660
actgcagaaa atattgatga ggcggcaaaa gaactt                                696

<210> SEQ ID NO 77
<211> LENGTH: 232
<212> TYPE: PRT
<213> ORGANISM: Artificial Sequence
<220> FEATURE:
<223> OTHER INFORMATION: Synthetic

<400> SEQUENCE: 77

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Ser Phe Leu Ala Thr Thr Leu Glu Arg
                85                  90                  95

Ile Glu Lys Asn Phe Val Ile Thr Asp Pro Arg Leu Pro Asp Asn Pro
            100                 105                 110

Ile Ile Phe Ala Ser Asp Ser Phe Leu Gln Leu Thr Glu Tyr Ser Arg
        115                 120                 125

Glu Glu Ile Leu Gly Arg Asn Cys Arg Phe Leu Gln Gly Pro Glu Thr
    130                 135                 140

Asp Arg Ala Thr Val Arg Lys Ile Arg Asp Ala Ile Asp Asn Gln Thr
145                 150                 155                 160

Glu Val Thr Val Gln Leu Ile Asn Tyr Thr Lys Ser Gly Lys Lys Phe
                165                 170                 175

Trp Asn Leu Phe His Leu Gln Pro Met Arg Asp Gln Lys Gly Asp Val
            180                 185                 190

Gln Tyr Phe Ile Gly Val Gln Leu Asp Gly Thr Glu His Val Arg Asp
        195                 200                 205

Ala Ala Glu Arg Glu Gly Val Met Leu Ile Lys Lys Thr Ala Glu Asn
    210                 215                 220

Ile Asp Glu Ala Ala Lys Glu Leu
225                 230

<210> SEQ ID NO 78
<211> LENGTH: 603
<212> TYPE: DNA
<213> ORGANISM: Artificial Sequence
<220> FEATURE:
<223> OTHER INFORMATION: Synthetic

<400> SEQUENCE: 78

```
atgaaagcgt taacggccag gcaacaagag gtgtttgatc tcatccgtga tcacatcagc    60
cagacaggta tgccgccgac gcgtgcggaa atcgcgcagc gtttggggtt ccgttcccca   120
aacgcggctg aagaacatct gaaggcgctg gcacgcaaag gcgttattga aattgtttcc   180
ggcgcatcac gcgggattcg tctgttgcag gaagaggaag aagggttgcc gctggtaggt   240
cgtgtggctg ccggtgaacc gtcccagaat tttgtgataa ctgatgcaag cttgccggat   300
aatcccatcg tctatgcaag ccgaggcttt taacgctaa ctggttattc ccttgatcag    360
attctaggtc gaaactgtcg tttccttcaa ggccctgaaa cagatccacg agctgtcgat   420
aagatccgaa atgccatcac aaaggagtg acacatcag tgtgtcttct taattaccgt    480
caagatggta caccttttg gaatctgttt tttgttgctg gtctacgaga ttcaaagggc    540
aatattgtta actatgttgg tgtgcagagt aaagtttctg aagattacgc caagttgcta   600
gtg                                                                603
```

<210> SEQ ID NO 79
<211> LENGTH: 201
<212> TYPE: PRT
<213> ORGANISM: Artificial Sequence
<220> FEATURE:
<223> OTHER INFORMATION: Synthetic

<400> SEQUENCE: 79

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Ser Gln Asn Phe Val Ile Thr Asp Ala
                85                  90                  95

Ser Leu Pro Asp Asn Pro Ile Val Tyr Ala Ser Arg Gly Phe Leu Thr
            100                 105                 110

-continued

```
Leu Thr Gly Tyr Ser Leu Asp Gln Ile Leu Gly Arg Asn Cys Arg Phe
            115                 120                 125

Leu Gln Gly Pro Glu Thr Asp Pro Arg Ala Val Asp Lys Ile Arg Asn
        130                 135                 140

Ala Ile Thr Lys Gly Val Asp Thr Ser Val Cys Leu Leu Asn Tyr Arg
145                 150                 155                 160

Gln Asp Gly Thr Thr Phe Trp Asn Leu Phe Phe Val Ala Gly Leu Arg
                165                 170                 175

Asp Ser Lys Gly Asn Ile Val Asn Tyr Val Gly Val Gln Ser Lys Val
            180                 185                 190

Ser Glu Asp Tyr Ala Lys Leu Leu Val
        195                 200
```

<210> SEQ ID NO 80
<211> LENGTH: 765
<212> TYPE: DNA
<213> ORGANISM: Artificial Sequence
<220> FEATURE:
<223> OTHER INFORMATION: Synthetic

<400> SEQUENCE: 80

```
atgtctacca agaagaaacc tttaactcaa gaacaattgg aggatgctag aaggttgaag     60
gccatctacg aaagaaaaa gaatgagtta gggctatctc aggaaagtgt ggccgacaag    120
atgggaatgg gccaatcagg tgttggtgct ttgttcaacg gtataaacgc attaaatgcc    180
tacaatgctg ccttactggc aaagatattg aaggtatctg tagaagagtt ctcaccttct    240
attgctcgtg aaatctatga atgtatgag gcggttagca tgcagccgtc tttgaggtca    300
gaatatggat cccatacgct ctacgctccc ggcggttatg acattatggg ctatctgatt    360
cagattatga caggccaaa ccccaagta gaactgggac ctgttgacac gtcagttgct    420
ctgattctgt gcgacctgaa gcaaaaagac acgccaattg tgtacgcctc ggaagctttt    480
ctctatatga caggatacag caatgcggag gtcttgggga gaaactgccg ttttcttcag    540
tcacccgacg aatggtcaa gccgaaatcg acaaggaagt acgtcgactc caacacgatc    600
aatacgatga ggaaagcgat tgataggaac gccgaggtgc aggttgaggt ggtcaatttt    660
aagaagaacg gccaacggtt tgtcaacttc ttgacgatga ttccggtgcg agatgaaaca    720
ggggaatacc ggtacagcat gggtttccag tgcgaaacgg aatga                   765
```

<210> SEQ ID NO 81
<211> LENGTH: 254
<212> TYPE: PRT
<213> ORGANISM: Artificial Sequence
<220> FEATURE:
<223> OTHER INFORMATION: Synthetic

<400> SEQUENCE: 81

```
Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
                20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Ala Lys Ile Leu Lys Val Ser Val Glu Glu Phe Ser Pro Ser
65                  70                  75                  80
```

Ile Ala Arg Glu Ile Tyr Glu Met Tyr Glu Ala Val Ser Met Gln Pro
                85                  90                  95

Ser Leu Arg Ser Glu Tyr Gly Ser His Thr Leu Tyr Ala Pro Gly Gly
            100                 105                 110

Tyr Asp Ile Met Gly Tyr Leu Ile Gln Ile Met Asn Arg Pro Asn Pro
        115                 120                 125

Gln Val Glu Leu Gly Pro Val Asp Thr Ser Val Ala Leu Ile Leu Cys
    130                 135                 140

Asp Leu Lys Gln Lys Asp Thr Pro Ile Val Tyr Ala Ser Glu Ala Phe
145                 150                 155                 160

Leu Tyr Met Thr Gly Tyr Ser Asn Ala Glu Val Leu Gly Arg Asn Cys
                165                 170                 175

Arg Phe Leu Gln Ser Pro Asp Gly Met Val Lys Pro Lys Ser Thr Arg
            180                 185                 190

Lys Tyr Val Asp Ser Asn Thr Ile Asn Thr Met Arg Lys Ala Ile Asp
        195                 200                 205

Arg Asn Ala Glu Val Gln Val Glu Val Val Asn Phe Lys Lys Asn Gly
    210                 215                 220

Gln Arg Phe Val Asn Phe Leu Thr Met Ile Pro Val Arg Asp Glu Thr
225                 230                 235                 240

Gly Glu Tyr Arg Tyr Ser Met Gly Phe Gln Cys Glu Thr Glu
                245                 250

<210> SEQ ID NO 82
<211> LENGTH: 645
<212> TYPE: DNA
<213> ORGANISM: Artificial Sequence
<220> FEATURE:
<223> OTHER INFORMATION: Synthetic

<400> SEQUENCE: 82
atgaaaccag taacgttata cgatgtcgca gagtatgccg gtgtctctca tcagaccgtt      60
tccaacgtgg tgaaccaggc cagccacgtt tctgcgaaaa cgcgggaaaa agtggaagcg     120
gcgatggcgg agctgaatta cattcccaac cgcgtggcac aacaactggc gggcaaacag     180
tcgttgggat cccatacgct ctacgctccc ggcggttatg acattatggg ctatctgatt     240
cagattatga caggccaaa ccccaagta gaactgggac ctgttgacac gtcagttgct     300
ctgattctgt gcgacctgaa gcaaaaagac acgccaattg tgtacgcctc ggaagctttt     360
ctctatatga caggatacag caatgcggag gtcttgggga gaaactgccg ttttcttcag     420
tcacccgacg gaatggtcaa gccgaaatcg acaaggaagt acgtcgactc caacacgatc     480
aatacgatga ggaaagcgat tgataggaac gccgaggtgc aggttgaggt ggtcaatttt     540
aagaagaacg gccaacggtt tgtcaacttc ttgacgatga ttccggtgcg agatgaaaca     600
ggggaatacc ggtacagcat gggtttccag tgcgaaacgg aatga                     645

<210> SEQ ID NO 83
<211> LENGTH: 214
<212> TYPE: PRT
<213> ORGANISM: Artificial Sequence
<220> FEATURE:
<223> OTHER INFORMATION: Synthetic

<400> SEQUENCE: 83

Met Lys Pro Val Thr Leu Tyr Asp Val Ala Glu Tyr Ala Gly Val Ser
1               5                   10                  15

His Gln Thr Val Ser Asn Val Val Asn Gln Ala Ser His Val Ser Ala

```
                20                  25                  30
Lys Thr Arg Glu Lys Val Glu Ala Ala Met Ala Glu Leu Asn Tyr Ile
             35                  40                  45

Pro Asn Arg Val Ala Gln Gln Leu Ala Gly Lys Gln Ser Leu Gly Ser
 50                  55                  60

His Thr Leu Tyr Ala Pro Gly Gly Tyr Asp Ile Met Gly Tyr Leu Ile
 65                  70                  75                  80

Gln Ile Met Asn Arg Pro Asn Pro Gln Val Glu Leu Gly Pro Val Asp
                 85                  90                  95

Thr Ser Val Ala Leu Ile Leu Cys Asp Leu Lys Gln Lys Asp Thr Pro
            100                 105                 110

Ile Val Tyr Ala Ser Glu Ala Phe Leu Tyr Met Thr Gly Tyr Ser Asn
            115                 120                 125

Ala Glu Val Leu Gly Arg Asn Cys Arg Phe Leu Gln Ser Pro Asp Gly
        130                 135                 140

Met Val Lys Pro Lys Ser Thr Arg Lys Tyr Val Asp Ser Asn Thr Ile
145                 150                 155                 160

Asn Thr Met Arg Lys Ala Ile Asp Arg Asn Ala Glu Val Gln Val Glu
                165                 170                 175

Val Val Asn Phe Lys Lys Asn Gly Gln Arg Phe Val Asn Phe Leu Thr
            180                 185                 190

Met Ile Pro Val Arg Asp Glu Thr Gly Glu Tyr Arg Tyr Ser Met Gly
        195                 200                 205

Phe Gln Cys Glu Thr Glu
    210

<210> SEQ ID NO 84
<211> LENGTH: 654
<212> TYPE: DNA
<213> ORGANISM: Artificial Sequence
<220> FEATURE:
<223> OTHER INFORMATION: Synthetic

<400> SEQUENCE: 84
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaaggatc ccatacgctc tacgctcccg gcggttatga cattatgggc     240
tatctgattc agattatgaa caggccaaac ccccaagtag aactgggacc tgttgacacg     300
tcagttgctc tgattctgtg cgacctgaag caaaaagaca cgccaattgt gtacgcctcg     360
gaagcttttc tctatatgac aggatacagc aatgcggagg tcttggggag aaactgccgt     420
tttcttcagt cacccgacgg aatggtcaag ccgaaatcga caggaagta cgtcgactcc     480 aacacgatca atacgatgag gaaagcgatt gataggaacg ccgaggtgca ggttgaggtg     540
gtcaatttta agaagaacgg ccaacggttt gtcaacttct tgacgatgat tccggtgcga     600
gatgaaacag gggaataccg gtacagcatg ggtttccagt gcgaaacgga atga          654

<210> SEQ ID NO 85
<211> LENGTH: 217
<212> TYPE: PRT
<213> ORGANISM: Artificial Sequence
<220> FEATURE:
<223> OTHER INFORMATION: Synthetic

<400> SEQUENCE: 85
```

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
50                  55                  60

Glu Gly Ser His Thr Leu Tyr Ala Pro Gly Gly Tyr Asp Ile Met Gly
65                  70                  75                  80

Tyr Leu Ile Gln Ile Met Asn Arg Pro Asn Pro Gln Val Glu Leu Gly
                85                  90                  95

Pro Val Asp Thr Ser Val Ala Leu Ile Leu Cys Asp Leu Lys Gln Lys
                100                 105                 110

Asp Thr Pro Ile Val Tyr Ala Ser Glu Ala Phe Leu Tyr Met Thr Gly
                115                 120                 125

Tyr Ser Asn Ala Glu Val Leu Gly Arg Asn Cys Arg Phe Leu Gln Ser
    130                 135                 140

Pro Asp Gly Met Val Lys Pro Lys Ser Thr Arg Lys Tyr Val Asp Ser
145                 150                 155                 160

Asn Thr Ile Asn Thr Met Arg Lys Ala Ile Asp Arg Asn Ala Glu Val
                165                 170                 175

Gln Val Glu Val Val Asn Phe Lys Lys Asn Gly Gln Arg Phe Val Asn
                180                 185                 190

Phe Leu Thr Met Ile Pro Val Arg Asp Glu Thr Gly Glu Tyr Arg Tyr
                195                 200                 205

Ser Met Gly Phe Gln Cys Glu Thr Glu
    210                 215

<210> SEQ ID NO 86
<211> LENGTH: 648
<212> TYPE: DNA
<213> ORGANISM: Artificial Sequence
<220> FEATURE:
<223> OTHER INFORMATION: Synthetic

<400> SEQUENCE: 86
atgtctaggc tagataagag caaagtcatc aattccgcgt tggaattact taacgaagta     60
ggtattgagg gtttgactac gagaaaacta gcgcaaaaat tgggtgtgga acaaccaaca    120
ctatactggc acgttaagaa taaacgtgca ttattagacg cattagccat cgagatgctg    180
gatagacacg gatcccatac gctctacgct cccggcggtt atgacattat gggctatctg    240
attcagatta tgaacaggcc aaaccccaa gtagaactgg gacctgttga cacgtcagtt    300
gctctgattc tgtgcgacct gaagcaaaaa gacacgccaa ttgtgtacgc ctcggaagct    360
tttctctata tgacaggata cagcaatgcg gaggtcttgg ggagaaactg ccgttttctt    420
cagtcacccg acggaatggt caagccgaaa tcgacaagga agtacgtcga ctccaacacg    480
atcaatacga tgaggaaagc gattgatagg aacgccgagg tgcaggttga ggtggtcaat    540
tttaagaaga acggccaacg gtttgtcaac ttcttgacga tgattccggt gcagagatga a    600 acagggaat accggtacag catgggtttc cagtgcgaaa cggaatga                   648

<210> SEQ ID NO 87
<211> LENGTH: 215
<212> TYPE: PRT

<213> ORGANISM: Artificial Sequence
<220> FEATURE:
<223> OTHER INFORMATION: Synthetic

<400> SEQUENCE: 87

```
Met Ser Arg Leu Asp Lys Ser Lys Val Ile Asn Ser Ala Leu Glu Leu
1               5                   10                  15
Leu Asn Glu Val Gly Ile Glu Gly Leu Thr Thr Arg Lys Leu Ala Gln
                20                  25                  30
Lys Leu Gly Val Glu Gln Pro Thr Leu Tyr Trp His Val Lys Asn Lys
            35                  40                  45
Arg Ala Leu Leu Asp Ala Leu Ala Ile Glu Met Leu Asp Arg His Gly
50                  55                  60
Ser His Thr Leu Tyr Ala Pro Gly Gly Tyr Asp Ile Met Gly Tyr Leu
65                  70                  75                  80
Ile Gln Ile Met Asn Arg Pro Asn Pro Gln Val Glu Leu Gly Pro Val
                85                  90                  95
Asp Thr Ser Val Ala Leu Ile Leu Cys Asp Leu Lys Gln Lys Asp Thr
            100                 105                 110
Pro Ile Val Tyr Ala Ser Glu Ala Phe Leu Tyr Met Thr Gly Tyr Ser
        115                 120                 125
Asn Ala Glu Val Leu Gly Arg Asn Cys Arg Phe Leu Gln Ser Pro Asp
130                 135                 140
Gly Met Val Lys Pro Lys Ser Thr Arg Lys Tyr Val Asp Ser Asn Thr
145                 150                 155                 160
Ile Asn Thr Met Arg Lys Ala Ile Asp Arg Asn Ala Glu Val Gln Val
                165                 170                 175
Glu Val Val Asn Phe Lys Lys Asn Gly Gln Arg Phe Val Asn Phe Leu
            180                 185                 190
Thr Met Ile Pro Val Arg Asp Glu Thr Gly Glu Tyr Arg Tyr Ser Met
        195                 200                 205
Gly Phe Gln Cys Glu Thr Glu
210                 215
```

<210> SEQ ID NO 88
<211> LENGTH: 1533
<212> TYPE: DNA
<213> ORGANISM: Artificial Sequence
<220> FEATURE:
<223> OTHER INFORMATION: Synthetic

<400> SEQUENCE: 88

```
atgaaagcgt taacggccag gcaacaagag gtgtttgatc tcatccgtga tcacatcagc    60
cagacaggta tgccgccgac gcgtgcggaa atcgcgcagc gtttgggggtt ccgttcccca   120 aacgcggctg aaaagcatct gaaggcgctg gcacgcaaag gcgttattga aattgtttcc   180
ggcgcatcac gcgggattcg tctgttgcag gaagaggaag aagggttgcc gctggtaggt   240
cgtgtggctg ccggtgaacc ccatacgctc tacgctcccg gcggttatga cattatgggc   300
tatctgattc agattatgaa caggccaaac ccccaagtag aactgggacc tgttgacacg   360
tcagttgctc tgattctgtg cgacctgaag caaaagacac gccaattgt gtacgcctcg   420 gaagctttc tctatatgac aggatacagc aatgcggagg tcttggggag aaactgccgt   480
tttcttcagt cacccgacgg aatggtcaag ccgaaatcga caggaagta cgtcgactcc   540 aacacgatca atacgatgag gaaagcgatt gataggaacg ccgaggtgca ggttgaggtg   600 gtcaattta agaagaacgg ccaacggttt gtcaacttct tgacgatgat tccggtgcga   660
```

```
gatgaaacag gggaataccg gtacagcatg ggtttccagt gcgaaacgga aactagtgcg    720
gccgcggact acaaggatga cgacgacaag ttccggaccg gttccaagac acccccccac    780
ggtaccatgc agggttctgt gacagagttt ctaaaaccgc gcctggttga tatcgagcaa    840
gtgagttcga cgcacgccaa ggtgacccct gagcctttag agcgtggctt tggccatact    900
ctgggtaacg cactgcgccg tattctgctc tcatcgatgc cggggttgcgc ggtgaccgag    960 gttgagattg atggtgtact acatgagtac agcaccaaag aaggcgttca ggaagatatc    1020
ctggaaatcc tgctcaacct gaaagggctg gcggtgagag ttcagggcaa agatgaagtt    1080
attcttacct tgaataaatc tggcattggc cctgtgactg cagccgatat cacccacgac    1140
ggtgatgtcg aaatcgtcaa gccgcagcac gtgatctgcc acctgaccga tgagaacgcg    1200
tctattagca tgcgtatcaa agttcagcgc ggtcgtggtt atgtgccggc ttctacccga    1260
attcattcgg aagaagatga gcgcccaatc ggccgtctgc tggtcgacgc atgctacagc    1320
cctgtggagc gtattgccta caatgttgaa gcagcgcgtg tagaacagcg taccgacctg    1380
gacaagctgg tcatcgaaat ggaaaccaac ggcacaatcg atcctgaaga ggcgattcgt    1440
cgtgcggcaa ccattctggc tgaacaactg gaagctttcg ttgacttacg tgatgtacgt    1500
cagcctgaag tgaaagaaga gaaaccagag taa                                 1533
```

<210> SEQ ID NO 89
<211> LENGTH: 510
<212> TYPE: PRT
<213> ORGANISM: Artificial Sequence
<220> FEATURE:
<223> OTHER INFORMATION: Synthetic

<400> SEQUENCE: 89

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Lys His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro His Thr Leu Tyr Ala Pro Gly Gly Tyr
                85                  90                  95

Asp Ile Met Gly Tyr Leu Ile Gln Ile Met Asn Arg Pro Asn Pro Gln
            100                 105                 110

Val Glu Leu Gly Pro Val Asp Thr Ser Val Ala Leu Ile Leu Cys Asp
        115                 120                 125

Leu Lys Gln Lys Asp Thr Pro Ile Val Tyr Ala Ser Glu Ala Phe Leu
    130                 135                 140

Tyr Met Thr Gly Tyr Ser Asn Ala Glu Val Leu Gly Arg Asn Cys Arg
145                 150                 155                 160

Phe Leu Gln Ser Pro Asp Gly Met Val Lys Pro Lys Ser Thr Arg Lys
                165                 170                 175

Tyr Val Asp Ser Asn Thr Ile Asn Thr Met Arg Lys Ala Ile Asp Arg
            180                 185                 190

Asn Ala Glu Val Gln Val Glu Val Val Asn Phe Lys Lys Asn Gly Gln
        195                 200                 205
```

Arg Phe Val Asn Phe Leu Thr Met Ile Pro Val Arg Asp Glu Thr Gly
        210                 215                 220

Glu Tyr Arg Tyr Ser Met Gly Phe Gln Cys Glu Thr Glu Thr Ser Ala
225                 230                 235                 240

Ala Ala Asp Tyr Lys Asp Asp Asp Lys Phe Arg Thr Gly Ser Lys
                245                 250                 255

Thr Pro Pro His Gly Thr Met Gln Gly Ser Val Thr Glu Phe Leu Lys
                260                 265                 270

Pro Arg Leu Val Asp Ile Glu Gln Val Ser Ser Thr His Ala Lys Val
            275                 280                 285

Thr Leu Glu Pro Leu Glu Arg Gly Phe Gly His Thr Leu Gly Asn Ala
290                 295                 300

Leu Arg Arg Ile Leu Leu Ser Ser Met Pro Gly Cys Ala Val Thr Glu
305                 310                 315                 320

Val Glu Ile Asp Gly Val Leu His Glu Tyr Ser Thr Lys Glu Gly Val
                325                 330                 335

Gln Glu Asp Ile Leu Glu Ile Leu Leu Asn Leu Lys Gly Leu Ala Val
                340                 345                 350

Arg Val Gln Gly Lys Asp Glu Val Ile Leu Thr Leu Asn Lys Ser Gly
            355                 360                 365

Ile Gly Pro Val Thr Ala Ala Asp Ile Thr His Asp Gly Asp Val Glu
370                 375                 380

Ile Val Lys Pro Gln His Val Ile Cys His Leu Thr Asp Glu Asn Ala
385                 390                 395                 400

Ser Ile Ser Met Arg Ile Lys Val Gln Arg Gly Arg Gly Tyr Val Pro
                405                 410                 415

Ala Ser Thr Arg Ile His Ser Glu Glu Asp Glu Arg Pro Ile Gly Arg
                420                 425                 430

Leu Leu Val Asp Ala Cys Tyr Ser Pro Val Glu Arg Ile Ala Tyr Asn
            435                 440                 445

Val Glu Ala Ala Arg Val Glu Gln Arg Thr Asp Leu Asp Lys Leu Val
450                 455                 460

Ile Glu Met Glu Thr Asn Gly Thr Ile Asp Pro Glu Glu Ala Ile Arg
465                 470                 475                 480

Arg Ala Ala Thr Ile Leu Ala Glu Gln Leu Glu Ala Phe Val Asp Leu
                485                 490                 495

Arg Asp Val Arg Gln Pro Glu Val Lys Glu Glu Lys Pro Glu
            500                 505                 510

<210> SEQ ID NO 90
<211> LENGTH: 1053
<212> TYPE: DNA
<213> ORGANISM: Artificial Sequence
<220> FEATURE:
<223> OTHER INFORMATION: Synthetic

<400> SEQUENCE: 90
atggcacgcg taactgttca ggacgctgta gagaaaattg gtaaccgttt tgacctggta      60
ctggtcgccg cgcgtcgcgc tcgtcagatg caggtaggcg aaaggatcc gctggtaccg      120 gaagaaaacg ataaaaccac tgtaatcgcg ctgcgcgaaa tcgaagaagg tctgatcaac      180
aaccagatcc tcgacgttcg cgaacgccag aacagcaag agcaggaagc cgctgaatta      240
caagccgtta ccgctattgc tgaaggtcgt gcggccgcgg actacaagga tgacgacgac      300
aagttccgga ccggttccaa gacacccccc cacactagta tgaaagcgtt aacggccagg      360

```
caacaagagg tgtttgatct catccgtgat cacatcagcc agacaggtat gccgccgacg    420
cgtgcggaaa tcgcgcagcg tttggggttc cgttccccaa acgcggctga aaagcatctg    480
aaggcgctgg cacgcaaagg cgttattgaa attgtttccg gcgcatcacg cgggattcgt    540
ctgttgcagg aagaggaaga agggttgccg ctggtaggtc gtgtggctgc cggtgaaccc    600
catacgctct acgctcccgg cggttatgac attatgggct atctgattca gattatgaac    660
aggccaaacc cccaagtaga actgggacct gttgacacgt cagttgctct gattctgtgc    720
gacctgaagc aaaaagacac gccaattgtg tacgcctcgg aagcttttct ctatatgaca    780
ggatacagca atgcggaggt cttggggaga aactgccgtt ttcttcagtc acccgacgga    840
atggtcaagc cgaaatcgac aaggaagtac gtcgactcca acacgatcaa tacgatgagg    900
aaagcgattg ataggaacgc cgaggtgcag gttgaggtgg tcaattttaa gaagaacggc    960
caacggtttg tcaacttctt gacgatgatt ccggtgcgag atgaaacagg ggaataccgg   1020
tacagcatgg gtttccagtg cgaaacggaa tga                                1053
```

<210> SEQ ID NO 91
<211> LENGTH: 350
<212> TYPE: PRT
<213> ORGANISM: Artificial Sequence
<220> FEATURE:
<223> OTHER INFORMATION: Synthetic

<400> SEQUENCE: 91

```
Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
                20                  25                  30

Gly Gly Lys Asp Pro Leu Val Pro Glu Glu Asn Asp Lys Thr Thr Val
            35                  40                  45

Ile Ala Leu Arg Glu Ile Glu Glu Gly Leu Ile Asn Asn Gln Ile Leu
        50                  55                  60

Asp Val Arg Glu Arg Gln Glu Gln Gln Glu Gln Ala Ala Glu Leu
65                  70                  75                  80

Gln Ala Val Thr Ala Ile Ala Glu Gly Arg Ala Ala Asp Tyr Lys
                85                  90                  95

Asp Asp Asp Asp Lys Phe Arg Thr Gly Ser Lys Thr Pro Pro His Thr
            100                 105                 110

Ser Met Lys Ala Leu Thr Ala Arg Gln Gln Glu Val Phe Asp Leu Ile
        115                 120                 125

Arg Asp His Ile Ser Gln Thr Gly Met Pro Pro Thr Arg Ala Glu Ile
130                 135                 140

Ala Gln Arg Leu Gly Phe Arg Ser Pro Asn Ala Ala Glu Lys His Leu
145                 150                 155                 160

Lys Ala Leu Ala Arg Lys Gly Val Ile Glu Ile Val Ser Gly Ala Ser
                165                 170                 175

Arg Gly Ile Arg Leu Leu Gln Glu Glu Glu Gly Leu Pro Leu Val
            180                 185                 190

Gly Arg Val Ala Ala Gly Glu Pro His Thr Tyr Ala Pro Gly Gly
        195                 200                 205

Tyr Asp Ile Met Gly Tyr Leu Ile Gln Ile Met Asn Arg Pro Asn Pro
    210                 215                 220

Gln Val Glu Leu Gly Pro Val Asp Thr Ser Val Ala Leu Ile Leu Cys
225                 230                 235                 240
```

```
Asp Leu Lys Gln Lys Asp Thr Pro Ile Val Tyr Ala Ser Glu Ala Phe
            245                 250                 255

Leu Tyr Met Thr Gly Tyr Ser Asn Ala Glu Val Leu Gly Arg Asn Cys
        260                 265                 270

Arg Phe Leu Gln Ser Pro Asp Gly Met Val Lys Pro Lys Ser Thr Arg
            275                 280                 285

Lys Tyr Val Asp Ser Asn Thr Ile Asn Thr Met Arg Lys Ala Ile Asp
290                 295                 300

Arg Asn Ala Glu Val Gln Val Glu Val Val Asn Phe Lys Lys Asn Gly
305                 310                 315                 320

Gln Arg Phe Val Asn Phe Leu Thr Met Ile Pro Val Arg Asp Glu Thr
                325                 330                 335

Gly Glu Tyr Arg Tyr Ser Met Gly Phe Gln Cys Glu Thr Glu
            340                 345                 350

<210> SEQ ID NO 92
<211> LENGTH: 1584
<212> TYPE: DNA
<213> ORGANISM: Artificial Sequence
<220> FEATURE:
<223> OTHER INFORMATION: Synthetic

<400> SEQUENCE: 92
atgtctacca agaagaaacc tttaactcaa gaacaattgg aggatgctag aaggttgaag      60
gccatctacg aaaagaaaaa gaatgagtta gggctatctc aggaaagtgt ggccgacaag     120
atgggaatgg ccaatcagg tgttggtgct ttgttcaacg gataaacgc attaaatgcc      180 tacaatgctg ccttactggc aaagatattg aaggtatctg tagaagagtt ctcaccttct     240
attgctcgtg aaatctatga atgtatgag gcggttagca tgcagccgtc tttgaggtca     300
gaatatggat cccatacgct ctacgctccc ggcggttatg acattatggg ctatctgatt    360
cagattatga caggccaaa cccccaagta gaactgggac ctgttgacac gtcagttgct    420
ctgattctgt gcgacctgaa gcaaaaagac acgccaattg tgtacgcctc ggaagctttt    480
ctctatatga caggatacag caatgcggag gtcttgggga gaaactgccg ttttcttcag    540
tcacccgacg gaatggtcaa gccgaaatcg acaaggaagt acgtcgactc caacacgatc    600
aatacgatga ggaaagcgat tgataggaac gccgaggtgc aggttgaggt ggtcaatttt    660
aagaagaacg gccaacggtt tgtcaacttc ttgacgatga ttccggtgcg agatgaaaca    720
ggggaatacc ggtacagcat gggttttcca gtgcgaaacgg aaactagtgc ggccgcggac    780
tacaaggatg acgacgacaa gttccggacc ggttccaaga cacccccccca cggtaccatg    840 cagggttctg tgacagagtt tctaaaaccg cgcctggttg atatcgagca agtgagttcg    900
acgcacgcca aggtgaccct tgagccttta gagcgtggct ttggccatac tctgggtaac    960
gcactgcgcc gtattctgct ctcatcgatg ccgggttgcg cggtgaccga ggttgagatt   1020
gatggtgtac tacatgagta cagcaccaaa gaaggcgttc aggaagatat cctggaaatc   1080
ctgctcaacc tgaaagggct ggcggtgaga gttcagggca agatgaagt tattcttacc   1140 ttgaataaat ctggcattgg ccctgtgact gcagccgata tcacccacga cggtgatgtc   1200
gaaatcgtca agccgcagca cgtgatctgc cacctgaccg atgagaacgc gtctattagc   1260
atgcgtatca agttcagcg cggtcgtggt tatgtgccgg cttctacccg aattcattcg   1320
gaagaagatg agcgcccaat cggccgtctg ctggtcgacg catgctacag ccctgtggag   1380
cgtattgcct acaatgttga agcagcgcgt gtagaacagc gtaccgacct ggacaagctg   1440
```

-continued

```
gtcatcgaaa tggaaaccaa cggcacaatc gatcctgaag aggcgattcg tcgtgcggca    1500
accattctgg ctgaacaact ggaagctttc gttgacttac gtgatgtacg tcagcctgaa    1560
gtgaaagaag agaaaccaga gtaa                                            1584
```

<210> SEQ ID NO 93
<211> LENGTH: 527
<212> TYPE: PRT
<213> ORGANISM: Artificial Sequence
<220> FEATURE:
<223> OTHER INFORMATION: Synthetic

<400> SEQUENCE: 93

```
Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
                20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Gly Ser His Thr Leu Tyr Ala Pro Gly Gly
            100                 105                 110

Tyr Asp Ile Met Gly Tyr Leu Ile Gln Ile Met Asn Arg Pro Asn Pro
        115                 120                 125

Gln Val Glu Leu Gly Pro Val Asp Thr Ser Val Ala Leu Ile Leu Cys
    130                 135                 140

Asp Leu Lys Gln Lys Asp Thr Pro Ile Val Tyr Ala Ser Glu Ala Phe
145                 150                 155                 160

Leu Tyr Met Thr Gly Tyr Ser Asn Ala Glu Val Leu Gly Arg Asn Cys
                165                 170                 175

Arg Phe Leu Gln Ser Pro Asp Gly Met Val Lys Pro Lys Ser Thr Arg
            180                 185                 190

Lys Tyr Val Asp Ser Asn Thr Ile Asn Thr Met Arg Lys Ala Ile Asp
        195                 200                 205

Arg Asn Ala Glu Val Gln Val Glu Val Val Asn Phe Lys Lys Asn Gly
    210                 215                 220

Gln Arg Phe Val Asn Phe Leu Thr Met Ile Pro Val Arg Asp Glu Thr
225                 230                 235                 240

Gly Glu Tyr Arg Tyr Ser Met Gly Phe Gln Cys Glu Thr Glu Thr Ser
                245                 250                 255

Ala Ala Ala Asp Tyr Lys Asp Asp Asp Lys Phe Arg Thr Gly Ser
            260                 265                 270

Lys Thr Pro Pro His Gly Thr Met Gln Gly Ser Val Thr Glu Phe Leu
        275                 280                 285

Lys Pro Arg Leu Val Asp Ile Glu Gln Val Ser Ser Thr His Ala Lys
    290                 295                 300

Val Thr Leu Glu Pro Leu Glu Arg Gly Phe Gly His Thr Leu Gly Asn
305                 310                 315                 320

Ala Leu Arg Arg Ile Leu Leu Ser Ser Met Pro Gly Cys Ala Val Thr
                325                 330                 335
```

Glu Val Glu Ile Asp Gly Val Leu His Glu Tyr Ser Thr Lys Glu Gly
              340                 345                 350

Val Gln Glu Asp Ile Leu Glu Ile Leu Leu Asn Leu Lys Gly Leu Ala
          355                 360                 365

Val Arg Val Gln Gly Lys Asp Glu Val Ile Leu Thr Leu Asn Lys Ser
370                 375                 380

Gly Ile Gly Pro Val Thr Ala Ala Asp Ile Thr His Asp Gly Asp Val
385                 390                 395                 400

Glu Ile Val Lys Pro Gln His Val Ile Cys His Leu Thr Asp Glu Asn
              405                 410                 415

Ala Ser Ile Ser Met Arg Ile Lys Val Gln Arg Gly Arg Gly Tyr Val
          420                 425                 430

Pro Ala Ser Thr Arg Ile His Ser Glu Glu Asp Glu Arg Pro Ile Gly
              435                 440                 445

Arg Leu Leu Val Asp Ala Cys Tyr Ser Pro Val Glu Arg Ile Ala Tyr
          450                 455                 460

Asn Val Glu Ala Ala Arg Val Glu Gln Arg Thr Asp Leu Asp Lys Leu
465                 470                 475                 480

Val Ile Glu Met Glu Thr Asn Gly Thr Ile Asp Pro Glu Glu Ala Ile
              485                 490                 495

Arg Arg Ala Ala Thr Ile Leu Ala Glu Gln Leu Glu Ala Phe Val Asp
          500                 505                 510

Leu Arg Asp Val Arg Gln Pro Glu Val Lys Glu Lys Pro Glu
          515                 520                 525

<210> SEQ ID NO 94
<211> LENGTH: 1104
<212> TYPE: DNA
<213> ORGANISM: Artificial Sequence
<220> FEATURE:
<223> OTHER INFORMATION: Synthetic

<400> SEQUENCE: 94
atggcacgcg taactgttca ggacgctgta gagaaaattg gtaaccgttt tgacctggta      60
ctggtcgccg cgcgtcgcgc tcgtcagatg caggtaggcg aaaggatcc gctggtaccg      120 gaagaaaacg ataaaaccac tgtaatcgcg ctgcgcgaaa tcgaagaagg tctgatcaac      180
aaccagatcc tcgacgttcg cgaacgccag aacagcaag agcaggaagc cgctgaatta      240
caagccgtta ccgctattgc tgaaggtcgt gcggccgcgg actacaagga tgacgacgac      300
aagttccgga ccggttccaa gacacccccc cacactagta tgtctaccaa gagaaacct      360 ttaactcaag aacaattgga ggatgctaga aggttgaagg ccatctacga aagaaaaag      420 aatgagttag gctatctca ggaaagtgtg gccgacaaga tgggaatggg ccaatcaggt      480
gttggtgctt tgttcaacgg gataaacgca ttaaatgcct acaatgctgc cttactggca      540
aagatattga aggtatctgt agaagagttc tcaccttcta ttgctcgtga atctatgaa      600 atgtatgagg cggttagcat gcagccgtct ttgaggtcag aatatggatc ccatacgctc      660
tacgctcccg gcggttatga cattatgggc tatctgattc agattatgaa caggccaaac      720
ccccaagtag aactgggacc tgttgacacg tcagttgctc tgattctgtg cgacctgaag      780
caaaaagaca cgccaattgt gtacgcctcg gaagcttttc tctatatgac aggatacagc      840
aatgcggagt cttgggggag aaactgccgt tttcttcagt cacccgacgg aatggtcaag      900
ccgaaatcga caaggaagta cgtcgactcc aacacgatca atacgatgag gaaagcgatt      960

```
gataggaacg ccgaggtgca ggttgaggtg gtcaatttta agaagaacgg ccaacggttt   1020
gtcaacttct tgacgatgat tccggtgcga gatgaaacag gggaataccg gtacagcatg   1080
ggtttccagt gcgaaacgga atga                                          1104
```

<210> SEQ ID NO 95
<211> LENGTH: 367
<212> TYPE: PRT
<213> ORGANISM: Artificial Sequence
<220> FEATURE:
<223> OTHER INFORMATION: Synthetic

<400> SEQUENCE: 95

```
Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
            20                  25                  30

Gly Gly Lys Asp Pro Leu Val Pro Glu Glu Asn Asp Lys Thr Thr Val
        35                  40                  45

Ile Ala Leu Arg Glu Ile Glu Glu Gly Leu Ile Asn Asn Gln Ile Leu
    50                  55                  60

Asp Val Arg Glu Arg Gln Glu Gln Gln Glu Glu Ala Ala Glu Leu
65                  70                  75                  80

Gln Ala Val Thr Ala Ile Ala Glu Gly Arg Ala Ala Ala Asp Tyr Lys
                85                  90                  95

Asp Asp Asp Asp Lys Phe Arg Thr Gly Ser Lys Thr Pro Pro His Thr
            100                 105                 110

Ser Met Ser Thr Lys Lys Lys Pro Leu Thr Gln Glu Gln Leu Glu Asp
        115                 120                 125

Ala Arg Arg Leu Lys Ala Ile Tyr Glu Lys Lys Lys Asn Glu Leu Gly
    130                 135                 140

Leu Ser Gln Glu Ser Val Ala Asp Lys Met Gly Met Gly Gln Ser Gly
145                 150                 155                 160

Val Gly Ala Leu Phe Asn Gly Ile Asn Ala Leu Asn Ala Tyr Asn Ala
                165                 170                 175

Ala Leu Leu Ala Lys Ile Leu Lys Val Ser Val Glu Glu Phe Ser Pro
            180                 185                 190

Ser Ile Ala Arg Glu Ile Tyr Glu Met Tyr Glu Ala Val Ser Met Gln
        195                 200                 205

Pro Ser Leu Arg Ser Glu Tyr Gly Ser His Thr Leu Tyr Ala Pro Gly
    210                 215                 220

Gly Tyr Asp Ile Met Gly Tyr Leu Ile Gln Ile Met Asn Arg Pro Asn
225                 230                 235                 240

Pro Gln Val Glu Leu Gly Pro Val Asp Thr Ser Val Ala Leu Ile Leu
                245                 250                 255

Cys Asp Leu Lys Gln Lys Asp Thr Pro Ile Val Tyr Ala Ser Glu Ala
            260                 265                 270

Phe Leu Tyr Met Thr Gly Tyr Ser Asn Ala Glu Val Leu Gly Arg Asn
        275                 280                 285

Cys Arg Phe Leu Gln Ser Pro Asp Gly Met Val Lys Pro Lys Ser Thr
    290                 295                 300

Arg Lys Tyr Val Asp Ser Asn Thr Ile Asn Thr Met Arg Lys Ala Ile
305                 310                 315                 320

Asp Arg Asn Ala Glu Val Gln Val Glu Val Val Asn Phe Lys Lys Asn
                325                 330                 335
```

Gly Gln Arg Phe Val Asn Phe Leu Thr Met Ile Pro Val Arg Asp Glu
                340                 345                 350

Thr Gly Glu Tyr Arg Tyr Ser Met Gly Phe Gln Cys Glu Thr Glu
        355                 360                 365

<210> SEQ ID NO 96
<211> LENGTH: 1464
<212> TYPE: DNA
<213> ORGANISM: Artificial Sequence
<220> FEATURE:
<223> OTHER INFORMATION: Synthetic

<400> SEQUENCE: 96

```
atgaaaccag taacgttata cgatgtcgca gagtatgccg gtgtctctca tcagaccgtt    60
tccaacgtgg tgaaccaggc cagccacgtt tctgcgaaaa cgcgggaaaa agtggaagcg   120
gcgatggcgg agctgaatta cattcccaac cgcgtggcac aacaactggc gggcaaacag   180
tcgttgggat cccatacgct ctacgctccc ggcggttatg acattatggg ctatctgatt   240
cagattatga caggccaaa ccccccaagta gaactgggac ctgttgacac gtcagttgct   300
ctgattctgt gcgacctgaa gcaaaaagac acgccaattg tgtacgcctc ggaagctttt   360
ctctatatga caggatacag caatgcggag gtcttgggga gaaactgccg ttttcttcag   420
tcacccgacg aatggtcaa gccgaaatcg acaaggaagt acgtcgactc caacacgatc   480
aatacgatga ggaaagcgat gataggaac gccgaggtgc aggttgaggt ggtcaatttt   540
aagaagaacg gccaacggtt tgtcaacttc ttgacgatga ttccggtgcg agatgaaaca   600
ggggaatacc ggtacagcat gggtttccag tgcgaaacgg aaactagtgc ggccgcggac   660
tacaaggatg acgacgacaa gttccggacc ggttccaaga cacccccca cggtaccatg   720 cagggttctg tgacagagtt tctaaaaccg cgcctggttg atatcgagca agtgagttcg   780
acgcacgcca aggtgaccct tgagccttta gagcgtggct ttggccatac tctgggtaac   840
gcactgcgcc gtattctgct ctcatcgatg ccgggttgcg cggtgaccga ggttgagatt   900
gatggtgtac tacatgagta cagcaccaaa gaaggcgttc aggaagatat cctggaaatc   960
ctgctcaacc tgaaagggct ggcggtgaga gttcagggca agatgaagt tattcttacc  1020 ttgaataaat ctggcattgg ccctgtgact gcagccgata tcacccacga cggtgatgtc  1080
gaaatcgtca agccgcagca cgtgatctgc cacctgaccg atgagaacgc gtctattagc  1140
atgcgtatca aagttcagcg cggtcgtggt tatgtgccgg cttctacccg aattcattcg  1200
gaagaagatg agcgcccaat cggccgtctg ctggtcgacg catgctacag ccctgtggag  1260
cgtattgcct acaatgttga agcagcgcgt gtagaacagc gtaccgacct ggacaagctg  1320
gtcatcgaaa tggaaaccaa cggcacaatc gatcctgaag aggcgattcg tcgtgcggca  1380
accattctgg ctgaacaact ggaagctttc gttgacttac gtgatgtacg tcagcctgaa  1440
gtgaaagaag agaaaccaga gtaa                                        1464
```

<210> SEQ ID NO 97
<211> LENGTH: 487
<212> TYPE: PRT
<213> ORGANISM: Artificial Sequence
<220> FEATURE:
<223> OTHER INFORMATION: Synthetic

<400> SEQUENCE: 97

Met Lys Pro Val Thr Leu Tyr Asp Val Ala Glu Tyr Ala Gly Val Ser
1               5                   10                  15

```
His Gln Thr Val Ser Asn Val Val Asn Gln Ala Ser His Val Ser Ala
             20                  25                  30

Lys Thr Arg Glu Lys Val Glu Ala Ala Met Ala Glu Leu Asn Tyr Ile
         35                  40                  45

Pro Asn Arg Val Ala Gln Gln Leu Ala Gly Lys Gln Ser Leu Gly Ser
     50                  55                  60

His Thr Leu Tyr Ala Pro Gly Gly Tyr Asp Ile Met Gly Tyr Leu Ile
 65                  70                  75                  80

Gln Ile Met Asn Arg Pro Asn Pro Gln Val Glu Leu Gly Pro Val Asp
                 85                  90                  95

Thr Ser Val Ala Leu Ile Leu Cys Asp Leu Lys Gln Lys Asp Thr Pro
                100                 105                 110

Ile Val Tyr Ala Ser Glu Ala Phe Leu Tyr Met Thr Gly Tyr Ser Asn
            115                 120                 125

Ala Glu Val Leu Gly Arg Asn Cys Arg Phe Leu Gln Ser Pro Asp Gly
        130                 135                 140

Met Val Lys Pro Lys Ser Thr Arg Lys Tyr Val Asp Ser Asn Thr Ile
145                 150                 155                 160

Asn Thr Met Arg Lys Ala Ile Asp Arg Asn Ala Glu Val Gln Val Glu
                165                 170                 175

Val Val Asn Phe Lys Lys Asn Gly Gln Arg Phe Val Asn Phe Leu Thr
            180                 185                 190

Met Ile Pro Val Arg Asp Glu Thr Gly Glu Tyr Arg Tyr Ser Met Gly
        195                 200                 205

Phe Gln Cys Glu Thr Glu Thr Ser Ala Ala Asp Tyr Lys Asp Asp
210                 215                 220

Asp Asp Lys Phe Arg Thr Gly Ser Lys Thr Pro Pro His Gly Thr Met
225                 230                 235                 240

Gln Gly Ser Val Thr Glu Phe Leu Lys Pro Arg Leu Val Asp Ile Glu
                245                 250                 255

Gln Val Ser Ser Thr His Ala Lys Val Thr Leu Glu Pro Leu Glu Arg
            260                 265                 270

Gly Phe Gly His Thr Leu Gly Asn Ala Leu Arg Arg Ile Leu Leu Ser
        275                 280                 285

Ser Met Pro Gly Cys Ala Val Thr Glu Val Glu Ile Asp Gly Val Leu
290                 295                 300

His Glu Tyr Ser Thr Lys Glu Gly Val Gln Glu Asp Ile Leu Glu Ile
305                 310                 315                 320

Leu Leu Asn Leu Lys Gly Leu Ala Val Arg Val Gln Gly Lys Asp Glu
                325                 330                 335

Val Ile Leu Thr Leu Asn Lys Ser Gly Ile Gly Pro Val Thr Ala Ala
            340                 345                 350

Asp Ile Thr His Asp Gly Asp Val Glu Ile Val Lys Pro Gln His Val
        355                 360                 365

Ile Cys His Leu Thr Asp Glu Asn Ala Ser Ile Ser Met Arg Ile Lys
        370                 375                 380

Val Gln Arg Gly Arg Gly Tyr Val Pro Ala Ser Thr Arg Ile His Ser
385                 390                 395                 400

Glu Glu Asp Glu Arg Pro Ile Gly Arg Leu Leu Val Asp Ala Cys Tyr
                405                 410                 415

Ser Pro Val Glu Arg Ile Ala Tyr Asn Val Glu Ala Ala Arg Val Glu
            420                 425                 430

Gln Arg Thr Asp Leu Asp Lys Leu Val Ile Glu Met Glu Thr Asn Gly
```

```
                435                 440                 445
Thr Ile Asp Pro Glu Glu Ala Ile Arg Arg Ala Ala Thr Ile Leu Ala
    450                 455                 460

Glu Gln Leu Glu Ala Phe Val Asp Leu Arg Asp Val Arg Gln Pro Glu
465                 470                 475                 480

Val Lys Glu Glu Lys Pro Glu
                485

<210> SEQ ID NO 98
<211> LENGTH: 984
<212> TYPE: DNA
<213> ORGANISM: Artificial Sequence
<220> FEATURE:
<223> OTHER INFORMATION: Synthetic

<400> SEQUENCE: 98
atggcacgcg taactgttca ggacgctgta gagaaaattg gtaaccgttt tgacctggta      60
ctggtcgccg cgcgtcgcgc tcgtcagatg caggtaggcg gaaaggatcc gctggtaccg     120
gaagaaaacg ataaaaccac tgtaatcgcg ctgcgcgaaa tcgaagaagg tctgatcaac     180
aaccagatcc tcgacgttcg cgaacgccag gaacagcaag agcaggaagc cgctgaatta     240
caagccgtta ccgctattgc tgaaggtcgt gcggccgcgg actacaagga tgacgacgac     300
aagttccgga ccggttccaa gacaccccc cacactagta tgaaaccagt aacgttatac      360
gatgtcgcag agtatgccgg tgtctctcat cagaccgttt ccaacgtggt gaaccaggcc     420
agccacgttt ctgcgaaaac gcgggaaaaa gtggaagcgg cgatggcgga gctgaattac     480
attcccaacc gcgtggcaca caactggcg ggcaaacagt cgttgggatc ccatacgctc      540
tacgctcccg gcggttatga cattatgggc tatctgattc agattatgaa caggccaaac     600
ccccaagtag aactgggacc tgttgacacg tcagttgctc tgattctgtg cgacctgaag     660
caaaaagaca cgccaattgt gtacgcctcg gaagcttttc tctatatgac aggatacagc     720
aatgcggagg tcttggggag aaactgccgt tttcttcagt cacccgacgg aatggtcaag     780
ccgaaatcga caaggaagta cgtcgactcc aacacgatca atacgatgag gaaagcgatt     840
gataggaacg ccgaggtgca ggttgaggtg gtcaattta agaagaacgg ccaacggttt      900
gtcaacttct tgacgatgat tccggtgcga gatgaaacag gggaataccg gtacagcatg     960
ggtttccagt gcgaaacgga atga                                            984

<210> SEQ ID NO 99
<211> LENGTH: 327
<212> TYPE: PRT
<213> ORGANISM: Artificial Sequence
<220> FEATURE:
<223> OTHER INFORMATION: Synthetic

<400> SEQUENCE: 99

Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
            20                  25                  30

Gly Gly Lys Asp Pro Leu Val Pro Glu Glu Asn Asp Lys Thr Thr Val
        35                  40                  45

Ile Ala Leu Arg Glu Ile Glu Glu Gly Leu Ile Asn Asn Gln Ile Leu
    50                  55                  60

Asp Val Arg Glu Arg Gln Glu Gln Gln Glu Gln Glu Ala Ala Glu Leu
65                  70                  75                  80
```

Gln Ala Val Thr Ala Ile Ala Glu Gly Arg Ala Ala Asp Tyr Lys
                85                  90                  95

Asp Asp Asp Asp Lys Phe Arg Thr Gly Ser Lys Thr Pro His Thr
            100                 105                 110

Ser Met Lys Pro Val Thr Leu Tyr Asp Val Ala Glu Tyr Ala Gly Val
        115                 120                 125

Ser His Gln Thr Val Ser Asn Val Val Asn Gln Ala Ser His Val Ser
    130                 135                 140

Ala Lys Thr Arg Glu Lys Val Glu Ala Ala Met Ala Glu Leu Asn Tyr
145                 150                 155                 160

Ile Pro Asn Arg Val Ala Gln Gln Leu Ala Gly Lys Gln Ser Leu Gly
                165                 170                 175

Ser His Thr Leu Tyr Ala Pro Gly Gly Tyr Asp Ile Met Gly Tyr Leu
            180                 185                 190

Ile Gln Ile Met Asn Arg Pro Asn Pro Gln Val Glu Leu Gly Pro Val
        195                 200                 205

Asp Thr Ser Val Ala Leu Ile Leu Cys Asp Leu Lys Gln Lys Asp Thr
    210                 215                 220

Pro Ile Val Tyr Ala Ser Glu Ala Phe Leu Tyr Met Thr Gly Tyr Ser
225                 230                 235                 240

Asn Ala Glu Val Leu Gly Arg Asn Cys Arg Phe Leu Gln Ser Pro Asp
                245                 250                 255

Gly Met Val Lys Pro Lys Ser Thr Arg Lys Tyr Val Asp Ser Asn Thr
            260                 265                 270

Ile Asn Thr Met Arg Lys Ala Ile Asp Arg Asn Ala Glu Val Gln Val
        275                 280                 285

Glu Val Val Asn Phe Lys Lys Asn Gly Gln Arg Phe Val Asn Phe Leu
    290                 295                 300

Thr Met Ile Pro Val Arg Asp Glu Thr Gly Glu Tyr Arg Tyr Ser Met
305                 310                 315                 320

Gly Phe Gln Cys Glu Thr Glu
                325

<210> SEQ ID NO 100
<211> LENGTH: 1473
<212> TYPE: DNA
<213> ORGANISM: Artificial Sequence
<220> FEATURE:
<223> OTHER INFORMATION: Synthetic

<400> SEQUENCE: 100
atgaagctac tgtcttctat cgaacaagca tgcgatattt gccgacttaa aaagctcaag      60
tgctccaaag aaaaaccgaa gtgcgccaag tgtctgaaga caactgggag gtgtcgctac     120
tctcccaaaa ccaaaaggtc tccgctgact agggcacatc tgacagaagt ggaatcaagg     180
ctagaaagac tggaaggatc ccatacgctc tacgctcccg gcggttatga cattatgggc     240
tatctgattc agattatgaa caggccaaac ccccaagtag aactgggacc tgttgacacg     300
tcagttgctc tgattctgtg cgacctgaag caaaaagaca cgccaattgt gtacgcctcg     360
gaagcttttc tctatatgac aggatacagc aatgcggagg tcttgggcag aaactgccgt     420
tttcttcagt cacccgacgg aatggtcaag ccgaaatcga caggaagta cgtcgactcc     480 aacacgatca atacgatgag gaaagcgatt gataggaacg ccgaggtgca ggttgaggtg     540
gtcaatttta agaagaacgg ccaacggttt gtcaacttct tgacgatgat tccggtgcga     600

```
gatgaaacag gggaataccg gtacagcatg ggtttccagt gcgaaacgga aactagtgcg   660
gccgcggact acaaggatga cgacgacaag ttccggaccg gttccaagac acccccccac   720
ggtaccatgc agggttctgt gacagagttt ctaaaaccgc gcctggttga tatcgagcaa   780
gtgagttcga cgcacgccaa ggtgacccct gagcctttag agcgtggctt tggccatact   840
ctgggtaacg cactgcgccg tattctgctc tcatcgatgc cggggttgcgc ggtgaccgag   900
gttgagattg atggtgtact acatgagtac agcaccaaag aaggcgttca ggaagatatc   960
ctggaaatcc tgctcaacct gaaagggctg gcggtgagag ttcagggcaa agatgaagtt  1020
attcttacct tgaataaatc tggcattggc cctgtgactg cagccgatat cacccacgac  1080
ggtgatgtcg aaatcgtcaa gccgcagcac gtgatctgcc acctgaccga tgagaacgcg  1140
tctattagca tgcgtatcaa agttcagcgc ggtcgtggtt atgtgccggc ttctacccga  1200
attcattcgg aagaagatga cgcccaatc ggccgtctgc tggtcgacgc atgctacagc  1260
cctgtggagc gtattgccta caatgttgaa gcagcgcgtg tagaacagcg taccgacctg  1320
gacaagctgg tcatcgaaat ggaaaccaac ggcacaatcg atcctgaaga ggcgattcgt  1380
cgtgcggcaa ccattctggc tgaacaactg gaagctttcg ttgacttacg tgatgtacgt  1440
cagcctgaag tgaaagaaga gaaaccagag taa                                1473
```

<210> SEQ ID NO 101
<211> LENGTH: 490
<212> TYPE: PRT
<213> ORGANISM: Artificial Sequence
<220> FEATURE:
<223> OTHER INFORMATION: Synthetic

<400> SEQUENCE: 101

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gly Ser His Thr Leu Tyr Ala Pro Gly Gly Tyr Asp Ile Met Gly
65                  70                  75                  80

Tyr Leu Ile Gln Ile Met Asn Arg Pro Asn Pro Gln Val Glu Leu Gly
                85                  90                  95

Pro Val Asp Thr Ser Val Ala Leu Ile Leu Cys Asp Leu Lys Gln Lys
            100                 105                 110

Asp Thr Pro Ile Val Tyr Ala Ser Glu Ala Phe Leu Tyr Met Thr Gly
        115                 120                 125

Tyr Ser Asn Ala Glu Val Leu Gly Arg Asn Cys Arg Phe Leu Gln Ser
    130                 135                 140

Pro Asp Gly Met Val Lys Pro Lys Ser Thr Arg Lys Tyr Val Asp Ser
145                 150                 155                 160

Asn Thr Ile Asn Thr Met Arg Lys Ala Ile Asp Arg Asn Ala Glu Val
                165                 170                 175

Gln Val Glu Val Val Asn Phe Lys Lys Asn Gly Gln Arg Phe Val Asn
            180                 185                 190

Phe Leu Thr Met Ile Pro Val Arg Asp Glu Thr Gly Glu Tyr Arg Tyr
        195                 200                 205
```

```
Ser Met Gly Phe Gln Cys Glu Thr Glu Thr Ser Ala Ala Ala Asp Tyr
    210                 215                 220

Lys Asp Asp Asp Lys Phe Arg Thr Gly Ser Lys Thr Pro Pro His
225                 230                 235                 240

Gly Thr Met Gln Gly Ser Val Thr Glu Phe Leu Lys Pro Arg Leu Val
                245                 250                 255

Asp Ile Glu Gln Val Ser Ser Thr His Ala Lys Val Thr Leu Glu Pro
                260                 265                 270

Leu Glu Arg Gly Phe Gly His Thr Leu Gly Asn Ala Leu Arg Arg Ile
            275                 280                 285

Leu Leu Ser Ser Met Pro Gly Cys Ala Val Thr Glu Val Glu Ile Asp
290                 295                 300

Gly Val Leu His Glu Tyr Ser Thr Lys Glu Gly Val Gln Glu Asp Ile
305                 310                 315                 320

Leu Glu Ile Leu Leu Asn Leu Lys Gly Leu Ala Val Arg Val Gln Gly
                325                 330                 335

Lys Asp Glu Val Ile Leu Thr Leu Asn Lys Ser Gly Ile Gly Pro Val
                340                 345                 350

Thr Ala Ala Asp Ile Thr His Asp Gly Asp Val Glu Ile Val Lys Pro
                355                 360                 365

Gln His Val Ile Cys His Leu Thr Asp Glu Asn Ala Ser Ile Ser Met
            370                 375                 380

Arg Ile Lys Val Gln Arg Gly Arg Gly Tyr Val Pro Ala Ser Thr Arg
385                 390                 395                 400

Ile His Ser Glu Glu Asp Glu Arg Pro Ile Gly Arg Leu Leu Val Asp
                405                 410                 415

Ala Cys Tyr Ser Pro Val Glu Arg Ile Ala Tyr Asn Val Glu Ala Ala
                420                 425                 430

Arg Val Glu Gln Arg Thr Asp Leu Asp Lys Leu Val Ile Glu Met Glu
            435                 440                 445

Thr Asn Gly Thr Ile Asp Pro Glu Glu Ala Ile Arg Arg Ala Ala Thr
            450                 455                 460

Ile Leu Ala Glu Gln Leu Glu Ala Phe Val Asp Leu Arg Asp Val Arg
465                 470                 475                 480

Gln Pro Glu Val Lys Glu Glu Lys Pro Glu
                485                 490

<210> SEQ ID NO 102
<211> LENGTH: 993
<212> TYPE: DNA
<213> ORGANISM: Artificial Sequence
<220> FEATURE:
<223> OTHER INFORMATION: Synthetic

<400> SEQUENCE: 102
atggcacgcg taactgttca ggacgctgta gagaaaattg gtaaccgttt tgacctggta      60
ctggtcgccg cgcgtcgcgc tcgtcagatg caggtaggcg aaaggatcc gctggtaccg      120 gaagaaaacg ataaaaccac tgtaatcgcg ctgcgcgaaa tcgaagaagg tctgatcaac      180
aaccagatcc tcgacgttcg cgaacgccag aacagcaag agcaggaagc cgctgaatta      240
caagccgtta ccgctattgc tgaaggtcgt gcggccgcgg actacaagga tgacgacgac      300
aagttccgga ccggttccaa gacaccccc cacactagta tgaagctact gtcttctatc      360
gaacaagcat gcgatatttg ccgacttaaa aagctcaagt gctccaaaga aaaccgaag      420 tgcgccaagt gtctgaagaa caactgggag tgtcgctact ctcccaaaac caaaaggtct      480
```

```
ccgctgacta gggcacatct gacagaagtg gaatcaaggc tagaaagact ggaaggatcc    540
catacgctct acgctcccgg cggttatgac attatgggct atctgattca gattatgaac    600
aggccaaacc cccaagtaga actgggacct gttgacacgt cagttgctct gattctgtgc    660
gacctgaagc aaaaagacac gccaattgtg tacgcctcgg aagcttttct ctatatgaca    720
ggatacagca atgcggaggt cttggggaga aactgccgtt ttcttcagtc acccgacgga    780
atggtcaagc cgaaatcgac aaggaagtac gtcgactcca acacgatcaa tacgatgagg    840
aaagcgattg ataggaacgc cgaggtgcag gttgaggtgg tcaatttaa gaagaacggc    900 caacggtttg tcaacttctt gacgatgatt ccggtgcgag atgaaacagg ggaataccgg    960
tacagcatgg gtttccagtg cgaaacgaaa tga                                993
```

<210> SEQ ID NO 103
<211> LENGTH: 330
<212> TYPE: PRT
<213> ORGANISM: Artificial Sequence
<220> FEATURE:
<223> OTHER INFORMATION: Synthetic

<400> SEQUENCE: 103

```
Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
            20                  25                  30

Gly Gly Lys Asp Pro Leu Val Pro Glu Glu Asn Asp Lys Thr Thr Val
        35                  40                  45

Ile Ala Leu Arg Glu Ile Glu Glu Gly Leu Ile Asn Asn Gln Ile Leu
    50                  55                  60

Asp Val Arg Glu Arg Gln Glu Gln Gln Glu Glu Ala Ala Glu Leu
65                  70                  75                  80

Gln Ala Val Thr Ala Ile Ala Glu Gly Arg Ala Ala Ala Asp Tyr Lys
                85                  90                  95

Asp Asp Asp Asp Lys Phe Arg Thr Gly Ser Lys Thr Pro Pro His Thr
            100                 105                 110

Ser Met Lys Leu Leu Ser Ser Ile Glu Gln Ala Cys Asp Ile Cys Arg
        115                 120                 125

Leu Lys Lys Leu Lys Cys Ser Lys Glu Lys Pro Lys Cys Ala Lys Cys
    130                 135                 140

Leu Lys Asn Asn Trp Glu Cys Arg Tyr Ser Pro Lys Thr Lys Arg Ser
145                 150                 155                 160

Pro Leu Thr Arg Ala His Leu Thr Glu Val Glu Ser Arg Leu Glu Arg
                165                 170                 175

Leu Glu Gly Ser His Thr Leu Tyr Ala Pro Gly Gly Tyr Asp Ile Met
            180                 185                 190

Gly Tyr Leu Ile Gln Ile Met Asn Arg Pro Asn Pro Gln Val Glu Leu
        195                 200                 205

Gly Pro Val Asp Thr Ser Val Ala Leu Ile Leu Cys Asp Leu Lys Gln
    210                 215                 220

Lys Asp Thr Pro Ile Val Tyr Ala Ser Glu Ala Phe Leu Tyr Met Thr
225                 230                 235                 240

Gly Tyr Ser Asn Ala Glu Val Leu Gly Arg Asn Cys Arg Phe Leu Gln
                245                 250                 255

Ser Pro Asp Gly Met Val Lys Pro Lys Ser Thr Arg Lys Tyr Val Asp
            260                 265                 270
```

```
Ser Asn Thr Ile Asn Thr Met Arg Lys Ala Ile Asp Arg Asn Ala Glu
            275                 280                 285

Val Gln Val Glu Val Val Asn Phe Lys Lys Asn Gly Gln Arg Phe Val
        290                 295                 300

Asn Phe Leu Thr Met Ile Pro Val Arg Asp Glu Thr Gly Glu Tyr Arg
305                 310                 315                 320

Tyr Ser Met Gly Phe Gln Cys Glu Thr Glu
                325                 330

<210> SEQ ID NO 104
<211> LENGTH: 1467
<212> TYPE: DNA
<213> ORGANISM: Artificial Sequence
<220> FEATURE:
<223> OTHER INFORMATION: Synthetic

<400> SEQUENCE: 104
```

| | | | | | |
|---|---|---|---|---|---|
| atgtctaggc | tagataagag | caaagtcatc | aattccgcgt | tggaattact | taacgaagta | 60 |
| ggtattgagg | gtttgactac | gagaaaacta | gcgcaaaaat | tgggtgtgga | acaaccaaca | 120 |
| ctatactggc | acgttaagaa | taaacgtgca | ttattagacg | cattagccat | cgagatgctg | 180 |
| gatagacacg | gatcccatac | gctctacgct | cccggcggtt | atgacattat | gggctatctg | 240 |
| attcagatta | tgaacaggcc | aaaccccccaa | gtagaactgg | gacctgttga | cacgtcagtt | 300 |
| gctctgattc | tgtgcgacct | gaagcaaaaa | gacacgccaa | ttgtgtacgc | ctcggaagct | 360 |
| tttctctata | tgacaggata | cagcaatgcg | gaggtcttgg | ggagaaactg | ccgttttctt | 420 |
| cagtcacccg | acggaatggt | caagccgaaa | tcgacaagga | agtacgtcga | ctccaacacg | 480 |
| atcaatacga | tgaggaaagc | gattgatagg | aacgccgagg | tgcaggttga | ggtggtcaat | 540 |
| tttaagaaga | acggccaacg | gtttgtcaac | ttcttgacga | tgattccggt | gcgagatgaa | 600 |
| acagggaat | accggtacag | catgggtttc | cagtgcgaaa | cggaaactag | tgcggccgcg | 660 |
| gactacaagg | atgacgacga | caagttccgg | accggttcca | agacaccccc | ccacggtacc | 720 |
| atgcagggtt | ctgtgacaga | gtttctaaaa | ccgcgcctgg | ttgatatcga | gcaagtgagt | 780 |
| tcgacgcacg | ccaaggtgac | ccttgagcct | ttagagcgtg | gctttggcca | tactctgggt | 840 |
| aacgcactgc | gccgtattct | gctctcatcg | atgcggggt | gcgcggtgac | cgaggttgag | 900 |
| attgatggtg | tactacatga | gtacagcacc | aaagaaggcg | ttcaggaaga | tatcctggaa | 960 |
| atcctgctca | acctgaaagg | gctggcggtg | agagttcagg | gcaaagatga | agttattctt | 1020 |
| accttgaata | aatctggcat | tggccctgtg | actgcagccg | atatcaccca | cgacggtgat | 1080 |
| gtcgaaatcg | tcaagccgca | gcacgtgatc | tgccacctga | ccgatgagaa | cgcgtctatt | 1140 |
| agcatgcgta | tcaaagttca | gcgcggtcgt | ggttatgtgc | cggcttctac | ccgaattcat | 1200 |
| tcggaagaag | atgagcgccc | aatcggccgt | ctgctggtcg | acgcatgcta | cagccctgtg | 1260 |
| gagcgtattg | cctacaatgt | tgaagcagcg | cgtgtagaac | agcgtaccga | cctggacaag | 1320 |
| ctggtcatcg | aaatggaaac | caacggcaca | atcgatcctg | aagaggcgat | cgtcgtgcg | 1380 |
| gcaaccattc | tggctgaaca | actggaagct | ttcgttgact | tacgtgatgt | acgtcagcct | 1440 |
| gaagtgaaag | aagagaaacc | agagtaa | | | | 1467 |

```
<210> SEQ ID NO 105
<211> LENGTH: 488
<212> TYPE: PRT
<213> ORGANISM: Artificial Sequence
<220> FEATURE:
```

<223> OTHER INFORMATION: Synthetic

<400> SEQUENCE: 105

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His Gly
    50                  55                  60

Ser His Thr Leu Tyr Ala Pro Gly Gly Tyr Asp Ile Met Gly Tyr Leu
65                  70                  75                  80

Ile Gln Ile Met Asn Arg Pro Asn Pro Gln Val Glu Leu Gly Pro Val
                85                  90                  95

Asp Thr Ser Val Ala Leu Ile Leu Cys Asp Leu Lys Gln Lys Asp Thr
            100                 105                 110

Pro Ile Val Tyr Ala Ser Glu Ala Phe Leu Tyr Met Thr Gly Tyr Ser
        115                 120                 125

Asn Ala Glu Val Leu Gly Arg Asn Cys Arg Phe Leu Gln Ser Pro Asp
    130                 135                 140

Gly Met Val Lys Pro Lys Ser Thr Arg Lys Tyr Val Asp Ser Asn Thr
145                 150                 155                 160

Ile Asn Thr Met Arg Lys Ala Ile Asp Arg Asn Ala Glu Val Gln Val
                165                 170                 175

Glu Val Val Asn Phe Lys Lys Asn Gly Gln Arg Phe Val Asn Phe Leu
            180                 185                 190

Thr Met Ile Pro Val Arg Asp Glu Thr Gly Glu Tyr Arg Tyr Ser Met
        195                 200                 205

Gly Phe Gln Cys Glu Thr Glu Thr Ser Ala Ala Ala Asp Tyr Lys Asp
    210                 215                 220

Asp Asp Asp Lys Phe Arg Thr Gly Ser Lys Thr Pro Pro His Gly Thr
225                 230                 235                 240

Met Gln Gly Ser Val Thr Glu Phe Leu Lys Pro Arg Leu Val Asp Ile
                245                 250                 255

Glu Gln Val Ser Ser Thr His Ala Lys Val Thr Leu Glu Pro Leu Glu
            260                 265                 270

Arg Gly Phe Gly His Thr Leu Gly Asn Ala Leu Arg Arg Ile Leu Leu
        275                 280                 285

Ser Ser Met Pro Gly Cys Ala Val Thr Glu Val Glu Ile Asp Gly Val
    290                 295                 300

Leu His Glu Tyr Ser Thr Lys Glu Gly Val Gln Glu Asp Ile Leu Glu
305                 310                 315                 320

Ile Leu Leu Asn Leu Lys Gly Leu Ala Val Arg Val Gln Gly Lys Asp
                325                 330                 335

Glu Val Ile Leu Thr Leu Asn Lys Ser Gly Ile Gly Pro Val Thr Ala
            340                 345                 350

Ala Asp Ile Thr His Asp Gly Asp Val Glu Ile Val Lys Pro Gln His
        355                 360                 365

Val Ile Cys His Leu Thr Asp Glu Asn Ala Ser Ile Ser Met Arg Ile
    370                 375                 380

Lys Val Gln Arg Gly Arg Gly Tyr Val Pro Ala Ser Thr Arg Ile His
385                 390                 395                 400
```

```
Ser Glu Glu Asp Glu Arg Pro Ile Gly Arg Leu Leu Val Asp Ala Cys
                405                 410                 415

Tyr Ser Pro Val Glu Arg Ile Ala Tyr Asn Val Glu Ala Ala Arg Val
            420                 425                 430

Glu Gln Arg Thr Asp Leu Asp Lys Leu Val Ile Glu Met Glu Thr Asn
        435                 440                 445

Gly Thr Ile Asp Pro Glu Ala Ile Arg Arg Ala Thr Ile Leu
    450                 455                 460

Ala Glu Gln Leu Glu Ala Phe Val Asp Leu Arg Asp Val Arg Gln Pro
465                 470                 475                 480

Glu Val Lys Glu Glu Lys Pro Glu
            485
```

<210> SEQ ID NO 106
<211> LENGTH: 987
<212> TYPE: DNA
<213> ORGANISM: Artificial Sequence
<220> FEATURE:
<223> OTHER INFORMATION: Synthetic

<400> SEQUENCE: 106

```
atggcacgcg taactgttca ggacgctgta gagaaaattg gtaaccgttt tgacctggta      60
ctggtcgccg cgcgtcgcgc tcgtcagatg caggtaggcg gaaaggatcc gctggtaccg     120
gaagaaaacg ataaaaccac tgtaatcgcg ctgcgcgaaa tcgaagaagg tctgatcaac     180
aaccagatcc tcgacgttcg cgaacgccag aacagcaag agcaggaagc cgctgaatta     240
caagccgtta ccgctattgc tgaaggtcgt gcggccgcgg actacaagga tgacgacgac     300
aagttccgga ccggttccaa gacacccccc cacactagta tgtctaggct agataagagc     360
aaagtcatca attccgcgtt ggaattactt aacgaagtag gtattgaggg tttgactacg     420
agaaaactag cgcaaaaatt gggtgtggaa caaccaacac tatactggca cgttaagaat     480
aaacgtgcat tattagacgc attagccatc gagatgctgg atagacacgg atcccatacg     540
ctctacgctc ccggcggtta tgacattatg gctatctga ttcagattat gaacaggcca      600
aaccccaag tagaactggg acctgttgac acgtcagttg ctctgattct gtgcgacctg      660
aagcaaaaag acacgccaat tgtgtacgcc tcggaagctt ttctctatat gacaggatac     720
agcaatgcgg aggtcttggg gagaaactgc cgttttcttc agtcacccga cggaatggtc     780
aagccgaaat cgacaaggaa gtacgtcgac tccaacacga tcaatacgat gaggaaagcg     840
attgatagga acgccgaggt gcaggttgag gtggtcaatt ttaagaagaa cggccaacgg     900
tttgtcaact tcttgacgat gattccggtg cgagatgaaa cagggggaata ccggtacagc     960
atgggttttcc agtgcgaaac ggaatga                                        987
```

<210> SEQ ID NO 107
<211> LENGTH: 328
<212> TYPE: PRT
<213> ORGANISM: Artificial Sequence
<220> FEATURE:
<223> OTHER INFORMATION: Synthetic

<400> SEQUENCE: 107

```
Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
            20                  25                  30

Gly Gly Lys Asp Pro Leu Val Pro Glu Glu Asn Asp Lys Thr Thr Val
```

```
                35                  40                  45
Ile Ala Leu Arg Glu Ile Glu Glu Gly Leu Ile Asn Asn Gln Ile Leu
             50                  55                  60
Asp Val Arg Glu Arg Gln Gln Gln Glu Gln Ala Ala Glu Leu
 65                  70                  75                  80
Gln Ala Val Thr Ala Ile Ala Glu Gly Arg Ala Ala Asp Tyr Lys
                 85                  90                  95
Asp Asp Asp Asp Lys Phe Arg Thr Gly Ser Lys Thr Pro Pro His Thr
                100                 105                 110
Ser Met Ser Arg Leu Asp Lys Ser Lys Val Ile Asn Ser Ala Leu Glu
                115                 120                 125
Leu Leu Asn Glu Val Gly Ile Glu Gly Leu Thr Thr Arg Lys Leu Ala
            130                 135                 140
Gln Lys Leu Gly Val Glu Gln Pro Thr Leu Tyr Trp His Val Lys Asn
145                 150                 155                 160
Lys Arg Ala Leu Leu Asp Ala Leu Ala Ile Glu Met Leu Asp Arg His
                165                 170                 175
Gly Ser His Thr Leu Tyr Ala Pro Gly Gly Tyr Asp Ile Met Gly Tyr
                180                 185                 190
Leu Ile Gln Ile Met Asn Arg Pro Asn Pro Gln Val Glu Leu Gly Pro
                195                 200                 205
Val Asp Thr Ser Val Ala Leu Ile Leu Cys Asp Leu Lys Gln Lys Asp
210                 215                 220
Thr Pro Ile Val Tyr Ala Ser Glu Ala Phe Leu Tyr Met Thr Gly Tyr
225                 230                 235                 240
Ser Asn Ala Glu Val Leu Gly Arg Asn Cys Arg Phe Leu Gln Ser Pro
                245                 250                 255
Asp Gly Met Val Lys Pro Lys Ser Thr Arg Lys Tyr Val Asp Ser Asn
                260                 265                 270
Thr Ile Asn Thr Met Arg Lys Ala Ile Asp Arg Asn Ala Glu Val Gln
            275                 280                 285
Val Glu Val Val Asn Phe Lys Lys Asn Gly Gln Arg Phe Val Asn Phe
        290                 295                 300
Leu Thr Met Ile Pro Val Arg Asp Glu Thr Gly Glu Tyr Arg Tyr Ser
305                 310                 315                 320
Met Gly Phe Gln Cys Glu Thr Glu
                325
```

<210> SEQ ID NO 108
<211> LENGTH: 2403
<212> TYPE: DNA
<213> ORGANISM: Artificial Sequence
<220> FEATURE:
<223> OTHER INFORMATION: Synthetic

<400> SEQUENCE: 108

```
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtggggtctc ccatgcgag      180 agtagggaac tgccaggcat caaataaaac gaaaggctca gtcgaaagac tgggcctttc     240
gttttatctg ttgtttgcgc tagcggatcc tgttttttttg atcgttttca caaaatgga    300 agtccacagt cttgacaggg aaaatgcagc ggcgtagctt ttatgctgta tataaaacca     360
gtggttatat gtacagtatt tattttttaac ttattgtttt aaaagtcaaa gaggatttta     420
```

```
taatggtgag caagggcgag gaggataaca tggccatcat caaggagttc atgcgcttca      480
aggtgcacat ggagggctcc gtgaacggcc acgagttcga gatcgaggc gagggcgagg       540 gccgccccta cgagggcacc cagaccgcca agctgaaggt gaccaagggt ggccccctgc      600
ccttcgcctg ggacatcctg tcccctcagt tcatgtacgg ctccaaggcc tacgtgaagc      660
accccgccga catccccgac tacttgaagc tgtccttccc cgagggcttc aagtgggagc      720
gcgtgatgaa cttcgaggac ggcggcgtgg tgaccgtgac ccaggactcc tccctgcagg      780
acggcgagtt catctacaag gtgaagctgc gcggcaccaa cttcccctcc gacggccccg      840
taatgcagaa gaagaccatg ggctgggagg cctcctccga gcggatgtac cccgaggacg      900
gcgccctgaa gggcgagatc aagcagaggc tgaagctgaa ggacggcggc cactacgacg      960
ctgaggtcaa gaccacctac aaggccaaga agcccgtgca gctgcccggc gcctacaacg     1020
tcaacatcaa gttggacatc acctcccaca acgaggacta caccatcgtg aacagtacg      1080 aacgcgccga gggccgccac tccaccggcg gcatggacga gctgtacaag taaagatctg     1140
cttgatccgg ctgctaacaa agcccgaaag gaagctgagt tggctgctgc caccgctgag     1200
caataactag cataacccct tggggcctct aaacgggtct tgaggggttt tttgctgaaa     1260
ggaggaacta tatccggatc tggcgtaata gcgaagaggc ccgcaccgat cgcccttccc     1320
aacagttgga gctcgtgcgc ggaaccccta tttgtttatt tttctaaata cattcaaata     1380
tgtatccgct catgagacaa taaccctgat aaatgcttca ataatattga aaaggaagc      1440 atatgaaagc gttaacggcc aggcaacaag aggtgtttga tctcatccgt gatcacatca     1500
gccagacagg tatgccgccg acgcgtgcgg aaatcgcgca gcgtttgggg ttccgttccc     1560
caaacgcggc tgaagaacat ctgaaggcgc tggcacgcaa aggcgttatt gaaattgttt     1620
ccggcgcatc acgcgggatt cgtctgttgc aggaagagga agaaggggttg ccgctggtag    1680 gtcgtgtggc tgccggtgaa ccgcatacgc tctacgctcc cggcggttat gacattatgg     1740
gctatctgat tcagattatg aacaggccaa accccccaagt agaactggga cctgttgaca    1800
cgtcagttgc tctgattctg tgcgacctga agcaaaaaga cacgccaatt gtgtacgcct     1860
cggaagcttt tctctatatg acaggataca gcaatgcgga ggtcttgggg agaaactgcc     1920
gttttcttca gtcacccgac ggaatggtca gccgaaatc gacaaggaag tacgtcgact      1980
ccaacacgat caatacgatg aggaaagcga ttgataggca cgccgaggtg caggttgagg     2040
tggtcaattt taagaagaac ggccaacggt ttgtcaactt cttgacgatg attccggtgc     2100
gagatgaaac aggggaatac cggtacagca tgggtttcca gtgcgaaacg gaatgagaat     2160
tccccctgtt ttggcggatg agagaagatt ttcagcctga tacagattaa atcagaacgc     2220
agaagcggtc tgataaaaca gaatttgcct ggcggcagta gcgcggtggt cccacctgac     2280
cccatgccga actcagaagt gaaacgccgt agcgccgatg gtagtgtggg gtctccccat     2340
gcgagagtag ggaactgcca ggcatcaaat aaaacgaaag gctcagtcga agactgggc     2400 ctt                                                                  2403
```

<210> SEQ ID NO 109
<211> LENGTH: 645
<212> TYPE: DNA
<213> ORGANISM: Artificial Sequence
<220> FEATURE:
<223> OTHER INFORMATION: Synthetic

<400> SEQUENCE: 109

```
atgaaaccag taacgttata cgatgtcgca gagtatgccg gtgtctctta tcagaccgtt    60
tcccgcgtgg tgaaccaggc cagccacgtt tctgcgaaaa cgcgggaaaa agtggaagcg   120
gcgatggcgg agctgaatta cattcccaac cgcgtggcac aacaactggc gggcaaacag   180
tcgttgggat cccatacgct ctacgctccc ggcggttatg acattatggg ctatctgatt   240
cagattatga acaggccaaa cccccaagta gaactgggac ctgttgacac gtcagttgct   300
ctgattctgt gcgacctgaa gcaaaaagac acgccaattg tgtacgcctc ggaagctttt   360
ctctatatga caggatacag caatgcggag gtcttgggga gaaactgccg ttttcttcag   420
tcacccgacg gaatggtcaa gccgaaatcg acaaggaagt acgtcgactc caacacgatc   480
aatacgatga ggaaagcgat tgataggaac gccgaggtgc aggttgaggt ggtcaatttt   540
aagaagaacg gccaacggtt tgtcaacttc ttgacgatga ttccggtgcg agatgaaaca   600
ggggaatacc ggtacagcat gggtttccag tgcgaaacgg aatga                  645
```

<210> SEQ ID NO 110
<211> LENGTH: 214
<212> TYPE: PRT
<213> ORGANISM: Artificial Sequence
<220> FEATURE:
<223> OTHER INFORMATION: Synthetic

<400> SEQUENCE: 110

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Gly Ser
    50                  55                  60

His Thr Leu Tyr Ala Pro Gly Gly Tyr Asp Ile Met Gly Tyr Leu Ile
65                  70                  75                  80

Gln Ile Met Asn Arg Pro Asn Pro Gln Val Glu Leu Gly Pro Val Asp
                85                  90                  95

Thr Ser Val Ala Leu Ile Leu Cys Asp Leu Lys Gln Lys Asp Thr Pro
            100                 105                 110

Ile Val Tyr Ala Ser Glu Ala Phe Leu Tyr Met Thr Gly Tyr Ser Asn
        115                 120                 125

Ala Glu Val Leu Gly Arg Asn Cys Arg Phe Leu Gln Ser Pro Asp Gly
    130                 135                 140

Met Val Lys Pro Lys Ser Thr Arg Lys Tyr Val Asp Ser Asn Thr Ile
145                 150                 155                 160

Asn Thr Met Arg Lys Ala Ile Asp Arg Asn Ala Glu Val Gln Val Glu
                165                 170                 175

Val Val Asn Phe Lys Lys Asn Gly Gln Arg Phe Val Asn Phe Leu Thr
            180                 185                 190

Met Ile Pro Val Arg Asp Glu Thr Gly Glu Tyr Arg Tyr Ser Met Gly
        195                 200                 205

Phe Gln Cys Glu Thr Glu
    210

<210> SEQ ID NO 111
<211> LENGTH: 1785
<212> TYPE: DNA
<213> ORGANISM: Artificial Sequence
<220> FEATURE:
<223> OTHER INFORMATION: Synthetic

<400> SEQUENCE: 111

| | | | | | |
|---|---|---|---|---|---|
| tcattccgtt | tcgcactgga | aacccatgct | gtaccggtat | tccctgtttt | catctcgcac | 60 |
| cggaatcatc | gtcaagaagt | tgacaaaccg | ttggccgttc | ttcttaaaat | tgaccacctc | 120 |
| aacctgcacc | tcggcgttcc | tatcaatcgc | tttcctcatc | gtattgatcg | tgttggagtc | 180 |
| gacgtacttc | cttgtcgatt | tcggcttgac | cattccgtcg | ggtgactgaa | gaaaacggca | 240 |
| gtttctcccc | aagacctccg | cattgctgta | tcctgtcata | tagagaaaag | cttccgaggc | 300 |
| gtacacaatt | ggcgtgtctt | tttgcttcag | gtcgcacaga | atcagagcaa | ctgacgtgtc | 360 |
| aacaggtccc | agttctactt | ggggggtttgg | cctgttcata | atctgaatca | gatagcccat | 420 |
| aatgtcataa | ccgccgggag | cgtagagcgt | atgggatccc | aacgactgtt | tgcccgccag | 480 |
| ttgttgtgcc | acgcggttgg | gaatgtaatt | cagctccgcc | atcgccgctt | ccacttttc | 540 |
| ccgcgttttc | gcagaaacgt | ggctggcctg | gttcaccacg | cgggaaacgg | tctgataaga | 600 |
| gacaccggca | tactctgcga | catcgtataa | cgttactggt | ttcatcaaaa | tcgtctccct | 660 |
| ccgtttgaat | atttgattga | tcgtaaccag | atgaagcact | cttttccacta | tccctacagt | 720 |
| gttatggctt | gaacaatcac | gaaacaataa | ttggtacgta | cgatctttca | gccgactcaa | 780 |
| acatcaaatc | ttacaaatgt | agtctttgaa | agtattacat | atgtaagatt | taaatgcaac | 840 |
| cgttttttcg | gaaggaaatg | atgacctcgt | ttccaccgga | attagcttgg | taccagctat | 900 |
| tgtaacataa | tcggtacggg | ggtgaaaaag | ctaacgaaaa | agggagcgga | aaagaatgat | 960 |
| gtaagcgtga | aaatttttt | atcttatcac | ttgaaattgg | aagggagatt | ctttattata | 1020 |
| agaattgtgg | aattgtgagc | ggataacaat | tcccaattaa | aggaggaagg | atccatggtg | 1080 |
| agcaagggcg | aggaggataa | catggccatc | atcaaggagt | tcatgcgctt | caaggtgcac | 1140 |
| atggagggct | ccgtgaacgg | ccacgagttc | gagatcgagg | gcgagggcga | gggccgcccc | 1200 |
| tacgagggca | cccagaccgc | caagctgaag | gtgaccaagg | gtggccccct | gcccttcgcc | 1260 |
| tgggacatcc | tgtcccctca | gttcatgtac | ggctccaagg | cctacgtgaa | gcaccccgcc | 1320 |
| gacatccccg | actacttgaa | gctgtccttc | cccgagggct | tcaagtggga | gcgcgtgatg | 1380 |
| aacttcgagg | acggcggcgt | ggtgaccgtg | acccaggact | cctccctgca | ggacggcgag | 1440 |
| ttcatctaca | aggtgaagct | gcgcggcacc | aacttcccct | ccgacggccc | cgtaatgcag | 1500 |
| aagaagacca | tgggctggga | ggcctcctcc | gagcggatgt | accccgagga | cggcgccctg | 1560 |
| aagggcgaga | tcaagcagag | gctgaagctg | aaggacggcg | ccactacga | cgctgaggtc | 1620 |
| aagaccacct | acaaggccaa | gaagcccgtg | cagctgcccg | gcgcctacaa | cgtcaacatc | 1680 |
| aagttggaca | tcacctccca | caacgaggac | tacaccatcg | tggaacagta | cgaacgcgcc | 1740 |
| gagggccgcc | actccaccgg | cggcatggac | gagctgtaca | agtaa | | 1785 |

<210> SEQ ID NO 112
<211> LENGTH: 1126
<212> TYPE: DNA
<213> ORGANISM: Artificial Sequence
<220> FEATURE:
<223> OTHER INFORMATION: Synthetic

<400> SEQUENCE: 112

| | | | | | |
|---|---|---|---|---|---|
| gatgtactgt | acatccatac | agtaactcac | aggggctgga | ttgattgtgt | aggctggagc | 60 |
| tgcttcgaag | ttcctatact | ttctagagaa | taggaacttc | ggaataggaa | cttcatttaa | 120 |

| | |
|---|---|
| atggcgcgcc ttacgcccccg ccctgccact catcgcagta ctgttgtatt cattaagcat | 180 |
| ctgccgacat ggaagccatc acaaacggca tgatgaacct gaatcgccag cggcatcagc | 240 |
| accttgtcgc cttgcgtata atatttgccc atggtgaaaa cggggggcgaa gaagttgtcc | 300 |
| atattggcca cgtttaaatc aaaactggtg aaactcaccc agggattggc tgagacgaaa | 360 |
| aacatattct caataaaccc tttagggaaa taggccaggt tttcaccgta acacgccaca | 420 |
| tcttgcgaat atatgtgtag aaactgccgg aaatcgtcgt ggtattcact ccagagcgat | 480 |
| gaaaacgttt cagtttgctc atggaaaacg gtgtaacaag ggtgaacact atcccatatc | 540 |
| accagctcac cgtctttcat tgccatacgt aattccggat gagcattcat caggcgggca | 600 |
| agaatgtgaa taaaggccgg ataaaacttg tgcttatttt tctttacggt ctttaaaaag | 660 |
| gccgtaatat ccagctgaac ggtctggtta taggtacatt gagcaactga ctgaaatgcc | 720 |
| tcaaaatgtt ctttacgatg ccattgggat atatcaacgg tggtatatcc agtgattttt | 780 |
| ttctccattt tagcttcctt agctcctgaa aatctcgaca actcaaaaaa tacgcccggt | 840 |
| agtgatctta tttcattatg gtgaaagttg gaacctctta cgtgccgatc aacgtctcat | 900 |
| tttcgccaaa agttggccca gggcttcccg gtatcaacag ggacaccagg atttatttat | 960 |
| tctgcgaagt gatcttccgt cacaggtagg cgcgccgaag ttcctatact ttctagaaa | 1020 |
| taggaacttc ggaataggaa ctaaggagga tattcatatg gaccatggct aattcccatg | 1080 |
| taaatttagg attaatcctg gaactttttt tgtcgcccag ccaatg | 1126 |

<210> SEQ ID NO 113
<211> LENGTH: 1574
<212> TYPE: DNA
<213> ORGANISM: Artificial Sequence
<220> FEATURE:
<223> OTHER INFORMATION: Synthetic

<400> SEQUENCE: 113

| | |
|---|---|
| gaaagcgtta acggccaggc aacaagaggt gtttgatctc atcctgagcg attgtgtagg | 60 |
| ctggagctgc ttcgaagttc ctatactttc tagagaatag gaacttcgga ataggaactt | 120 |
| caagatcccc tcacgctgcc gcaagcactc agggcgcaag ggctgctaaa ggaagcggaa | 180 |
| cacgtagaaa gccagtccgc agaaacggtg ctgaccccgg atgaatgtca gctactgggc | 240 |
| tatctggaca agggaaaacg caagcgcaaa gagaaagcag gtagcttgca gtgggcttac | 300 |
| atggcgatag ctagactggg cggttttatg gacagcaagc gaaccggaat tgccagctgg | 360 |
| ggcgccctct ggtaaggttg ggaagccctg caaagtaaac tggatggctt tcttgccgcc | 420 |
| aaggatctga tggcgcaggg gatcaagatc tgatcaagag acaggatgag gatcgtttcg | 480 |
| catgattgaa caagatggat tgcacgcagg ttctccggcc gcttgggtgg agaggctatt | 540 |
| cggctatgac tgggcacaac agacaatcgg ctgctctgat gccgccgtgt tccggctgtc | 600 |
| agcgcagggg cgcccggttc ttttgtcaa gaccgacctg tccggtgccc tgaatgaact | 660 |
| gcaggacgag gcagcgcggc tatcgtggct ggccacgacg ggcgttcctt gcgcagctgt | 720 |
| gctcgacgtt gtcactgaag cgggaaggga ctggctgcta ttgggcgaag tgccggggca | 780 |
| ggatctcctg tcatctcacc ttgctcctgc cgagaaagta tccatcatgg ctgatgcaat | 840 |
| gcggcggctg catacgcttg atccggctac ctgcccattc gaccaccaag cgaaacatcg | 900 |
| catcgagcga gcacgtactc ggatggaagc cggtcttgtc gatcaggatg atctggacga | 960 |
| agagcatcag gggctcgcgc cagccgaact gttcgccagg ctcaaggcgc gcatgcccga | 1020 |
| cggcgaggat ctcgtcgtga cccatggcga tgcctgcttg ccgaatatca tggtggaaaa | 1080 |

```
tggccgcttt tctggattca tcgactgtgg ccggctgggt gtggcggacc gctatcagga   1140
catagcgttg gctacccgtg atattgctga agagcttggc ggcgaatggg ctgaccgctt   1200
cctcgtgctt tacggtatcg ccgctcccga ttcgcagcgc atcgccttct atcgccttct   1260
tgacgagttc ttctgagcgg gactctgggg ttcgaaatga ccgaccaagc gacgcccaac   1320
ctgccatcac gagatttcga ttccaccgcc gccttctatg aaaggttggg cttcggaatc   1380
gttttccggg acgccggctg gatgatcctc cagcgcgggg atctcatgct ggagttcttc   1440
gcccacccca gcttcaaaag cgctctgaag ttcctatact ttctagagaa taggaacttc   1500
ggaataggaa ctaaggagga tattcatatg gcgagtttaa accaattgtc gttgaccttc   1560
gtcagcagag cttc                                                     1574
```

<210> SEQ ID NO 114
<211> LENGTH: 1588
<212> TYPE: DNA
<213> ORGANISM: Artificial Sequence
<220> FEATURE:
<223> OTHER INFORMATION: Synthetic

<400> SEQUENCE: 114

```
cttatcagac cgcctgatat gacgtggtca cgccacatca ggcaatacaa atgagcgatt     60
gtgtaggctg gagctgcttc gaagttccta tactttctag aataggaa cttcggaata      120 ggaacttcaa gatcccctca cgctgccgca agcactcagg gcgcaagggc tgctaaagga   180
agcggaacac gtagaaagcc agtccgcaga acggtgctg accccggatg aatgtcagct    240
actgggctat ctggacaagg gaaaacgcaa gcgcaaagag aaagcaggta gcttgcagtg    300
ggcttacatg gcgatagcta gactgggcgg ttttatggac agcaagcgaa ccggaattgc    360
cagctggggc gccctctggt aaggttggga agccctgcaa agtaaactgg atggcttcct   420
tgccgccaag gatctgatgg cgcaggggat caagatctga tcaagagaca ggatgaggat    480
cgtttcgcat gattgaacaa gatggattgc acgcaggttc tccggccgct tgggtggaga    540
ggctattcgg ctatgactgg gcacaacaga caatcggctg ctctgatgcc gccgtgttcc    600
ggctgtcagc gcaggggcgc ccggttcttt ttgtcaagac cgacctgtcc ggtgccctga    660
atgaactgca ggacgaggca gcgcggctat cgtggctggc cacgacgggc gttccttgcg    720
cagctgtgct cgacgttgtc actgaagcgg gaagggactg gctgctattg ggcgaagtgc    780
cggggcagga tctcctgtca tctcaccttg ctcctgccga gaaagtatcc atcatggctg    840
atgcaatgcg gcggctgcat acgcttgatc cggctacctg cccattcgac caccaagcga    900
aacatcgcat cgagcgagca cgtactcgga tggaagccgg tcttgtcgat caggatgatc    960
tggacgaaga gcatcagggg ctcgcgccag ccgaactgtt cgccaggctc aaggcgcgca  1020
tgcccgacgg cgaggatctc gtcgtgaccc atggcgatgc ctgcttgccg aatatcatgg   1080
tggaaaatgg ccgcttttct ggattcatcg actgtggccg gctgggtgtg gcggaccgct   1140
atcaggacat agcgttggct acccgtgata ttgctgaaga gcttggcggc gaatgggctg   1200
accgcttcct cgtgctttac ggtatcgccg ctcccgattc gcagcgcatc gccttctatc   1260
gccttcttga cgagttcttc tgagcggact ctggggttcg aaatgaccga ccaagcgac    1320 gcccaacctg ccatcacgag atttcgattc caccgccgcc ttctatgaaa ggttgggctt   1380
cggaatcgtt ttccgggacg ccggctggat gatcctccag cgcggggatc tcatgctgga  1440
gttcttcgcc cacccagct tcaaaagcgc tctgaagttc ctatactttc tagagaatag   1500
```
gaacttcgga ataggaacta aggaggatat tcatatgagt cgcatcctca catgcccagt    1560
ttctcaaaga ttttgttgag ttttcct                                        1588

<210> SEQ ID NO 115
<211> LENGTH: 1574
<212> TYPE: DNA
<213> ORGANISM: Artificial Sequence
<220> FEATURE:
<223> OTHER INFORMATION: Synthetic

<400> SEQUENCE: 115
aggacgctgt agagaaaatt ggtaaccgtt ttgacctggt actgtgagcg attgtgtagg      60
ctggagctgc ttcgaagttc ctatactttc tagagaatag gaacttcgga ataggaactt    120
caagatcccc tcacgctgcc gcaagcactc agggcgcaag ggctgctaaa ggaagcggaa    180
cacgtagaaa gccagtccgc agaaacggtg ctgaccccgg atgaatgtca gctactgggc    240
tatctggaca agggaaaacg caagcgcaaa gagaaagcag gtagcttgca gtgggcttac    300
atggcgatag ctagactggg cggttttatg gacagcaagc gaaccggaat tgccagctgg    360
ggcgccctct ggtaaggttg gaagccctg caaagtaaac tggatggctt tcttgccgcc     420
aaggatctga tggcgcaggg gatcaagatc tgatcaagac aggatgagga tcgtttcg     480 catgattgaa caagatggat tgcacgcagg ttctccggcc gcttgggtgg agaggctatt    540
cggctatgac tgggcacaac agacaatcgg ctgctctgat gccgccgtgt tccggctgtc    600
agcgcagggg cgcccggttc tttttgtcaa gaccgacctg tccggtgccc tgaatgaact    660
gcaggacgag gcagcgcggc tatcgtggct ggccacgacg ggcgttcctt gcgcagctgt    720
gctcgacgtt gtcactgaag cgggaaggga ctggctgcta ttgggcgaag tgccggggca    780
ggatctcctg tcatctcacc ttgctcctgc cgagaaagta tccatcatgg ctgatgcaat    840
gcggcggctg catacgcttg atccggctac ctgcccattc gaccaccaag cgaaacatcg    900
catcgagcga gcacgtactc ggatggaagc cggtcttgtc gatcaggatg atctggacga    960
agagcatcag gggctcgcgc cagccgaact gttcgccagg ctcaaggcgc gcatgcccga   1020
cggcgaggat ctcgtcgtga cccatggcga tgcctgcttg ccgaatatca tggtggaaaa   1080
tggccgcttt tctggattca tcgactgtgg ccggctgggt gtggcggacc gctatcagga   1140
catagcgttg gctacccgtg atattgctga agagcttggc ggcgaatggg ctgaccgctt   1200
cctcgtgctt tacggtatcg ccgctcccga ttcgcagcgc atcgccttct atcgccttct   1260
tgacgagttc ttctgagcgg gactctgggg ttcgaaatga ccgaccaagc gacgcccaac   1320
ctgccatcac gagatttcga ttccaccgcc gccttctatg aaaggttggg cttcggaatc   1380
gttttccggg acgccggctg atgatcctc cagcgcgggg atctcatgct ggagttcttc    1440
gcccacccca gcttcaaaag cgctctgaag ttcctatact ttctagagaa taggaacttc   1500
ggaataggaa ctaaggagga tattcatatg caagagcagg aagccgctga attacaagcc   1560
gttaccgcta ttgc                                                     1574

<210> SEQ ID NO 116
<211> LENGTH: 2427
<212> TYPE: DNA
<213> ORGANISM: Artificial Sequence
<220> FEATURE:
<223> OTHER INFORMATION: Synthetic

<400> SEQUENCE: 116
gaagctctgc tgacgaaggt caacgacaat tggtttaaac tcgctatttt cgtgcgcgga     60

```
accectattt gtttattttt ctaaatacat tcaaatatgt atccgctcat gagacaataa      120
ccctgataaa tgcttcaata atattgaaaa aggaagcata tgaaagcgtt aacggccagg      180
caacaagagg tgtttgatct catccgtgat cacatcagcc agacaggtat gccgccgacg      240
cgtgcgaaaa tcgcgcagcg tttggggttc cgttccccaa acgcggctga aaagcatctg      300
aaggcgctgg cacgcaaagg cgttattgaa attgtttccg gcgcatcacg cgggattcgt      360
ctgttgcagg aagaggaaga agggttgccg ctggtaggtc gtgtggctgc cggtgaaccg      420
ggtggcggtg gatcccatac gctctacgct cccggcggtt atgacattat gggctatctg      480
attcagatta tgaacaggcc aaaccccccaa gtagaactgg gacctgttga cacgtcagtt      540
gctctgattc tgtgcgacct gaagcaaaaa gacacgccaa ttgtgtacgc ctcggaagct      600
tttctctata tgacaggata cagcaatgcg gaggtcttgg ggagaaactg ccgtttttctt      660 cagtcacccg acggaatggt caagccgaaa tcgacaagga agtacgtcga ctccaacacg      720
atcaatacga tgaggaaagc gattgatagg aacgccgagg tgcaggttga ggtggtcaat      780
tttaagaaga acggccaacg gtttgtcaac ttcttgacga tgattccggt gcgagatgaa      840
acaggggaat accggtacag catgggtttc cagtgcgaaa cggaatgacc cgaattcgcg      900
attgtgtagg ctggagctgc ttcgaagttc ctatactttc tagagaatag gaacttcgga      960
ataggaactt caagatcccc tcacgctgcc gcaagcactc agggcgcaag ggctgctaaa     1020
ggaagcggaa cacgtagaaa gccagtccgc agaaacggtg ctgaccccgg atgaatgtca     1080
gctactgggc tatctggaca agggaaaacg caagcgcaaa gagaaagcag gtagcttgca     1140
gtgggcttac atggcgatag ctagactggg cggttttatg gacagcaagc gaaccggaat     1200
tgccagctgg ggcgccctct ggtaaggttg gaagccctg caaagtaaac tggatggctt     1260
tcttgccgcc aaggatctga tggcgcaggg gatcaagatc tgatcaagag acaggatgag     1320
gatcgtttcg catgattgaa caagatggat tgcacgcagg ttctccggcc gcttgggtgg     1380
agaggctatt cggctatgac tgggcacaac agacaatcgg ctgctctgat gccgccgtgt     1440
tccggctgtc agcgcagggg cgcccggttc ttttttgtcaa gaccgacctg tccggtgccc     1500
tgaatgaact gcaggacgag gcagcgcggc tatcgtggct ggccacgacg ggcgttcctt     1560
gcgcagctgt gctcgacgtt gtcactgaag cgggaaggga ctggctgcta ttgggcgaag     1620
tgccggggca ggatctcctg tcatctcacc ttgctcctgc cgagaaagta tccatcatgg     1680
ctgatgcaat gcggcggctg catacgcttg atccggctac ctgcccattc gaccaccaag     1740
cgaaacatcg catcgagcga gcacgtactc ggatggaagc cggtcttgtc gatcaggatg     1800
atctggacga agagcatcag gggctcgcgc cagccgaact gttcgccagg ctcaaggcgc     1860
gcatgcccga cggcgaggat ctcgtcgtga cccatggcga tgcctgcttg ccgaatatca     1920
tggtggaaaa tggccgcttt tctggattca tcgactgtgg ccggctgggt gtggcggacc     1980
gctatcagga catagcgttg ctacccgtga tattgctga agagcttggc ggcgaatggg     2040
ctgaccgctt cctcgtgctt tacggtatcg ccgctcccga ttcgcagcgc atcgccttct     2100
atcgccttct tgacgagttc ttctgagcgg actctgggg ttcgaaatga ccgaccaagc     2160
gacgcccaac ctgccatcac gagatttcga ttccaccgcc gccttctatg aaaggttggg     2220
cttcggaatc gttttccggg acgccggctg gatgatcctc cagcgcgggg atctcatgct     2280
ggagttcttc gcccacccca gcttcaaaag cgctctgaag ttcctatact ttctagagaa     2340
taggaacttc ggaataggaa ctaaggagga tattcatgag tatatacagc aaaaggcgat     2400
```

```
tttggaacca taaactgcac aataaac                                            2427
```

<210> SEQ ID NO 117
<211> LENGTH: 1400
<212> TYPE: DNA
<213> ORGANISM: Artificial Sequence
<220> FEATURE:
<223> OTHER INFORMATION: Synthetic

<400> SEQUENCE: 117

```
ctgttttggc ggatgagaga agattttcag cctgatacag attaaatcag aacgcagaag         60
cggtctgata aaacagaatt tgcctggcgg cagtagcgcg gtggtcccac ctgaccccat        120
gccgaactca gaagtgaaac gccgtagcgc cgatggtagt gtggggtctc cccatgcgag        180
agtagggaac tgccaggcat caaataaaac gaaaggctca gtcgaaagac tgggcctttc        240
gttttatctg ttgtttgcgc tagcggatcc tgttttttg atcgttttca caaaatgga         300
agtccacagt cttgacaggg aaaatgcagc ggcgtagctt ttatgctgta tataaaacca        360
gtggttatat gtacagtatt tattttaac ttattgtttt aaaagtcaaa gaggatttta        420
taatggtgag caagggcgag gaggataaca tggccatcat caaggagttc atgcgcttca        480
aggtgcacat ggagggctcc gtgaacggcc acgagttcga gatcgagggc gagggcgagg        540
gccgccccta cgagggcacc cagaccgcca agctgaaggt gaccaagggt ggccccctgc        600
ccttcgcctg ggacatcctg tcccctcagt tcatgtacgg ctccaaggcc tacgtgaagc        660
accccgccga catccccgac tacttgaagc tgtccttccc cgagggcttc aagtgggagc        720
gcgtgatgaa cttcgaggac ggcggcgtgg tgaccgtgac ccaggactcc tccctgcagg        780
acggcgagtt catctacaag gtgaagctgc gcggcaccaa cttcccctcc gacggccccg        840
taatgcagaa gaagaccatg ggctgggagg cctcctccga gcggatgtac cccgaggacg        900
gcgccctgaa gggcgagatc aagcagaggc tgaagctgaa ggacggcggc cactacgacg        960
ctgaggtcaa gaccacctac aaggccaaga agcccgtgca gctgcccggc gcctacaacg       1020
tcaacatcaa gttggacatc acctcccaca acgaggacta caccatcgtg aacagtacg        1080
aacgcgccga gggccgccac tccaccggcg gcatggacga gctgtacaag taagaattcc       1140
ccctgttttg gcggatgaga gaagattttc agcctgatac agattaaatc agaacgcaga       1200
agcggtctga taaaacagaa tttgcctggc ggcagtagcg cggtggtccc acctgacccc       1260
atgccgaact cagaagtgaa acgccgtagc gccgatggta gtgtggggtc tccccatgcg       1320
agagtaggga actgccaggc atcaaataaa acgaaaggct cagtcgaaag actgggcctt       1380
tcgttttatc tgttgtttgc                                                  1400
```

<210> SEQ ID NO 118
<211> LENGTH: 3740
<212> TYPE: DNA
<213> ORGANISM: Artificial Sequence
<220> FEATURE:
<223> OTHER INFORMATION: Synthetic

<400> SEQUENCE: 118

```
ctgttttggc ggatgagaga agattttcag cctgatacag attaaatcag aacgcagaag         60
cggtctgata aaacagaatt tgcctggcgg cagtagcgcg gtggtcccac ctgaccccat        120
gccgaactca gaagtgaaac gccgtagcgc cgatggtagt gtggggtctc cccatgcgag        180
agtagggaac tgccaggcat caaataaaac gaaaggctca gtcgaaagac tgggcctttc        240
gttttatctg ttgtttgcgc tagcggatcc tgttttttg atcgttttca caaaatgga         300
```

```
agtccacagt cttgacaggg aaaatgcagc ggcgtagctt ttatgctgta tataaaacca    360
gtggttatat gtacagtatt tattttaac ttattgtttt aaaagtcaaa gaggataagc     420
ttatggtcgt tttacaacgt cgtgactggg aaaaccctgg cgttacccaa cttaatcgcc    480
ttgcagcaca tcccccttc gccagctggc gtaatagcga agaggcccgc accgatcgcc     540
cttcccaaca gttgcgcagc ctgaatggcg aatggcgctt tgcctggttt ccggcaccag    600
aagcggtgcc ggaaagctgg ctggagtgcg atcttcctga ggccgatact gtcgtcgtcc    660
cctcaaactg gcagatgcac ggttacgatg cgcccatcta caccaacgta acctatccca    720
ttacggtcaa tccgccgttt gttcccacgg agaatccgac gggttgttac tcgctcacat    780
ttaatgttga tgaaagctgg ctacaggaag gccagacgcg aattattttt gatggcgtta    840
actcggcgtt tcatctgtgg tgcaacgggc gctgggtcgg ttacggccag acagtcgtt    900 tgccgtctga atttgacctg agcgcatttt tacgcgccgg agaaaaccgc ctcgcggtga    960
tggtgctgcg ttggagtgac ggcagttatc tggaagatca ggatatgtgg cggatgagcg    1020
gcattttccg tgacgtctcg ttgctgcata accgactac acaaatcagc gatttccatg    1080
ttgccactcg ctttaatgat gatttcagcc gcgctgtact ggaggctgaa gttcagatgt    1140
gcggcgagtt gcgtgactac ctacgggtaa cagtttcttt atggcagggt gaaacgcagg    1200
tcgccagcgg caccgcgcct ttcggcggtg aaattatcga tgagcgtggt ggttatgccg    1260
atcgcgtcac actacgtctg aacgtcgaaa acccgaaact gtggagcgcc gaaatcccga    1320
atctctatcg tgcggtggtt gaactgcaca ccgccgacgg cacgctgatt gaagcagaag    1380
cctgcgatgt cggtttccgc gaggtgcgga ttgaaaatgg tctgctgctg ctgaacggca    1440
agccgttgct gattcgaggc gttaaccgtc acgagcatca tcctctgcat ggtcaggtca    1500
tggatgagca gacgatggtg caggatatcc tgctgatgaa gcagaacaac tttaacgccg    1560
tgcgctgttc gcattatccg aaccatccgc tgtggtacac gctgtgcgac cgctacggcc    1620
tgtatgtggt ggatgaagcc aatattgaaa cccacggcat ggtgccaatg aatcgtctga    1680
ccgatgatcc gcgctggcta ccggcgatga gcgaacgcgt aacgcgaatg gtgcagcgcg    1740
atcgtaatca cccgagtgtg atcatctggt cgctggggga tgaatcaggc cacggcgcta    1800
atcacgacgc gctgtatcgc tggatcaaat ctgtcgatcc ttcccgcccg gtgcagtatg    1860
aaggcggcgg agccgacacc acggccaccg atattatttg cccgatgtac gcgcgcgtgg    1920
atgaagacca gcccttcccg gctgtgccga atggtccat caaaaaatgg ctttcgctac      1980
ctggagagac gcgcccgctg atcctttgcg aatacgccca cgcgatgggt aacagtcttg    2040
gcggtttcgc taaatactgg caggcgtttc gtcagtatcc ccgtttacag ggcggcttcg    2100
tctgggactg gtggatcag tcgctgatta aatatgatga aaacggcaac ccgtggtcgg     2160
cttacggcgg tgattttggc gatacgccga acgatcgcca gttctgtatg aacggtctgg    2220
tctttgccga ccgcacgccg catccagcgc tgacggaagc aaaacaccag cagcagtttt    2280
tccagttccg tttatccggg caaaccatcg aagtgaccag cgaatacctg ttccgtcata    2340
gcgataacga gctcctgcac tggatggtgg cgctggatgg taagccgctg gcaagcggtg    2400
aagtgcctct ggatgtcgct ccacaaggta aacagttgat tgaactgcct gaactaccgc    2460
agccggagag cgccgggcaa ctctggctca cagtacgcgt agtgcaaccg aacgcgaccg    2520
catggtcaga agccgggcac atcagcgcct ggcagcagtg cgtctggcg gaaaacctca    2580 gtgtgacgct ccccgccgcg tcccacgcca tcccgcatct gaccaccagc gaaatggatt    2640
```

| tttgcatcga gctgggtaat aagcgttggc aatttaaccg ccagtcaggc tttcttcac | 2700 |
| agatgtggat tggcgataaa aaacaactgc tgacgccgct gcgcgatcag ttcacccgtg | 2760 |
| caccgctgga taacgacatt ggcgtaagtg aagcgacccg cattgaccct aacgcctggg | 2820 |
| tcgaacgctg gaaggcggcg ggccattacc aggccgaagc agcgttgttg cagtgcacgg | 2880 |
| cagatacact tgctgatgcg gtgctgatta cgaccgctca cgcgtggcag catcagggga | 2940 |
| aaaccttatt tatcagccgg aaaacctacc ggattgatgg tagtggtcaa atggcgatta | 3000 |
| ccgttgatgt tgaagtggcg agcgatacac cgcatccggc gcggattggc ctgaactgcc | 3060 |
| agctggcgca ggtagcagag cgggtaaact ggctcggatt agggccgcaa gaaaactatc | 3120 |
| ccgaccgcct tactgccgcc tgttttgacc gctgggatct gccattgtca gacatgtata | 3180 |
| ccccgtacgt cttcccgagc gaaaacggtc tgcgctgcgg gacgcgcgaa ttgaattatg | 3240 |
| gcccacacca gtggcgcggc gacttccagt tcaacatcag ccgctacagt caacagcaac | 3300 |
| tgatggaaac cagccatcgc catctgctgc acgcggaaga aggcacatgg ctgaatatcg | 3360 |
| acggtttcca tatggggatt ggtggcgacg actcctggag cccgtcagta tcggcggaat | 3420 |
| tccagctgag cgccggtcgc taccattacc agttggtctg gtgtcaaaaa taaagatctc | 3480 |
| ccctgttttg gcggatgaga gaagattttc agcctgatac agattaaatc agaacgcaga | 3540 |
| agcggtctga taaaacagaa tttgcctggc ggcagtagcg cggtggtccc acctgacccc | 3600 |
| atgccgaact cagaagtgaa acgccgtagc gccgatggta gtgtggggtc tccccatgcg | 3660 |
| agagtaggga actgccaggc atcaaataaa acgaaaggct cagtcgaaag actgggcctt | 3720 |
| tcgttttatc tgttgtttgc | 3740 |

<210> SEQ ID NO 119
<211> LENGTH: 1319
<212> TYPE: DNA
<213> ORGANISM: Artificial Sequence
<220> FEATURE:
<223> OTHER INFORMATION: Synthetic

<400> SEQUENCE: 119

| ctgttttggc ggatgagaga agattttcag cctgatacag attaaatcag aacgcagaag | 60 |
| cggtctgata aaacagaatt tgcctggcgg cagtagcgcg gtggtcccac ctgacccat | 120 |
| gccgaactca gaagtgaaac gccgtagcgc cgatggtagt gtggggtctc ccatgcgag | 180 |
| agtagggaac tgccaggcat caaataaaac gaaaggctca gtcgaaagac tgggcctttc | 240 |
| gttttatctg ttgtttgcgc tagcggatcc atagggttga tctttgttgt cactggatgt | 300 |
| actgtacatc catacagtaa ctcacagggg ctggattgat tatggtgagc aagggcgagg | 360 |
| aggataacat ggccatcatc aaggagttca tgcgcttcaa ggtgcacatg gagggctccg | 420 |
| tgaacggcca cgagttcgag atcgagggcg agggcgaggg ccgcccctac gagggcaccc | 480 |
| agaccgccaa gctgaaggtg accaagggtg gccccctgcc cttcgcctgg gacatcctgt | 540 |
| cccctcagtt catgtacggc tccaaggcct acgtgaagca ccccgccgac atccccgact | 600 |
| acttgaagct gtccttcccc gagggcttca gtgggagcg cgtgatgaac ttcgaggacg | 660 |
| gcggcgtggt gaccgtgacc caggactcct ccctgcagga cggcgagttc atctacaagg | 720 |
| tgaagctgcg cggcaccaac ttcccctccg acggccccgt aatgcagaag aagaccatgg | 780 |
| gctgggaggc ctcctccgag cggatgtacc ccgaggacgg cgccctgaag ggcgagatca | 840 |
| agcagaggct gaagctgaag gacggcggcc actacgacgc tgaggtcaag accacctaca | 900 |
| aggccaagaa gcccgtgcag ctgcccggcg cctacaacgt caacatcaag ttggacatca | 960 |

```
cctcccacaa cgaggactac accatcgtgg aacagtacga acgcgccgag ggccgccact    1020
ccaccggcgg catggacgag ctgtacaagt aagaattccc cctgttttgg cggatgagag    1080
aagattttca gcctgataca gattaaatca gaacgcagaa gcggtctgat aaaacagaat    1140
ttgcctggcg gcagtagcgc ggtggtccca cctgacccca tgccgaactc agaagtgaaa    1200
cgccgtagcg ccgatggtag tgtggggtct ccccatgcga gagtagggaa ctgccaggca    1260
tcaaataaaa cgaaaggctc agtcgaaaga ctgggccttt cgttttatct gttgtttgc     1319
```

<210> SEQ ID NO 120
<211> LENGTH: 1348
<212> TYPE: DNA
<213> ORGANISM: Artificial Sequence
<220> FEATURE:
<223> OTHER INFORMATION: Synthetic

<400> SEQUENCE: 120

```
ctgttttggc ggatgagaga agattttcag cctgatacag attaaatcag aacgcagaag      60
cggtctgata aaacagaatt tgcctggcgg cagtagcgcg gtggtcccac ctgacccccat    120 gccgaactca gaagtgaaac gccgtagcgc cgatggtagt gtggggtctc ccatgcgag     180 agtagggaac tgccaggcat caaataaaac gaaaggctca gtcgaaagac tgggcctttc    240
gttttatctg ttgtttgcgc tagcggatcc gcctatgcag cgacaaatat tgatagcctg    300
aatcagtatt gatctgctgg caagaacaga ctactgtata taaaaacagt ataacttcag    360
gcagattatt atggtgagca agggcgagga ggataacatg gccatcatca aggagttcat    420
gcgcttcaag gtgcacatgg agggctccgt gaacggccac gagttcgaga tcgagggcga    480
gggcgagggc cgcccctacg agggcaccca gaccgccaag ctgaaggtga ccaagggtgg    540
ccccctgccc ttcgcctggg acatcctgtc ccctcagttc atgtacggct ccaaggccta    600
cgtgaagcac cccgccgaca tccccgacta cttgaagctg tccttcccg agggcttcaa     660 gtgggagcgc gtgatgaact cgaggacgg cggcgtggtg accgtgaccc aggactcctc     720
cctgcaggac ggcgagttca tctacaaggt gaagctgcgc ggcaccaact tcccctccga    780
cggccccgta atgcagaaga agaccatggg ctgggaggcc tcctccgagc ggatgtaccc    840
cgaggacggc gccctgaagg gcgagatcaa gcagaggctg aagctgaagg acggcggcca    900
ctacgacgct gaggtcaaga ccacctacaa ggccaagaag cccgtgcagc tgcccggcgc    960
ctacaacgtc aacatcaagt tggacatcac ctcccacaac gaggactaca ccatcgtgga   1020
acagtacgaa cgcgccgagg ccgccactc caccggcggc atggacgagc tgtacaagta    1080
agaattcccc ctgttttggc ggatgagaga agattttcag cctgatacag attaaatcag   1140
aacgcagaag cggtctgata aaacagaatt tgcctggcgg cagtagcgcg gtggtcccac   1200 ctgacccccat gccgaactca gaagtgaaac gccgtagcgc cgatggtagt gtggggtctc  1260
cccatgcgag agtagggaac tgccaggcat caaataaaac gaaaggctca gtcgaaagac   1320
tgggcctttc gttttatctg ttgtttgc                                      1348
```

<210> SEQ ID NO 121
<211> LENGTH: 1348
<212> TYPE: DNA
<213> ORGANISM: Artificial Sequence
<220> FEATURE:
<223> OTHER INFORMATION: Synthetic

<400> SEQUENCE: 121

```
ctgttttggc ggatgagaga agattttcag cctgatacag attaaatcag aacgcagaag    60
cggtctgata aaacagaatt tgcctggcgg cagtagcgcg gtggtcccac ctgaccccat   120
gccgaactca gaagtgaaac gccgtagcgc cgatggtagt gtggggtctc cccatgcgag   180
agtagggaac tgccaggcat caaataaaac gaaaggctca gtcgaaagac tgggcctttc   240
gttttatctg ttgtttgcgc tagcggatcc caatttctac aaaacacttg atactgtatg   300
agcatacagt ataattgctt caacagaaca tattgactat ccggtattac ccggcatgac   360
aggagtaaaa atggtgagca agggcgagga ggataacatg gccatcatca aggagttcat   420
gcgcttcaag gtgcacatgg agggctccgt gaacggccac gagttcgaga tcgagggcga   480
gggcgagggc cgcccctacg agggcaccca gaccgccaag ctgaaggtga ccaagggtgg   540
ccccctgccc ttcgcctggg acatcctgtc cctcagttc atgtacggct ccaaggccta   600
cgtgaagcac cccgccgaca tccccgacta cttgaagctg tccttccccg agggcttcaa   660
gtgggagcgc gtgatgaact tcgaggacgg cggcgtggtg accgtgaccc aggactcctc   720
cctgcaggac ggcgagttca tctacaaggt gaagctgcgc ggcaccaact cccccctcga   780
cggccccgta atgcagaaga agaccatggg ctgggaggcc tcctccgagc ggatgtaccc   840
cgaggacggc gccctgaagg gcgagatcaa gcagaggctg aagctgaagg acggcggcca   900
ctacgacgct gaggtcaaga ccacctacaa ggccaagaag cccgtgcagc tgcccggcgc   960
ctacaacgtc aacatcaagt tggacatcac ctcccacaac gaggactaca ccatcgtgga  1020
acagtacgaa cgcgccgagg gccgccactc caccggcggc atggacgagc tgtacaagta  1080
agaattcccc ctgttttggc ggatgagaga agattttcag cctgatacag attaaatcag  1140
aacgcagaag cggtctgata aaacagaatt tgcctggcgg cagtagcgcg gtggtcccac  1200
ctgaccccat gccgaactca gaagtgaaac gccgtagcgc cgatggtagt gtggggtctc  1260
cccatgcgag agtagggaac tgccaggcat caaataaaac gaaaggctca gtcgaaagac  1320
tgggcctttc gttttatctg ttgtttgc                                     1348
```

<210> SEQ ID NO 122
<211> LENGTH: 1322
<212> TYPE: DNA
<213> ORGANISM: Artificial Sequence
<220> FEATURE:
<223> OTHER INFORMATION: Synthetic

<400> SEQUENCE: 122

```
ctgttttggc ggatgagaga agattttcag cctgatacag attaaatcag aacgcagaag    60
cggtctgata aaacagaatt tgcctggcgg cagtagcgcg gtggtcccac ctgaccccat   120
gccgaactca gaagtgaaac gccgtagcgc cgatggtagt gtggggtctc cccatgcgag   180
agtagggaac tgccaggcat caaataaaac gaaaggctca gtcgaaagac tgggcctttc   240
gttttatctg ttgtttgcgc tagcggatcc tatctaacac cgtgcgtgtt gactatttta   300
cctctggcgg tgataatggt tgcatgtact aaggaggtac tagtatggtg agcaagggcg   360
aggaggataa catggccatc atcaaggagt tcatgcgctt caaggtgcac atggagggct   420
ccgtgaacgg ccacgagttc gagatcgagg gcgagggcga gggccgcccc tacgagggca   480
cccagaccgc caagctgaag gtgaccaagg gtggcccccct gcccttcgcc tgggacatcc   540
tgtcccctca gttcatgtac ggctccaagg cctacgtgaa gcaccccgcc gacatccccg   600
actacttgaa gctgtccttc cccgagggct tcaagtggga gcgcgtgatg aacttcgagg   660
acggcggcgt ggtgaccgtg acccaggact cctcccctgca ggacggcgag ttcatctaca   720
```

```
aggtgaagct gcgcggcacc aacttcccct ccgacggccc cgtaatgcag aagaagacca      780
tgggctggga ggcctcctcc gagcggatgt accccgagga cggcgccctg aagggcgaga      840
tcaagcagag gctgaagctg aaggacggcg gccactacga cgctgaggtc aagaccacct      900
acaaggccaa gaagcccgtg cagctgcccg gcgcctacaa cgtcaacatc aagttggaca      960
tcacctccca caacgaggac tacaccatcg tggaacagta cgaacgcgcc gagggccgcc     1020
actccaccgg cggcatggac gagctgtaca agtaagaatt ccccctgttt tggcggatga     1080
gagaagattt tcagcctgat acagattaaa tcagaacgca gaagcggtct gataaaacag     1140
aatttgcctg gcggcagtag cgcggtggtc ccacctgacc ccatgccgaa ctcagaagtg     1200
aaacgccgta gcgccgatgg tagtgtgggg tctccccatg cgagagtagg gaactgccag     1260
gcatcaaata aaacgaaagg ctcagtcgaa agactgggcc tttcgtttta tctgttgttt     1320
gc                                                                   1322

<210> SEQ ID NO 123
<211> LENGTH: 1340
<212> TYPE: DNA
<213> ORGANISM: Artificial Sequence
<220> FEATURE:
<223> OTHER INFORMATION: Synthetic

<400> SEQUENCE: 123
ctgttttggc ggatgagaga agattttcag cctgatacag attaaatcag aacgcagaag       60
cggtctgata aaacagaatt tgcctggcgg cagtagcgcg gtggtcccac ctgaccccat      120
gccgaactca gaagtgaaac gccgtagcgc cgatggtagt gtggggtctc cccatgcgag      180
agtagggaac tgccaggcat caaataaaac gaaaggctca gtcgaaagac tgggcctttc      240
gttttatctg ttgtttgcgc tagcggatcc ggaaattaat acgactcact ataggggaat      300
ttttagcgct aaaaattccc ctgtagaaat aattttgttt aactttaata aggagatata      360
ccatggtgag caagggcgag gaggataaca tggccatcat caaggagttc atgcgcttca      420
aggtgcacat ggagggctcc gtgaacggcc acgagttcga gatcgagggc gagggcgagg      480
ccgcccccta cgagggcacc cagaccgcca agctgaaggt gaccaagggt ggccccctgc      540
ccttcgcctg ggacatcctg tcccctcagt tcatgtacgg ctccaaggcc tacgtgaagc      600
accccgccga catccccgac tacttgaagc tgtccttccc cgagggcttc aagtgggagc      660
gcgtgatgaa cttcgaggac ggcggcgtgg tgaccgtgac ccaggactcc tccctgcagg      720
acggcgagtt catctacaag gtgaagctgc gcggcaccaa cttcccctcc gacggccccg      780
taatgcagaa gaagaccatg gctgggagg cctcctccga gcggatgtac cccgaggacg      840
gcgccctgaa gggcgagatc aagcagaggc tgaagctgaa ggacggcggc cactacgacg      900
ctgaggtcaa gaccacctac aaggccaaga gcccgtgca gctgcccggc gcctacaacg      960
tcaacatcaa gttggacatc acctcccaca acgaggacta caccatcgtg gaacagtacg     1020
aacgcgccga gggccgccac tccaccggcg gcatggacga gctgtacaag taagaattcc     1080 ccctgtttg gcggatgaga gaagattttc agcctgatac agattaaatc agaacgcaga     1140
agcggtctga taaaacagaa tttgcctggc ggcagtagcg cggtggtccc acctgacccc     1200
atgccgaact cagaagtgaa acgccgtagc gccgatggta gtgtggggtc tccccatgcg     1260
agagtaggga actgccaggc atcaaataaa acgaaaggct cagtcgaaag actgggcctt     1320
tcgttttatc tgttgtttgc                                                1340
```

<210> SEQ ID NO 124
<211> LENGTH: 1337
<212> TYPE: DNA
<213> ORGANISM: Artificial Sequence
<220> FEATURE:
<223> OTHER INFORMATION: Synthetic

<400> SEQUENCE: 124

```
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtggggtctc cccatgcgag     180
agtagggaac tgccaggcat caaataaaac gaaaggctca gtcgaaagac tgggcctttc     240
gtttatctg ttgtttgcgc tagcggatcc ggaaattaat acgactcact ataggggcgg     300
agtactgtcc tccgcccctg tagaaataat tttgtttaac tttaataagg agatatacca     360
tggtgagcaa gggcgaggag gataacatgg ccatcatcaa ggagttcatg cgcttcaagg     420
tgcacatgga gggctccgtg aacggccacg agttcgagat cgagggcgag ggcgagggcc     480
gccctacga gggcacccag accgccaagc tgaaggtgac caagggtggc cccctgccct     540
cgcctggga catcctgtcc cctcagttca tgtacggctc caaggcctac gtgaagcacc     600
ccgccgacat ccccgactac ttgaagctgt ccttccccga gggcttcaag tgggagcgcg     660
tgatgaactt cgaggacggc ggcgtggtga ccgtgaccca ggactcctcc ctgcaggacg     720
gcgagttcat ctacaaggtg aagctgcgcg gcaccaactt cccctccgac ggccccgtaa     780
tgcagaagaa gaccatgggc tgggaggcct cctccgagcg gatgtacccc gaggacggcg     840
ccctgaaggg cgagatcaag cagaggctga agctgaagga cggcggccac tacgacgctg     900
aggtcaagac cacctacaag gccaagaagc ccgtgcagct gcccggcgcc tacaacgtca     960
acatcaagtt ggacatcacc tcccacaacg aggactacac catcgtggaa cagtacgaac    1020
gcgccgaggg ccgccactcc accggcggca tggacgagct gtacaagtaa gaattccccc    1080
tgttttggcg gatgagagaa gattttcagc ctgatacaga ttaaatcaga acgcagaagc    1140
ggtctgataa aacagaattt gcctggcggc agtagcgcgg tggtcccacc tgaccccatg    1200
ccgaactcag aagtgaaacg ccgtagcgcc gatggtagtg tggggtctcc ccatgcgaga    1260
gtagggaact gccaggcatc aaataaaacg aaaggctcag tcgaaagact gggcctttcg    1320
ttttatctgt tgtttgc                                                   1337
```

<210> SEQ ID NO 125
<211> LENGTH: 1339
<212> TYPE: DNA
<213> ORGANISM: Artificial Sequence
<220> FEATURE:
<223> OTHER INFORMATION: Synthetic

<400> SEQUENCE: 125

```
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtggggtctc cccatgcgag     180
agtagggaac tgccaggcat caaataaaac gaaaggctca gtcgaaagac tgggcctttc     240
gtttatctg ttgtttgcgc tagcggatcc ggaaattaat acgactcact ataggggtcc     300
ctatcagtga tagagacccc tgtagaaata attttgttta actttaataa ggagatatac     360
catggtgagc aagggcgagg aggataacat ggccatcatc aaggagttca tgcgcttcaa     420
```

```
ggtgcacatg agggctccg tgaacggcca cgagttcgag atcgagggcg agggcgaggg    480
ccgcccctac gagggcaccc agaccgccaa gctgaaggtg accaagggtg ccccctgcc    540 cttcgcctgg gacatcctgt cccctcagtt catgtacggc tccaaggcct acgtgaagca    600
ccccgccgac atcccgact acttgaagct gtccttcccc gagggcttca gtgggagcg    660 cgtgatgaac ttcgaggacg gcggcgtggt gaccgtgacc caggactcct ccctgcagga    720
cggcgagttc atctacaagg tgaagctgcg cggcaccaac ttcccctccg acggccccgt    780
aatgcagaag aagaccatgg gctgggaggc ctcctccgag cggatgtacc ccgaggacgg    840
cgccctgaag ggcgagatca agcagaggct gaagctgaag gacggcggcc actacgacgc    900
tgaggtcaag accacctaca aggccaagaa gcccgtgcag ctgcccggcg cctacaacgt    960
caacatcaag ttggacatca cctcccacaa cgaggactac accatcgtgg aacagtacga    1020
acgcgccgag ggccgccact ccaccggcgg catggacgag ctgtacaagt aagaattccc    1080
cctgttttgg cggatgagag aagattttca gcctgataca gattaaatca gaacgcagaa    1140
gcggtctgat aaaacagaat tgcctggcg gcagtagcgc ggtggtccca cctgacccca    1200
tgccgaactc agaagtgaaa cgccgtagcg ccgatggtag tgtggggtct ccccatgcga    1260
gagtagggaa ctgccaggca tcaaataaaa cgaaaggctc agtcgaaaga ctgggccttt    1320
cgttttatct gttgtttgc                                                1339

<210> SEQ ID NO 126
<211> LENGTH: 1370
<212> TYPE: DNA
<213> ORGANISM: Artificial Sequence
<220> FEATURE:
<223> OTHER INFORMATION: Synthetic

<400> SEQUENCE: 126
ctgttttggc ggatgagaga agattttcag cctgatacag attaaatcag aacgcagaag    60
cggtctgata aaacagaatt tgcctggcgg cagtagcgcg gtggtccac ctgacccat    120 gccgaactca gaagtgaaac gccgtagcgc cgatggtagt gtggggtctc cccatgcgag    180
agtagggaac tgccaggcat caaataaaac gaaaggctca gtcgaaagac tgggcctttc    240
gttttatctg ttgtttgcgc tagcggatcc ctgtatataa aaccagtggt tatatgtaca    300
gtaccattag gcaccccggg ctttacactt tatgcttccg gctcgtatgt tgtgtcgacc    360
gagcggataa caatttcaca caggaaaagc ttatggtgag caagggcgag gaggataaca    420
tggccatcat caaggagttc atgcgcttca aggtgcacat ggagggctcc gtgaacggcc    480
acgagttcga gatcgagggc gagggcgagg ccgcccta cgagggcacc cagaccgcca    540
agctccgact acttgaagct gtccttcccc gagggcttca gtgggagcg cgtgatgaag    600 gtgaccaagg gtggccccct gcccttcgcc tgggacatcc tgtcccctca gttcatgtac    660
ggctccaagg cctacgtgaa gcaccccgcc gacatccgaa cttcgaggac ggcggcgtgg    720
tgaccgtgac ccaggactcc tccctgcagg acggcgagtt catctacaag gtgaagctgc    780
gcggcaccaa cttccctcc gacggccccg taatgcagaa gaagaccatg gctgggagg    840 cctcctccga gcggatgtac cccgaggacg gcgccctgaa gggcgagatc aagcagaggc    900
tgaagctgaa ggacggcggc cactacgacg ctgaggtcaa gaccacctac aaggccaaga    960
agcccgtgca gctgcccggc gcctacaacg tcaacatcaa gttggacatc acctcccaca    1020
acgaggacta caccatcgtg gaacagtacg aacgcgccga gggccgccac tccaccggcg    1080
```

```
gcatggacga gctgtacaag taagaattcc ccctgttttg gcggatgaga gaagattttc    1140
agcctgatac agattaaatc agaacgcaga agcggtctga taaaacagaa tttgcctggc    1200
ggcagtagcg cggtggtccc acctgacccc atgccgaact cagaagtgaa acgccgtagc    1260
gccgatggta gtgtggggtc tccccatgcg agagtaggga actgccaggc atcaaataaa    1320
acgaaaggct cagtcgaaag actgggcctt tcgttttatc tgttgtttgc               1370

<210> SEQ ID NO 127
<211> LENGTH: 1384
<212> TYPE: DNA
<213> ORGANISM: Artificial Sequence
<220> FEATURE:
<223> OTHER INFORMATION: Synthetic

<400> SEQUENCE: 127
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtggggtctc cccatgcgag     180
agtagggaac tgccaggcat caaataaaac gaaaggctca gtcgaaagac tgggcctttc     240
gttttatctg ttgtttgcgc tagcggatcc tatctaacac cgtgcgtgtt gactatttta     300
cctctggcgg tgataatgca ttaggcaccc gggctttac actttatgct tccggctcgt     360
atgttgtgtc gaccgagcgg ataacaattt cacacaggaa aagcttatgg tgagcaaggg     420
cgaggaggat aacatggcca tcatcaagga gttcatgcgc ttcaaggtgc acatggaggg     480
ctccgtgaac ggccacgagt cgagatcga gggcgagggc gagggccgcc ctacgaggg      540 cacccagacc gccaagctga aggtgaccaa gggtggcccc ctgcccttcg cctgggacat     600
cctgtcccct cagttcatgt acggctccaa ggcctacgtg aagcaccccg ccgacatccc     660
cgactacttg aagctgtcct tccccgaggg cttcaagtgg gagcgcgtga tgaacttcga     720
ggacggcggc gtggtgaccg tgacccagga ctcctccctg caggacgcg agttcatcta     780 caaggtgaag ctgcgcggca ccaacttccc ctccgacggc ccgtaatgc agaagaagac     840 catgggctgg gaggcctcct ccgagcgat gtaccccgag gacggcgcc tgaagggcga     900 gatcaagcag aggctgaagc tgaaggacgg cggccactac gacgctgagg tcaagaccac     960
ctacaaggcc aagaagcccg tgcagctgcc cggcgcctac aacgtcaaca tcaagttgga    1020
catcacctcc cacaacgagg actacaccat cgtggaacag tacgaacgcg ccgagggccg    1080
ccactccacc ggcggcatgg acgagctgta caagtaagaa ttcccctgt ttggcggat    1140 gagagaagat tttcagcctg atacagatta aatcagaacg cagaagcggt ctgataaaac    1200
agaatttgcc tggcggcagt agcgcggtgg tcccacctga ccccatgccg aactcagaag    1260
tgaaacgccg tagcgccgat ggtagtgtgg ggtctcccca tgcgagagta gggaactgcc    1320
aggcatcaaa taaaacgaaa ggctcagtcg aaagactggg cctttcgttt tatctgttgt    1380
ttgc                                                                  1384

<210> SEQ ID NO 128
<211> LENGTH: 1356
<212> TYPE: DNA
<213> ORGANISM: Artificial Sequence
<220> FEATURE:
<223> OTHER INFORMATION: Synthetic

<400> SEQUENCE: 128
ctgttttggc ggatgagaga agattttcag cctgatacag attaaatcag aacgcagaag      60
```

```
cggtctgata aaacagaatt tgcctggcgg cagtagcgcg gtggtcccac ctgaccccat    120
gccgaactca gaagtgaaac gccgtagcgc cgatggtagt gtggggtctc cccatgcgag    180
agtagggaac tgccaggcat caaataaaac gaaaggctca gtcgaaagac tgggcctttc    240
gttttatctg ttgtttgcgc tagcggatcc aattttttagc gctaaaaatt cattaggcac    300
cccgggcttt acactttatg cttccggctc gtatgttgtg tcgaccgagc ggataacaat    360
ttcacacagg aaaagcttat ggtgagcaag ggcgaggagg ataacatggc catcatcaag    420
gagttcatgc gcttcaaggt gcacatggag ggctccgtga acggccacga gttcgagatc    480
gagggcgagg gcgagggccg cccctacgag ggcacccaga ccgccaagct gaaggtgacc    540
aagggtggcc ccctgccctt cgcctgggac atcctgtccc ctcagttcat gtacggctcc    600
aaggcctacg tgaagcaccc cgccgacatc cccgactact tgaagctgtc cttccccgag    660
ggcttcaagt gggagcgcgt gatgaacttc gaggacggcg gcgtggtgac cgtgacccag    720
gactcctccc tgcaggacgg cgagttcatc tacaaggtga agctgcgcgg caccaacttc    780
ccctccgacg gccccgtaat gcagaagaag accatgggct gggaggcctc ctccgagcgg    840
atgtaccccg aggacggcgc cctgaagggc gagatcaagc agaggctgaa gctgaaggac    900
ggcggccact acgacgctga ggtcaagacc acctacaagg ccaagaagcc cgtgcagctg    960
cccggcgcct acaacgtcaa catcaagttg gacatcacct cccacaacga ggactacacc   1020
atcgtggaac agtacgaacg cgccgagggc cgccactcca ccggcggcat ggacgagctg   1080
tacaagtaag aattccccct gttttggcgg atgagagaag attttcagcc tgatacagat   1140
taaatcagaa cgcagaagcg gtctgataaa acagaatttg cctggcggca gtagcgcggt   1200
ggtcccacct gaccccatgc cgaactcaga agtgaaacgc cgtagcgccg atggtagtgt   1260
ggggtctccc catgcgagag tagggaactg ccaggcatca aataaaacga aaggctcagt   1320
cgaaagactg gcctttcgt tttatctgtt gtttgc                              1356
```

<210> SEQ ID NO 129  
<211> LENGTH: 1372  
<212> TYPE: DNA  
<213> ORGANISM: Artificial Sequence  
<220> FEATURE:  
<223> OTHER INFORMATION: Synthetic

<400> SEQUENCE: 129

```
ctgtttggc ggatgagaga agattttcag cctgatacag attaaatcag aacgcagaag     60
cggtctgata aacagaatt tgcctggcgg cagtagcgcg gtggtcccac ctgaccccat    120
gccgaactca gaagtgaaac gccgtagcgc cgatggtagt gtggggtctc cccatgcgag    180
agtagggaac tgccaggcat caaataaaac gaaaggctca gtcgaaagac tgggcctttc    240
gttttatctg ttgtttgcgc tagcggatcc cggagtactg tcctccgagc ggagtactgt    300
cctccgcatt aggcacccg ggctttacac tttatgcttc cggctcgtat gttgtgtcga    360
ccgagcggat aacaatttca cacaggaaaa gcttatggtg agcaagggcg aggaggataa    420
catggccatc atcaaggagt tcatgcgctt caaggtgcac atggagggct ccgtgaacgg    480
ccacgagttc gagatcgagg gcgagggcga gggccgcccc tacgagggca cccagaccgc    540
caagctgaag gtgaccaagg gtggcccct gcccttcgcc tgggacatcc tgtcccctca    600
gttcatgtac ggctccaagg cctacgtgaa gcaccccgcc gacatccccg actacttgaa    660
gctgtccttc cccgagggct tcaagtggga gcgcgtgatg aacttcgagg acggcggcgt    720
```

```
ggtgaccgtg acccaggact cctccctgca ggacggcgag ttcatctaca aggtgaagct    780
gcgcggcacc aacttcccct ccgacggccc cgtaatgcag aagaagacca tgggctggga    840
ggcctcctcc gagcggatgt accccgagga cggcgccctg aagggcgaga tcaagcagag    900
gctgaagctg aaggacggcg ccactacga cgctgaggtc aagaccacct acaaggccaa    960
gaagcccgtg cagctgcccg cgcctacaa cgtcaacatc aagttggaca tcacctccca   1020
caacgaggac tacaccatcg tggaacagta cgaacgcgcc gagggccgcc actccaccgg   1080
cggcatggac gagctgtaca agtaagaatt ccccctgttt tggcggatga gagaagattt   1140
tcagcctgat acagattaaa tcagaacgca gaagcggtct gataaaacag aatttgcctg   1200
gcggcagtag cgcggtggtc ccacctgacc ccatgccgaa ctcagaagtg aaacgccgta   1260
gcgccgatgg tagtgtgggg tctccccatg cgagagtagg gaactgccag gcatcaaata   1320
aaacgaaagg ctcagtcgaa agactgggcc tttcgtttta tctgttgttt gc           1372

<210> SEQ ID NO 130
<211> LENGTH: 1376
<212> TYPE: DNA
<213> ORGANISM: Artificial Sequence
<220> FEATURE:
<223> OTHER INFORMATION: Synthetic

<400> SEQUENCE: 130
ctgttttggc ggatgagaga agattttcag cctgatacag attaaatcag aacgcagaag     60
cggtctgata aaacagaatt tgcctggcgg cagtagcgcg gtggtcccac ctgaccccat    120
gccgaactca gaagtgaaac gccgtagcgc cgatggtagt gtggggtctc ccatgcgag    180 agtagggaac tgccaggcat caaataaaac gaaaggctca gtcgaaagac tgggcctttc    240
gttttatctg ttgtttgcgc tagcggatcc tccctatcag tgatagagag ctccctatca    300
gtgatagaga cattaggcac cccgggcttt acactttatg cttccggctc gtatgttgtg    360
tcgaccgagg ggataacaat ttcacacagg aaaagcttat ggtgagcaag ggcgaggagg    420
ataacatggc catcatcaag gagttcatgc gcttcaaggt gcacatggag ggctccgtga    480
acggccacga gttcgagatc gagggcgagg gcgaggccg cccctacgag ggcacccaga    540
ccgccaagct gaaggtgacc aagggtggcc cctgcccctt cgcctgggac atcctgtccc    600
ctcagttcat gtacggctcc aaggcctacg tgaagcaccc cgccgacatc ccgactact    660 tgaagctgtc cttccccgag ggcttcaagt gggagcgcgt gatgaacttc gaggacggcg    720
gcgtggtgac cgtgacccag gactcctccc tgcaggacgg cgagttcatc tacaaggtga    780
agctgcgcgg caccaacttc ccctccgacg gccccgtaat gcagaagaag accatgggct    840
gggaggcctc ctccgagcgg atgtaccccg aggacggcgc cctgaagggc gagatcaagc    900
agaggctgaa gctgaaggac ggcggccact acgacgctga ggtcaagacc acctacaagg    960
ccaagaagcc cgtgcagctg cccgcgcct acaacgtcaa catcaagttg gacatcacct   1020
cccacaacga ggactacacc atcgtggaac agtacgaacg cgccgagggc cgccactcca   1080
ccggcggcat ggacgagctg tacaagtaag aattccccct gttttggcgg atgagagaag   1140
attttcagcc tgatacagat taaatcagaa cgcagaagcg gtctgataaa acagaatttg   1200
cctggcggca gtagcgcggt ggtcccacct gaccccatgc cgaactcaga agtgaaacgc   1260
cgtagcgccg atggtagtgt ggggtctccc catgcgagag tagggaactg ccaggcatca   1320
aataaaacga aaggctcagt cgaaagactg ggcctttcgt tttatctgtt gtttgc        1376
```

-continued

<210> SEQ ID NO 131
<211> LENGTH: 714
<212> TYPE: DNA
<213> ORGANISM: Bacteriophage lambda

<400> SEQUENCE: 131

```
atgagcacaa aaagaaaacc attaacacaa gagcagcttg aggacgcacg tcgccttaaa      60
gcaatttatg aaaaaaagaa aaatgaactt ggcttatccc aggaatctgt cgcagacaag     120
atggggatgg ggcagtcagg cgttggtgct ttatttaatg gcatcaatgc attaaatgct     180
tataacgccg cattgcttgc aaaaattctc aaagttagcg ttgaagaatt tagcccttca     240
atcgccagag aaatctacga gatgtatgaa gcggttagta tgcagccgtc acttagaagt     300
gagtatgagt accctgtttt ttctcatgtt caggcaggga tgttctcacc tgagcttaga     360
acctttacca aagtgatgc ggagagatgg gtaagcacaa ccaaaaaagc cagtgattct     420
gcattctggc ttgaggttga aggtaattcc atgaccgcac caacaggctc aagccaagc     480
tttcctgacg gaatgttaat tctcgttgac cctgagcagg ctgttgagcc aggtgatttc     540
tgcatagcca gacttggggg tgatgagttt accttcaaga aactgatcag ggatagcggt     600
caggtgtttt tacaaccact aaacccacag tacccaatga tcccatgcaa tgagagttgt     660
tccgttgtgg ggaaagttat cgctagtcag tggcctgaag agacgtttgg ctaa           714
```

<210> SEQ ID NO 132
<211> LENGTH: 237
<212> TYPE: PRT
<213> ORGANISM: Bacteriophage lambda

<400> SEQUENCE: 132

Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
            20                  25                  30

Ser Gln Glu Ser Val Ala Asp Lys Met Gly Met Gly Gln Ser Gly Val
        35                  40                  45

Gly Ala Leu Phe Asn Gly Ile Asn Ala Leu Asn Ala Tyr Asn Ala Ala
    50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly

Lys Val Ile Ala Ser Gln Trp Pro Glu Glu Thr Phe Gly
225             230             235

<210> SEQ ID NO 133
<211> LENGTH: 2369
<212> TYPE: DNA
<213> ORGANISM: Artificial Sequence
<220> FEATURE:
<223> OTHER INFORMATION: Synthetic

<400> SEQUENCE: 133

| | | | | | |
|---|---|---|---|---|---|
| ctgttttggc | ggatgagaga | agattttcag | cctgatacag | attaaatcag | aacgcagaag | 60 |
| cggtctgata | aaacagaatt | tgcctggcgg | cagtagcgcg | gtggtcccac | ctgaccccat | 120 |
| gccgaactca | gaagtgaaac | gccgtagcgc | cgatggtagt | gtggggtctc | ccatgcgag | 180 |
| agtagggaac | tgccaggcat | caaataaaac | gaaaggctca | gtcgaaagac | tgggcctttc | 240 |
| gttttatctg | ttgtttgcgc | tagcggatcc | tgttttttg | atcgttttca | caaaaatgga | 300 |
| agtccacagt | cttgacaggg | aaaatgcagc | ggcgtagctt | ttatgctgta | tataaaacca | 360 |
| gtggttatat | gtacagtatt | tatttttaac | ttattgtttt | aaaagtcaaa | gaggatttta | 420 |
| taatgagcac | aaaaaagaaa | ccattaacac | aagagcagct | tgaggacgca | cgtcgcctta | 480 |
| aagcaattta | tgaaaaaaag | aaaaatgaac | ttggcttatc | ccaggaatct | gtcgcagaca | 540 |
| agatggggat | ggggcagtca | ggcgttggtg | ctttatttaa | tggcatcaat | gcattaaatg | 600 |
| cttataacgc | cgcattgctt | gcaaaaattc | tcaaagttag | cgttgaagaa | tttagccctt | 660 |
| caatcgccag | agaaatctac | gagatgtatg | aagcggttag | tatgcagccg | tcacttagaa | 720 |
| gtgagtatga | gtaccctgtt | ttttctcatg | ttcaggcagg | gatgttctca | cctgagctta | 780 |
| gaacctttac | caaaggtgat | gcggagagat | gggtaagcac | aaccaaaaaa | gccagtgatt | 840 |
| ctgcattctg | gcttgaggtt | gaaggtaatt | ccatgaccgc | accaacaggc | tccaagccaa | 900 |
| gctttcctga | cggaatgtta | attctcgttg | accctgagca | ggctgttgag | ccaggtgatt | 960 |
| tctgcatagc | cagacttggg | ggtgatgagt | ttaccttcaa | gaaactgatc | agggatagcg | 1020 |
| gtcaggtgtt | tttacaacca | ctaaacccac | agtacccaat | gatcccatgc | aatgagagtt | 1080 |
| gttccgttgt | ggggaaagtt | atcgctagtc | agtggcctga | agagacgttt | ggctaaagat | 1140 |
| ctgcttgatc | cggctgctaa | caaagcccga | aggaagctg | agttggctgc | tgccaccgct | 1200 |
| gagcaataac | tagcataacc | ccttggggcc | tctaaacggg | tcttgagggg | ttttttgctg | 1260 |
| aaaggaggaa | ctatatccgg | atctggcgta | atagcgaaga | ggcccgcacc | gatcgcccttt | 1320 |
| cccaacagtt | ggagctctat | ctaacaccgt | gcgtgttgac | tattttacct | ctggcggtga | 1380 |
| taatggttgc | atgtactaag | gaggtactag | tatggtgagc | aagggcgagg | aggataacat | 1440 |
| ggccatcatc | aaggagttca | tgcgcttcaa | ggtgcacatg | gagggctccg | tgaacggcca | 1500 |
| cgagttcgag | atcgagggcg | agggcgaggg | ccgcccctac | gagggcaccc | agaccgccaa | 1560 |
| gctgaaggtg | accaagggtg | gccccctgcc | cttcgcctgg | gacatcctgt | cccctcagtt | 1620 |
| catgtacggc | tccaaggcct | acgtgaagca | ccccgccgac | atccccgact | acttgaagct | 1680 |
| gtccttcccc | gagggcttca | gtgggagcg | cgtgatgaac | ttcgaggacg | gcggcgtggt | 1740 |
| gaccgtgacc | caggactcct | ccctgcagga | cggcgagttc | atctacaagg | tgaagctgcg | 1800 |
| cggcaccaac | ttcccctccg | acggccccgt | aatgcagaag | aagaccatgg | gctgggaggc | 1860 |
| ctcctccgag | cggatgtacc | ccgaggacgg | cgccctgaag | ggcgagatca | agcagaggct | 1920 |

```
gaagctgaag gacggcggcc actacgacgc tgaggtcaag accacctaca aggccaagaa    1980
gcccgtgcag ctgcccggcg cctacaacgt caacatcaag ttggacatca cctcccacaa    2040
cgaggactac accatcgtgg aacagtacga acgcgccgag ggccgccact ccaccggcgg    2100
catggacgag ctgtacaagt aagaattccc cctgttttgg cggatgagag aagattttca    2160
gcctgataca gattaaatca gaacgcagaa gcggtctgat aaaacagaat tgcctggcg    2220 gcagtagcgc ggtggtccca cctgacccca tgccgaactc agaagtgaaa cgccgtagcg    2280
ccgatggtag tgtggggtct ccccatgcga gagtagggaa ctgccaggca tcaaataaaa    2340
cgaaaggctc agtcgaaaga ctgggccttt                                    2369
```

<210> SEQ ID NO 134
<211> LENGTH: 2303
<212> TYPE: DNA
<213> ORGANISM: Artificial Sequence
<220> FEATURE:
<223> OTHER INFORMATION: Synthetic

<400> SEQUENCE: 134

```
ctgttttggc ggatgagaga agattttcag cctgatacag attaaatcag aacgcagaag     60
cggtctgata aaacagaatt tgcctggcgg cagtagcgcg gtggtcccac ctgacccat    120 gccgaactca gaagtgaaac gccgtagcgc cgatggtagt gtggggtctc cccatgcgag    180
agtagggaac tgccaggcat caaataaaac gaaaggctca gtcgaaagac tgggcctttc    240
gttttatctg ttgtttgcgc tagcggatcc tgttttttg atcgttttca caaaatgga    300 agtccacagt cttgacaggg aaaatgcagc ggcgtagctt ttatgctgta tataaaacca    360
gtggttatat gtacagtatt tattttaac ttattgtttt aaaagtcaaa gaggatttta    420
taatgagcac aaaaaagaaa ccattaacac aagagcagct tgaggacgca cgtcgcctta    480 aagcaatta tgaaaaaag aaaaatgaac ttggcttatc ccaggaatct gtcgcagaca    540
agatggggat ggggcagtca ggcgttggtg ctttatttaa tggcatcaat gcattaaatg    600
cttataacgc cgcattgctt gcaaaaattc tcaaagttag cgttgaagaa tttagccctt    660
caatcgccag agaaatctac gagatgtatg aagcggttag tatgcagccg tcacttagaa    720
gtgagtatga gtaccctgtt ttttctcatg ttcaggcagg gatgttctca cctgagctta    780
gaacctttac caaaggtgat gcggagagat gggtaagcac aaccaaaaaa gccagtgatt    840
ctgcattctg gcttgaggtt gaaggtaatt ccatgaccgc accaacaggc tccaagccaa    900
gctttcctga cggaatgtta attctcgttg accctgagca ggctgttgag ccaggtgatt    960
tctgcatagc cagacttggg ggtgatgagt ttaccttcaa gaaactgatc agggatagcg   1020
gtcaggtgtt tttacaacca ctaaacccac agtaccaat gatcccatgc aatgagagtt   1080
gttccgttgt ggggaaagtt atcgctagtc agtggcctga agagacgttt ggctaaagat   1140
ctgcttgatc cggctgctaa caaagcccga aggaagctg agttggctgc tgccaccgct   1200
gagcaataac tagcataacc ccttggggcc tctaaacggg tcttgagggg ttttttgctg   1260
aaaggaggaa ctatatccgg atctggcgta atagcgaaga ggcccgcacc gatcgccctt   1320
cccaacagtt ggagctctat ctaacaccgt gcgtgttgac tattttacct ctggcggtga   1380
taatggttgc atgtactaag gaggtactag tatgatgcaa ccatcaatca aacctgctga   1440
cgagcattca gctggcgata tcattgcgcg catcggcagc ctgacgcgta tgctgcgcga   1500
cagtttgcgg gaactggggc tggatcaggc cattgccgaa gcggcggaag ccatccccga   1560
tgcgcgcgat cgtttgtact atgttgtgca gatgaccgcc caggctgcgg agcgggcgct   1620
```

-continued

| | |
|---|---|
| gaacagtgtt gaggcgtcac aaccgcatca ggatcaaatg gagaaatcag caaaagcgtt | 1680 |
| aacccaacgt tgggatgact ggtttgccga tccgattgac cttgccgacg cccgtgaact | 1740 |
| ggtaacagat acacgacaat ttctggcaga tgtacccgcg cataccagct ttactaacgc | 1800 |
| gcaactgctg gaaatcatga tggcgcagga ttttcaggat ctcaccgggc aggtcattaa | 1860 |
| gcggatgatg gatgtcattc aggagatcga acgccagttg ctgatggtgc tgttggaaaa | 1920 |
| catcccggaa caggagtcgc gtccaaaacg tgaaaccag agtttgctta atggacctca | 1980 |
| ggtcgatacc agcaaagccg tgtggtagc cagtcaggat caggtggacg atttgttgga | 2040 |
| tagtcttgga ttttgagaat tcccctgtt ttggcggatg agagaagatt ttcagcctga | 2100 |
| tacagattaa atcagaacgc agaagcggtc tgataaaaca gaatttgcct ggcggcagta | 2160 |
| gcgcggtggt cccacctgac ccatgccga actcagaagt gaaacgccgt agcgccgatg | 2220 |
| gtagtgtggg gtctccccat gcgagagtag ggaactgcca ggcatcaaat aaaacgaaag | 2280 |
| gctcagtcga aagactgggc ctt | 2303 |

<210> SEQ ID NO 135
<211> LENGTH: 2900
<212> TYPE: DNA
<213> ORGANISM: Artificial Sequence
<220> FEATURE:
<223> OTHER INFORMATION: Synthetic

<400> SEQUENCE: 135

| | |
|---|---|
| ctgtttggc ggatgagaga agattttcag cctgatacag attaaatcag aacgcagaag | 60 |
| cggtctgata aacagaatt tgcctggcgg cagtagcgcg gtggtcccac ctgaccccat | 120 |
| gccgaactca gaagtgaaac gccgtagcgc cgatggtagt gtgggtctc ccatgcgag | 180 |
| agtagggaac tgccaggcat caaataaaac gaaaggctca gtcgaaagac tgggcctttc | 240 |
| gttttatctg ttgtttgcgc tagcggatcc tgttttttg atcgttttca caaaatgga | 300 |
| agtccacagt cttgacaggg aaaatgcagc ggcgtagctt ttatgctgta tataaaacca | 360 |
| gtggttatat gtacagtatt tattttaac ttattgtttt aaaagtcaaa gaggatttta | 420 |
| taatgagcac aaaaagaaa ccattaacac aagagcagct tgaggacgca cgtcgcctta | 480 |
| aagcaatta tgaaaaaaag aaaaatgaac ttggcttatc ccaggaatct gtcgcagaca | 540 |
| agatggggat ggggcagtca ggcgttggtg ctttatttaa tggcatcaat gcattaaatg | 600 |
| cttataacgc cgcattgctt gcaaaaattc tcaaagttag cgttgaagaa tttagccctt | 660 |
| caatcgccag agaaatctac gagatgtatg aagcggttag tatgcagccg tcacttagaa | 720 |
| gtgagtatga gtaccctgtt ttttctcatg ttcaggcagg gatgttctca cctgagctta | 780 |
| gaacctttac caaaggtgat gcggagagat gggtaagcac aaccaaaaaa gccagtgatt | 840 |
| ctgcattctg gcttgaggtt gaaggtaatt ccatgaccgc accaacaggc tccaagccaa | 900 |
| gctttcctga cggaatgtta attctcgttg accctgagca ggctgttgag ccaggtgatt | 960 |
| tctgcatagc cagacttggg ggtgatgagt ttaccttcaa gaaactgatc agggatagcg | 1020 |
| gtcaggtgtt tttacaacca ctaaacccac agtacccaat gatcccatgc aatgagagtt | 1080 |
| gttccgttgt ggggaaagtt atcgctagtc agtggcctga agacgtttt ggctaaagat | 1140 |
| ctgcttgatc cggctgctaa caaagcccga aaggaagctg agttggctgc tgccaccgct | 1200 |
| gagcaataac tagcataacc ccttggggcc tctaaacggg tcttgagggg ttttttgctg | 1260 |
| aaaggaggaa ctatatccgg atctggcgta atagcgaaga ggcccgcacc gatcgccctt | 1320 |

```
cccaacagtt ggagctctat ctaacaccgt gcgtgttgac tattttacct ctggcggtga    1380
taatggttgc atgtactaag gaggtactag tatgaagatg ccagaaaaac atgacctgtt    1440
ggccgccatt ctcgcggcaa aggaacaagg catcgggca atccttgcgt ttgcaatggc     1500
gtaccttcgc ggcagatata atggcggtgc gtttacaaaa acagtaatcg acgcaacgat    1560
gtgcgccatt atcgcctggt tcattcgtga ccttctcgac ttcgccggac taagtagcaa    1620
tctcgcttat ataacgagcg tgtttatcgg ctacatcggt actgactcga ttggttcgct    1680
tatcaaacgc ttcgctgcta aaaagccgg agtagaagat ggtagaaatc aataatcaac     1740
gtaaggcgtt cctcgatatg ctggcgtggt cggagggaac tgataacgga cgtcagaaaa    1800
ccagaaatca tggttatgac gtcattgtag gcggagagct atttactgat tactccgatc    1860
accctcgcaa acttgtcacg ctaaacccaa aactcaaatc aacaggcgcc ggacgctacc    1920
agcttctttc ccgttggtgg gatgcctacc gcaagcagct tggcctgaaa gacttctctc    1980
cgaaaagtca ggacgctgtg gcattgcagc agattaagga gcgtggcgct ttacctatga    2040
ttgatcgtgg tgatatccgt caggcaatcg accgttgcag caatatctgg gcttcactgc    2100
cgggcgctgg ttatggtcag ttcgagcata aggctgacag cctgattgca aaattcaaag    2160
aagcgggcgg aacggtcaga gagattgatg tatgagcaga gtcaccgcga ttatctccgc    2220
tctggttatc tgcatcatcg tctgcctgtc atgggctgtt aatcattacc gtgataacgc    2280
cattacctac aaagcccagc gcgacaaaaa tgccagagaa ctgaagctgg cgaacgcggc    2340
aattactgac atgcagatgc gtcagcgtga tgttgctgcg ctcgatgcaa aatacacgaa    2400
ggagttagct gatgctaaag ctgaaaatga tgctctgcgt gatgatgttg ccgctggtcg    2460
tcgtcggttg cacatcaaag cagtctgtca gtcagtgcgt gaagccacca ccgcctccgg    2520
cgtggataat gcagcctccc cccgactggc agacaccgct gaacgggatt atttcaccct    2580
cagagagagg ctgatcacta tgcaaaaaca actggaagga acccagaagt atattaatga    2640
gcagtgcaga taggaattcc ccctgttttg gcggatgaga aagattttc agcctgatac     2700 agattaaatc agaacgcaga agcggtctga taaaacagaa tttgcctggc ggcagtagcg    2760
cggtggtccc acctgacccc atgccgaact cagaagtgaa acgccgtagc gccgatggta    2820
gtgtggggtc tccccatgcg agagtaggga actgccaggc atcaaataaa acgaaaggct    2880
cagtcgaaag actgggcctt                                                2900
```

```
<210> SEQ ID NO 136
<211> LENGTH: 108
<212> TYPE: DNA
<213> ORGANISM: Artificial Sequence
<220> FEATURE:
<223> OTHER INFORMATION: Synthetic

<400> SEQUENCE: 136
gtgcgcggaa ccctatttg tttattttc taaatacatt caaatatgta tccgctcatg     60
agacaataac cctgataaat gcttcaataa tattgaaaaa ggaagcat                 108

<210> SEQ ID NO 137
<211> LENGTH: 115
<212> TYPE: PRT
<213> ORGANISM: Neurospora crassa

<400> SEQUENCE: 137

Cys Ala Leu Ile Leu Cys Asp Leu Lys Gln Lys Asp Thr Pro Ile Val
1               5                   10                  15
```

```
Tyr Ala Ser Glu Ala Phe Leu Tyr Met Thr Gly Tyr Ser Asn Ala Glu
                20                  25                  30

Val Leu Gly Arg Asn Cys Arg Phe Leu Gln Ser Pro Asp Gly Met Val
            35                  40                  45

Lys Pro Lys Ser Thr Arg Lys Tyr Val Asp Ser Asn Thr Ile Asn Thr
 50                  55                  60

Met Arg Lys Ala Ile Asp Arg Asn Ala Glu Val Gln Val Glu Val Val
 65                  70                  75                  80

Asn Phe Lys Lys Asn Gly Gln Arg Phe Val Asn Phe Leu Thr Met Ile
                85                  90                  95

Pro Val Arg Asp Glu Thr Gly Glu Tyr Arg Tyr Ser Met Gly Phe Gln
            100                 105                 110

Cys Glu Thr
    115

<210> SEQ ID NO 138
<211> LENGTH: 116
<212> TYPE: PRT
<213> ORGANISM: Neurospora crassa

<400> SEQUENCE: 138

Cys Ala Phe Val Val Cys Asp Val Thr Leu Asn Asp Cys Pro Ile Ile
 1               5                  10                  15

Tyr Tyr Val Ser Asp Asn Phe Gln Asn Leu Thr Gly Tyr Ser Arg His
                20                  25                  30

Glu Ile Val Gly Arg Asn Cys Arg Phe Leu Gln Ala Pro Asp Gly Asn
            35                  40                  45

Val Glu Ala Gly Thr Lys Arg Glu Phe Val Glu Asn Asn Ala Val Tyr
 50                  55                  60

Thr Leu Lys Lys Thr Ile Ala Glu Gly Gln Ile Gln Gln Ser Leu
 65                  70                  75                  80

Ile Asn Tyr Arg Lys Gly Gly Lys Pro Phe Leu Asn Leu Thr Met
                85                  90                  95

Ile Pro Ile Pro Trp Asp Thr Glu Glu Ile Arg Tyr Phe Ile Gly Phe
            100                 105                 110

Gln Ile Asp Leu
    115

<210> SEQ ID NO 139
<211> LENGTH: 112
<212> TYPE: PRT
<213> ORGANISM: Arabidopsis thaliana

<400> SEQUENCE: 139

Pro Ser Phe Ile Val Ser Asp Ala Leu Glu Pro Asp Phe Leu Ile Tyr
 1               5                  10                  15

Val Asn Arg Val Phe Glu Val Phe Thr Gly Tyr Arg Ala Asp Glu Val
                20                  25                  30

Leu Gly Arg Asn Cys Arg Phe Leu Gln Tyr Arg Asp Pro Arg Ala Gln
            35                  40                  45

Arg Arg His Pro Leu Val Asp Pro Val Val Ser Glu Ile Arg Arg
 50                  55                  60

Cys Leu Glu Glu Gly Ile Glu Phe Gln Gly Glu Leu Leu Asn Phe Arg
 65                  70                  75                  80

Lys Asp Gly Thr Pro Leu Val Asn Arg Leu Arg Leu Ala Pro Ile Arg
                85                  90                  95
```

```
Asp Asp Asp Gly Thr Ile Thr His Val Ile Gly Ile Gln Val Phe Ser
            100                 105                 110
```

<210> SEQ ID NO 140
<211> LENGTH: 104
<212> TYPE: PRT
<213> ORGANISM: Vaucheria frigida

<400> SEQUENCE: 140

```
Gln Asn Phe Val Ile Thr Asp Ala Ser Leu Pro Asp Asn Pro Ile Val
1               5                   10                  15

Tyr Ala Ser Arg Gly His Leu Thr Leu Thr Gly Tyr Ser Leu Asp Gln
            20                  25                  30

Ile Leu Gly Arg Asn Cys Arg Phe Leu Gln Gly Pro Glu Thr Asp Pro
        35                  40                  45

Arg Ala Val Asp Lys Ile Arg Asn Ala Ile Thr Lys Gly Val Asp Thr
    50                  55                  60

Ser Val Cys Leu Leu Asn Tyr Arg Gln Asp Gly Thr Thr Phe Trp Asn
65                  70                  75                  80

Leu Phe Phe Val Ala Gly Leu Arg Asp Ser Lys Gly Asn Ile Val Asn
                85                  90                  95

Tyr Val Gly Val Gln Ser Lys Val
            100
```

<210> SEQ ID NO 141
<211> LENGTH: 104
<212> TYPE: PRT
<213> ORGANISM: Avena sativa

<400> SEQUENCE: 141

```
Gln Thr Phe Val Val Ser Asp Ala Ser Arg Pro Gly His Pro Ile Met
1               5                   10                  15

Tyr Ala Ser Ala Gly Phe Phe Asn Met Thr Gly Tyr Thr Ser Lys Glu
            20                  25                  30

Val Val Gly Arg Asn Cys Arg Phe Leu Gln Gly Ser Gly Thr Asp Pro
        35                  40                  45

Ala Glu Ile Ala Lys Ile Arg Gln Ala Leu Ala Asp Gly Ser Asn Tyr
    50                  55                  60

Cys Gly Arg Val Leu Asn Tyr Lys Lys Asp Gly Thr Ala Phe Trp Asn
65                  70                  75                  80

Leu Leu Thr Ile Ala Pro Ile Lys Asp Glu Glu Gly Arg Val Leu Lys
                85                  90                  95

Phe Ile Gly Met Gln Val Glu Val
            100
```

<210> SEQ ID NO 142
<211> LENGTH: 105
<212> TYPE: PRT
<213> ORGANISM: Avena sativa

<400> SEQUENCE: 142

```
Lys Asn Phe Val Ile Thr Asp Pro Arg Leu Pro Asp Asn Pro Ile Ile
1               5                   10                  15

Phe Ala Ser Asp Ser Phe Leu Gln Leu Thr Glu Tyr Ser Arg Glu
            20                  25                  30

Glu Ile Leu Gly Arg Asn Cys Arg Phe Leu Gln Gly Pro Glu Thr Asp
        35                  40                  45

Arg Ala Thr Val Arg Lys Ile Arg Asp Ala Ile Asp Asn Gln Thr Glu
```

```
            50                  55                  60
Val Thr Val Gln Leu Ile Asn Tyr Thr Lys Ser Gly Lys Lys Phe Trp
 65                  70                  75                  80

Asn Leu Phe His Leu Gln Pro Met Arg Asp Gln Lys Gly Asp Val Gln
                 85                  90                  95

Tyr Phe Ile Gly Val Gln Leu Asp Gly
            100                 105
```

<210> SEQ ID NO 143
<211> LENGTH: 43
<212> TYPE: DNA
<213> ORGANISM: Artificial Sequence
<220> FEATURE:
<223> OTHER INFORMATION: Synthetic

<400> SEQUENCE: 143
taactcacag gggctggatt gattgtgtag gctggagctg ctt             43

<210> SEQ ID NO 144
<211> LENGTH: 42
<212> TYPE: DNA
<213> ORGANISM: Artificial Sequence
<220> FEATURE:
<223> OTHER INFORMATION: Synthetic

<400> SEQUENCE: 144
gatgtactgt acatccatac agtaactcac aggggctgga tt              42

<210> SEQ ID NO 145
<211> LENGTH: 43
<212> TYPE: DNA
<213> ORGANISM: Artificial Sequence
<220> FEATURE:
<223> OTHER INFORMATION: Synthetic

<400> SEQUENCE: 145
ttccaggatt aatcctaaat ttacatggga attagccatg gtc             43

<210> SEQ ID NO 146
<211> LENGTH: 44
<212> TYPE: DNA
<213> ORGANISM: Artificial Sequence
<220> FEATURE:
<223> OTHER INFORMATION: Synthetic

<400> SEQUENCE: 146
cattggctgg gcgacaaaaa aagttccagg attaatccta aatt            44

<210> SEQ ID NO 147
<211> LENGTH: 44
<212> TYPE: DNA
<213> ORGANISM: Artificial Sequence
<220> FEATURE:
<223> OTHER INFORMATION: Synthetic

<400> SEQUENCE: 147
caacaagagg tgtttgatct catcctgagc gattgtgtag gctg            44

<210> SEQ ID NO 148
<211> LENGTH: 37
<212> TYPE: DNA
<213> ORGANISM: Artificial Sequence
<220> FEATURE:
<223> OTHER INFORMATION: Synthetic

<400> SEQUENCE: 148
gaaagcgtta acggccaggc aacaagaggt gtttgat     37

<210> SEQ ID NO 149
<211> LENGTH: 42
<212> TYPE: DNA
<213> ORGANISM: Artificial Sequence
<220> FEATURE:
<223> OTHER INFORMATION: Synthetic

<400> SEQUENCE: 149
acgacaattg gtttaaactc gccatatgaa tatcctcctt ag     42

<210> SEQ ID NO 150
<211> LENGTH: 42
<212> TYPE: DNA
<213> ORGANISM: Artificial Sequence
<220> FEATURE:
<223> OTHER INFORMATION: Synthetic

<400> SEQUENCE: 150
gaagctctgc tgacgaaggt caacgacaat tggtttaaac tc     42

<210> SEQ ID NO 151
<211> LENGTH: 45
<212> TYPE: DNA
<213> ORGANISM: Artificial Sequence
<220> FEATURE:
<223> OTHER INFORMATION: Synthetic

<400> SEQUENCE: 151
ggtcacgcca catcaggcaa tacaaatgag cgattgtgta ggctg     45

<210> SEQ ID NO 152
<211> LENGTH: 45
<212> TYPE: DNA
<213> ORGANISM: Artificial Sequence
<220> FEATURE:
<223> OTHER INFORMATION: Synthetic

<400> SEQUENCE: 152
cttatcagac cgcctgatat gacgtggtca cgccacatca ggcaa     45

<210> SEQ ID NO 153
<211> LENGTH: 44
<212> TYPE: DNA
<213> ORGANISM: Artificial Sequence
<220> FEATURE:
<223> OTHER INFORMATION: Synthetic

<400> SEQUENCE: 153
aactgggcat gtgaggatgc gactcatatg aatatcctcc ttag     44

<210> SEQ ID NO 154
<211> LENGTH: 46
<212> TYPE: DNA
<213> ORGANISM: Artificial Sequence
<220> FEATURE:
<223> OTHER INFORMATION: Synthetic

<400> SEQUENCE: 154
aggaaaaact caacaaaatc tttgagaaac tgggcatgtg aggatg     46

<210> SEQ ID NO 155
<211> LENGTH: 42

```
<212> TYPE: DNA
<213> ORGANISM: Artificial Sequence
<220> FEATURE:
<223> OTHER INFORMATION: Synthetic

<400> SEQUENCE: 155
gtaaccgttt tgacctggta ctgtgagcga ttgtgtaggc tg                        42

<210> SEQ ID NO 156
<211> LENGTH: 40
<212> TYPE: DNA
<213> ORGANISM: Artificial Sequence
<220> FEATURE:
<223> OTHER INFORMATION: Synthetic

<400> SEQUENCE: 156
aggacgctgt agagaaaatt ggtaaccgtt ttgacctggt                           40

<210> SEQ ID NO 157
<211> LENGTH: 43
<212> TYPE: DNA
<213> ORGANISM: Artificial Sequence
<220> FEATURE:
<223> OTHER INFORMATION: Synthetic

<400> SEQUENCE: 157
aattcagcgg cttcctgctc ttgcatatga atatcctcct tag                      43

<210> SEQ ID NO 158
<211> LENGTH: 41
<212> TYPE: DNA
<213> ORGANISM: Artificial Sequence
<220> FEATURE:
<223> OTHER INFORMATION: Synthetic

<400> SEQUENCE: 158
gcaatagcgg taacggcttg taattcagcg gcttcctgct c                         41

<210> SEQ ID NO 159
<211> LENGTH: 31
<212> TYPE: DNA
<213> ORGANISM: Artificial Sequence
<220> FEATURE:
<223> OTHER INFORMATION: Synthetic

<400> SEQUENCE: 159
cccctcgagc tgccaccgct gagcaataac t                                   31

<210> SEQ ID NO 160
<211> LENGTH: 30
<212> TYPE: DNA
<213> ORGANISM: Artificial Sequence
<220> FEATURE:
<223> OTHER INFORMATION: Synthetic

<400> SEQUENCE: 160
cccgaattct cattccgttt cgcactggaa                                     30

<210> SEQ ID NO 161
<211> LENGTH: 32
<212> TYPE: DNA
<213> ORGANISM: Artificial Sequence
<220> FEATURE:
<223> OTHER INFORMATION: Synthetic

<400> SEQUENCE: 161
```
cccgaattcg cgattgtgta ggctggagct gc                                    32

<210> SEQ ID NO 162
<211> LENGTH: 38
<212> TYPE: DNA
<213> ORGANISM: Artificial Sequence
<220> FEATURE:
<223> OTHER INFORMATION: Synthetic

<400> SEQUENCE: 162
cttttgctgt atatactcat gaatatcctc cttagttc                              38

<210> SEQ ID NO 163
<211> LENGTH: 40
<212> TYPE: DNA
<213> ORGANISM: Artificial Sequence
<220> FEATURE:
<223> OTHER INFORMATION: Synthetic

<400> SEQUENCE: 163
gtttatggtt ccaaaatcgc cttttgctgt atatactcat                            40

<210> SEQ ID NO 164
<211> LENGTH: 40
<212> TYPE: DNA
<213> ORGANISM: Artificial Sequence
<220> FEATURE:
<223> OTHER INFORMATION: Synthetic

<400> SEQUENCE: 164
gggctcgagg tttattgtgc agtttatggt tccaaaatcg                            40

<210> SEQ ID NO 165
<211> LENGTH: 43
<212> TYPE: DNA
<213> ORGANISM: Artificial Sequence
<220> FEATURE:
<223> OTHER INFORMATION: Synthetic

<400> SEQUENCE: 165
attggtttaa actcgctatt ttcgtgcgcg gaacccctat ttg                        43

<210> SEQ ID NO 166
<211> LENGTH: 40
<212> TYPE: DNA
<213> ORGANISM: Artificial Sequence
<220> FEATURE:
<223> OTHER INFORMATION: Synthetic

<400> SEQUENCE: 166
ctgctgacga aggtcaacga caattggttt aaactcgcta                            40

<210> SEQ ID NO 167
<211> LENGTH: 25
<212> TYPE: DNA
<213> ORGANISM: Artificial Sequence
<220> FEATURE:
<223> OTHER INFORMATION: Synthetic

<400> SEQUENCE: 167
gaagctctgc tgacgaaggt caacg                                            25

<210> SEQ ID NO 168
<211> LENGTH: 30
<212> TYPE: DNA
<213> ORGANISM: Artificial Sequence
<220> FEATURE:
<223> OTHER INFORMATION: Synthetic

<400> SEQUENCE: 168
gtttattgtg cagtttatgg ttccaaaatc    30

<210> SEQ ID NO 169
<211> LENGTH: 24
<212> TYPE: DNA
<213> ORGANISM: Artificial Sequence
<220> FEATURE:
<223> OTHER INFORMATION: Synthetic

<400> SEQUENCE: 169
cccctcgagc atgaaagcgt taac    24

<210> SEQ ID NO 170
<211> LENGTH: 30
<212> TYPE: DNA
<213> ORGANISM: Artificial Sequence
<220> FEATURE:
<223> OTHER INFORMATION: Synthetic

<400> SEQUENCE: 170
cggttcaccg gcagccacac gacctaccag    30

<210> SEQ ID NO 171
<211> LENGTH: 36
<212> TYPE: DNA
<213> ORGANISM: Artificial Sequence
<220> FEATURE:
<223> OTHER INFORMATION: Synthetic

<400> SEQUENCE: 171
ctgccggtga accgcatacg ctctacgctc ccggcg    36

<210> SEQ ID NO 172
<211> LENGTH: 30
<212> TYPE: DNA
<213> ORGANISM: Artificial Sequence
<220> FEATURE:
<223> OTHER INFORMATION: Synthetic

<400> SEQUENCE: 172
cccgaattct cattccgttt cgcactggaa    30

<210> SEQ ID NO 173
<211> LENGTH: 31
<212> TYPE: DNA
<213> ORGANISM: Artificial Sequence
<220> FEATURE:
<223> OTHER INFORMATION: Synthetic

<400> SEQUENCE: 173
cccgaattcc tgccaccgct gagcaataac t    31

<210> SEQ ID NO 174
<211> LENGTH: 32
<212> TYPE: DNA
<213> ORGANISM: Artificial Sequence
<220> FEATURE:
<223> OTHER INFORMATION: Synthetic

<400> SEQUENCE: 174
gggctcgagc cctggctgtg gtgatgatgg tg    32

<210> SEQ ID NO 175
<211> LENGTH: 30
<212> TYPE: DNA
<213> ORGANISM: Artificial Sequence
<220> FEATURE:
<223> OTHER INFORMATION: Synthetic

<400> SEQUENCE: 175
cggttcaccg gcagccacac gacctaccag 30

<210> SEQ ID NO 176
<211> LENGTH: 30
<212> TYPE: DNA
<213> ORGANISM: Artificial Sequence
<220> FEATURE:
<223> OTHER INFORMATION: Synthetic

<400> SEQUENCE: 176
tgtcgtgggc atacgctcta cgctcccggc 30

<210> SEQ ID NO 177
<211> LENGTH: 27
<212> TYPE: DNA
<213> ORGANISM: Artificial Sequence
<220> FEATURE:
<223> OTHER INFORMATION: SEQ ID NO.

<400> SEQUENCE: 177
gtgtttcata cgctctacgc tcccggc 27

<210> SEQ ID NO 178
<211> LENGTH: 27
<212> TYPE: DNA
<213> ORGANISM: Artificial Sequence
<220> FEATURE:
<223> OTHER INFORMATION: Synthetic

<400> SEQUENCE: 178
tataagcata cgctctacgc tcccggc 27

<210> SEQ ID NO 179
<211> LENGTH: 27
<212> TYPE: DNA
<213> ORGANISM: Artificial Sequence
<220> FEATURE:
<223> OTHER INFORMATION: Synthetic

<400> SEQUENCE: 179
ggatcccata cgctctacgc tcccggc 27

<210> SEQ ID NO 180
<211> LENGTH: 27
<212> TYPE: DNA
<213> ORGANISM: Artificial Sequence
<220> FEATURE:
<223> OTHER INFORMATION: Synthetic

<400> SEQUENCE: 180
gaacctcata cgctctacgc tcccggc 27

<210> SEQ ID NO 181
<211> LENGTH: 39
<212> TYPE: DNA
<213> ORGANISM: Artificial Sequence
<220> FEATURE:
<223> OTHER INFORMATION: Synthetic

<400> SEQUENCE: 181
ctggccgagg ccgctgccca tacgctctac gctcccggc                                   39

<210> SEQ ID NO 182
<211> LENGTH: 45
<212> TYPE: DNA
<213> ORGANISM: Artificial Sequence
<220> FEATURE:
<223> OTHER INFORMATION: Synthetic

<400> SEQUENCE: 182
accgagttcc ccggcgtgga ccagcatacg ctctacgctc ccggc                            45

<210> SEQ ID NO 183
<211> LENGTH: 28
<212> TYPE: DNA
<213> ORGANISM: Artificial Sequence
<220> FEATURE:
<223> OTHER INFORMATION: Synthetic

<400> SEQUENCE: 183
ggctgcaggt gcgcggaacc cctatttg                                               28

<210> SEQ ID NO 184
<211> LENGTH: 31
<212> TYPE: DNA
<213> ORGANISM: Artificial Sequence
<220> FEATURE:
<223> OTHER INFORMATION: Synthetic

<400> SEQUENCE: 184
ggctcgagta ctcatatgct tccttttca a                                            31

<210> SEQ ID NO 185
<211> LENGTH: 28
<212> TYPE: DNA
<213> ORGANISM: Artificial Sequence
<220> FEATURE:
<223> OTHER INFORMATION: Synthetic

<400> SEQUENCE: 185
ggctgcaggt gcgcggaacc cctatttg                                               28

<210> SEQ ID NO 186
<211> LENGTH: 31
<212> TYPE: DNA
<213> ORGANISM: Artificial Sequence
<220> FEATURE:
<223> OTHER INFORMATION: Synthetic

<400> SEQUENCE: 186
ggctcgagta ctcatatgct tccttttca a                                            31

<210> SEQ ID NO 187
<211> LENGTH: 26
<212> TYPE: DNA
<213> ORGANISM: Artificial Sequence
<220> FEATURE:
<223> OTHER INFORMATION: Synthetic

<400> SEQUENCE: 187
gattccatat gaaagcgtta acggcc                                                 26

<210> SEQ ID NO 188

<211> LENGTH: 30
<212> TYPE: DNA
<213> ORGANISM: Artificial Sequence
<220> FEATURE:
<223> OTHER INFORMATION: Synthetic

<400> SEQUENCE: 188
cccctcgagt cattccgttt cgcactggaa                                    30

<210> SEQ ID NO 189
<211> LENGTH: 25
<212> TYPE: DNA
<213> ORGANISM: Artificial Sequence
<220> FEATURE:
<223> OTHER INFORMATION: Synthetic

<400> SEQUENCE: 189
gctctgattc tgtgcgacct gaagc                                         25

<210> SEQ ID NO 190
<211> LENGTH: 27
<212> TYPE: DNA
<213> ORGANISM: Artificial Sequence
<220> FEATURE:
<223> OTHER INFORMATION: Synthetic

<400> SEQUENCE: 190
gcatgacgtg tcaacaggtc ccagttc                                       27

<210> SEQ ID NO 191
<211> LENGTH: 25
<212> TYPE: DNA
<213> ORGANISM: Artificial Sequence
<220> FEATURE:
<223> OTHER INFORMATION: Synthetic

<400> SEQUENCE: 191
gaggccaaac ccccaagtag aactg                                         25

<210> SEQ ID NO 192
<211> LENGTH: 26
<212> TYPE: DNA
<213> ORGANISM: Artificial Sequence
<220> FEATURE:
<223> OTHER INFORMATION: Synthetic

<400> SEQUENCE: 192
ttcataatct gaatcagata gcccat                                        26

<210> SEQ ID NO 193
<211> LENGTH: 24
<212> TYPE: DNA
<213> ORGANISM: Artificial Sequence
<220> FEATURE:
<223> OTHER INFORMATION: Synthetic

<400> SEQUENCE: 193
gctgattcag attatgaaca ggcc                                          24

<210> SEQ ID NO 194
<211> LENGTH: 26
<212> TYPE: DNA
<213> ORGANISM: Artificial Sequence
<220> FEATURE:
<223> OTHER INFORMATION: Synthetic

<400> SEQUENCE: 194

```
cagcccataa tgtcataacc gccggg                                          26

<210> SEQ ID NO 195
<211> LENGTH: 29
<212> TYPE: DNA
<213> ORGANISM: Artificial Sequence
<220> FEATURE:
<223> OTHER INFORMATION: Synthetic

<400> SEQUENCE: 195
gctgattcag attatgaaga ggccaaacc                                       29

<210> SEQ ID NO 196
<211> LENGTH: 28
<212> TYPE: DNA
<213> ORGANISM: Artificial Sequence
<220> FEATURE:
<223> OTHER INFORMATION: Synthetic

<400> SEQUENCE: 196
cagcccataa tgtcataacc gccgggag                                        28

<210> SEQ ID NO 197
<211> LENGTH: 26
<212> TYPE: DNA
<213> ORGANISM: Artificial Sequence
<220> FEATURE:
<223> OTHER INFORMATION: Synthetic

<400> SEQUENCE: 197
tcccagatta tgaacaggcc aaaccc                                          26

<210> SEQ ID NO 198
<211> LENGTH: 25
<212> TYPE: DNA
<213> ORGANISM: Artificial Sequence
<220> FEATURE:
<223> OTHER INFORMATION: Synthetic

<400> SEQUENCE: 198
cagatagccc ataatgtcat aaccg                                           25

<210> SEQ ID NO 199
<211> LENGTH: 26
<212> TYPE: DNA
<213> ORGANISM: Artificial Sequence
<220> FEATURE:
<223> OTHER INFORMATION: Synthetic

<400> SEQUENCE: 199
gcgcagatta tgaacaggcc aaaccc                                          26

<210> SEQ ID NO 200
<211> LENGTH: 25
<212> TYPE: DNA
<213> ORGANISM: Artificial Sequence
<220> FEATURE:
<223> OTHER INFORMATION: Synthetic

<400> SEQUENCE: 200
cagatagccc ataatgtcat aaccg                                           25

<210> SEQ ID NO 201
<211> LENGTH: 26
<212> TYPE: DNA
```

<213> ORGANISM: Artificial Sequence
<220> FEATURE:
<223> OTHER INFORMATION: Synthetic

<400> SEQUENCE: 201
gccaaacccc caagtagaac tgggac                                         26

<210> SEQ ID NO 202
<211> LENGTH: 25
<212> TYPE: DNA
<213> ORGANISM: Artificial Sequence
<220> FEATURE:
<223> OTHER INFORMATION: Synthetic

<400> SEQUENCE: 202
ctgcgcataa tctgaatcag atagc                                          25

<210> SEQ ID NO 203
<211> LENGTH: 40
<212> TYPE: DNA
<213> ORGANISM: Artificial Sequence
<220> FEATURE:
<223> OTHER INFORMATION: Synthetic

<400> SEQUENCE: 203
gctgccggtg aaccgtcctt cttggctact acacttgaac                          40

<210> SEQ ID NO 204
<211> LENGTH: 32
<212> TYPE: DNA
<213> ORGANISM: Artificial Sequence
<220> FEATURE:
<223> OTHER INFORMATION: Synthetic

<400> SEQUENCE: 204
acgggctcga gaataagttc ttttgccgcc tc                                  32

<210> SEQ ID NO 205
<211> LENGTH: 26
<212> TYPE: DNA
<213> ORGANISM: Artificial Sequence
<220> FEATURE:
<223> OTHER INFORMATION: Synthetic

<400> SEQUENCE: 205
gattccatat gaaagcgtta acggcc                                         26

<210> SEQ ID NO 206
<211> LENGTH: 29
<212> TYPE: DNA
<213> ORGANISM: Artificial Sequence
<220> FEATURE:
<223> OTHER INFORMATION: Synthetic

<400> SEQUENCE: 206
atcggttcac cggcagccac acgacctac                                      29

<210> SEQ ID NO 207
<211> LENGTH: 40
<212> TYPE: DNA
<213> ORGANISM: Artificial Sequence
<220> FEATURE:
<223> OTHER INFORMATION: Synthetic

<400> SEQUENCE: 207
gctgccggtg aaccgtcctt cttggctact acacttgaac                          40

<210> SEQ ID NO 208
<211> LENGTH: 32
<212> TYPE: DNA
<213> ORGANISM: Artificial Sequence
<220> FEATURE:
<223> OTHER INFORMATION: Synthetic

<400> SEQUENCE: 208
ctactacaca cacgaagttc ttttgccgcc tc                                32

<210> SEQ ID NO 209
<211> LENGTH: 27
<212> TYPE: DNA
<213> ORGANISM: Artificial Sequence
<220> FEATURE:
<223> OTHER INFORMATION: Synthetic

<400> SEQUENCE: 209
ggcgcatatg tctaccaaga agaaacc                                     27

<210> SEQ ID NO 210
<211> LENGTH: 29
<212> TYPE: DNA
<213> ORGANISM: Artificial Sequence
<220> FEATURE:
<223> OTHER INFORMATION: Synthetic

<400> SEQUENCE: 210
cccggatcca tattctgacc tcaaagacg                                   29

<210> SEQ ID NO 211
<211> LENGTH: 28
<212> TYPE: DNA
<213> ORGANISM: Artificial Sequence
<220> FEATURE:
<223> OTHER INFORMATION: Synthetic

<400> SEQUENCE: 211
ggcgcatatg aaaccagtaa cgttatac                                    28

<210> SEQ ID NO 212
<211> LENGTH: 28
<212> TYPE: DNA
<213> ORGANISM: Artificial Sequence
<220> FEATURE:
<223> OTHER INFORMATION: Synthetic

<400> SEQUENCE: 212
cccggatccc aacgactgtt tgcccgcc                                    28

<210> SEQ ID NO 213
<211> LENGTH: 25
<212> TYPE: DNA
<213> ORGANISM: Artificial Sequence
<220> FEATURE:
<223> OTHER INFORMATION: Synthetic

<400> SEQUENCE: 213
cgtttccaac gtggtgaacc aggcc                                       25

<210> SEQ ID NO 214
<211> LENGTH: 25
<212> TYPE: DNA
<213> ORGANISM: Artificial Sequence
<220> FEATURE:

```
<223> OTHER INFORMATION: Synthetic

<400> SEQUENCE: 214
cgtttccaac gtggtgaacc aggcc                                          25

<210> SEQ ID NO 215
<211> LENGTH: 28
<212> TYPE: DNA
<213> ORGANISM: Artificial Sequence
<220> FEATURE:
<223> OTHER INFORMATION: Synthetic

<400> SEQUENCE: 215
ggcgcatatg aagctactgt cttctatc                                       28

<210> SEQ ID NO 216
<211> LENGTH: 29
<212> TYPE: DNA
<213> ORGANISM: Artificial Sequence
<220> FEATURE:
<223> OTHER INFORMATION: Synthetic

<400> SEQUENCE: 216
cccggatcct tccagtcttt ctagccttg                                      29

<210> SEQ ID NO 217
<211> LENGTH: 27
<212> TYPE: DNA
<213> ORGANISM: Artificial Sequence
<220> FEATURE:
<223> OTHER INFORMATION: Synthetic

<400> SEQUENCE: 217
ggcgcatatg tctaggctag ataagag                                        27

<210> SEQ ID NO 218
<211> LENGTH: 28
<212> TYPE: DNA
<213> ORGANISM: Artificial Sequence
<220> FEATURE:
<223> OTHER INFORMATION: Synthetic

<400> SEQUENCE: 218
cccggatccg tgtctatcca gcatctcg                                       28

<210> SEQ ID NO 219
<211> LENGTH: 26
<212> TYPE: DNA
<213> ORGANISM: Artificial Sequence
<220> FEATURE:
<223> OTHER INFORMATION: Synthetic

<400> SEQUENCE: 219
gcggcatatg gcacgcgtaa ctgttc                                         26

<210> SEQ ID NO 220
<211> LENGTH: 37
<212> TYPE: DNA
<213> ORGANISM: Artificial Sequence
<220> FEATURE:
<223> OTHER INFORMATION: Synthetic

<400> SEQUENCE: 220
tccttgtagt ccgcggccgc acgaccttca gcaatag                             37
```

```
<210> SEQ ID NO 221
<211> LENGTH: 59
<212> TYPE: DNA
<213> ORGANISM: Artificial Sequence
<220> FEATURE:
<223> OTHER INFORMATION: Synthetic

<400> SEQUENCE: 221
catggggggg tgtcttggaa ccggtccgga acttgtcgtc gtcatccttg tagtccgcg        59

<210> SEQ ID NO 222
<211> LENGTH: 38
<212> TYPE: DNA
<213> ORGANISM: Artificial Sequence
<220> FEATURE:
<223> OTHER INFORMATION: Synthetic

<400> SEQUENCE: 222
cgttaacgct ttcatactag tgtgggggg tgtcttgg                                38

<210> SEQ ID NO 223
<211> LENGTH: 25
<212> TYPE: DNA
<213> ORGANISM: Artificial Sequence
<220> FEATURE:
<223> OTHER INFORMATION: Synthetic

<400> SEQUENCE: 223
atgaaagcgt taacggccag gcaac                                             25

<210> SEQ ID NO 224
<211> LENGTH: 30
<212> TYPE: DNA
<213> ORGANISM: Artificial Sequence
<220> FEATURE:
<223> OTHER INFORMATION: Synthetic

<400> SEQUENCE: 224
cccgaattct cattccgttt cgcactggaa                                        30

<210> SEQ ID NO 225
<211> LENGTH: 29
<212> TYPE: DNA
<213> ORGANISM: Artificial Sequence
<220> FEATURE:
<223> OTHER INFORMATION: Synthetic

<400> SEQUENCE: 225
gggactagta tgagcacaaa aaagaaacc                                         29

<210> SEQ ID NO 226
<211> LENGTH: 27
<212> TYPE: DNA
<213> ORGANISM: Artificial Sequence
<220> FEATURE:
<223> OTHER INFORMATION: Synthetic

<400> SEQUENCE: 226
gggactagta tgaaaccagt aacgtta                                           27

<210> SEQ ID NO 227
<211> LENGTH: 30
<212> TYPE: DNA
<213> ORGANISM: Artificial Sequence
<220> FEATURE:
<223> OTHER INFORMATION: Synthetic
```

<400> SEQUENCE: 227
cccactagta tgaagctact gtcttctatc                                      30

<210> SEQ ID NO 228
<211> LENGTH: 30
<212> TYPE: DNA
<213> ORGANISM: Artificial Sequence
<220> FEATURE:
<223> OTHER INFORMATION: Synthetic

<400> SEQUENCE: 228
cccactagta tgtctaggct agataagagc                                      30

<210> SEQ ID NO 229
<211> LENGTH: 26
<212> TYPE: DNA
<213> ORGANISM: Artificial Sequence
<220> FEATURE:
<223> OTHER INFORMATION: Synthetic

<400> SEQUENCE: 229
gattccatat gaaagcgtta acggcc                                          26

<210> SEQ ID NO 230
<211> LENGTH: 43
<212> TYPE: DNA
<213> ORGANISM: Artificial Sequence
<220> FEATURE:
<223> OTHER INFORMATION: Synthetic

<400> SEQUENCE: 230
ccttgtagtc cgcggccgca ctagtttccg tttcgcactg gaa                       43

<210> SEQ ID NO 231
<211> LENGTH: 31
<212> TYPE: DNA
<213> ORGANISM: Artificial Sequence
<220> FEATURE:
<223> OTHER INFORMATION: Synthetic

<400> SEQUENCE: 231
cctgcatggt accgtggggg ggtgtcttgg a                                    31

<210> SEQ ID NO 232
<211> LENGTH: 30
<212> TYPE: DNA
<213> ORGANISM: Artificial Sequence
<220> FEATURE:
<223> OTHER INFORMATION: Synthetic

<400> SEQUENCE: 232
catggtacca tgcagggttc tgtgacagag                                      30

<210> SEQ ID NO 233
<211> LENGTH: 31
<212> TYPE: DNA
<213> ORGANISM: Artificial Sequence
<220> FEATURE:
<223> OTHER INFORMATION: Synthetic

<400> SEQUENCE: 233
gccctcgagt tactctggtt tctcttcttt c                                    31

<210> SEQ ID NO 234
<211> LENGTH: 26

```
<212> TYPE: DNA
<213> ORGANISM: Artificial Sequence
<220> FEATURE:
<223> OTHER INFORMATION: Synthetic

<400> SEQUENCE: 234
gggcatatga gcacaaaaaa gaaacc                                           26

<210> SEQ ID NO 235
<211> LENGTH: 24
<212> TYPE: DNA
<213> ORGANISM: Artificial Sequence
<220> FEATURE:
<223> OTHER INFORMATION: Synthetic

<400> SEQUENCE: 235
gggcatatga aaccagtaac gtta                                             24

<210> SEQ ID NO 236
<211> LENGTH: 27
<212> TYPE: DNA
<213> ORGANISM: Artificial Sequence
<220> FEATURE:
<223> OTHER INFORMATION: Synthetic

<400> SEQUENCE: 236
ccccatatga agctactgtc ttctatc                                          27

<210> SEQ ID NO 237
<211> LENGTH: 27
<212> TYPE: DNA
<213> ORGANISM: Artificial Sequence
<220> FEATURE:
<223> OTHER INFORMATION: Synthetic

<400> SEQUENCE: 237
ccccatatgt ctaggctaga taagagc                                          27

<210> SEQ ID NO 238
<211> LENGTH: 58
<212> TYPE: DNA
<213> ORGANISM: Artificial Sequence
<220> FEATURE:
<223> OTHER INFORMATION: Synthetic

<400> SEQUENCE: 238
gatcgttttc acaaaaatgg aagtccacag tcttgacagg gaaaatgcag cggcgtag        58

<210> SEQ ID NO 239
<211> LENGTH: 35
<212> TYPE: DNA
<213> ORGANISM: Artificial Sequence
<220> FEATURE:
<223> OTHER INFORMATION: Synthetic

<400> SEQUENCE: 239
ggggatcctg ttttttttgat cgttttcaca aaaat                                35

<210> SEQ ID NO 240
<211> LENGTH: 59
<212> TYPE: DNA
<213> ORGANISM: Artificial Sequence
<220> FEATURE:
<223> OTHER INFORMATION: Synthetic

<400> SEQUENCE: 240
```
tataaaatcc tctttgactt ttaaaacaat aagttaaaaa taaatactgt acatataac        59

<210> SEQ ID NO 241
<211> LENGTH: 34
<212> TYPE: DNA
<213> ORGANISM: Artificial Sequence
<220> FEATURE:
<223> OTHER INFORMATION: Synthetic

<400> SEQUENCE: 241
cgcccttgct caccattata aaatcctctt tgac        34

<210> SEQ ID NO 242
<211> LENGTH: 34
<212> TYPE: DNA
<213> ORGANISM: Artificial Sequence
<220> FEATURE:
<223> OTHER INFORMATION: Synthetic

<400> SEQUENCE: 242
cgcccttgct caccattata aaatcctctt tgac        34

<210> SEQ ID NO 243
<211> LENGTH: 26
<212> TYPE: DNA
<213> ORGANISM: Artificial Sequence
<220> FEATURE:
<223> OTHER INFORMATION: Synthetic

<400> SEQUENCE: 243
atggtgagca agggcgagga gctgtt        26

<210> SEQ ID NO 244
<211> LENGTH: 30
<212> TYPE: DNA
<213> ORGANISM: Artificial Sequence
<220> FEATURE:
<223> OTHER INFORMATION: Synthetic

<400> SEQUENCE: 244
ggggaattct tacttgtaca gctcgtccat        30

<210> SEQ ID NO 245
<211> LENGTH: 35
<212> TYPE: DNA
<213> ORGANISM: Artificial Sequence
<220> FEATURE:
<223> OTHER INFORMATION: Synthetic

<400> SEQUENCE: 245
caagtaagaa ttccccctgt tttggcggat gagag        35

<210> SEQ ID NO 246
<211> LENGTH: 35
<212> TYPE: DNA
<213> ORGANISM: Artificial Sequence
<220> FEATURE:
<223> OTHER INFORMATION: Synthetic

<400> SEQUENCE: 246
caagtaagaa ttccccctgt tttggcggat gagag        35

<210> SEQ ID NO 247
<211> LENGTH: 29
<212> TYPE: DNA
<213> ORGANISM: Artificial Sequence

```
<220> FEATURE:
<223> OTHER INFORMATION: Synthetic

<400> SEQUENCE: 247
gacctcgagc gcagcctgaa tggcgaatg                                29

<210> SEQ ID NO 248
<211> LENGTH: 27
<212> TYPE: DNA
<213> ORGANISM: Artificial Sequence
<220> FEATURE:
<223> OTHER INFORMATION: Synthetic

<400> SEQUENCE: 248
cgggatccat ttcgcgggat cgagatc                                  27

<210> SEQ ID NO 249
<211> LENGTH: 29
<212> TYPE: DNA
<213> ORGANISM: Artificial Sequence
<220> FEATURE:
<223> OTHER INFORMATION: Synthetic

<400> SEQUENCE: 249
cccgctagcg gatccatagg gttgatctt                                29

<210> SEQ ID NO 250
<211> LENGTH: 26
<212> TYPE: DNA
<213> ORGANISM: Artificial Sequence
<220> FEATURE:
<223> OTHER INFORMATION: Synthetic

<400> SEQUENCE: 250
gggggtacca tttcgcggga tcgaga                                   26

<210> SEQ ID NO 251
<211> LENGTH: 31
<212> TYPE: DNA
<213> ORGANISM: Artificial Sequence
<220> FEATURE:
<223> OTHER INFORMATION: Synthetic

<400> SEQUENCE: 251
cccggtaccc ccctgttttg gcggatgaga g                             31

<210> SEQ ID NO 252
<211> LENGTH: 31
<212> TYPE: DNA
<213> ORGANISM: Artificial Sequence
<220> FEATURE:
<223> OTHER INFORMATION: Synthetic

<400> SEQUENCE: 252
cccgctagcg caaacaacag ataaaacgaa a                             31

<210> SEQ ID NO 253
<211> LENGTH: 31
<212> TYPE: DNA
<213> ORGANISM: Artificial Sequence
<220> FEATURE:
<223> OTHER INFORMATION: Synthetic

<400> SEQUENCE: 253
cccaagctta tggtcgtttt acaacgtcgt g                             31
```

<210> SEQ ID NO 254
<211> LENGTH: 31
<212> TYPE: DNA
<213> ORGANISM: Artificial Sequence
<220> FEATURE:
<223> OTHER INFORMATION: Synthetic

<400> SEQUENCE: 254
cctagatctt tattttttgac accagaccaa c                              31

<210> SEQ ID NO 255
<211> LENGTH: 34
<212> TYPE: DNA
<213> ORGANISM: Artificial Sequence
<220> FEATURE:
<223> OTHER INFORMATION: Synthetic

<400> SEQUENCE: 255
cccagatctc ccctgttttg gcggatgaga gaag                            34

<210> SEQ ID NO 256
<211> LENGTH: 33
<212> TYPE: DNA
<213> ORGANISM: Artificial Sequence
<220> FEATURE:
<223> OTHER INFORMATION: Synthetic

<400> SEQUENCE: 256
cccaagctta tcctctttga cttttaaaac aat                             33

<210> SEQ ID NO 257
<211> LENGTH: 28
<212> TYPE: DNA
<213> ORGANISM: Artificial Sequence
<220> FEATURE:
<223> OTHER INFORMATION: Synthetic

<400> SEQUENCE: 257
cccggatcca tagggttgat ctttgttg                                   28

<210> SEQ ID NO 258
<211> LENGTH: 34
<212> TYPE: DNA
<213> ORGANISM: Artificial Sequence
<220> FEATURE:
<223> OTHER INFORMATION: Synthetic

<400> SEQUENCE: 258
gcccttgctc accataatca atccagcccc tgtg                            34

<210> SEQ ID NO 259
<211> LENGTH: 34
<212> TYPE: DNA
<213> ORGANISM: Artificial Sequence
<220> FEATURE:
<223> OTHER INFORMATION: Synthetic

<400> SEQUENCE: 259
cccggatccc aatttctaca aaacacttga tact                            34

<210> SEQ ID NO 260
<211> LENGTH: 37
<212> TYPE: DNA
<213> ORGANISM: Artificial Sequence
<220> FEATURE:
<223> OTHER INFORMATION: Synthetic

```
<400> SEQUENCE: 260
cgcccttgct caccattttt actcctgtca tgccggg                              37

<210> SEQ ID NO 261
<211> LENGTH: 30
<212> TYPE: DNA
<213> ORGANISM: Artificial Sequence
<220> FEATURE:
<223> OTHER INFORMATION: Synthetic

<400> SEQUENCE: 261
cccggatccg cctatgcagc gacaaatatt                                      30

<210> SEQ ID NO 262
<211> LENGTH: 37
<212> TYPE: DNA
<213> ORGANISM: Artificial Sequence
<220> FEATURE:
<223> OTHER INFORMATION: Synthetic

<400> SEQUENCE: 262
cgcccttgct caccataata atctgcctga agttata                              37

<210> SEQ ID NO 263
<211> LENGTH: 36
<212> TYPE: DNA
<213> ORGANISM: Artificial Sequence
<220> FEATURE:
<223> OTHER INFORMATION: Synthetic

<400> SEQUENCE: 263
tatctaacac cgtgcgtgtt gactatttta cctctg                               36

<210> SEQ ID NO 264
<211> LENGTH: 27
<212> TYPE: DNA
<213> ORGANISM: Artificial Sequence
<220> FEATURE:
<223> OTHER INFORMATION: Synthetic

<400> SEQUENCE: 264
cccggatcct atctaacacc gtgcgtg                                         27

<210> SEQ ID NO 265
<211> LENGTH: 32
<212> TYPE: DNA
<213> ORGANISM: Artificial Sequence
<220> FEATURE:
<223> OTHER INFORMATION: Synthetic

<400> SEQUENCE: 265
gcaaccatta tcaccgccag aggtaaaata gt                                   32

<210> SEQ ID NO 266
<211> LENGTH: 34
<212> TYPE: DNA
<213> ORGANISM: Artificial Sequence
<220> FEATURE:
<223> OTHER INFORMATION: Synthetic

<400> SEQUENCE: 266
agtacctcct tagtacatgc aaccattatc accg                                 34

<210> SEQ ID NO 267
```

```
<211> LENGTH: 34
<212> TYPE: DNA
<213> ORGANISM: Artificial Sequence
<220> FEATURE:
<223> OTHER INFORMATION: Synthetic

<400> SEQUENCE: 267
gcccttgctc accatactag tacctcctta gtac                              34

<210> SEQ ID NO 268
<211> LENGTH: 27
<212> TYPE: DNA
<213> ORGANISM: Artificial Sequence
<220> FEATURE:
<223> OTHER INFORMATION: Synthetic

<400> SEQUENCE: 268
atggtgagca agggcgagga gctgttc                                      27

<210> SEQ ID NO 269
<211> LENGTH: 30
<212> TYPE: DNA
<213> ORGANISM: Artificial Sequence
<220> FEATURE:
<223> OTHER INFORMATION: Synthetic

<400> SEQUENCE: 269
ggggaattct tacttgtaca gctcgtccat                                   30

<210> SEQ ID NO 270
<211> LENGTH: 30
<212> TYPE: DNA
<213> ORGANISM: Artificial Sequence
<220> FEATURE:
<223> OTHER INFORMATION: Synthetic

<400> SEQUENCE: 270
cccggatccg gaaattaata cgactcacta                                   30

<210> SEQ ID NO 271
<211> LENGTH: 29
<212> TYPE: DNA
<213> ORGANISM: Artificial Sequence
<220> FEATURE:
<223> OTHER INFORMATION: Synthetic

<400> SEQUENCE: 271
gggactagtt ctccttatta agttaaac                                     29

<210> SEQ ID NO 272
<211> LENGTH: 31
<212> TYPE: DNA
<213> ORGANISM: Artificial Sequence
<220> FEATURE:
<223> OTHER INFORMATION: Synthetic

<400> SEQUENCE: 272
ctaaaaattc ccctgtagaa ataattttgt t                                 31

<210> SEQ ID NO 273
<211> LENGTH: 32
<212> TYPE: DNA
<213> ORGANISM: Artificial Sequence
<220> FEATURE:
<223> OTHER INFORMATION: Synthetic

<400> SEQUENCE: 273
```
cgctaaaaat tccctatag tgagtcgtat ta                                  32

<210> SEQ ID NO 274
<211> LENGTH: 29
<212> TYPE: DNA
<213> ORGANISM: Artificial Sequence
<220> FEATURE:
<223> OTHER INFORMATION: Synthetic

<400> SEQUENCE: 274
gtcctccgcc cctgtagaaa taattttgt                                     29

<210> SEQ ID NO 275
<211> LENGTH: 31
<212> TYPE: DNA
<213> ORGANISM: Artificial Sequence
<220> FEATURE:
<223> OTHER INFORMATION: Synthetic

<400> SEQUENCE: 275
agtactccgc ccctatagtg agtcgtatta a                                  31

<210> SEQ ID NO 276
<211> LENGTH: 29
<212> TYPE: DNA
<213> ORGANISM: Artificial Sequence
<220> FEATURE:
<223> OTHER INFORMATION: Synthetic

<400> SEQUENCE: 276
tgatagagac ccctgtagaa ataattttg                                     29

<210> SEQ ID NO 277
<211> LENGTH: 32
<212> TYPE: DNA
<213> ORGANISM: Artificial Sequence
<220> FEATURE:
<223> OTHER INFORMATION: Synthetic

<400> SEQUENCE: 277
ctgataggga cccctatagt gagtcgtatt aa                                 32

<210> SEQ ID NO 278
<211> LENGTH: 60
<212> TYPE: DNA
<213> ORGANISM: Artificial Sequence
<220> FEATURE:
<223> OTHER INFORMATION: Synthetic

<400> SEQUENCE: 278
aggcaccccg ggctttacac tttatgcttc cggctcgtat gttgtgtcga ccgagcggat   60

<210> SEQ ID NO 279
<211> LENGTH: 31
<212> TYPE: DNA
<213> ORGANISM: Artificial Sequence
<220> FEATURE:
<223> OTHER INFORMATION: Synthetic

<400> SEQUENCE: 279
ccggatccca ttaggcaccc cgggctttac a                                  31

<210> SEQ ID NO 280
<211> LENGTH: 43
<212> TYPE: DNA

<213> ORGANISM: Artificial Sequence
<220> FEATURE:
<223> OTHER INFORMATION: Synthetic

<400> SEQUENCE: 280
ccccaagctt ttcctgtgtg aaagtcttat ccgctcggtc gac         43

<210> SEQ ID NO 281
<211> LENGTH: 30
<212> TYPE: DNA
<213> ORGANISM: Artificial Sequence
<220> FEATURE:
<223> OTHER INFORMATION: Synthetic

<400> SEQUENCE: 281
cccaagctta tggtgagcaa gggcgaggag         30

<210> SEQ ID NO 282
<211> LENGTH: 33
<212> TYPE: DNA
<213> ORGANISM: Artificial Sequence
<220> FEATURE:
<223> OTHER INFORMATION: Synthetic

<400> SEQUENCE: 282
acaggatccg ctagcgcaaa caacagataa aac         33

<210> SEQ ID NO 283
<211> LENGTH: 36
<212> TYPE: DNA
<213> ORGANISM: Artificial Sequence
<220> FEATURE:
<223> OTHER INFORMATION: Synthetic

<400> SEQUENCE: 283
gttatatgta cagtaccatt aggcaccccg ggcttt         36

<210> SEQ ID NO 284
<211> LENGTH: 38
<212> TYPE: DNA
<213> ORGANISM: Artificial Sequence
<220> FEATURE:
<223> OTHER INFORMATION: Synthetic

<400> SEQUENCE: 284
cactggtttt atatacaggg atccgctagc gcaaacaa         38

<210> SEQ ID NO 285
<211> LENGTH: 45
<212> TYPE: DNA
<213> ORGANISM: Artificial Sequence
<220> FEATURE:
<223> OTHER INFORMATION: Synthetic

<400> SEQUENCE: 285
tattttacct ctggcggtga taatgcatta ggcaccccgg gcttt         45

<210> SEQ ID NO 286
<211> LENGTH: 43
<212> TYPE: DNA
<213> ORGANISM: Artificial Sequence
<220> FEATURE:
<223> OTHER INFORMATION: Synthetic

<400> SEQUENCE: 286
gtcaacacgc acggtgttag ataggatccg ctagcgcaaa caa         43

<210> SEQ ID NO 287
<211> LENGTH: 30
<212> TYPE: DNA
<213> ORGANISM: Artificial Sequence
<220> FEATURE:
<223> OTHER INFORMATION: Synthetic

<400> SEQUENCE: 287
gctcacaatt cattaggcac cccgggcttt                                    30

<210> SEQ ID NO 288
<211> LENGTH: 30
<212> TYPE: DNA
<213> ORGANISM: Artificial Sequence
<220> FEATURE:
<223> OTHER INFORMATION: Synthetic

<400> SEQUENCE: 288
gctcacaatt ggatccgcta gcgcaaacaa                                    30

<210> SEQ ID NO 289
<211> LENGTH: 37
<212> TYPE: DNA
<213> ORGANISM: Artificial Sequence
<220> FEATURE:
<223> OTHER INFORMATION: Synthetic

<400> SEQUENCE: 289
cggagtactg tcctccgcat taggcacccc gggcttt                            37

<210> SEQ ID NO 290
<211> LENGTH: 39
<212> TYPE: DNA
<213> ORGANISM: Artificial Sequence
<220> FEATURE:
<223> OTHER INFORMATION: Synthetic

<400> SEQUENCE: 290
ctcggaggac agtactccgg gatccgctag cgcaaacaa                          39

<210> SEQ ID NO 291
<211> LENGTH: 40
<212> TYPE: DNA
<213> ORGANISM: Artificial Sequence
<220> FEATURE:
<223> OTHER INFORMATION: Synthetic

<400> SEQUENCE: 291
ctccctatca gtgatagaga cattaggcac cccgggcttt                         40

<210> SEQ ID NO 292
<211> LENGTH: 40
<212> TYPE: DNA
<213> ORGANISM: Artificial Sequence
<220> FEATURE:
<223> OTHER INFORMATION: Synthetic

<400> SEQUENCE: 292
ctctctatca ctgataggga ggatccgcta gcgcaaacaa                         40

<210> SEQ ID NO 293
<211> LENGTH: 31
<212> TYPE: DNA
<213> ORGANISM: Artificial Sequence
<220> FEATURE:

<223> OTHER INFORMATION: Synthetic

<400> SEQUENCE: 293
cccggtaccc ccctgttttg gcggatgaga g                               31

<210> SEQ ID NO 294
<211> LENGTH: 30
<212> TYPE: DNA
<213> ORGANISM: Artificial Sequence
<220> FEATURE:
<223> OTHER INFORMATION: Synthetic

<400> SEQUENCE: 294
gggagatctt tacttgtaca gctcgtccat                                 30

<210> SEQ ID NO 295
<211> LENGTH: 35
<212> TYPE: DNA
<213> ORGANISM: Artificial Sequence
<220> FEATURE:
<223> OTHER INFORMATION: Synthetic

<400> SEQUENCE: 295
cgaagcttga agatctgctt gatccggctg caaac                           35

<210> SEQ ID NO 296
<211> LENGTH: 26
<212> TYPE: DNA
<213> ORGANISM: Artificial Sequence
<220> FEATURE:
<223> OTHER INFORMATION: Synthetic

<400> SEQUENCE: 296
gggggtacca tttcgcggga tcgaga                                     26

<210> SEQ ID NO 297
<211> LENGTH: 35
<212> TYPE: DNA
<213> ORGANISM: Artificial Sequence
<220> FEATURE:
<223> OTHER INFORMATION: Synthetic

<400> SEQUENCE: 297
ggggatcctg ttttttgat cgttttcaca aaaat                            35

<210> SEQ ID NO 298
<211> LENGTH: 25
<212> TYPE: DNA
<213> ORGANISM: Artificial Sequence
<220> FEATURE:
<223> OTHER INFORMATION: Synthetic

<400> SEQUENCE: 298
tataaaatcc tctttgactt ttaaa                                      25

<210> SEQ ID NO 299
<211> LENGTH: 35
<212> TYPE: DNA
<213> ORGANISM: Artificial Sequence
<220> FEATURE:
<223> OTHER INFORMATION: Synthetic

<400> SEQUENCE: 299
aaagaggatt ttataatgag cacaaaaaag aaacc                           35

```
<210> SEQ ID NO 300
<211> LENGTH: 30
<212> TYPE: DNA
<213> ORGANISM: Artificial Sequence
<220> FEATURE:
<223> OTHER INFORMATION: Synthetic

<400> SEQUENCE: 300
gggagatctt tagccaaacg tctcttcagg                                       30

<210> SEQ ID NO 301
<211> LENGTH: 36
<212> TYPE: DNA
<213> ORGANISM: Artificial Sequence
<220> FEATURE:
<223> OTHER INFORMATION: Synthetic

<400> SEQUENCE: 301
tatctaacac cgtgcgtgtt gactatttta cctctg                                36

<210> SEQ ID NO 302
<211> LENGTH: 27
<212> TYPE: DNA
<213> ORGANISM: Artificial Sequence
<220> FEATURE:
<223> OTHER INFORMATION: Synthetic

<400> SEQUENCE: 302
cccgagctct atctaacacc gtgcgtg                                          27

<210> SEQ ID NO 303
<211> LENGTH: 32
<212> TYPE: DNA
<213> ORGANISM: Artificial Sequence
<220> FEATURE:
<223> OTHER INFORMATION: Synthetic

<400> SEQUENCE: 303
gcaaccatta tcaccgccag aggtaaaata gt                                    32

<210> SEQ ID NO 304
<211> LENGTH: 34
<212> TYPE: DNA
<213> ORGANISM: Artificial Sequence
<220> FEATURE:
<223> OTHER INFORMATION: Synthetic

<400> SEQUENCE: 304
agtacctcct tagtacatgc aaccattatc accg                                  34

<210> SEQ ID NO 305
<211> LENGTH: 34
<212> TYPE: DNA
<213> ORGANISM: Artificial Sequence
<220> FEATURE:
<223> OTHER INFORMATION: Synthetic

<400> SEQUENCE: 305
gcccttgctc accatactag tacctcctta gtac                                  34

<210> SEQ ID NO 306
<211> LENGTH: 27
<212> TYPE: DNA
<213> ORGANISM: Artificial Sequence
<220> FEATURE:
<223> OTHER INFORMATION: Synthetic
```

<400> SEQUENCE: 306
atggtgagca agggcgagga gctgttc                                      27

<210> SEQ ID NO 307
<211> LENGTH: 30
<212> TYPE: DNA
<213> ORGANISM: Artificial Sequence
<220> FEATURE:
<223> OTHER INFORMATION: Synthetic

<400> SEQUENCE: 307
ggggaattct tacttgtaca gctcgtccat                                   30

<210> SEQ ID NO 308
<211> LENGTH: 35
<212> TYPE: DNA
<213> ORGANISM: Artificial Sequence
<220> FEATURE:
<223> OTHER INFORMATION: Synthetic

<400> SEQUENCE: 308
caagtaagaa ttcccccctgt tttggcggat gagag                            35

<210> SEQ ID NO 309
<211> LENGTH: 32
<212> TYPE: DNA
<213> ORGANISM: Artificial Sequence
<220> FEATURE:
<223> OTHER INFORMATION: Synthetic

<400> SEQUENCE: 309
gggctcgagc aaacaacaga taaaacgaaa gg                                32

<210> SEQ ID NO 310
<211> LENGTH: 29
<212> TYPE: DNA
<213> ORGANISM: Artificial Sequence
<220> FEATURE:
<223> OTHER INFORMATION: Synthetic

<400> SEQUENCE: 310
gacctcgagc gcagcctgaa tggcgaatg                                    29

<210> SEQ ID NO 311
<211> LENGTH: 30
<212> TYPE: DNA
<213> ORGANISM: Artificial Sequence
<220> FEATURE:
<223> OTHER INFORMATION: Synthetic

<400> SEQUENCE: 311
caggagctcc aactgttggg aagggcgatc                                   30

<210> SEQ ID NO 312
<211> LENGTH: 34
<212> TYPE: DNA
<213> ORGANISM: Artificial Sequence
<220> FEATURE:
<223> OTHER INFORMATION: Synthetic

<400> SEQUENCE: 312
cccactagta tgatgcaacc atcaatcaaa cctg                              34

<210> SEQ ID NO 313
<211> LENGTH: 30

```
<212> TYPE: DNA
<213> ORGANISM: Artificial Sequence
<220> FEATURE:
<223> OTHER INFORMATION: Synthetic

<400> SEQUENCE: 313
ggggaattct caaaatccaa gactatccaa                                    30

<210> SEQ ID NO 314
<211> LENGTH: 34
<212> TYPE: DNA
<213> ORGANISM: Artificial Sequence
<220> FEATURE:
<223> OTHER INFORMATION: Synthetic

<400> SEQUENCE: 314
cccactagta tgaagatgcc agaaaaacat gacc                               34

<210> SEQ ID NO 315
<211> LENGTH: 31
<212> TYPE: DNA
<213> ORGANISM: Artificial Sequence
<220> FEATURE:
<223> OTHER INFORMATION: Synthetic

<400> SEQUENCE: 315
cccgaattct aggcatttat actccgctgg a                                  31

<210> SEQ ID NO 316
<211> LENGTH: 29
<212> TYPE: DNA
<213> ORGANISM: Artificial Sequence
<220> FEATURE:
<223> OTHER INFORMATION: Synthetic

<400> SEQUENCE: 316
cccactagta tgttcaatga attaaatgc                                     29

<210> SEQ ID NO 317
<211> LENGTH: 28
<212> TYPE: DNA
<213> ORGANISM: Artificial Sequence
<220> FEATURE:
<223> OTHER INFORMATION: Synthetic

<400> SEQUENCE: 317
cccgaattct tataaccttt tcccgtac                                      28

<210> SEQ ID NO 318
<211> LENGTH: 29
<212> TYPE: DNA
<213> ORGANISM: Artificial Sequence
<220> FEATURE:
<223> OTHER INFORMATION: Synthetic

<400> SEQUENCE: 318
cccgagctcg tgcgcggaac ccctatttg                                     29

<210> SEQ ID NO 319
<211> LENGTH: 30
<212> TYPE: DNA
<213> ORGANISM: Artificial Sequence
<220> FEATURE:
<223> OTHER INFORMATION: Synthetic

<400> SEQUENCE: 319
```

```
cccgaattct cattccgttt cgcactggaa                              30

<210> SEQ ID NO 320
<211> LENGTH: 31
<212> TYPE: DNA
<213> ORGANISM: Artificial Sequence
<220> FEATURE:
<223> OTHER INFORMATION: Synthetic

<400> SEQUENCE: 320
cccctcgagc tgccaccgct gagcaataac t                            31

<210> SEQ ID NO 321
<211> LENGTH: 30
<212> TYPE: DNA
<213> ORGANISM: Artificial Sequence
<220> FEATURE:
<223> OTHER INFORMATION: Synthetic

<400> SEQUENCE: 321
gccggtaccg agcgtcgaga tcccggacac                              30

<210> SEQ ID NO 322
<211> LENGTH: 33
<212> TYPE: DNA
<213> ORGANISM: Artificial Sequence
<220> FEATURE:
<223> OTHER INFORMATION: Synthetic

<400> SEQUENCE: 322
agggagacga ttttgatgaa accagtaacg tta                          33

<210> SEQ ID NO 323
<211> LENGTH: 36
<212> TYPE: DNA
<213> ORGANISM: Artificial Sequence
<220> FEATURE:
<223> OTHER INFORMATION: Synthetic

<400> SEQUENCE: 323
ttaattgcgt tgcgctcatt ccgtttcgca ctggaa                       36

<210> SEQ ID NO 324
<211> LENGTH: 30
<212> TYPE: DNA
<213> ORGANISM: Artificial Sequence
<220> FEATURE:
<223> OTHER INFORMATION: Synthetic

<400> SEQUENCE: 324
caaaatcgtc tccctccgtt tgaatatttg                              30

<210> SEQ ID NO 325
<211> LENGTH: 29
<212> TYPE: DNA
<213> ORGANISM: Artificial Sequence
<220> FEATURE:
<223> OTHER INFORMATION: Synthetic

<400> SEQUENCE: 325
gcgcaacgca attaatgtga gttaaggcc                               29

<210> SEQ ID NO 326
<211> LENGTH: 29
<212> TYPE: DNA
<213> ORGANISM: Artificial Sequence
```

```
<220> FEATURE:
<223> OTHER INFORMATION: Synthetic

<400> SEQUENCE: 326
cccggatcca tggtgagcaa gggcgagga                                          29

<210> SEQ ID NO 327
<211> LENGTH: 30
<212> TYPE: DNA
<213> ORGANISM: Artificial Sequence
<220> FEATURE:
<223> OTHER INFORMATION: Synthetic

<400> SEQUENCE: 327
gggtctagat tacttgtaca gctcgtccat                                         30
```

LIGHT-SWITCHABLE GENE EXPRESSION SYSTEM AND THE METHODS FOR CONTROLLING GENE EXPRESSION IN PROKARYOTIC BACTERIUM

FIELD OF INVENTION

The invention relates to the fields of genetic engineering and synthetic biology, especially, relates to gene expression, and more especially, relates to an inducible gene expression system based on light-switchable proteins and a method of regulating the gene expression in prokaryotic bacterium by using this expression system.

BACKGROUND OF INVENTION

In the field of genetic engineering, precise controlling gene expression plays an important role in studying gene function and life processes of living organisms. Gene expression system in prokaryotic bacterium is much simpler relative to the complex gene expression system in eukaryotic cells. Take the most widely used prokaryotic bacterium $E.\ coli$ for example, the first step is the transcription of DNA into RNA by RNA polymerase. The RNA polymerase of $E.\ coli$ consists of five subunits; its molecular weight is about 480 Kd, it contains $\alpha$, $\beta$, $\beta'$, $\sigma$ four different polypeptides, there are two molecular of $\alpha$ polypeptide, so the holoenzyme is $\alpha_2\beta\beta'$ $\sigma$. $\alpha$ subunit is linked with the formation of tetramer core enzyme ($\alpha_2\beta\beta'$) of RNA polymerase; $\beta$ subunit contains the binding site of nucleoside triphosphate; $\beta'$ subunit has the binding site of DNA template; $\sigma$ is only linked with the initiation of RNA transcription and is not unrelated to the elongation of chain. Once transcription initiates, $\sigma$ is released and the elongation of chain is catalyzed by tetramer core enzyme. So the function of $\sigma$ is recognition of the transcriptional initiation signal and enabling binding of RNA polymerase to the promoter region. The initiation signal in DNA, also as "initiation sequence", is termed as promoter. The promoter of $E.\ coli$ consists of $-10$ region and $-35$ region, $-10$ region locates at 10 bp upstream of the transcriptional start point and contains the conserved sequence of six bases TATATA which is the tight binding site of RNA polymerase. Another conserved sequence of six bases TTGACA is located at 35 bp upstream of the transcriptional start point, $-35$ region provides the recognition signal of RNA polymerase; the promoter activity of $E.\ coli$ depends on the base contents of $-10$ and $-35$ regions and space length between $-10$ and $-35$ regions. Although the core enzyme can bind to the DNA, it mainly results from the non-specific electrostatic attraction between basic protein and acidic nucleic acid, the DNA is still double helix, $\sigma$ subunit can alter the affinity of RNA polymerase and DNA and significantly increase the binding constant and residence time of the enzyme and promoter. The core enzyme contacts with DNA with the help of $\sigma$ subunit and forms non-specific complex, such complex is not stable and the enzyme can slide along with the DNA chain. The holoenzyme rapidly recognizes the promoter with the help of $\sigma$ subunit and binds to it to form relaxed closed promoter complex. The RNA polymerase binds to DNA surface and the recognition is located at the $-35$ region of promoter. Then the conformation of DNA changes to form the open promoter complex, at this time, the enzyme binds tightly to the promoter, untwists the double strands of DNA at $-10$ region and recognizes the template strand. It is easy to untwist the DNA strands due to the region containing rich A-T base. Once the formation of open complex, DNA continues to be untwisted and the enzyme moves to the transcription start point. $Bacillus$ is another widely used prokaryotic bacteria and is gram-positive bacterium. Somewhat differently, $Bacillus$ contains many kinds of RNA polymerases and $\sigma$ which recognize different promoter sequences.

The gene expression systems of prokaryotic bacteria can be divided into two types, the first is constitutive expression which enables the independent continuous expression of target gene without induction. The other is inducible gene expression system which can be divided into small chemical induced gene expression system and physical methods induced gene expression system according to the inducers. For the small chemical induced gene expression system, IPTG is the mostly used inducer. IPTG is the analogue of lactose and has extremely strong induction ability, it is very stable and cannot be metabolized by bacteria. The inducer of current most widely used expression vectors containing T7 promoter, lac promoter, Tac promoter and grac promoter is IPTG. Expression systems using arabinose and tryptophan as the inducers have been used more and more, arabinose and tryptophan have the advantages of no toxicity and tight regulation. The discovery of $Mn^{2+}$, $Fe^{2+}$, $Cu^+$ et al metal ions sensing proteins attracts peoples' eyes to use the metal ions binding proteins to induce protein expression. Using the changes of temperature to induce gene expression is widely used in physical methods induced gene expression system, such as the temperature sensitive mutant of lad which repress the promoter activity at 30° C. and loose its activity and cannot repress the promoter activity at 42° C. Ultraviolet (UV)-regulated "cage" (Caged) technology [Keyes, W M and A A Mills, Trends Biotechnology, 2003, 21 (2): 53-55][1] is another widely used physical methods inducible gene expression system.

Although many of those methods have been widely used, there exist some potential problems: (1) some inducers have great toxicity and are expensive (IPTG), it is not suitable to expression recombinant proteins for gene therapy; (2) in metal ions inducible gene expression systems, the recognition of metal ion sensing proteins to metal ions lacks specificity, different metal ions of the same family or the same period can be recognized by the same sensing protein to activate the transcription, so the transcription can be interfered many metal ions in the internal environment of prokaryotic bacteria cells. Additionally, the low valence metal ions can be oxidized by the oxidizing environment of prokaryotic bacteria cells, resulting in interference of transcriptional activation by the metal ions that need strict oxidizing environment; (3) In the temperature inducible gene expression systems, the increase of external temperature can activate the heat shock proteins of $E.\ coli$ to affect the stability of products, some proteins are difficult to fold correctly, the UV-induced cage technology may cause irreversible damage to cells; (4) the most importantly, chemical inducers only can temporally regulate gene expression, but cannot spatially regulate the gene expression in specific cells and tissues.

Nevertheless, light is easy to be spatiotemporally manipulated, has no toxicity to cells and is easy to obtain. In recent years, light-regulated proteins (also known as photosensitive protein) was found in the biological clock systems of some organisms, its functions can be significantly affected by light illumination. We aimed to engineer the natural existing transcription factor to obtain artificial light-sensitive transcription factor based on molecular design, and in turn construct light-switchable gene expression system in prokaryotic bacterium. However, studies on light-regulated transcription factors have been rarely reported, there are only two systems. Anselm Levskaya et al. reported a light regulated protein expression system based on the phytochrome Cph1 and EnvZ/OmpR two-component of *E. coli* in 2005 [Levskaya, A. et al, Nature, 2005. 438(7067): p. 441-2.][2]. In the dark conditions, the light-switchable transcription factor autophosphorylated and bond to OmpR dependent ompC promoter, and then initiated the transcription and expression of target gene. Upon red light illumination, the autophosphorylation of light-switchable transcription factor was inhibited and could not bind to ompC promoter, so the transcription and expression of target gene could not be activated. In the following years, this light regulated protein expression system was modified by the same group to obtain multi-color co-regulated protein expression systems [Tabor, J. J. et al., J Mol Biol, 2011. 405(2): p. 315-24, Tabor, J. J. et al., Cell, 2009. 137(7): p. 1272-81.][3, 4]. Keith Moffat group developed another novel light-switchable transcription factor YF1 which was based on blue light sensitive protein YtvA from *Bacillus subtilis* and FixL protein from *Bradyrhizobium japonicum* [Moglich, A. et al., J Mol Biol, 2009. 385(5): p. 1433-44, Ohlendorf, R. et al., J Mol Biol, 2012. 416, 534-542.][5, 6]. Gene expression from the light regulated gene expression system based on YF1 was repressed upon blue light illumination, and high gene expression occurred without blue light. However, both of the two systems had marked limitations. In addition to the light-switchable transcription factor and reporter system, the first system is very complex, it is necessary to introduce ho1 and pcyA genes into cells to obtain the required phycocyanobilin from haem, which significantly increases the work of system construction. The second system has high leak expression even upon blue light illumination and has only dozens of the induction ratio, so it is difficult to precisely control gene expression. The above described disadvantages limit the use of these two systems in prokaryotic bacterium. Until now, except for the used photosensitive proteins Cph1 and YtvA, there are some other known photosensitive proteins: the photosensitive proteins using flavin as the chromophore (also called flavin-containing protein family blue light receptor), which can be divided into three groups: first is photoreceptors with light-oxygen-voltage (LOV) domain, such as phytochrome; the second is photolyase-like cryptochromes; the third is blue light using FAD (BLUF) family that is found in recent years.

Phytochrome is the most common photoreceptor containing LOV domain, such as phototropin 1, white collar-1 (WC-1), white collar-2 (WC-2), photoactive yellow protein (PYP), Phy3, VVD, etc. Phytochrome is usually a membrane-coupled kinase which can autophosphorylate and alters its activity to regulate specific physiological processes upon blue light exposure. Most phytochromes have Serine/Threonine kinase domain at the C-terminal and two LOV domains with flavin at the N-terminal. With the illumination of blue light, the LOV domain and flavin bind covalently to form a cysteinyl-flavin adduct which can cause the conformation change of flavin-binding pocket and then enable the kinase domain at the C-terminal to alter the kinase activity. This process is reversible. The most successful light regulated gene expression system in eukaryotic cells is based on photosensitive protein VIVID. Yang's group [Wang, X. et al., Nat Methods, 2012. p. 266-269.][7] developed a eukaryotic light-switchable gene expression system based on the formation of homodimer of blue light sensitive protein VIVID from *Neurospora crassa* after blue light illumination. In this system, light-switchable transcription factor consists of three or four polypeptides, the ability of dimerization of the recombinant light-switchable transcription factor changed after blue light illumination, the dimerized transcription factor bond to the reaction element of the target transcription unit nucleotide sequence, to regulate (initiate/repress) the transcription and expression of the target gene via the synergistic effect on the promoter in the target transcription unit by the transcriptional activation/repression domain of the third polypeptide in this fusion protein and other transcriptional co-factors derived from the recruitment host cells. This system is considered as the best gene expression system of eukaryotic cells due to the following advantages: simplicity, fast induction kinetics, high induction ratio, good reversibility and high spatiotemporal resolution. However, it is a pity that the transcription and translation mechanism of prokaryotic bacteria differs from that of eukaryotic cells, so this system cannot be used in prokaryotic bacteria. Masayuki Yazaw et al. [Yazawa, M. et al., Nat Biotechnol, 2009. 27(10): p. 941-5] also developed a eukaryotic light regulated gene expression system based on the interaction of FKF1 (flavin-binding, kelch repeat, f box 1) and GI (GIGANTEA) from *Arabidopsis thaliana* upon blue light illumination, but its application was limited for the low induction ratio and complexity of the system.

Cryptochromes from *Arabidopsis thaliana* are the first separated blue light photosensitive plant proteins, of which some have been well studied, such as cryptochrome1 (CRY1), cryptochrome 2 (CRY2), phytochrome A (phyA) and phytochrome B (phyB), their functions were regulated by the light of circadian rhythm to control growth and movement of plants. The amino acid sequences and fluorophore of cryptochromes are the similar to photofragmentation proteins, the molecular weight of most cryptochromes is about 70 kD-80 kD, it contains conservative PHR domain (relevant to photofragmentation enzyne) at the N terminal and unknown domain with great differences in length at the C terminal, the PHR domain can non-covalently bind to flavin. Based on the interaction of *Arabidopsis* CRY2 and CIB1 (CRY-interacting bHLH1) protein upon blue light illumination, people developed a light regulated gene expression system in eukaryotic cells [Kennedy, M. J. et al, Nat Methods, 2010. 7(12): p. 973-5.][8].

Difference between blue light photoreceptor proteins with BLUF domain and photoreceptor proteins with LOV domain is that no adduct is generated between BLUF and flavin after light irradiation, but it will lead to 10 nm red-shift absorbance due to the comformation change of chromophore. The most well studied BLUF domain containing photoreceptor is AppA, which is a repressor of anti-transcription from *Rhodobacter sphaeroides*. AppA and transcription factor PpsR combine to form AppA-PpsR2 complex and enable PpsR not to bind with DNA in darkness; bright blue light irradiation may enable AppA to dissociate from the complex, and the released PpsR forms a tetramer and bind to a specific DNA sequence to repress the gene transcription [Pandey, R. et al, FEBS J, 2012.][9].

Haifeng Ye et al. [Ye, H. et al, Science, 2011. 332(6037): p. 1565-8.][10] developed a blue light activated light induced gene expression system of eukaryotic cells based on melanopsin and intracellular signaling. Melanopsin is a photosensitive protein of certain retinal cells. Upon blue light illumination, melanopsin rapidly triggers the influx of $Ca^{2+}$ into cells, after a series of cascade, calmodulin activates the serine/threonine phosphatase calcineurin, which dephosphorylates the transcription factor NFAT, the dephosphorylated transcription factor NFAT enters into nucleus and bind to the NFAT-dependent promoter to activate transcription and translation of target genes. The drawback of this system is that it is involved in intracellular signaling, resulting in poor stability and interrupting normal life activities by affecting cell signaling.

In relative to eukaryotic cells, prokaryotic bacteria have advantages of fast proliferation, low costs and high expression of foreign proteins (even can reach 90% of the total proteins), enabling it more suitable for large scale production of interested proteins. As described above, the most widely used gene expression systems today utilize chemical substances as the inducers, which have reasonable desirable induction performance, low leakage expression and high expression levels. However, many of gene expression systems have side-effect and potential toxicity due to their pleiotropic effect. Besides, the chemical inducers cannot precisely control gene expression at high spatial resolution. Up to now, there are only a few of gene expression systems controlled by physical methods, raise of temperature results in side-effect. Few photosensitive protein based gene expression systems have been developed, but the complexity and low induction ratio may limit their wide application.

In summary, it is considered that a more excellent gene expression system of prokaryotic bacteria can be created to overcome the shortcomings of previous studies and it can be widely used in biomedical researches. After painstaking studies, the inventers have created a novel light-switchable gene expression system in prokaryotic bacterium. It has an excellent capacity to control the gene expression and it can spatiotemporally regulate the gene expression.

Accordingly, the first object of the invention is to provide a novel light-switchable gene expression system of prokaryotic bacterium.

The second object of the invention is to provide a method of the regulation of gene expression by using said light-switchable gene expression system in prokaryotic bacterium.

The third object of the invention is to provide a prokaryotic expression vector containing said light-switchable gene expression system.

The fourth object of the invention is to provide a method of the regulation of life processes (such as bacteria mobility, lysis) of prokaryotic bacterium.

The fifth object of the invention is to provide a kit comprising a prokaryotic expression vector containing said light controllable gene expression system or a prokaryotic bacterium strain containing a light-switchable transcription factor in its genome.

SUMMARY OF INVENTION

The invention relates to a light-switchable gene expression system of prokaryotic bacterium, comprising two parts: a) a gene encoding a recombinant light-switchable transcription factor, said recombinant light-switchable transcription factor is one fusion protein including the first polypeptide as DNA-binding domain and the second polypeptide as light-switchable domain; b) a target transcription unit, including promoter or promoter-reaction element or reaction element-promoter containing at least one reaction element, recognized/bound by the first polypeptide, and the nucleic acid sequence to be transcribed.

In the light-switchable gene expression system according to the invention, the recombinant light-switchable transcription factor is a recombinant light-switchable DNA-binding protein. The capacity of the light-switchable DNA-binding protein binding to the reaction element is significantly changed before and after illumination, resulting in the direct repression or initiation of the transcription and translation of genes.

The first polypeptide in the recombinant light-switchable transcription factor is a DNA-binding domain which is able to specifically recognize the reaction element, but unable to bind the reaction element or only have a weak binding affinity. The binding to the reaction element needs the assistance of the second polypeptide. The first polypeptide and the second polypeptide can be linked each other directly or operatively.

The first polypeptide can be selected from the helix-turn-helix DNA-binding domain, zinc finger motif or zinc cluster DNA-binding domain, leucine zipper DNA-binding domain, winged helix DNA-binding domain, winged helix-turn-helix DNA-binding domain, helix-loop-helix DNA-binding domain, high mobility family DNA-binding domain and B3 DNA-binding domain. The second polypeptide is a light-switchable domain usually derived from the class of the photosensitive proteins containing flavin chromophore. The first polypeptide and the second polypeptide can be linked directly or operatively via a linker peptide. The amino acid number of the linker peptide is variable (such as 0-10 or more).

The first polypeptide can be further selected from DNA binding domain of *E. coli* LexA protein, DNA binding domain of λ phage cI repression protein, DNA binding domain of LacI repression protein, DNA binding domain of yeast Gal4 protein, and DNA binding domain of tetracycline combination protein TetR, and their truncated mutants and/or mutants containing 80%-99% homologous amino acid sequence.

The second polypeptide is selected from the photosensitive domains of the photosensitive proteins containing flavin chromophore and photosensitive domains of the photosensitive proteins containing LOV-domain.

The second polypeptide can be further selected from LOV domain of *Neurospora crassa* VIVID, AsLOV2 domain of oat phytochrome gene 1, AuLOV domain in aureochrome1 of *Stramenopile algae Vaucheria frigida*, LOV domain of PpSB1-LOV in *Pseudomonas putida*, and their truncated mutants or those mutants containing 15%-99% identical or 36%-99% similar amino acid sequence.

In the light-switchable gene expression system according to the invention, the promoter-the nucleic acid sequence to be transcribed, or the promoter-the reaction element-the nucleic acid sequence to be transcribed, or the reaction element-the promoter element-the nucleic acid sequence to be transcribed in target transcription unit can be linked each other directly or operatively.

The reaction element is a DNA motif which can be specifically recognized and bound by the first polypeptide. The reaction element is selected from LexA binding element, cI binding element, LacI binding element, Gal4 binding element and TetR binding element.

The promoter is selected from colE promoter, sulA promoter, recA promoter, umuDC promoter and lac minimal promoter of *E. coli*, T7 promoter of T7 phage and grac promoter of *Bacillus subtilis*.

In the light-switchable gene expression system according to the invention, the recombinant light-switchable transcription factor can also contain additional peptides, such as the third polypeptide that can recruit other components of RNA polymerase. The first polypeptide, second polypeptide and third polypeptide can be linked each other directly or operatively. The third peptide is selected from *E. coli* ω protein, α protein, and their mutants containing 36%-99% homologous amino acid sequence.

The invention also relates to a prokaryotic expression vector containing the light-switchable gene expression system according to the invention. The prokaryotic expression vector can only contain the gene encoding the recombinant light-switchable transcriptional factor, or only contain the target transcription unit. The target transcription unit contains a promoter but leaving a vacancy for the nucleic acid sequence to be transcribed, or a promoter-a reaction element but leaving a vacancy for the nucleic acid sequence to be transcribed, or a reaction element-a promoter but leaving a vacancy for the nucleic acid sequence to be transcribed. The prokaryotic expression vector can also contain both the gene encoding the recombinant light-switchable transcriptional factor and the target transcription unit.

The gene encoding said recombinant light-switchable transcription factor in expression vector has a nucleotide sequence selected from SEQ. ID. NO: 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 109.

The invention also relates to a prokaryotic bacteria strain whose genome is integrated with the recombinant light-switchable transcription factor in the light-switchable gene expression system according to the invention.

The invention also relates to a method for the regulation of gene expression in prokaryotic cells by using the light-switchable gene expression system according the invention, comprising the following steps:

a) constructing the light-switchable gene expression system in a prokaryotic plasmid expression vector;

b) introducing the construct into the prokaryotic cells containing said gene being regulated; and c) inducing the prokaryotic cells via illumination to express said gene being regulated.

In the above method, the illumination comprises the selection and the control of light sources. The light sources include, but are not limited to, LED lamp, incandescent lamp, fluorescent lamp and laser; and the illumination method includes the selection of the quantity, time, intensity and frequency of the illumination. The spatial expression control of the target gene, using scan, projection, optical molds, etc., also falls into the range of the invention.

The invention also relates to methods for the regulation of prokaryotic bacterium life processes by using said light-switchable gene expression system, such as mobility, lysis etc.

The invention further relates to a kit containing the prokaryotic bacteria (such as *E. coli*) expression vector comprising the light-switchable gene expression system or the prokaryotic bacterium strain integration of the frame of light-switchable transcription factor in said light-switchable gene expression system, as well as the directions. The kit can also contain the prokaryotic expression vector comprising the target transcription unit composed of the target transcription factor but leaving a vacancy for the nucleic acid sequence to be transcribed.

DETAILED DESCRIPTION OF INVENTION

The invention provides a photosensitive polypeptide-based light-switchable gene expression system useful for the regulation of target gene expression with high spatiotemporal resolution in prokaryotic cells. The light-switchable gene expression system of the invention relates to at least two portions. The first portion is a nucleotide sequence (encoding the recombinant light-switchable transcription factor fusion protein) being able to express in the prokaryotic cells. This fusion protein is composed of two polypeptides, wherein the first polypeptide is its DNA-binding domain; the second polypeptide is a light-switchable domain. The second portion is a nucleotide sequence of the target transcription unit composed of promoter and the nucleic acid sequence to be transcribed, or promoter-reaction element and the nucleic acid sequence to be transcribed, or reaction element-promoter element and the nucleic acid sequence to be transcribed, wherein the reaction element is a DNA nucleotide motif recognized/bound by the first polypeptide in the above-mentioned recombinant light-switchable transcription factor fusion protein; The first polypeptide and second polypeptide in the first portion is preferred to be a truncated functional active fragment (i.e. Domain) of the proteins involved. The first and second portions of the light-switchable gene expression system can be constructed in one or two prokaryotic expression vectors, respectively.

These two portions will be transformed into prokaryotic cells by using different conventional methods, or the first portion will be integrated into genome of prokaryotic cells by using conventional knock-out methods, to express the recombinant light-switchable transcription factor fusion protein. The illumination of appropriate wavelength light can result in the change of dimerization ability of the light-switchable second polypeptide, then the change of dimerization ability of the whole recombinant light-switchable transcription factor. The dimerized transcription factor can bind to the reaction element in the second portion, i.e., target transcription unit nucleotide sequence, to directly repress the transcription and expression of the target gene via preventing the binding of RNA polymerase to promoter region, or to activate the transcription and expression of the target gene via recruit other components of RNA polymerase to promoter region.

The light-switchable gene expression system of the invention can utilize the illumination which is hardly damaging cells or the body, to regulate the target gene expression in prokaryotic host cells at high spatiotemporal resolution.

The light-switchable gene expression system can utilize different light sources and illumination conditions to regulate the target gene expression in prokaryotic host cells.

The light-switchable gene expression system can regulate the life processes of prokaryotic bacterium via inducing expression of certain proteins, such as mobility and lysis. The used light is cheap, easy to be obtained and non-toxic to cells.

Definition and Explanation of Terms Used Herein

"host cell" refers to the prokaryotic cells in the invention, it can be original prokaryotic cells without modifications, it also can be commercial prokaryotic cells whose genome have been modified, such as the widely used BL21, JM109 (DE3), DH5α, *Bacillus subtilis* WB800, it also can be the prokaryotic cells whose genome have been modified from commercial strains, such as the *E. coli* strain JM109(DE3, sulA⁻,LexA⁻) whose sulA gene and LexA gene in the genome have been deleted, it also can be the prokaryotic cells whose genome has been integrated with the said light-switchable transcription factor.

"Target protein" is also known as "interested protein" and refers to any useful protein, for example, useful prokaryotic protein, including natural or artificial modification or mutation proteins in need of expression in *E. coli* host cells for the preventive or therapeutic or other purposes.

"Report protein", one of target proteins, refers to a useful protein which expression is easy to be detected. In order to facilitate the detection for effect of the inventive photosensitive polypeptide-based light-switchable target gene expression system, the known widely used report proteins can be selected as following: firefly luciferase (Fluc), green fluorescent protein (GFP), chloramphenicol acetyltransferase (CAT), β-galactosidase (LacZ), etc. However, the light-switchable target protein gene expression system is not limited to express a report protein, but may be used for the expression of any useful target protein.

"Gene of a target protein", "encoding nucleotide sequence of a target protein", "nucleotide sequence encoding target protein" and its abbreviation "target gene", as used herein, have the same meaning. They can be used interchangeably and refer to the gene encoding target protein, generally double-strands DNA sequence. This gene can be contained in the chromosomal DNA sequence of the host cells or in artificial expression vectors, such as the target transcription unit sequence of the invention. Similarly, "report gene" means a gene encoding a report protein.

"Transcription" as used herein specifically refers to a process wherein a target gene is transcribed by RNA polymerase to produce RNA carrying this gene information in the prokaryotic host cells.

"Expression", "gene expression of a target protein" and "gene expression", as used herein, have the same meaning. They can be used interchangeably and refer to both a target gene DNA sequence being transcribed to RNA (mRNA or antisense RNA) carrying this gene information and the information carried by this RNA being translated to produce the target protein, that is, both the messenger RNA production via transcription and the target protein production via translation are called as expression. As herein, these two meanings are included, mainly referring to produce the target protein.

"Transcription regulation" as used herein specifically refers to regulation of gene transcription in prokaryotic cells.

"Transcription factor" and "transcription factor fusion protein" as herein have the same meaning. They can be used interchangeably, and refer to the prokaryote transcription factor. It is usually a protein. It may be natural or artificially modified or fused proteins composed of the polypeptide able to recognize/bind to the reaction element nucleotide sequence in the target transcription unit and the polypeptide able to the gene transcription via itself or via recruiting other components of RNA polymerase. Depending on the different composition, the transcription factors can be divided into "transcriptional activation factor" and "transcriptional repression factor".

"Target transcription unit" refers to a artificial DNA sequence composed of a promoter containing reaction element and a nucleic acid sequence to be transcribed (not a protein), wherein the reaction element is located in the promoter or upstream of –35 region or downstream of –10 region; and the nucleic acid sequence to be transcribed is located downstream of the promoter. The reaction element, promoter and nucleic acid sequence to be transcribed can be connected directly or operatively, i.e., separated by several nucleotides.

"Reaction element" refers to one or more cis-DNA motifs recognized/bound specifically by a transcription factor. Different transcription factors have their corresponding different reaction elements; and the binding domain contained in the transcription factor can bind to this DNA motif. When a transcription factor has bound specifically to its corresponding reaction element, promoter activities are repressed or activated by the transcription factor itself or via recruiting other components. According to the invention, the reaction refers to a DNA motif able to be recognized/bound specifically by the first polypeptide in the recombinant light-switchable transcription factor, for example, a LexA reaction element is the long 16 bp DNA motif (Sequence 11).

"Promoter" refers to a DNA sequence which can start and lead to its downstream gene transcription to produce RNA, which is required for gene expression. Promoter may be a naturally or artificially modified promoter. Prokaryote promoter is very important for mRNA synthesis and consists of two highly conserved and separated regions. Pribnow box, also termed as TATA box or –10 region, is a A-T rich region containing 6-8 bases. The Pribnow box sequences of the promoters from different source differ slightly. The region consisting of 10 bp bases locating 35 bp upstream the transcription start point is termed as –35 region. The *E. coli* RNA polymerase recognizes and binds to promoter when transcription. –35 region bind to the σ subunit of RNA polymerase and –10 region binds to the core enzyme of RNA polymerase, the DNA is unwind to form single strand near the transcription start point, phosphodiester bond forms between the first and second nucleotide by RNA polymerase, and RNA polymerase moves forward to form new RNA strand.

"Vector", "expression vector", "gene expression vector" and "recombinant gene expression vector" have the same meaning. They can be used interchangeably and refer to a vector able to express recombinant target proteins in prokaryotic cells.

"Transformation" refers to a process that the prokaryotic host cells uptake the exogenous gene-carrying expression vector through physical or chemical methods. The methods for the host cells transformed with the expression vectors can be found in Sambrooka et al (Molecular Cloning, A laboratory Manual, Second Edition, Cold Spring Harbor Press (1989) and other related textbooks.

In the light-switchable gene expression system of prokaryotic cells in the invention, the recombinant light-switchable transcription factor in the first portion is a fusion protein formed by tandem connection of two or three functional polypeptide fragments via direct peptide bonds or via a linker peptide. Under illumination of an appropriate wavelength light, such fusion protein can bind to the reaction element in the second portion, i.e., target transcription unit nucleotide sequence of the system, so as to initiate or directly repress the expression of the target protein gene in the transcription unit by itself or via recruiting other components of RNA polymerase.

As used herein, "recombinant light-switchable transcription factor fusion protein" and "recombinant light-switchable transcription factor" have the same meaning and can be used interchangeably.

The recombinant light-switchable transcription factor of the invention comprises the first polypeptide which is able to specifically recognize said reaction element in the target transcription unit nucleotide sequence, but unable to bind the reaction element or only have a weak binding affinity. The first polypeptide can only bind to the reaction component after homogenous dimerization of the transcription factor occurring with the assistance of the second polypeptide. The first polypeptide can derive from the DNA recognizing/binding domain of any known protein or their analogues (the mutant and truncation of binding domain having the similar or stronger binding capacity). The first polypeptide can be selected from: the helix-turn-helix DNA-binding domain, zinc finger motif or zinc cluster DNA-binding domain, leucine zipper DNA-binding domain, winged helix DNA-binding domain, winged helix-turn-helix DNA-binding domain, helix-loop-helix DNA-binding domain, high mobility family DNA-binding domain and B3 DNA-binding domain. The first polypeptide of the invention includes, but not limited to DNA-binding domain of LexA protein (SEQ. ID. NO:2), DNA-binding domain of λ phage cI repression protein (SEQ. ID. NO:4), DNA-binding domain of Lac repression protein LacI (SEQ. ID. NO:6), DNA-binding domain of Gal4 protein (SEQ. ID. NO:8), DNA-binding domain of tetracycline repression protein TetR (SEQ. ID. NO:10) etc., and their truncated mutants and/or mutants containing 80%-99% homologous amino acid sequence. More preferably are selected from DNA-binding domains of LexA protein and cI protein.

LexA protein is a transcriptional repression protein present in $E.\ coli$ cells, and it can regulate the transcription of more than 20 genes and recognize/bind to 16 bp palindromic structure $CTGT(N)_8ACAG$ of upstream reaction element of gene promoter to prevent the downstream gene transcription by RNA polymerase. LexA contains 202 amino acids with a winged helix-turn-helix DNA-binding domain, wherein the 1-87 amino acids are useful for specific recognition of DNA and the 88-202 amino acids, useful for dimerization. Only dimerized LexA can specifically bind to the corresponding reaction element and the monomer cannot. LexA exists in the dimeric form in normal cells. When the cells are stimulated by an internal or external SOS signal, the dimerized LexA is cut by certain enzymes (such as RecA) in vivo and dissociated from the DNA, resulting in the activation of the gene previously repressed by LexA, $E.\ coli$ initiates the repair function to the SOS[11, 12][Schnarr, M. et al, Biochimie, 1991. 73(4): p. 423-31, Little, J. W. et al, Cell, 1982. 29(1): p. 11-22.]. LexA-based double hybrid system has also been used for researching the interaction of gene expression and proteins. For example, MATCHMAKER™ yeast LexA Two-Hybrid System (Clontech) is based on this system.

The cI protein is a transcription repression protein encoded by λ phage cI gene, and it can prevent the transcription activity of λ left and right early promoters, resulting in the production of protein unable to perform cell duplication and cell division. The cI protein contains 236 amino acids with a helix-turn-helix DNA-binding domain, wherein 1-102 amino acids are useful for specific recognition of DNA and 132-236 amino acids, useful for dimerization. Only dimerized cI can specifically bind to the corresponding reaction element. The homogenous dimer of cI protein can recognize/bind to two operon sequences, $P_L$ and $P_R$, each contains three recognizing/binding sites, OL1, OL2 and OL3 for $P_L$, and OR1, OR2 and OR3 for $P_R$, respectively. The cI protein has stronger ability to bind to OR1. The conserved DNA sequence is showed as SEQ. ID. NO:71. The monomer cI protein almost has no such binding ability [Burz, D. S. et al, Biochemistry 33 (28), 8399-8405 (1994), Hu, J. C. et al, Science 250 (4986), 1400-1403 (1990)][13, 14].

Lac repression protein LacI can specifically recognize/bind to the $E.\ coli$ lactose operon to regulate transcription and translation of corresponding genes. LacI protein consists of DNA recognizing/binding domain at the N terminal (1-62 amino acids), core domain (63-340 amino acids) and the tetramerization domain at the C terminal (341-357 amino acids). Its specifically recognizing/binding conserved sequence is GAATTGTGAGCGCTCACAATT (SEQ ID NO:13), only dimerized or tetramerized LacI can bind to the DNA, but monomer LacI almost cannot [Lewis, M. et al, Science 271 (5253), 1247-1254 (1996), Friedman, A. M. et al, Science, 1995. 268(5218): p. 1721-7.][15,16].

Gal4 is a transcriptional activation domain of $Saccharomyces\ cerevisiae$ (the encoding gene is Gal4), and it is able to recognize/bind to the upstream reaction element-UASG motif [a 17 bp sequence 5'-CGGRNNRCYNYNYNC-NCCG-3' (SEQ ID NO:14, R refers to purine, Y refers to pyrimidine, N refers to deoxynucleotide)]. Gal4 regulates the expression of galactose inducible genes, such as GAL1, GAL2, GAL7, GAL10 and MEL1. The N terminal of GAL4 is DNA recognizing/binding domain, C terminal is transactivation domain (AD). The DNA recognizing/binding domain contains a Zinc cluster, also termed as Zn(2)-Cys(6) double cluster. Gal4 plays its role to bind to the reaction element in need of the formation of a homogeneous dimer [Kraulis, P. J. et al, Nature, 1992. 356(6368): p. 448-50, Marmorstein, R. et al, Nature, 1992. 356(6368): p. 408-14.][17, 18]. Gal4/UAS-based double hybrid system is an effective tool for researching the gene expression. For example, this Gal4/UAS system has been used in Check-Mate™ Mammalian Two-Hybrid System (Promega).

Tetracycline repression protein (TetR), a transcription factor resided in many Gram-negative bacteria, represses the transcription of corresponding genes via the bind to specific DNA motifs. TetR protein has a helix-turn-helix DNA-binding domain. The monomer of TetR protein can form the homogenous dimer for recognition/binding to the operon containing a specific DNA sequence (SEQ. ID. NO:70), but the monomer of TetR protein itself almost has no such binding ability [Wissmann, A. et al., EMBO J 10 (13), 4145-4152 (1991), Ramos, J. L. et al., Microbiol Mol Biol Rev 69 (2), 326-356 (2005)][19, 20].

In a preferred embodiment of the invention, the first polypeptide is the 1-87 amino acid sequence of DNA-binding domain of LexA protein (its nucleic acid and protein sequences are SEQ. ID. NO:1 and SEQ. ID. NO:2, respectively), i.e., truncated DNA-binding domain which cannot bind to the reaction element alone (SEQ. ID. NO:11). In another preferred embodiment of the invention, the first polypeptide is the 1-102 amino acid sequence of DNA-binding domain of cI protein (its nucleic acid and protein sequences are SEQ. ID. NO:3 and SEQ. ID. NO:3, respectively), i.e., truncated DNA-binding domain which also can not bind to the reaction element alone (SEQ. ID. NO:12). In another preferred embodiment of the invention, the first polypeptide is the 1-62 amino acid sequence of DNA-binding domain of LacI protein (its nucleic acid and protein sequences are SEQ. ID. NO:5 and SEQ. ID. NO:6, respectively), i.e., truncat Tetracycline repression protein ed DNA-binding domain which cannot bind to the reaction element alone (SEQ. ID. NO:13). In another preferred embodiment of the invention, the first polypeptide is the 1-65 amino acid sequence of DNA-binding domain of Gal4 protein (its nucleic acid and protein sequences are SEQ. ID. NO:7 and SEQ. ID. NO:8, respectively), i.e., truncated DNA-binding domain which cannot bind to the reaction element alone (SEQ. ID. NO:14). In another preferred embodiment of the invention, the first polypeptide is the 1-63 amino acid sequence of DNA-binding domain of TetR protein (its nucleic acid and protein sequences are SEQ. ID. NO:9 and SEQ. ID. NO:10, respectively), i.e., truncated DNA-binding domain which cannot bind to the reaction element alone (SEQ. ID. NO:15).

The second polypeptide in the recombinant light-switchable transcription factor fusion protein of this invention is a photosensitive polypeptide derived from the photosensitive domain containing flavin chromophore (FMN or FAD). For example, the photosensitive protein contains light-O-voltage (LOV) domain, the photolyase-like cryptochromes and the blue light protein using FAD (BLUF), preferably, the photosensitive protein contains LOV domain. After the illumination with the appropriate wavelength light, the dimerization ability of the second polypeptide has been changed to alter the dimerization ability of the transcription factor, then the dimer of the transcription factor can bind to the corresponding reaction element, thereby to regulate the expression level of the target genes. The invention includes, but is not limited to, several preferred photosensitive proteins or their functionally active truncated fragments described below.

The most preferred second polypeptide of the invention is the light-switchable domain of *Neurospora crassa* VIVID protein and its mutants. VIVID exists in the cells of *Neurospora crassa* and it is a photosensitive protein involved in cellular signaling pathway regulated by blue-light. Under the illumination of blue light, it can form a dimer with flavin adenine dinucleotide (FAD) in a intermolecular reaction. Full-length VIVID protein contains 186 amino acids with only one photosensitive LOV domain. Studies have showed that VIVID-36, the truncated protein of VIVID protein (missing 36 amino acid sequence in the N-terminal), were more stable than the full-length VIVID protein, Meanwhile, without illumination, the half-life of VIVID-36 dimer formed by illumination with blue light for regaining its monomeric form is 180000 s; the VIVID-36 containing point mutation C71V has more strong dimerization ability. In a preferred embodiment of the invention, the second polypeptide is selected from one point-mutation-containing and 1-36 amino acid sequence deleted VIVID (C71V), VIVID (N56K) and VIVID (Y50W) mutants (their nucleic acid sequences are SEQ. ID. NO:16, 18 and 20, respectively; their amino acid sequences are SEQ. ID. NO:17, 19 and 21, respectively). In a more preferred embodiment of the invention, the second polypeptide is two point-mutation-containing and 1-36 amino acid sequence deleted VVD (N56K C71V), VVD (I52A C71V), VVD (I52S C71V and VVD (N56R C71V) mutants (The nucleic acid and protein sequences are SEQ. ID. NO:22, 24, 26, 28 and SEQ. ID. NO:23, 25, 27, 29 respectively).

The secondly preferred second polypeptide of the invention is LOV2 domain of *Avena sativa* phytochrome 1 (abbreviated as AsLOV2) [Peter, E., B. Dick, and S. A. Baeurle, Nat Commun, 2010. 1(8): 122]. The N-terminal of phytochrome 1 of *Avena sativa* is light-O-voltage (LOV) domain, LOV1 or LOV2, which can bind to flavin mononucleotide (FMN) to produce an additional compound under illumination of blue light. In the invention, LOV2 domain is linked to the first polypeptide, thus successfully resulting in the ability to bind to the corresponding reaction element for the first polypeptide in the transcription factor. The second polypeptide in the transcription factor LA containing AsLOV2 domain can bind to its corresponding reaction element in dark, resulting in repression of the expression of target gene, whereas this binding is weakening under illumination, resulting in the up-regulation of target gene expression level.

The thirdly preferred second polypeptide of the invention is LOV domain (abbreviated as AuLOV, its nucleic acid and protein sequences are SEQ. ID. NO:45 and SEQ. ID. NO:46 respectively) in the C-terminal of aureochrome1 of *Stramenopile algae Vaucheria frigida* [Takahashi, F. et al, Proc Natl Acad Sci USA, 2007. 104(49): 19625-19630]. The dimerization ability of the second polypeptide in the transcription factor LAu containing AuLOV domain has been enhanced after illumination, thus resulting in the down-regulation of target gene expression level.

The dimerization of the recombinant light-switchable transcription factor constituted from VIVID or AuLOV is enhanced by the illumination of a light with an appropriate wavelength thus resulting in the bind of the second polypeptide to the reaction element to start or down-regulate the transcription. However, the light-switchable transcription factor containing AsLOV2 is dimerized in the dark, and binds to the reaction element, resulting in repressing the transcription of target gene.

The homology of six different LOV domains derived from photosensitive proteins was analysed by using Accelry Discovery Studio 2.1. These LOV domains are derived from VIVID (Nc_VVD, its protein sequence is SEQ ID NO:137), White-collar-1 (Nc_Wc1, its protein sequence is SEQ ID NO:138), FKF1 (At_FKF1, its protein sequence is SEQ ID NO:139), aureochrome1 (Vf_Aureo1_LOV, its protein sequence is SEQ ID NO:140), oat phototropin 1 (As_phot_LOV1 and As_phot_LOV2, their protein sequences are SEQ ID NO:141 and SEQ ID NO:142, respectively). Results showed that these proteins have about 15% identical amino acids and about 36% similar sequences (FIG. 36).

In the light-switchable gene expression system of the invention, the recombinant light-switchable transcription factor can contain the third polypeptide which can recruit other components of RNA polymerase. The third polypeptide used in the invention includes, but is not limited to: ω domain and a domain from *E. coli* which have been widely used in *E. coli* one-hybrid system [Dove, S. L. et al., 1998. 12(5): p. 745-54, Dove, S. L. et al., Nature, 1997. 386(6625): p. 627-30.][21,22]. The third polypeptide link, directly or via a linker, with the first, the second polypeptides.

As described above, there are various options for each of the two or three polypeptides contained in the recombinant light-switchable transcription factor and various combination options for the two or three polypeptides to be connected to become a fusion protein. The fragments of the functional domain of each polypeptide with good activity are preferably used for the preparation of the recombinant light-switchable transcription factor fusion protein. Recombinant light-switchable transcription factor with strong regulatory ability (i.e. large differences of its gene expression level during the illumination and in the dark), selected by the expression in prokaryotic cells, are used to regulate the expression of the nucleic acid sequence to be transcribed. Whatever choices and combinations are, they fall into the range of the invention provided the gene expression regulated by illumination is achieved.

The second portion of the light-switchable gene expression system in prokaryotic cells is a target transcription unit composed of the promoter (specifically recognized/bound by the transcription factor)-nucleotide sequence to be transcribed, or promoter-reaction element-nucleotide sequence to be transcribed, or reaction element-promoter-nucleotide sequence to be transcribed. Specifically, the reaction element, a nucleotide motif, is dependent on the first polypeptide selected to be used in the recombinant light-switchable transcription factor fusion protein. In other words, the promoter, or promoter-reaction element, or reaction element-promoter, specific to the first polypeptide, must be selected based on the first polypeptide. For example, when the first polypeptide is the DNA recognition/binding domain of LexA, cI, LacI, Gal4 or TetR proteins, the corresponding reaction element should be a motif of SEQ. ID. NO:11, 12, 13, 14 or 15.

The reaction element of the invention corresponding to the light-switchable transcription factor is usually contained in nucleotide sequence of promoter, or is located downstream of −10 region. In the detailed embodiment of the invention, the promoter can contain: colE promoter, sulA promoter and recA promoter from *E. coli*, O12 promoter from λ phage, T7 promoter from T7 phage and grac promoter from *Bacillus subtilis* (The nucleic acid sequences are SEQ. ID. NO:34, 35, 36, 37, 38, 39, 40). Additionally, the reaction element can also locate upstream the −35 region of promoter; the third peptide of the light-switchable transcription factor can recruit other components of RNA polymerase to initiate the transcription of target gene. Based on the analysis of related literatures, the available promoters include, but not be limited to lac promoter (nucleic acid sequence is SEQ. ID. NO:41), the number of the upstream reaction element can differ from one to five. In the specific embodiments of the invention, the *E. coli* lac promoter is a preferable choice.

The person skilled in the art knows that so-called "operatively link" refers the connection between the reaction element and the promoter or among reaction elements is not a direct connection, but spaced by several nucleotides, provided the synergistic effect still exists.

In the target transcription unit of the invention, the downstream nucleotide sequence is a nucleotide sequence to be transcribed, a nucleotide sequence encoding the target protein or functional RNA. As above-mentioned, the target protein can be any useful protein. In order to verify the effects of the present system and to facilitate the detection, following exemplary report proteins have been used as target protein in the examples: Red fluorescent protein mCherry (its nuclei acid and amino acid sequence are SEQ. ID. NO:42 and SEQ. ID. NO:43, respectively), β-galactosidase (LacZ, its nuclei acid and protein sequence are SEQ. ID. NO:44 and SEQ. ID. NO:45, respectively), sulfhydryl oxidase Ero1 (its nuclei acid and protein sequence are SEQ. ID. NO:46 and SEQ. ID. NO:47, respectively). However, the target protein of the invention is not limited to these report proteins.

The first portion and the second portion of the light-switchable target protein gene expression system of the invention can be constituted in one prokaryotic expression vector or in two prokaryotic expression vectors, respectively, by using standard recombinant DNA technique. Such expression vectors can be introduced into various prokaryotic host cell population to express the interested target proteins.

The invention provides prokaryotic expression vectors containing recombinant light-switchable transcription factor fusion proteins composed of two or three polypeptides. In one embodiment of the invention, provided are prokaryotic expression vectors pLV-L0, pLV-L1, pLV-L2, pLV-L3, pLV-L4, pLV-L5, pLV-L6, pLV-L7, pALV-L0, pALV-L1, pALV-L2, pALV-L3, pALV-L4, pALV-L5, pALV-L6 and pLV-L7 of the recombinant light-switchable transcription factors LexA(1-87)-VVD36(C71V) (the light-switchable transcription factors are abbreviated as LV-L0, LV-L1, LV-L2, LV-L3, LV-L4, LV-L5, LV-L6, LV-L7, their nucleic acid sequences are SEQ. ID. NO:48, 50, 52, 54, 56, 58, 60, 62, their amino acid sequences are SEQ. ID. NO:49, 51, 53, 55, 57, 59, 61, 63), wherein the connection between LexA(1-87) and VVD36(C71V) is via different linker peptides. In a preferable embodiment of the invention, provided are the encoding nucleic acid sequences (SEQ. ID. NO:64, 66), amino acid sequences (SEQ. ID. NO:65, 67) and prokaryotic expression vectors pALV-L0 (N56K), pALV-L0(Y50W) of two recombinant light-switchable transcription factors LexA (1-87)-VVD wherein brackets are the mutation sites in VIVID. In another preferable embodiment of the invention, provided are the encoding nucleic acid sequence (SEQ. ID. NO:68, 70, 72, 74), amino acid sequence (SEQ. ID. NO:69, 71, 73, 75) and prokaryotic expression vector pALV-L0 (N56K C71V), pALV-L0 (I52A C71V), pALV-L0 (IS2S C71V) and pALV-L0(N56R C71V) of the four recombinant light-switchable transcription factors LexA(1-87)-VVD containing double mutants in VIVID. In another embodiment of the invention, provided are the encoding nucleic acid sequence (SEQ. ID. NO:76), amino acid sequence (SEQ. ID. NO:77) and prokaryotic expression vector pALA of the recombinant light-switchable transcription factor LexA(1-87)-AsLOV2 (abbreviated as LA). In another embodiment of the invention, provided are the encoding nucleic acid sequence (SEQ. ID. NO:78), amino acid sequence (SEQ. ID. NO:79) and prokaryotic expression vector pALAu of the recombinant light-switchable transcription factor LexA (1-87)-AuLOV (abbreviated as LAu). In another embodiment of the invention, provided are the encoding nucleic acid sequence (SEQ. ID. NO:80), amino acid sequence (SEQ. ID. NO:81) and prokaryotic expression vector pACV of the recombinant light-switchable transcription factor cI (1-102)-VVD36 (C71V) (abbreviated as CV). In another embodiment of the invention, provided are the encoding nucleic acid sequence (SEQ. ID. NO:82), amino acid sequence (SEQ. ID. NO:83) and prokaryotic expression vector pALaV of the recombinant light-switchable transcription factor Lad (1-62)-VVD36(C71V (abbreviated as LaV). In another embodiment of the invention, provided are the encoding nucleic acid sequence (SEQ. ID. NO:84), amino acid sequence (SEQ. ID. NO:85) and prokaryotic expression vector pAGV of the recombinant light-switchable transcription factor Gal4 (1-65)-VVD36 (C71V) (abbreviated as GV). In another embodiment of the invention, provided are the encoding nucleic acid sequence (SEQ. ID. NO:86), amino acid sequence (SEQ. ID. NO:87) and prokaryotic expression vector pATV of the recombinant light-switchable transcription factor TetR (1-63)-VVD36 (C71V) (abbreviated as TV). In another embodiment of the invention, provided are the encoding nucleic acid sequence (SEQ. ID. NO:88), amino acid sequence (SEQ. ID. NO:89) and prokaryotic expression vector pALVα of the recombinant light-switchable transcription factor LexA (1-87)-VVD36 (C71V)-α (abbreviated as LVα). In another embodiment of the invention, provided are the encoding nucleic acid sequence (SEQ. ID. NO:90), amino acid sequence (SEQ. ID. NO:91) and prokaryotic expression vector pAωLV of the recombinant light-switchable transcription factor ω-LexA (1-87)-VVD36(C71V) (abbreviated as ωLV). In another embodiment of the invention, provided are the encoding nucleic acid sequence (SEQ. ID. NO:92), amino acid sequence (SEQ. ID. NO:93) and prokaryotic expression vector pACVα of the recombinant light-switchable transcription factor cI (1-102)-VVD36 (C71V)-α (abbreviated as CVα). In another embodiment of the invention, provided are the encoding nucleic acid sequence (SEQ. ID. NO:94), amino acid sequence (SEQ. ID. NO:95) and prokaryotic expression vector pAωCV of the recombinant light-switchable transcription factor ω-cI (1-102)-VVD36 (C71V) (abbreviated as ωCV). In another embodiment of the invention, provided are the encoding nucleic acid sequence (SEQ. ID. NO:96), amino acid sequence (SEQ. ID. NO:97) and prokaryotic expression vector pALaVα of the recombinant light-switchable transcription factor Lad (1-62)-VVD36 (C71V)-α (abbreviated as LaVα). In another embodiment of the invention, provided are the encoding nucleic acid sequence (SEQ. ID. NO:98), amino acid sequence (SEQ. ID. NO:99) and prokaryotic expression vector pAωLaV of the recombinant light-switchable transcription factor ω-LacI (1-62)-VVD36 (C71V) (abbreviated as ωLaV). In another embodiment of the invention, provided are the encoding nucleic acid sequence (SEQ. ID. NO:100), amino acid sequence (SEQ. ID. NO:101) and prokaryotic expression vector pAGVα of the recombinant light-switchable transcription factor Gal4 (1-65)-VVD36(C71V)-α (abbreviated as GVα). In another embodiment of the invention, provided are the encoding nucleic acid sequence (SEQ. ID. NO:102), amino acid sequence (SEQ. ID. NO:103) and prokaryotic expression vector pAωGV of the recombinant light-switchable transcription factor ω-Gal4 (1-65)-VVD36 (C71V) (abbreviated as ωGV). In another embodiment of the invention, provided are the encoding nucleic acid sequence (SEQ. ID. NO:104), amino acid sequence (SEQ. ID. NO:105) and prokaryotic expression vector pATVα of the recombinant light-switchable transcription factor TetR (1-63)-VVD36 (C71V)-α (abbreviated as TVα). In another embodiment of the invention, provided are the encoding nucleic acid sequence (SEQ. ID. NO:106), amino acid sequence (SEQ. ID. NO: 107) and prokaryotic expression vector pAωTV of the recombinant light-switchable transcription factor ω-TetR (1-63)-VVD36 (C71V) (abbreviated as ωTV). In another embodiment of the invention, provided is the prokaryotic expression vector pD-colE-mCherry-Amp-LV containing both the recombinant light-switchable transcription factor LV-L0 and target transcription unit colE-mCherry (the nucleic acid sequence of ter-colE-mCherry-Amp-LV-ter is SEQ. ID. NO:108).

In another embodiment of the invention, provided is the prokaryotic expression vector pHT01-LaV(wt)-$P_{grac}$-m-Cherry containing both the recombinant light-switchable transcription factor LacI (1-62, wt)-VVD36 (C71V)(abbreviated as LaV(wt), its nucleic acid and protein sequences are SEQ. ID. NO:109 and SEQ. ID. NO:110 respectively) and target transcription unit $P_{grac}$-mCherry (the nucleic acid sequence of LaV(wt)-$P_{grac}$-mCherry is SEQ. ID. NO:111).

The invention also provides the prokaryotic expression vector containing the target transcription unit but leaving a vacancy for the nucleic acid sequence to be transcribed. This vacant location for the nucleic acid sequence can be replaced with the interested nucleotide sequence selected by the user himself, such as the gene encoding the target protein which is inserted into the expression vector of the invention by using standard recombinant DNA techniques, then this expression vector and above-mentioned expression vector containing the gene of the recombinant light-switchable transcription factor are used to co-transform prokaryotic host cells for the regulation of the expression of the nucleotide sequence (gene) to be transcribed. In the embodiment of the invention, the target transcription unit but leaving a vacancy for the nucleic acid sequence to be transcribed of the prokaryotic expression vector are: colE-nucleotide sequence to be transcribed corresponding to LexA, sulA-nucleotide sequence to be transcribed corresponding to LexA, RecA-the nucleotide sequence to be transcribed corresponding to LexA, umuDC-nucleotide sequence to be transcribed corresponding to LexA, LexA reaction element-lac minimal promoter-nucleotide sequence to be transcribed corresponding to LexA, $P_{\lambda O12}$-nucleotide sequence to be transcribed corresponding to cI, cI reaction element O12-lac minimal promoter-nucleotide sequence to be transcribed corresponding to cI, T7-lacI reaction element-nucleotide sequence to be transcribed corresponding to lad, lad reaction element-lac minimal promoter-nucleotide sequence to be transcribed corresponding to lad, T7-Gal4 reaction element-nucleotide sequence to be transcribed corresponding to Gal4, Gal4 reaction element-lac minimal promoter-nucleotide sequence to be transcribed corresponding to Gal4, T7-TetR reaction element-nucleotide sequence to be transcribed corresponding to TetR, TetR reaction element-lac minimal promoter-nucleotide sequence to be transcribed corresponding to TetR.

The invention also provides prokaryotic strains transformed with prokaryotic expression vectors containing genes encoding various recombinant light-switchable transcription factors or integrated with various recombinant light-switchable transcription factors in the genome, and provides prokaryotic expression vectors containing the target transcription unit composed of the promoter, or promoter-reaction element, or reaction element-promoter, but leaving an vacancy for the nucleotide sequence to be transcribed. The nucleotide sequence to be transcribed (target protein gene) selected by the user himself can be inserted into said vector by using standard recombinant DNA techniques, then this re-constructed vector can be used to transformed prokaryotic cells already transformed by the prokaryotic expression vector containing the recombinant light-switchable transcription factor or integrated with various recombinant light-switchable transcription factors in the genome. These prokaryotic bacteria cells can be cultured to express the interested gene or to study how to regulate the expression of the target gene.

The invention further provides a kit containing the expression vectors comprising two portions of the gene expression regulation system of the invention or the prokaryotic cells already transformed by these vectors or integrated with various recombinant light-switchable transcription factors in the genome. In one embodiment, some containers in the kit are filled, respectively, with the prokaryotic expression vector(s) containing one or more recombinant light-switchable transcription factor genes. In another embodiment, some containers in the kit are filled, respectively, with the prokaryotic expression vector(s) containing one or more recombinant light-switchable transcription factor genes, other containers are filled with the prokaryotic expression vector(s) containing the target transcription unit (promoter-nucleotide sequence to be transcribed, or promoter-reaction element-nucleotide sequence to be transcribed, or reaction element-promoter-nucleotide sequence to be transcribed). In a further embodiment, some containers in the kit are filled with prokaryotic cells already transformed with prokaryotic expression vectors containing the recombinant light-switchable transcription factor genes or integrated with various recombinant light-switchable transcription factors in the genome, other containers are filled with prokaryotic expression vectors containing the promoter-nucleotide sequence to be transcribed, or promoter-reaction element-nucleotide sequence to be transcribed, or reaction element-promoter-nucleotide sequence to be transcribed. The kit of the invention can also contain appropriate illumination control devices, such as LED lamp and its control devices. All kits of the invention will be equipped with a direction for the description of each component, its intended use and methods of application and provide relevant reference catalog.

The invention further provides a method for the regulation of gene expression in prokaryotic cells using the light-switchable gene expression system, comprising following steps:

a) constructing the light-switchable gene expression system in prokaryotic plasmid expression vectors;

b) introducing the construct into prokaryotic host cells; and c) inducing host cells via illumination to express the nucleotide being regulated.

The illumination method for inducing the gene expression in host cells comprising: selection and application of light sources. The light sources include, but not are limited to, LED lamp, incandescent lamp, fluorescent lamp and laser. In one embodiment of the invention, blue LED (460-470 nm) is selected as the light source. The illumination methods include illumination quantity, time, intensity and frequency as well as the spatial expression control of the target gene via scan, projection, optical molds, etc. They are also comprised in the range of the invention. In one embodiment of the invention, the illumination intensities are varying within 0-0.125 mW/cm$^2$. In another embodiment of the invention, the cellular target gene expression in different locations is regulated in the space using the printing projection film as a light mold. In another embodiment of the invention, the cellular target gene expression in different locations is regulated in the space using the neutral gray film as a light mold.

BRIEF DESCRIPTION OF DRAWINGS

Figure 36:
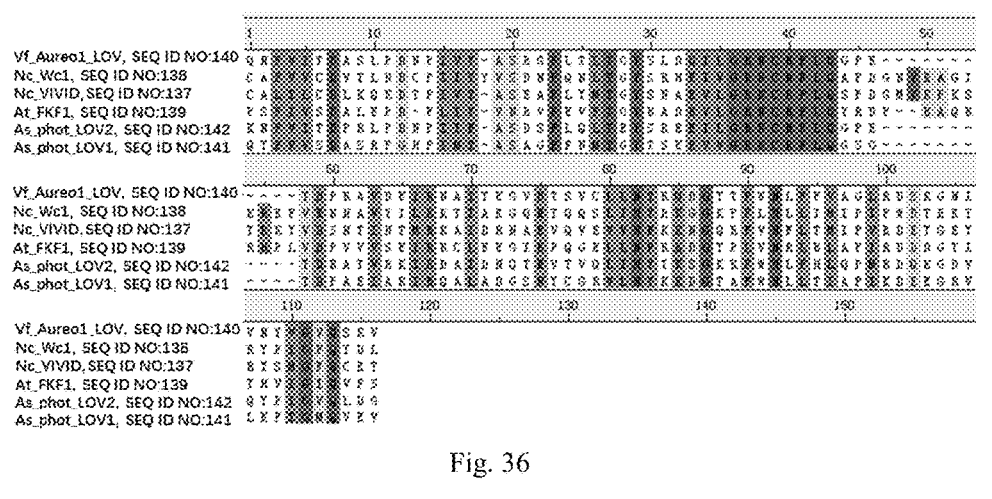

FIG. 36 shows homology analysis of LOV domains derived from six photosensitive proteins, wherein the black color represents 100% homologous amino acid sequence, the dark grey represents the higher homologous sequences and french gray represents the medium homologous Sequences.

PREFERABLE EMBODIMENTS

Figure 1:
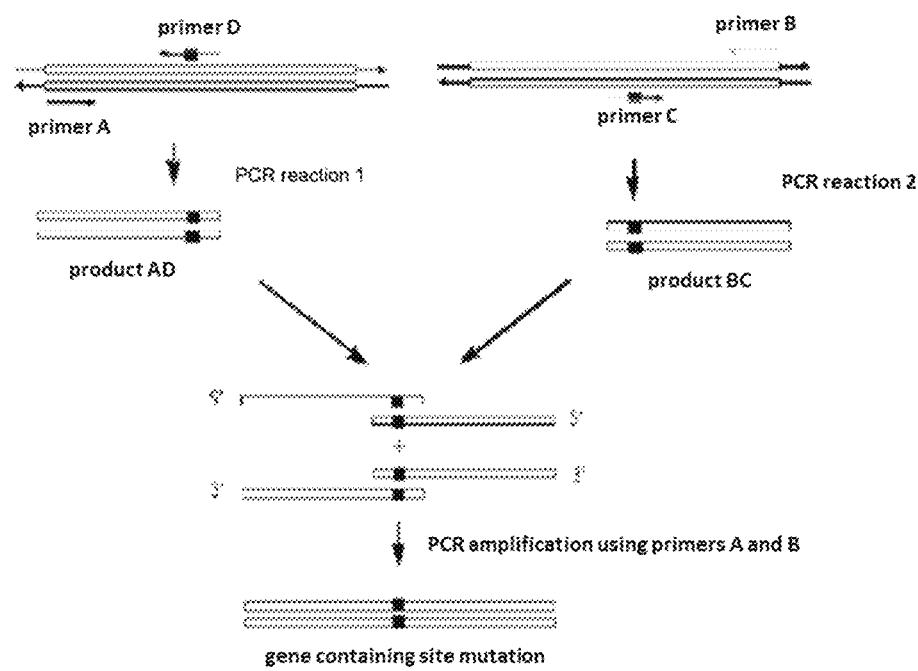
FIG. 1 shows the principle of overlapping PCR.
Figure 2:
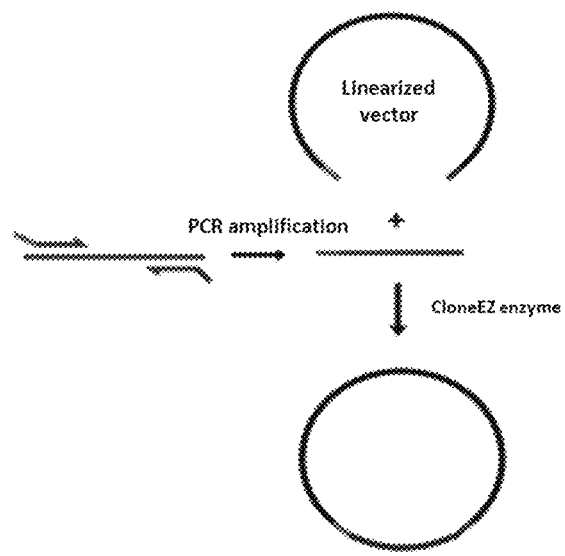
FIG. 2 is a schematic diagram of homologous recombination ligation.

The invention will be described in detail by using following examples. These examples are only used for the illustration of the invention without any restriction on the scope of protection. It is not difficult for those skilled in the art to successfully implement the invention on the basis of the examples with some modifications or alternatives. All these modifications or alternatives are within the scope of the attached claims. The methods used in the samples were the routine methods of molecular biology cloning in genetic engineering and cell biology field, such as: 《Lab Ref: A handbook of Recipes, Reagents, and Other Reference Tools for Use at the Bench》 written by Roskams, J. et al, 《Molecular Cloning: A Laboratory Manual》 (the third edition, August in 2002, Science press, Beijing) written by Sambrook J and Russell D W, and translated by Peitang Huang et al.; Chapters in book 《Short protocols in Protein Science》 (Science press, background) written by Coligan J. E. et al, and translated by Shentao Li et al.

pCDFDuet1 vector was purchased from Novagen company; pRSETb and pBAD/His A were purchased from Invitrogen company; pKD3, pKD, pCP20 and pKD46 were gifts from Prof. Jie Bao of East China University of Science and Technology. All the primers were synthesized, purified and identified via mass spectrometry by Shanghai Generay Biotech Co. Ltd. All the vectors obtained in the examples were verified via sequencing by BGI and JIE LI Biology Company. Taq DNA polymerase used in the examples was purchased from DongSheng Biotech Company; pfu DNA polymerase was purchased from TianGen Biotech (Beijing) Co. LtD., and PrimeStar DNA polymerase was purchased from TaKaRa. All the three polymerases contained corresponding buffer and dNTP when purchased. Restriction enzyme such as BamHI, BglII, HindIII, NdeI, XhoI, SacI, EcoRI, SpeI et al., T4 ligase and T4 phosphatase (T4 PNK) were purchased, together with 10× Tango™ buffer, from Fermentas. CloneEZ PCR clone kit was purchased from GenScript (Nanjing). Unless otherwise mentioned, inorganic salt chemical reagents were purchased from Sinopharm Chemical Reagent Co.; Kanamycin, Ampicillin and ONPG were purchased from Ameresco; 384 well white plates for luminescence detection and 384 well black plates for fluorescene detection were purchased from Grenier.

The kit for DNA purification was purchased from BBI (Canada); common plasmid kit was purchased from TianGen Biotech (Beijing) Co. LtD.; *E. coli* strain Mach1 was purchased from Invitrogen; *E. coli* strain JM109 (DE3) was purchased from Promega; *E. coli* strain BL21 (DE3) was purchased from Novagen;

Main equipments: Biotek Synergy 2 multi-mode microplate reader (BioTek, US), X-15R high speed refriger (Beckman, US), Microfuge22R high speed refriger (Beckman, US), PCR Amplifier (Biometra, Germany), In-Vivo Multispectral System FX (Kodak, US), Luminometer (Sanwa, Japan), electrophoresis apparatus (shanghai Biocolor BioScience &Technolgy Co.).

The meaning of abbreviations: h=hour, min=minute, s=second, μL=microliter, mL=milliliter, L=liter, bp=base pair, mM=millimole, μM=Micromolar.

20 Amino Acids and Abbreviations

| Name | Abbreviation by three letters | Abbreviation by one letter |
| --- | --- | --- |
| Glycine | Gly | G |
| Alanine | Ala | A |
| Valine | Val | V |
| Leucine | Leu | L |
| Isoleucine | Ile | I |
| Proline | Pro | P |
| Phenylalanine | Phe | F |
| Tyrosine | Tyr | Y |
| Tryptophan | Trp | W |
| Serine | Ser | S |
| Threonine | Thr | T |
| Cysteine | Cys | C |
| Methionine | Met | M |
| Asparagine | Asn | N |
| Glutamine | Gln | Q |
| Asparagic acid | Asp | D |
| Glutamate | Glu | E |
| Lysine | Lys | K |
| Arginine | Arg | R |
| Histidine | His | H |

Methods Used in the Examples (1) Polymerase Chain Reaction (PCR):

1. Amplification of Gene Fragment by PCR:

| The reaction system of PCR amplification of target gene | |
| --- | --- |
| Template | 0.5-1 μL |
| Forward primer (25 μM) | 0.5 μL |
| Reverse primer (25 μM) | 0.5 μL |
| 10 × pfu buffer | 5 μL |
| Pfu DNA polymerase | 0.5 μL |
| dNTP (10 mM) | 1 μL |
| ddH$_2$O | 41.5-42 μL |
| Total volume | 50 μL |

Amplification Process (Bp Represents the Number of Nucleotide being Amplified):

| Process of PCR amplification of target gene | | |
| --- | --- | --- |
| denaturation | 95° C. | 2-10 min |
| 30 cycles | 94-96° C. | 30-45 s |
| | 50-65° C. | 30-45 s |
| | 72° C. | bp/(600 bp/min) |
| extension | 72° C. | 10 min |

2. PCR Amplification of Long Fragment (>2500 bp):

| Reaction system of PCR amplification of long fragment(>2500 bp) | |
| --- | --- |
| template (10 pg-1 ng) | 1 μL |
| Forward primer (25 μM) | 0.5 μL |
| Reverse primer (25 μM) | 0.5 μL |
| 5 × PrimerSTAR buffer | 10 μL |
| PrimerSTAR DNA polymerase | 0.5 μL |
| dNTP (2.5 mM) | 4 μL |
| ddH$_2$O | 33.5 μL |
| Total volume | 50 μL |

Amplification Process (bp Represents the Number of Nucleotide being Amplified):

| Process of PCR amplification of long fragment | | |
| --- | --- | --- |
| denaturation | 95° C. | 5 min |
| 30 cycles | 98° C. | 10 s |
| | 50-68° C. | 5-15 s |
| | 72° C. | bp/(1000 bp/min) |
| extension | 72° C. | 10 min |

Or

| Process of PCR amplification of long fragment | | |
| --- | --- | --- |
| denaturation | 95° C. | 5 min |
| 30 cycels | 98° C. | 10 s |
| | 68° C. | bp /(1000 bp/min) |
| extension | 72° C. | 10 min |

(2) Reaction System of Restriction Enzyme

1. The System of Double Digestion of Plasmid (n Represents the Required ddH$_2$O to Reach the Total Volume (μL):

| The system of double digestion of plasmid | |
| --- | --- |
| plasmid | 20 μL (about 1.5 μg) |
| 10 × buffer | 5 μL |
| restriction enzyme 1 | 1-2 μL |
| restriction enzyme 2 | 1-2 μL |
| ddH$_2$O | n μL |
| Total volume | 50 μL |
| Reaction condition | 37° C., 1~7 h |

2. The System of Double Digestion of PCR Fragment (n Represents the Same Meaning as Above):

| The system of double digestion of PCR fragment | |
| --- | --- |
| PCR fragment | 15-25 μL(about1 μg) |
| 10 × buffer | 5 μL |
| restriction enzyme 1 | 1-2 μL |
| restriction enzyme 2 | 1-2 μL |
| ddH$_2$O | n μL |
| Total volume | 50 μL |
| Reaction condition | 37° C., 1~7 h |

3. The System of Ligating the PCR Fragment into Plasmid by Double Digestion:

| Ligation system | |
| --- | --- |
| DNA of PCR fragment after double digestion | 1-7 µL |
| Digested plasmids | 0.5-7 µL |
| 10 × T4 ligase buffer | 1 µL |
| T4 DNA ligase | 1 µL |
| ddH₂O | N µL |
| Total volume | 10 µL |
| Reaction condition | 16° C., 4~8 h |

Note:
The ratio of PCR fragment to digested plasmid is about 2:1-6:1.

(3) Cyclization Reaction of DNA Fragment after Phosphorylation at the 5' End:

The terminal of plasmid or genome from microorganism has phosphate group, but PCR product has no, so addition reaction of phosphate group at the 5' end of PCR product is necessary for the ligation of DNA molecular. Cyclization reaction refers to ligation of the 3' and 5' ends of linearized fragment.

| Reaction system of phosphorylation | |
| --- | --- |
| DNA of PCR product | 5-8 µL |
| 10 × T4 ligase buffer | 1 µL |
| T4 PNK | 1 µL |
| ddH₂O | 0-3 µL |
| Total volume | 10 µL |
| Reaction condition | 37° C., 30 min~2 h |

T4 PNK is the abbreviation of polynucleotide kinase which is used for addition reaction of phosphate group at the 5' end of DNA molecular. Cyclization reaction system of DNA fragment with 5' end phosphorylation:

| Cyclization reaction system | |
| --- | --- |
| Phosphorylation product | 10 µL |
| T4 ligase (5 U/µL) | 0.5 µL |
| Total volume | 10.5 µL |
| Reaction condition | 16° C., 4~16 h |

(4) Overlapping PCR

Overlapping PCR is commonly used in ligating two different genes. Such as FIG. 1, to ligate gene AD with gene BC, two pairs of primers A and D, C and B are used to amplify gene AD and gene BC, the 5' end of primer D and primer C contains certain length of complementary sequences. The amplified products AD and BC of the first round are used as the template of the second round after recovery. 10 cycles of conventional PCR progress is carried out from the second round, the PCR system is:

| Reaction system of PCR amplification of target gene | |
| --- | --- |
| AD | 1 µL |
| BC | 1 µL |
| 10 × pfu buffer | 5 µL |
| Pfu DNA polymerase | 0.5 µL |
| dNTP (10 mM) | 1 µL |
| ddH2O | 39.5 µL |
| Total volume | 48 µL |

Addition of primer A and primer B after the second round, additional 30 cycles of amplification is carried out to obtain the ligation product of AD and BC.

(5) Reverse PCR

Figure 3:
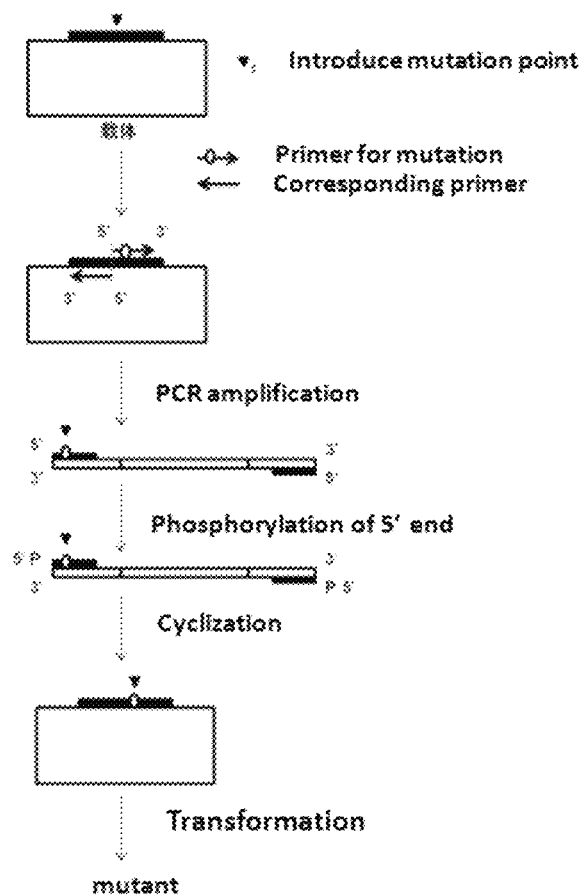
FIG. 3 shows the principle of reverse PCR.

Reverse PCR technology is used in the sample for site mutagenesis, truncation mutagenesis and insertion mutagenesis. The basic principle is based on the experiment progress of MutaBEST kit from Takara Company. As is shown in FIG. 3, reverse PCR primers are located at the mutation site; 5' end of one of the primers contains the mutation sequence. The amplification product undergoes purification, phosphorylation at the 5' end, cyclization, and then is transformed into competent cells.

(6) Preparation of Competent Cells and Transformation

Preparation of Competent Cells:

1. Pick single clone (such as Mach1) into 5 ml LB medium, culture at 37° C. overnight.

2. Transfer 0.5-1 ml of the overnight cultures to 50 ml LB medium, culture at 220 rpm/min for 3-5 h to reach OD600~0.5;

3. Incubate the cells on ice for 2 h;

4. Centrifuge the cells at 4000 rpm/min for 10 min at 4° C.

5. Discard the supernatant, resuspend cells with 5 mL of ice cold suspension buffer, mix completely and then add 45 ml of the suspension buffer after;

6. Keep the cells on ice for 45 min;

7. Centrifuge the cells at 4000 rpm/min for 10 min at 4° C., resuspend cells using 5 mL of ice stock buffer;

8. Dispense 100 uL to sterile Eppendorf vials. Snap-freeze in dry ice or −80° C.

Suspension buffer: $CaCl_2$ (100 mM), $MgCl_2$ (70 mM), NaAc (40 mM)

Stock buffer: 0.5 mL DMSO, 1.9 mL 80% glycerol, 1 mL 10×$CaCl_2$ (1M), 1 mL 10×$MgCl_2$ (700 mM), 1 mL 10×NaAc (400 mM), 4.6 mL ddH₂O Transformation:

1. take 100 ul competent cells to thaw on ice;

2. Add the ligation product, mix and incubate on ice for 30 min. Usually, the volume of ligation product should be less than 1/10 of competent cells;

3. Heat shock at 42° C. for 90 s, rapidly transfer the cells to ice for 5 min;

4. Add 500 µl LB and grow in 37° C. shaking incubator for 1 h.;

5. Centrifuge the cells at 4000 rpm/min for 3 min, resuspend cells using the remained 200 µl supernatant, and plate the cells onto a plate containing the appropriate antibiotic. Incubate plates at 37° C. overnight.

(7) Determination of mCherry Fluorescent Protein Expressed by *E. coli*

Single clones on the transformation plate is picked into 48-well plate, each well contains 700 µl LB, each sample has six replicates, the cells grow overnight at 30° C. The cells are diluted 200 folds into two 48-well plates containing fresh LB. Unless otherwise mentioned, the culture condition is 30° C., the speed of shaking incubator is 280 rpm/min, light intensity is 0.125 mW/cm². Cells are harvested by 4000 rpm for 20 min after 18 h. The supernatant is discarded and 200 µl PBS is added into each well, the cells are resuspended using the agitator. 5 µl of the cells is added into 96-well white plate, then 115 µl PBS is added into each well and mix completely, determine the OD600 using Biotek Synergy 2 multi-mode microplate reader. The OD600 of each well is adjusted to the same according to the OD600 value from the reader. After adjustment, 100 µl of the cells is added into 96-well plate for fluorescence determinant, the fluorescence of the cells is determined using Biotek Synergy 2 multi-mode microplate reader using the filters Ex590/20 and Em645/40. The dark samples are wrapped by aluminum foil; other manipulation methods are the same.

(8) Determination of β-Galactosidase Activity

Single clones on the transformation plate is picked into 48-well plate, each well contains 700 μl LB, each sample has six replicates, the cells grow overnight at 30° C. The cells are diluted 200 folds into two 48-well plates containing fresh LB, the cells are cultured in the light or in the dark at 30° C., the light intensity of blue light is 0.125 mW/cm². 5 μl of the cells is added to the 96-well white plate after 18 h, 20 μl of the membrane permeable solution is added into each well, shake the 96-well plate using agitator for 1 min and incubate the cells at 37° C. for 10 min. 150 μl of the substrate solution is added and the kinetics of OD420 is determined after 30 s shaking. The obtained slope of the curve is proportional to LacZ activity.

Preparation of Solutions for Determination of LacZ Activity:

Substrate solution: $Na_2HPO_4$ 60 mM, $NaH_2PO_4$ 40 mM, ONPG 1 mg/ml, β-mercaptoethanol 2.7 μl/ml.

Membrane permeable solution: $Na_2HPO_4$ 100 mM, KCl 20 mM, $MgSO_4$ 2 mM, CTAB 0.8 mg/ml, sodium deoxycholate 0.4 mg/ml, β-mercaptoethanol 5.4 μl/ml.

(9) Gene Knock-Out on *E. coli* Genome 1. transform pKD46 vector into the target strain, culture on the plate containing Ampicillin at 30° C. overnight.
2. Pick the single clone into 5 mL LB medium containing Ampicillin and culture overnight;
3. The overnight cells are diluted 100 folds into 50 ml 2×YT medium and culture at 30° C., add L-arabinose (final concentration is 30 mM) when the OD600 reaches about 0.2-0.3, culture at 30° C. for induction for 90 min;
4. The cells after induction are placed on ice for 1 h, centrifuge the cells at 4000 rpm for 10 min at 4° C. and discard the supernatant, resuspend the cells with 20 ml ice-cold $ddH_2O$, centrifuge the cells at 4000 rpm for 10 min at 4° C., repeat this process for 4 times. Resuspend the cells using 1.5 ml $ddH_2O$ for the last time, dispense 80-100 uL to each sterile Eppendorf vials.
5. Adding 10 μl linearized fragment used for knock-out into the competent cells, rapidly mix and add into the electroporation cuvette, put the electroporation cuvette in the electropolator for electrotransformation, add 500 μl fresh LB immediately after electrotransformation, recover the cells at 37° C. for 1-2 h.
6. Centrifuge the cells at 4000 rpm and plate the cells onto a plate containing the appropriate antibiotic. Incubate plates at 37° C. overnight; identify the positive clone the next day.

(10) Elimination of the Antibiotics Gene from the Genome of *E coli*

1. Transform pCP20 into the strain that is ready to eliminate the antibiotics gene, culture at 30° C. overnight.
2. Pick the single clone from the transformation plate into Eppendorf tube containing fresh LB (no antibiotics), culture the cells at 37° C. for 8 h for heat induction;
3. Transfer the Eppendorf tube to 42° C. and grow overnight to remove pCP20 plasmid, plate little cells onto a plate containing no antibiotics and grow at 37° C. overnight.
4. Identify the positive clone using corresponding primers.

(11) Transformation of *Bacillus subtilis* WB800

1. Grow *Bacillus subtilis* WB800 in a 3 mL LB broth overnight.
2. Transfer 2.6 ml of the overnight culture to 40 ml medium (LB+0.5 M sorbic alcohol) and culture at 37° C. with 200 rpm shaking to OD600=0.85~0.95.
3. Incubate the cells on ice for 10 min; centrifuge the cells at 5000 g for 5 min to harvest the cells.

4. Resuspend the cells with 50 ml ice-cold transformation medium (0.5 Msorbic alcohol, 0.5 Mmannitol, 10% glucose), 4° C. centrifuge the cells at 5000 g for 5 min, discard the supernatant. Repeat this process for 4 times.
5. Resuspend the cells with 1 ml transformation medium; dispense 120 μL to each sterile Eppendorf vials.
6. Add 50 ng DNA (1~8 μl) into 60 μL of the competent cells, incubate on ice for 2 min, add the cells into pre-cooled transformation medium, pulse once.
7. remove the cuvette and immediately add 1 ml RM (LB+0.5 Msorbic alcohol+0.38 M mannitol) to the cuvette, incubate the cells at 37° C. with 200 rpm shaking for 3 h, plate aliquots of the cells on plate. Incubate the plate at 37° C. overnight.

Preparation of the Solutions:

40 ml (LB+0.5 M sorbic alcohol): typtone 10 g/l, yeast extract 5 g/l, NaCl 10 g/l, 3.6 g sorbic alcohol pH=7.2

10 ml RM (0.5 M M sorbic alcohol, 0.38 M mannitol): 0.9 g sorbic alcohol, 0.7 g mannitol.

Two 50 ml centrifuge tubes, 0.22 μM filter.

Example 1: Construction of *E. coli* Strains JM109 (DE3,sulA⁻,LexA⁻), JM109(DE3, sulA⁻,LexA⁻, CheZ⁻), JM109(DE3,sulA⁻,LexA⁻,ω⁻), and JM109 (DE3,sulA⁻,LexA::Amp-LV-L0)

The linearized fragment containing the homologous arm of sulA gene at the ends used in sulA gene knock-out was amplified from pKD3 plasmid by PCR using primer P1, P2, P3 and P4 (SEQ ID NO: 112). The knock-out of sulA gene was carried out on the basis of JM109(DE3) strain, the resulted transitional strain was JM109(DE3,sulA::Cam). The linearized fragment containing the homologous arm of LexA gene at the ends used in LexA gene knock-out was amplified from pKD4 plasmid by PCR using primer P5, P6, P7 and P8 (SEQ ID NO: 113). The knock-out of LexA gene was carried out on the basis of JM109 (DE3, sulA::Cam) transitional strain, the resulted transitional strain was JM109 (DE3, sulA::Cam,LexA::kan). The Cam and Kan resistance genes of JM109 (DE3,sulA::Cam,LexA::kan) strain were removed, resulting in JM109(DE3,sulA⁻,LexA⁻) strain.

The linearized fragment containing the homologous arm of CheZ gene at the ends used in CheZ gene knock-out (SEQ ID NO: 114) was amplified from pKD4 plasmid by PCR using primer P9, P10, P11 and P12. The linearized fragment containing the homologous arm of w gene at the ends used in w gene knock-out (SEQ ID NO: 115) was amplified from pKD4 plasmid by PCR using primer P9, P10, P11 and P12. The knock-out of CheZ and w genes were carried out on the basis of JM109(DE3,sulA⁻,LexA⁻) strain, resulting in JM109(DE3,sulA⁻,LexA⁻,CheZ::kan) and JM109(DE3, sulA⁻,LexA⁻,ω::kan) strains, respectively. The kan resistance gene in the genome of these two strains was removed, resulting JM109 (DE3,sulA⁻,LexA⁻,ω⁻) strain.

```
Primers for the amplification of the linearized
fragment used in sulA gene-knock:
Forward primer 1 (P1):
5'-TAACTCACAGGGGCTGGATTGATTGTGTAGGCTGGAGCTGCTT-3'

Forward primer 2 (P2):
5'-GATGTACTGTACATCCATACAGTAACTCACAGGGGCTGGATT-3'

Reverse primer 1 (P3):
5'-TTCCAGGATTAATCCTAAATTTACATGGGAATTAGCCATGGTC-3'

Reverse primer 2 (P4):
5'-CATTGGCTGGGCGACAAAAAAAGTTCCAGGATTAATCCTAAATT-3'
```

-continued

Primers for the amplification of the linearized
fragment used in LexA gene-knock:
Forward primer 1 (P5):
5'-CAACAAGAGGTGTTTGATCTCATCCTGAGCGATTGTGTAGGCTG-3'

Forward primer 2 (P6):
5'-GAAAGCGTTAACGGCCAGGCAACAAGAGGTGTTTGAT-3'

Reverse primer 1 (P7):
5'-ACGACAATTGGTTTAAACTCGCCATATGAATATCCTCCTTAG-3'

Reverse primer 2 (P8):
5'-GAAGCTCTGCTGACGAAGGTCAACGACAATTGGTTTAAACTC-3'

Primers for the amplification of the linearized
fragment used in CheZ gene-knock:
Forward primer 1 (P9):
5'-GGTCACGCCACATCAGGCAATACAAATGAGCGATTGTGTAGGCTG-3'

Forward primer 2 (P10):
5'-CTTATCAGACCGCCTGATATGACGTGGTCACGCCACATCAGGCAA-3'

Reverse primer 1 (P11):
5'-AACTGGGCATGTGAGGATGCGACTCATATGAATATCCTCCTTAG-3'

Reverse primer 2 (P12):
5'-AGGAAAAACTCAACAAAATCTTTGAGAAACTGGGCATGTGAGGATG-3'

Primers for the amplification of the linearized
fragment used in ω gene-knock:
Forward primer 1 (P13):
5'-GTAACCGTTTTGACCTGGTACTGTGAGCGATTGTGTAGGCTG-3'

Forward primer 2 (P14):
5'-AGGACGCTGTAGAGAAAATTGGTAACCGTTTTGACCTGGT-3'

Reverse primer 1 (P15):
5'-AATTCAGCGGCTTCCTGCTCTTGCATATGAATATCCTCCTTAG-3'

Reverse primer 2 (P16):
5'-GCAATAGCGGTAACGGCTTGTAATTCAGCGGCTTCCTGCTC-3'

To obtain the JM109(DE3,sulA⁻,LexA::Amp-LV-L0) containing said recombinant light-switchable transcription factor LV-L0 encoding cassette, pALV-L0 was amplified by PCR using primers P17 and P18, kan gene fragment containing kan resistance gene encoding cassette was amplified from pKD4 by PCR using primers P19, P20, P21 and P22, and inserted into the linearized pALV-L0 by the same double digestion, the resulting vector was named as pALV-L0-kan. Amp-LV-L0-kan fragment amplified from pALV-L0-kan by PCR using primers P23, P24, P25 and P26, the nucleotide sequence is SEQ. ID. No:116. The knock-out was carried out on the basis of JM109(DE3, sulA⁻) strain, resulting in JM109(DE3,sulA⁻,LexA::AmpLV-L0-kan) strain whose kan resistance was removed from its genome to obtain JM109(DE3,sulA⁻,LexA::Amp-LV-L0) strain.

Primers for the amplification of pALV-L0 vector:
Forward primer (P17):
5'-CCCCTCGAGCTGCCACCGCTGAGCAATAACT-3'

Reverse primer (P18):
5'-CCCGAATTCTCATTCCGTTTCGCACTGGAA-3'

Primers for the amplification of kan
resistance gene:
Forward primer (P19):
5'-CCCGAATTCGCGATTGTGTAGGCTGGAGCTGC-3'

Reverse primer 1 (P20):
5'-CTTTTGCTGTATATACTCATGAATATCCTCCTTAGTTC-3'

Reverse primer 2 (P21):
5'-GTTTATGGTTCCAAAATCGCCTTTTGCTGTATATACTCAT-3'

Reverse primer 3 (P22):
5'-GGGCTCGAGGTTTATTGTGCAGTTTATGGTTCCAAAATCG-3'

Primers for the amplification of pALV-L0-kan
vector:
Forward primer 1 (P23):
5'-ATTGGTTTAAACTCGCTATTTTCGTGCGCGGAACCCCTATTTG-3'

Forward primer 2 (P24):
5'-CTGCTGACGAAGGTCAACGACAATTGGTTTAAACTCGCTA-3'

Forward primer 3 (P25):
5'-GAAGCTCTGCTGACGAAGGTCAACG-3'

Reverse primer (P26):
5'-GTTTATTGTGCAGTTTATGGTTCCAAAATC-3'

Example 2 Construction of Prokaryotic Bacterium Expression Vectors Containing T7 Promoter Driven Expression of Different Linkers of LexA (1-87)-VVD36(C71V)

Figures 4, 5:
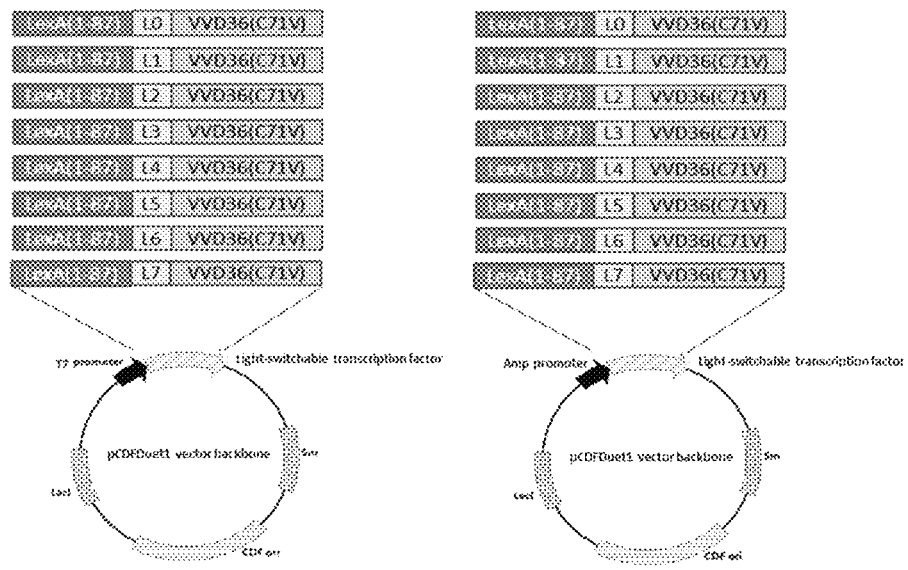
FIG. 4 is a schematic diagram of construction of T7 promoter driven expression of prokaryotic expression vectors containing the light-switchable transcription factors with different linkers. Top panel is schematic diagram of the light-switchable transcription factor fusion protein with different linkers. Bottom panel is schematic diagram of orbicular expression vectors, wherein the backbone of these vectors is pCDFDuet1.
FIG. 5 is a schematic diagram of construction of Amp promoter driven expression of prokaryotic expression vectors containing the light-switchable transcription factors with different linkers. Top panel is schematic diagram of the light-switchable transcription factor fusion protein with different linkers. Bottom panel is schematic diagram of orbicular expression vectors, wherein the backbone of these vectors is pCDFDuet1.

Gene fragment encoding 1-87 amino acid of LexA was amplified from the genome of JM109(DE3) using primers P27 and P28. VVD36 (C71V) gene fragment was amplified from pGAVP(C71V) plasmid (preserved by our lab, the corresponding paper: Wang, X. et al, Nat Methods, 2012.) using primers P29 and P30, LexA(1-87)-VVD36 (C71V) gene fragment was obtained by fusing LexA (1-87) to VVD36 (C71V) using overlaping PCR. pCDFDuet1 was amplified using P31 and P32, the obtained linearized vector was ligated with LexA(1-87)-VVD36(C71V) gene fragment by XhoI and EcoRI double digestion, the resulting vector was named as pLV-L0 containing the gene of recombinant light-switchable transcription factor LexA(1-87)-VVD36 (C71V) (abbreviated to LV-L0, SEQ. ID. No:48 (polynucleotide) and 49 (polypeptide)). On the basis of pLV-L0, the linker between LexA(1-87) and VVD36(C71V) was replaced using primers P33, P34, P35, P36, P37, P38, P39 and P40, the resulting plasmids containing seven different linkers (L1, L2, L3, L4, L5, L6 and L7) of the fusion protein LexA(1-87)-VVD36(C71V) were named as pLV-L1. pLV-L2, pLV-L3, pLV-L4, pLV-L5, pLV-L6 and pLV-L7, respectively (FIG. 4). The fusion protein polynucleotide encoding sequences are SEQ. ID. No: 50, 52, 54, 56, 58, 60 and 62; the amino acid sequences are SEQ. ID. No: 51, 53, 55, 57, 59, 61 and 63.

Primers for the amplification of LexA (1-87)
gene fragment:
Forward primer (P27):
5'-CCCCTCGAGCATGAAAGCGTTAAC-3'

Reverse primer (P28):
5'-CGGTTCACCGGCAGCCACACGACCTACCAG-3'

Primers for the amplification of VVD36 (C71V)
gene fragment:
Forward primer (P29):
5'-CTGCCGGTGAACCGCATACGCTCTACGCTCCCGGCG-3'

Reverse primer (P30):
5'-CCCGAATTCTCATTCCGTTTCGCACTGGAA-3'

-continued

Primers for the amplification of pCDFDuet1 vector:
Forward primer (P31):
5'-CCCGAATTCCTGCCACCGCTGAGCAATAACT-3'

Reverse primer (P32):
5'-GGGCTCGAGCCCTGGCTGTGGTGATGATGGTG-3'

Primers for changing the linkers of
LexA (1-87)-VVD36 (C71V):
The common reverse primer (P33):
5'-CGGTTCACCGGCAGCCACACGACCTACCAG-3'

Forward primer for linker 1 (P34):
5'-TGTCGTGGGCATACGCTCTACGCTCCCGGC-3'

Forward primer for linker 2 (P35):
5'-GTGTTTCATACGCTCTACGCTCCCGGC-3'

Forward primer for linker 3 (P36):
5'-TATAAGCATACGCTCTACGCTCCCGGC-3'

Forward primer for linker 4 (P37):
5'-GGATCCCATACGCTCTACGCTCCCGGC-3'

Forward primer for linker 5 (P38):
5'-GAACCTCATACGCTCTACGCTCCCGGC-3'

Forward primer for linker 6 (P39):
5'-CTGGCCGAGGCCGCTGCCCATACGCTCTACGCTCCCGGC-3'

Forward primer for linker 7 (P40):
5'-ACCGAGTTCCCCGGCGTGGACCAGCATACGCTCTACGCTCCCGGC-3'

Example 3 Construction of Prokaryotic Bacterium Expression Vectors Containing Amp Promoter Driven Expression of Different Linkers of LexA(1-87)-VVD36(C71V)

Amp promoter fragment was amplified from pRSETb vector by PCR using primers P41 and P42 (SEQ. ID. No:136 (polynucleotide)), pCDFDuet1 vector was amplified by PCR using P43 and P44, the obtained linearized fragment was ligated with Amp promoter fragment by NdeI and XhoI double digestion, the resulting plasmids was named as pAmp. LexA(1-87)-VVD36 (C71V) fragments containing different linkers constructed in example 2 were amplified using primers P45 and P46, the resulting LexA(1-87)-VVD36 (C71V) fragments containing different linkers were ligated into pAmp by NdeI and XhoI double digestion, the resulting plasmids were named as pALV-L0, pALV-L1, pALV-L2, pALV-L3, pALV-L4, pALV-L5, pALV-L6 and pALV-L7 containing the genes of recombinant protein LexA (1-87)-VVD36 (C71V) with eight different linkers (L0, L1, L2, L3, L4, L5, L6, L7) (FIG. 5, SEQ. ID. No: 48, 50, 52, 54, 56, 58, 60, 62 (polynucleotide) and 49, 51, 53, 55, 57, 59, 61, 63 (polypeptide)).

Primers for amplification of Amp promoter:
Forward primer (P41):
5'-GGCTGCAGGTGCGCGGAACCCCTATTTG-3'

Reverse primer (P42):
5'-GGCTCGAGTACTCATATGCTTCCTTTTTCAA-3'

Primers for amplification of pCDFDuet1 vector:
Forward primer (P43):
5'-GGCTGCAGGTGCGCGGAACCCCTATTTG-3'

Reverse primer (P44):
5'-GGCTCGAGTACTCATATGCTTCCTTTTTCAA-3'

Primers for amplification of LexA (87)-VVD36(C71V) containing different linkers:
Forward primer (P45):
5'-GATTCCATATGAAAGCGTTAACGGCC-3'

Reverse primer (P46):
5'-CCCCTCGAGTCATTCCGTTTCGCACTGGAA-3'

Figure 6:
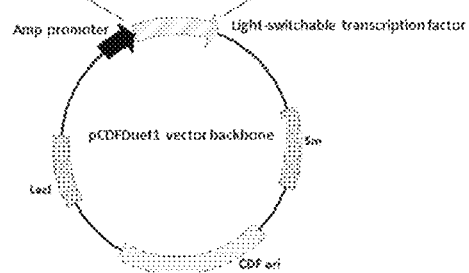
FIG. 6 is a schematic diagram of construction of prokaryotic expression vectors containing the light-switchable transcription factors with different VVD mutants, AsLOV2 or AuLOV as the second peptide. Top panel is schematic diagram of the light-switchable transcription factor fusion protein with different linkers. Bottom panel is schematic diagram of orbicular expression vectors, wherein the backbone of these vectors is pCDFDuet1.

Example 4 Construction of Prokaryotic Bacterium Expression Vectors Containing the Recombinant Light-Switchable Transcription Factor with Different VVD Mutants, Phot1-LOV2, and Aurochrome as the Second Polypeptide pALV-L0 vector was amplified by reverse PCR using primers P47 and P48, the resulting transitional vector was named as pALV-L0(wt). Prokaryotic bacterium expression vectors containing genes of the recombinant protein LexA (1-87)-VVD36 with VVD mutants N56K or Y50W or N56K C71V or I52A C71V or I52S C71V or N56R C71V were constructed by reverse PCR using primers P49 and P50, P51 and P52 for pALV-L0(wt) vector, P53 and P54, P55 and P56, P57 and P58, P59 and P60 for pALV-L0, the resulting vectors were named as pALV-L0 (N56K), pALV-L0 (Y50W), pALV-L0 (N56K C71V), pALV-L0 (I52A C71V), pALV-L0 (I52S C71V), and pALV-L0 (N56R C71V), respectively (FIG. 6, SEQ. ID. No: 64, 66, 68, 70, 72, 74, (polynucleotide) and 65, 67, 69, 71, 73, 75 (polypeptide)).

Primers for amplification of pALV-L0 (wt):
Forward primer (P47):
5'-GCTCTGATTCTGTGCGACCTGAAGC-3'

Reverse primer (P48):
5'-GCATGACGTGTCAACAGGTCCCAGTTC-3'

Primers for amplification of VVD36 (N56K) mutant:
Forward primer (P49):
5'-GAGGCCAAACCCCCAAGTAGAACTG-3'

Reverse primer (P50):
5'-TTCATAATCTGAATCAGATAGCCCAT-3'

Primers for amplification of VVD36 (Y50W) mutant:
Forward primer (P51):
5'-GCTGATTCAGATTATGAACAGGCC-3'

Reverse primer (P52):
5'-CAGCCCATAATGTCATAACCGCCGGG-3'

Primers for amplification of VVD36 (N56K C71V) mutant:
Forward primer (P53):
5'-GCTGATTCAGATTATGAAGAGGCCAAACC-3'

Reverse primer (P54):
5'-CAGCCCATAATGTCATAACCGCCGGGAG-3'

Primers for amplification of VVD36 (I52S C71V) mutant:
Forward primer (P55):
5'-TCCCAGATTATGAACAGGCCAAACCC-3'

Reverse primer (P56):
5'-CAGATAGCCCATAATGTCATAACCG-3'

Primers for amplification of VVD36 (I52A C71V) mutant:
Forward primer (P57):
5'-GCGCAGATTATGAACAGGCCAAACCC-3'

```
-continued
Reverse primer (P58):
5'-CAGATAGCCCATAATGTCATAACCG-3'

Primers for amplification of VVD36
(N56R C71V) mutant:
Forward primer (P59):
5'-GCCAAACCCCCAAGTAGAACTGGGAC-3'

Reverse primer (P60):
5'-CTGCGCATAATCTGAATCAGATAGC-3'
```

For constructing the expression vector containing light-switchable transcription factor with LOV2 domain of phototropin1 (abbreviated to AsLOV2, a kind gift from Gardner lab, The University of Texas at Dallas) as the second peptide, AsLOV2 gene fragment was amplified from cDNA using primers P61 and P62, LexA(1-87) gene fragment was amplified from pALV-L0 vector constructed in example 3 using primers P63 and P64, then AsLOV2 gene fragment and LexA(1-87) gene fragment were fused using overlapping PCR, the obtained recombinant gene fragment LexA(1-87)-AsLOV2 was ligated with pALV-L0 vector constructed in example 3 by NdeI and XhoI double digestion, the resulting vector was named as pALA containing recombinant protein LexA(1-87)-AsLOV2 (abbreviated to LA, SEQ. ID. No: 76 (polynucleotide) and 77 (polypeptide)).

```
Primers for amplification of AsLOV2 gene fragment:
Forward primer (P61):
5'-GCTGCCGGTGAACCGTCCTTCTTGGCTACTACACTTGAAC-3'

Reverse primer (P62):
5'-ACGGGCTCGAGAATAAGTTCTTTTGCCGCCTC-3'

Primers for amplification of LexA (1-87)
gene fragment:
Forward primer (P63):
5'-GATTCCATATGAAAGCGTTAACGGCC-3'

Reverse primer (P64):
5'-ATCGGTTCACCGGCAGCCACACGACCTAC-3'
```

For constructing the expression vector containing light-switchable transcription factor with LOV2 domain of aurochrome (abbreviated to AuLOV, a kind gift from Hironao Kataoka lab, Ritsumeikan University) as the second peptide, AuLOVgene fragment was amplified from cDNA using primers P65 and P66, and then was ligated with LexA(1-87) in this example using overlapping PCR, the obtained recombinant gene fragment LexA(1-87)-AsLOV2 was ligated with pALV-L0 vector constructed in example 3 by NdeI and XhoI double digestion, the resulting vector was named as pALAu containing recombinant protein LexA(1-87)-AuLOV (abbreviated to LAu, SEQ. ID. No: 78 (polynucleotide) and 79 (polypeptide)).

```
Forward primer (P65):
5'-GCTGCCGGTGAACCGTCCTTCTTGGCTACTACACTTGAAC-3'

Reverse primer (P66):
5'-CTACTACACACACGAAGTTCTTTTGCCGCCTC-3'
```

Figure 7:
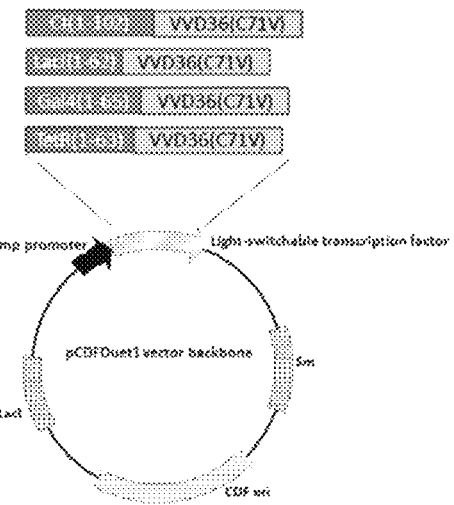
FIG. 7 is a schematic diagram of construction of prokaryotic expression vectors containing the light-switchable transcription factors with cI, LacI, Gal4 or TetR as the first peptide. Top panel is schematic diagram of the light-switchable transcription factor fusion protein with different linkers. Bottom panel is schematic diagram of orbicular expression vectors, wherein the backbone of these vectors is pCDFDuet1.

Example 5 Construction of Prokaryotic Bacterium Expression Vectors Containing the Light-Switchable Transcription Factors with cI, LacI, Gal4, and TetR as the First Polypeptide For constructing the expression vector containing light-switchable transcription factor with cI(1-102) as the first polypeptide, cI(1-102) gene fragment was amplified from the genome of λ phage by PCR using primers P67 and P68, the obtained fragment was ligated with pALV-L4 by NdeI and BamHI double digestion, the resulting vector was named as pACV containing recombinant light-switchable transcription factor with cI as the first peptide (FIG. 7), the corresponding recombinant light-switchable transcription factor was abbreviated to CV, whose polynucleotide and polypeptide sequence are SEQ. ID. No: 80 and SEQ. ID. No: 81, respectively.

```
Primers for amplification of cI (1-102):
Forward primer (P67):
5'-GGCGCATATGTCTACCAAGAAGAAACC-3'

Reverse primer (P68):
5'-CCCGGATCCATATTCTGACCTCAAAGACG-3'
```

For constructing the expression vector containing light-switchable transcription factor with lad (1-62) as the first polypeptide, the gene fragment of DNA binding domain (1-62 amino acid) was amplified from pCDFDuet1 vector (Novagen company) using primers P69 and P70 and ligated with pALV-L4 by NdeI and BamHI double digestion, the resulting transitional vector was named as pALaV(wt). pALaV (wt) was then amplified from pALaV (wt) vector by PCR using primers P71 and P72, the linearized vector fragment was phosphorylated and ligated to obtain the expression vector named as pALaV containing the recombinant light-switchable transcription factor with Lad (1-62) as the first peptide (FIG. 7), the corresponding recombinant light-switchable transcription factor was abbreviated to LaV, whose polynucleotide and polypeptide sequence are SEQ. ID. No: 82 and SEQ. ID. No: 83, respectively.

```
Primers for amplification of LacI (1-62):
Forward primer (P69):
5'-GGCGCATATGAAACCAGTAACGTTATAC-3'

Reverse primer (P70):
5'-CCCGGATCCCAACGACTGTTTGCCCGCC-3'

Primers for amplification of pALaV vector:
Forward primer (P71):
5'-CGTTTCCAACGTGGTGAACCAGGCC-3'

Reverse primer (P72):
5'-CGTTTCCAACGTGGTGAACCAGGCC-3'
```

For constructing the expression vector containing light-switchable transcription factor with Gal4(1-65) as the first polypeptide, gene fragment of Gal4(1-65) DNA binding domain was amplified from pBIND vector (Promega company) using primers P73 and P74, the obtained fragment was ligated with pALV-L4 by NdeI and BamHI double digestion, the resulting vector was named as pAGV containing recombinant light-switchable transcription factor with Gal4(1-65) as the first peptide (FIG. 7), the corresponding recombinant light-switchable transcription factor was abbreviated to GV, whose polynucleotide and polypeptide sequence are SEQ. ID. No: 84 and SEQ. ID. No: 85, respectively.

```
Primers for amplification of Gal4 (1-65):
Forward primer (P73):
5'-GGCGCATATGAAGCTACTGTCTTCTATC-3'

Reverse primer (P74):
5'-CCCGGATCCTTCCAGTCTTTCTAGCCTTG-3'
```

For constructing the E. coli expression vector containing light-switchable transcription factor with TetR(1-63) as the first polypeptide, gene fragment of TetR DNA binding domain (1-63 amino acid) synthesized by Shanghai Generay Biotech Co. Ltd. was amplified by PCR using primers P75 and P76, and then was ligated with pALV-L4 by NdeI and BamHI double digestion, the resulting vector was named as pATV containing recombinant light-switchable transcription factor with TetR(1-63) as the first peptide (FIG. 7), the corresponding recombinant light-switchable transcription factor was abbreviated to TV, whose polynucleotide and polypeptide sequence are SEQ. ID. No: 86 and SEQ. ID. No: 87, respectively.

```
Primers for amplification of TetR (1-63):
Forward primer (P75):
5'-GGCGCATATGTCTAGGCTAGATAAGAG-3'

Reverse primer (P76):
5'-CCCGGATCCGTGTCTATCCAGCATCTCG-3'
```

Figure 8:
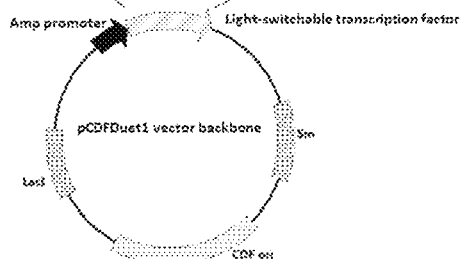
FIG. 8 is a schematic diagram of construction of prokaryotic expression vectors containing the light-switchable transcription factors with co as the third peptide. Top panel is schematic diagram of the light-switchable transcription factor fusion protein with different linkers. Bottom panel is schematic diagram of orbicular expression vectors, wherein the backbone of these vectors is pCDFDuet1.

Example 6 Construction of Prokaryotic Bacterium Expression Vectors Containing the Light-Switchable Transcription Factors with ω and α as the Third Polypeptide ω gene fragment was amplified from the genome of BL21(DE3) using primers P77 and P78, w-linker gene fragment was amplified by overlapping PCR using primers P77, P79 and P80, LV-L0 gene fragment was amplified from pALV-L0 constructed in example 3 using primers P81 and P82, the gene fragment of recombinant protein ω-linker-LV-L0 (abbreviated to ωAX, SEQ. ID. No:90 (polynucleotide) and SEQ. ID. No:91 (polypeptide)) was obtained by fusing ω-linker to LV-L0 gene fragment by overlapping PCR, and then was ligated with pALV-L0 vector constructed in example 3 by NdeI and XhoI double digestion, the resulting vector was named as pAωLV. CV, LaV, GV and TV gene fragments were amplified from pACV, pALaV, pAGV and pATV vectors constructed in example 5 using primers P82 and P83, P82 and P84, P82 and P85, P82 and P86, and then were ligated with pAωLV vector by SpeI and XhoI double digestion, the resulting plasmids were named as pAωCV, pAωLaV, pAωGV and pAωTV, respectively (FIG. 8). These recombinant transcription factors were abbreviated to ωCV, ωLaV, ωGV and ωTV respectively, the polynucleotide sequences are SEQ. ID. No: 94, 98, 102, 106 and polypeptide sequences are SEQ. ID. No: 95, 99, 103 and 107.

```
Primers for amplification of ω gene fragment:
Forward primer 1 (P77):
5'-GCGGCATATGGCACGCGTAACTGTTC-3'

Reverse primer 2 (P78):
5'-TCCTTGTAGTCCGCGGCCGCACGACCTTCAGCAATAG-3'

Primers for amplification of ω-linker gene
fragment:
Forward primer (P79):
5'-CATGGGGGGTGTCTTGGAACCGGTCCGGAACTTGTCGTCGTC

ATCCTTGTAGTCCGCG-3'

Reverse primer 2 (P80):
5'-CGTTAACGCTTTCATACTAGTGTGGGGGGTGTCTTGG-3'

Primers for amplification of LV-L0 gene fragment:
Forward primer (P81):
5'-ATGAAAGCGTTAACGGCCAGGCAAC-3'
```

```
Reverse primer (P82):
5'-CCCGAATTCTCATTCCGTTTCGCACTGGAA-3'

Primers for amplification of CV, LaV, GV and
TV gene fragments:
Forward primer (P83):
5'-GGGACTAGTATGAGCACAAAAAAGAAACC-3'

Forward primer (P84):
5'-GGGACTAGTATGAAACCAGTAACGTTA-3'

Forward primer (P85):
5'-CCCACTAGTATGAAGCTACTGTCTTCTATC-3'

Forward primer (P86):
5'-CCCACTAGTATGTCTAGGCTAGATAAGAGC-3'
```

Figure 9:
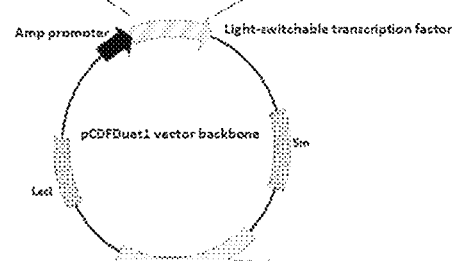
FIG. 9 is a schematic diagram of construction of prokaryotic expression vectors containing the light-switchable transcription factors with a as the third peptide. Top panel is schematic diagram of the light-switchable transcription factor fusion protein with different linkers. Bottom panel is schematic diagram of orbicular expression vectors, wherein the backbone of these vectors is pCDFDuet1.

For construction of prokaryotic bacterium expression vectors containing the light-switchable transcription factors with a as the third polypeptide, LV-L0 gene fragment was amplified from pALV-L0 vector constructed in example 3 using primers P87 and P88, LV-L0-linker was obtained by overlapping PCR using primers P87, P79 and P89, α gene fragment was amplified from the genome of BL21(DE3) using primers P90 and P91, LV-L0-linker gene fragment and a gene fragment were fused by overlapping PCR to obtain LV-L0-linker-α gene fragment (abbreviated to LVα, SEQ. ID. No:88 (polynucleotide) and 89 (polypeptide)) which was ligated with pALV-L0 vector by NdeI and XhoI double digestion, the resulting vector was named as pALVα. CV, LaV, GV and TV gene fragments were amplified from pACV, pALaV, pAGV and pATV vectors constructed in example 5 using primers P88 and P92, P88 and P93, P88 and P94, P88 and P95, and then were ligated with pALVα vector by NdeI and SpeI double digestion, the resulting plasmids were named as pACVα, pALaVα, pAGVα and pATVα, respectively (FIG. 9). These recombinant transcription factors were abbreviated to CVα, LaVα, GVα and TVα respectively, the polynucleotide sequences are SEQ. ID. No: 92, 96, 100, 104 and polypeptide sequences are SEQ. ID. No: 93, 97, 101 and 105.

```
Primers for amplification of LV-L0 gene fragment:
Forward primer 1 (P87):
5'-GATTCCATATGAAAGCGTTAACGGCC-3'

Reverse primer 2 (P88):
5'-CCTTGTAGTCCGCGGCCGCACTAGTTTCCGTTTCGCACTGGAA-3'

Primers for amplification of LV-L0-linker
gene fragment:
Reverse primer (P89):
5'-CCTGCATGGTACCGTGGGGGGGTGTCTTGGA-3'

Primers for amplification of α gene fragment:
Forward primer 1 (P90):
5'-CATGGTACCATGCAGGGTTCTGTGACAGAG-3'

Reverse primer 2 (P91):
5'-GCCCTCGAGTTACTCTGGTTTCTCTTCTTTC-3'

Primers for amplification of CV, LaV, GV and
TV gene fragments:
Forward primer (P92):
5'-GGGCATATGAGCACAAAAAAGAAACC-3'

Forward primer (P93):
5'-GGGCATATGAAACCAGTAACGTTA-3'

Forward primer (P94):
5'-CCCCATATGAAGCTACTGTCTTCTATC-3'

Forward primer (P95):
5'-CCCCATATGTCTAGGCTAGATAAGAGC-3'
```

Example 7 Construction of Prokaryotic Bacterium Expression Vectors Containing Target Transcription Units with the Reaction Elements of LexA, cI, LacI, Gal4 and TetR To detect the effect of recombinant light-switchable transcription factor with LexA as the first peptide on the transcriptional regulation of mCherry fluorescent protein and LacZ β galactosidase genes, prokaryotic bacterium expression vector containing the target transcription unit with LexA reaction element and fluorescent protein reporter gene was constructed. colE promoter fragment was amplified by overlapping PCR using primers P96, P97, P98, P99 and P100; mCherry gene fragment was amplified from pU5-mCherry vector (preserved by our lab, the corresponding paper: Wang, X. et al, Nat Methods, 2012.) using primers P101 and P102. rrnB transcription termination fragment was amplified from pBAD/His A vector by PCR using primiers P103 and P104; there three fragments were amplified by overlapping PCR to obtain colE-mCherry-rrnB gene fragment. pRSETb vector was amplified by primers P105 and P106, the obtained linearized fragment was ligated with colE-mCherry-rrnB gene fragment by BamHI and XhoI double digestion, the resulting transitional plasmid was amplified by primers P107 and P108, the obtained linearized fragment was digested by KpnI and NheI and then ligated with rrnB fragment amplified by primers P109 and P110, the resulting prokaryotic bacterium expression vector pB-colE-mCherry contains the target transcription unit with LexA reaction element and mCherry fluorescent protein reporter gene, the polynucleotide sequence is SEQ. ID. No:117. LacZ gene was amplified from the genome of BL21(DE3) using primers P111 and P112, pB-colE-mCherry vector was amplified using primers P113 and P114, the obtained LacZ gene fragment and linearized pB-colE-mCherry fragment were ligated after HindIII and BglII double digestion, the resulting prokaryotic bacterium expression vector pB-colE-LacZ contains the target transcription unit with LexA reaction element and LacZ 13 galactosidase gene, the polynucleotide sequence is SEQ. ID. No:118. sulA, RecA and umuDC fragments were amplified from the genome of JM109(DE3) strain using primers P115 and P116, P117 and P118, P119 and P120, and then were fused with mCherry gene fragment obtained in this sample, the resulting fragments sulA-mCherry, RecA-mCherry and umuDC-mCherry were ligated with pB-colE-mCherry by BamHI and EcoRI double digestion to generate other three prokaryotic bacterium expression vectors pB-sulA-mCherry, pB-umuDC-mCherry and pB-RecA-mCherry containing the target transcription unit with LexA reaction element and mCherry fluorescent protein gene, respectively (FIG. 10), the corresponding polynucleotide sequences are SEQ. ID. No:119, 120 and 121.

Primers for amplification of colE promoter fragment:
Forward primer 1(P96):
5'-GATCGTTTTCACAAAAATGGAAGTCCACAGTCTTGACAGGGAAAA

TGCAGCGGCGTAG-3'

Forward primer 2 (P97):
5'-GGGGATCCTGTTTTTTTGATCGTTTTCACAAAAAT-3'

Reverse primer 1 (P98):
5'-TATAAAATCCTCTTTGACTTTTAAAACAATAAGTTAAAAATAAATA

CTGTACATATAAC-3'

Reverse primer 2(P99):
5'-CGCCCTTGCTCACCATTATAAAATCCTCTTTGAC-3'

Reverse primer 3(P100):
5'-CGCCCTTGCTCACCATTATAAAATCCTCTTTGAC-3'

Primers for amplification of mCherry gene fragment:
Forward primer (P101):
5'-ATGGTGAGCAAGGGCGAGGAGCTGTTC-3'

Reverse primer (P102):
5'-GGGGAATTCTTACTTGTACAGCTCGTCCAT-3'

Primers for amplification of rrnB transcription terminator:
Forward primer (P103):
5'-CAAGTAAGAATTCCCCCTGTTTTGGCGGATGAGAG-3'

Reverse primer (P104):
5'-CAAGTAAGAATTCCCCCTGTTTTGGCGGATGAGAG-3'

Primers for amplification of pRSET vector:
Forward primer (P105):
5'-GACCTCGAGCGCAGCCTGAATGGCGAATG-3'

Reverse primer (P106):
5'-CGGGATCCATTTCGCGGGATCGAGATC-3'

Primers for amplification of the transitional vector:
Forward primer (P107):
5'-CCCGCTAGCGGATCCATAGGGTTGATCTT-3'

Reverse primer (P108):
5'-GGGGGTACCATTTCGCGGGATCGAGA-3'

Primers for amplification of rrnB transcription terminator:
Forward primer (P109):
5'-CCCGGTACCCCCCTGTTTTGGCGGATGAGAG-3'

Reverse primer (P110):
5'-CCCGCTAGCGCAAACAACAGATAAAACGAAA-3'

Primers for amplification of LacZ gene:
Forward primer (P111):
5'-CCCAAGCTTATGGTCGTTTTACAACGTCGTG-3'

Reverse primer (P112):
5'-CCTAGATCTTTATTTTTGACACCAGACCAAC-3'

Primers for amplification of pB-colE-mCherry vector:
Forward primer (P113):
5'-CCCAGATCTCCCCTGTTTTGGCGGATGAGAGAAG-3'

Reverse primer (P114):
5'-CCCAAGCTTATCCTCTTTGACTTTTAAAACAAT-3'

Primers for amplification of sulA promoter:
Forward primer (P115):
5'-CCCGGATCCATAGGGTTGATCTTTGTTG-3'

Reverse primer (P116):
5'-GCCCTTGCTCACCATAATCAATCCAGCCCCTGTG-3'

Primers for amplification of RecA promoter:
Forward primer (P117):
5'-CCCGGATCCCAATTTCTACAAAACACTTGATACT-3'

Reverse primer (P118):
5'-CGCCCTTGCTCACCATTTTTACTCCTGTCATGCCGGG-3'

Primers for amplification of umuDC promoter:
Forward primer (P119):
5'-CCCGGATCCGCCTATGCAGCGACAAATATT-3'

Reverse primer (P120):
5'-CGCCCTTGCTCACCATAATAATCTGCCTGAAGTTATA-3'

To detect the effect of recombinant light-switchable transcription factor with cI as the first peptide on the transcriptional regulation of mCherry fluorescent protein gene, prokaryotic bacterium expression vector containing the target transcription unit with cI reaction element and fluorescent protein reporter gene was constructed. $P_{\lambda O12}$ promoter fragment was amplified by overlapping PCR using primers P121, P122, P123, P124 and P125, mCherry fragment was amplified from pB-colE-mCherry vector using primers P126 and P127, $P_{\lambda O12}$-mCherry gene fragment was obtained by fusing $P_{\lambda O12}$ promoter fragment to mCherry gene fragment using overlapping PCR, and then was ligated with pB-colE-mCherry vector by BamHI and EcoRI double digestion, the resulting prokaryotic bacterium expression vector pB-$P_{\lambda O12}$-mCherry contains the target transcription unit with cI reaction element and mCherry fluorescent protein gene (FIG. 10), the polynucleotide sequence is SEQ. ID. No:122.

```
Primers for amplification of P<sub>λO12</sub> promoter:
Forward primer 1 (P121):
5'-TATCTAACACCGTGCGTGTTGACTATTTTACCTCTG-3'

Forward primer 2 (P122):
5'-CCCGGATCCTATCTAACACCGTGCGTG-3'

Reverse primer 1 (P123):
5'-GCAACCATTATCACCGCCAGAGGTAAAATAGT-3'

Reverse primer 2 (P124):
5'-AGTACCTCCTTAGTACATGCAACCATTATCACCG3'

Reverse primer 3 (P125):
5'-GCCCTTGCTCACCATACTAGTACCTCCTTAGTAC-3'

Primers for amplification of mCherry gene
fragment:
Forward primer (P126):
5'-ATGGTGAGCAAGGGCGAGGAGCTGTTC-3'

Reverse primer (P127):
5'-GGGGAATTCTTACTTGTACAGCTCGTCCAT-3'
```

Figure 10:
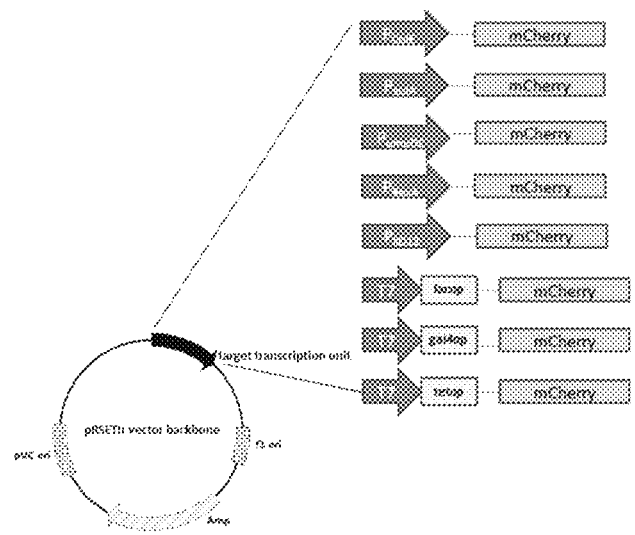
FIG. 10 is a schematic diagram of construction of prokaryotic expression vectors containing the target transcription units corresponding to LexA, cI, LacI, Gal4 or TetR. Top panel is a schematic diagram of respective target transcription units, and the bottom panel is a schematic diagram of orbicular expression vectors. The backbone of these vectors is pRSETb.

To detect the effect of recombinant light-switchable transcription factor with LacI, Gal4 or TetR as the first peptide on the transcriptional regulation of mCherry fluorescent protein gene, prokaryotic bacterium expression vector containing the target transcription unit with LacI, Gal4 or TetR reaction element and fluorescent protein reporter gene was constructed. T7 promoter-lac operator fragment was amplified from pCDFDuet1 vector using primers P128 and P129, the obtained fragment was ligated with pB-$P_{\lambda O12}$-mCherry vector by BamHI and SpeI double digestion, the resulting transitional vector was named as pB-T7lacop-mCherry (wt). pB-T7lacop-mCherry(wt) vector was amplified by PCR using primers P130 and P131, P132 and P133, P134 and P135, the obtained linearized vector fragments were phosphorylated by T4 PNK and ligated to obtain the prokaryotic expression vectors pB-T7lacop-mCherry, pB-T7galop-mCherry, pB-T7tetop-mCherry containing the target transcription unit with LacI, Gal4 or TetR reaction element, respectively (FIG. 10). The polynucleotide sequences are SEQ. ID. No:123, 124, 125.

```
Primers for amplification of T7 promoter-lac
operator:
Forward primer (P128):
5'-CCCGGATCCGGAAATTAATACGACTCACTA-3'

Reverse primer (P129):
5'-GGGACTAGTTCTCCTTATTAAAGTTAAAC-3'

Primers for amplification of the vector containing
the target transcription unit with LacI reaction
element:
Forward primer (P130):
5'-CTAAAAATTCCCCTGTAGAAATAATTTTGTT-3'

Reverse primer (P131):
5'-CGCTAAAAATTCCCCTATAGTGAGTCGTATTA-3'

Primers for amplification of the vector containing
the target transcription unit with Gal4 reaction
element:
Forward primer (P132):
5'-GTCCTCCGCCCCTGTAGAAATAATTTTGT-3'

Reverse primer (P133):
5'-AGTACTCCGCCCCTATAGTGAGTCGTATTAA-3'

Primers for amplification of the vector containing
the target transcription unit with TetR reaction
element:
Forward primer (P134):
5'-TGATAGAGACCCCTGTAGAAATAATTTTG-3'

Reverse primer (P135):
5'-CTGATAGGGACCCCTATAGTGAGTCGTATTAA-3'
```

Figures 11, 12:
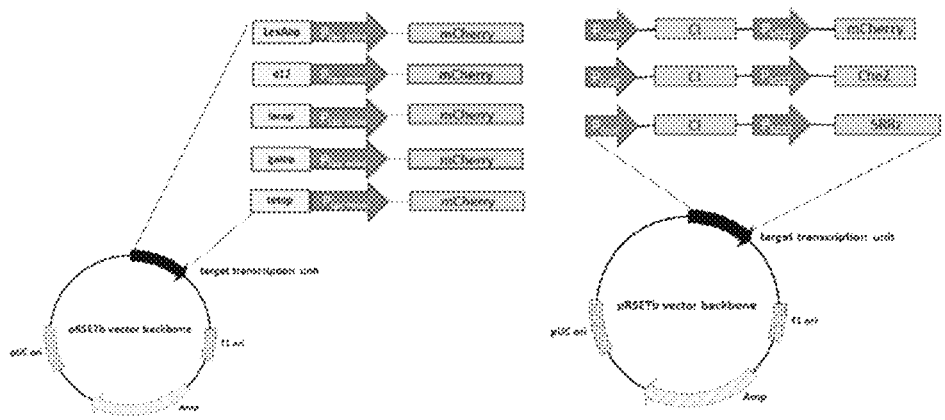
FIG. 11 is a schematic diagram of construction of prokaryotic expression vectors containing the target transcription units corresponding to LexA, cI, LacI, Gal4 or TetR regulated by the recombinant light-switchable transcription factors with co or a as the third peptide. Top panel is a schematic diagram of respective target transcription units, and the bottom panel is a schematic diagram of orbicular expression vectors. The backbone of these vectors is pRSETb.
FIG. 12 is a schematic diagram of construction of prokaryotic expression vectors using cI repressor for the indirect regulation. Top panel is a schematic diagram of respective target transcription units, and the bottom panel is a schematic diagram of orbicular expression vectors. The backbone of the vector is pRSETb.

Example 8 Construction of Prokaryotic Bacterium Expression Vectors Containing the Target Transcription Units with the Reaction Elements of LexA, cI, LacI, Gal4 or TetR and mCherry Fluorescent Protein Gene Corresponding to Recombinant Light-Switchable Transcription Factor with LexA, cI, LacI, Gal4 and TetR as the First Peptide, with ω and α as the Third Peptide For construction of prokaryotic bacterium expression vectors containing the target transcription unit of the light-switchable transcription factors with ω and α as the third polypeptide, lac minimal promoter was amplified using primers P136, P137 and P138, pB-colE-mCherry constructed in example 7 was amplified using primers P139 and P140, the linearized fragment was ligated with lac minimal promoter by BamHI and HindIII double digestion, the resulting transitional vector was named as pB-lac-mCherry. pB-lac-mCherry vector was amplified using primers P141 and P142, P143 and P144, P145 and P146, P147 and P148, P149 and P150, the obtained linearized fragment was phosphorylated and ligated to generate prokaryotic bacterium expression vectors containing the target transcription units with the reaction elements and mCherry fluorescent protein gene corresponding to recombinant light-switchable transcription factor with LexA, cI, lacI, Gal4 and TetR as the first peptide, with ω and α as the third peptide, these vectors were named as pB-lexAop-lac-mCherry, pB-o12-lac-mCherry, pB-lacop-lac-mCherry, pB-galop-lac-mCherry and pB-tetop-lac-mCherry (FIG. 11), the target transcription unit sequences are SEQ. ID. No:126, 127, 128, 129 and 130.

```
Primers for amplification of lac minimal promoter:
Forward primer 1 (P136):
5'-AGGCACCCCGGGCTTTACACTTTATGCTTCCGGCTCGTATGTTG
TGTCGACCGAGCGGAT-3'

Forward primer 2 (P137):
5'-CCGGATCCCATTAGGCACCCCGGGCTTTACA-3'

Reverse primer (P138):
5'-CCAAGCTTTTCCTGTGTGAAAGTCTTATCCGCTCGGTCGAC-3'
```

-continued
Primers for amplification of pB-colE-mCherry vector:
Forward primer (P139):
5'-CCCAAGCTTATGGTGAGCAAGGGCGAGGAG-3'

Reverse primer (P140):
5'-ACAGGATCCGCTAGCGCAAACAACAGATAAAAC-3'

Primers for PCR amplification of pB-lac-mCherry vector to generate the prokaryotic bacterium plasmids containing LexA target transcription unit:
Forward primer (P141):
5'-GTTATATGTACAGTACCATTAGGCACCCCGGGCTTT-3'

Reverse primer (P142):
5'-CACTGGTTTTATATACAGGGATCCGCTAGCGCAAACAA-3'

Primers for PCR amplification of pB-lac-mCherry vector to generate the prokaryotic bacterium plasmids containing cI target transcription unit:
Forward primer (P143):
5'-TATTTTACCTCTGGCGGTGATAATGCATTAGGCACCCCGGGCTTT-3'

Reverse primer (P144):
5'-GTCAACACGCACGGTGTTAGATAGGATCCGCTAGCGCAAACAA-3'

Primers for PCR amplification of pB-lac-mCherry vector to generate the prokaryotic bacterium plasmids containing lacI target transcription unit:
Forward primer (P145):
5'-GCTCACAATTCATTAGGCACCCCGGGCTTT-3'

Reverse primer (P146):
5'-GCTCACAATTGGATCCGCTAGCGCAAACAA-3'

Primers for PCR amplification of pB-lac-mCherry vector to generate the prokaryotic bacterium plasmids containing Gal4 target transcription unit:
Forward primer (P147):
5'-CGGAGTACTGTCCTCCGCATTAGGCACCCCGGGCTTT-3'

Reverse primer (P148):
5'-CTCGGAGGACAGTACTCCGGGATCCGCTAGCGCAAACAA-3'

Primers for PCR amplification of pB-lac-mCherry vector to generate the prokaryotic bacterium plasmids containing TetR target transcription unit:
Forward primer (P149):
5'-CTCCCTATCAGTGATAGAGACATTAGGCACCCCGGGCTTT-3'

Reverse primer (P150):
5'-CTCTCTATCACTGATAGGGAGGATCCGCTAGCGCAAACAA-3'

Example 9 Construction of Prokaryotic Bacterium Expression Vectors Containing cI Repressor for the Indirect Regulation For construction of prokaryotic bacterium expression vectors containing cI repressor for the indirect regulation, rrnB-colE-mCherry gene fragment obtained in example 7 was amplified using primers P151 and P152, pRSETb vector was amplified using primers P153 and P154, The obtained linearized fragment was ligated with rrnB-colE-mCherry gene fragment by KpnI and BglII double digestion to generate the transitional vector pB-rrnB-colE-mCherry. ColE promoter was amplified using primers P155 and P156, cI gene fragment (SEQ. ID. No:131 (polynucleotide) and 132 (polypeptide)) was amplified from the genome of λ phage using primers P157 and P158, colE-cI fragment was obtained by overlapping PCR and ligated with pB-rrnB-colE-mCherry vector by BamHI and BglII double digestion to generate the transitional vector pB-rrnB-colE-cI. P$\lambda_{O12}$ promoter fragment was amplified by overlapping PCR using primers P159, P160, P161, P162 and P163, mCherry fragment was amplified from pB-colE-mCherry vector using primers P164 and P165, rrnB transcription terminator fragment was amplified using primers P166 and P167, P$\lambda_{O12}$-mCherry-rrnB gene fragment was obtained by overlapping PCR. pB-rrnB-colE-mCherry constructed in this sample was amplified using primers P168 and P169, the obtained linearized fragment was ligated with P$\lambda_{O12}$-mCherry-rrnB by SacI and XhoI double digestion to generate the indirect regulation vector pB-colE-cI-P$\lambda_{O12}$-mCherry (FIG. 12), the polynucleotide sequence of the target transcription unit is SEQ. ID. No:133.

Primers for amplification of rrnB-colE-mCherry gene fragment:
Forward primer (P151):
5'-CCCGGTACCCCCCTGTTTTGGCGGATGAGAG-3'

Reverse primer (P152):
5'-GGGAGATCTTTACTTGTACAGCTCGTCCAT-3'

Primers for amplification of pRSETb vector:
Forward primer (P153):
5'-CGAAGCTTGAAGATCTGCTTGATCCGGCTGCAAAC-3'

Reverse primer (P154):
5'-GGGGGTACCATTTCGCGGGATCGAGA-3'

Primers for amplification of colE promoter:
Forward primer (P155):
5'-GGGGATCCTGTTTTTTTGATCGTTTTCACAAAAAT-3'

Reverse primer (P156):
5'-TATAAAATCCTCTTTGACTTTTAAA-3'

Primers for amplification of cI gene fragment:
Forward primer (P157):
5'-AAAGAGGATTTTATAATGAGCACAAAAAAGAAACC-3'

Reverse primer (P158):
5'-GGGAGATCTTTAGCCAAACGTCTCTTCAGG-3'

Primers for amplification of P$\lambda_{O12}$ promoter:
Forward primer 1 (P159):
5'-TATCTAACACCGTGCGTGTTGACTATTTTACCTCTG-3'

Forward primer 2 (P160):
5'-CCCGAGCTCTATCTAACACCGTGCGTG-3'

Reverse primer 1 (P161):
5'-GCAACCATTATCACCGCCAGAGGTAAAATAGT-3'

Reverse primer 2 (P162):
5'-AGTACCTCCTTAGTACATGCAACCATTATCACCG-3'

Reverse primer 3 (P163):
5'-GCCCTTGCTCACCATACTAGTACCTCCTTAGTAC-3'

Primers for amplification of mCherry gene fragment:
Forward primer (P164):
5'-ATGGTGAGCAAGGGCGAGGAGCTGTTC-3'

Reverse primer (P165):
5'-GGGGAATTCTTACTTGTACAGCTCGTCCAT-3'

Primers for amplification of rrnB transcription terminator:
Forward primer (P166):
5'-CAAGTAAGAATTCCCCCTGTTTTGGCGGATGAGAG-3'

Reverse primer (P167):
5'-GGGCTCGAGCAAACAACAGATAAAACGAAAGG-3'

```
-continued
Primers for amplification of pB-rrnB-colE-mCherry
vector:
Forward primer (P168):
5'-GACCTCGAGCGCAGCCTGAATGGCGAATG-3'

Reverse primer (P169):
5'-CAGGAGCTCCAACTGTTGGGAAGGGCGATC-3'
```

For construction of prokaryotic bacterium expression vectors containing cI repressor for the indirect regulation and CheZ or SRRz gene cassette as the reporter gene, CheZ gene and SRRz gene cassette were amplified from the genome of JM109(DE3) and λ phage using primers P170 and P171, P172 and P173, respectively, the obtained gene fragments were ligated with pB-colE-cI-$P_{\lambda O12}$-mCherry constructed in this sample by SpeI and EcoRI double digestion to generate the indirect regulation vectors pB-colE-cI-$P_{\lambda O12}$-CheZ and pB-colE-cI-$P_{\lambda O12}$-SRRz (FIG. 12), the polynucleotide sequences of the target transcription unit are SEQ. ID. No:134 and 135.

```
Primers for amplification of CheZ gene fragment:
Forward primer (P170):
5'-CCCACTAGTATGATGCAACCATCAATCAAACCTG-3'

Reverse primer (P171):
5'-GGGGAATTCTCAAAATCCAAGACTATCCAA-3'

Primers for amplification of SRRz gene cassette:
Forward primer (P172):
5'-CCCACTAGTATGAAGATGCCAGAAAAACATGACC-3'

Reverse primer (P173):
5'-CCCGAATTCTAGGCATTTATACTCCGCTGGA-3'
```

For large scale production of sulfhydryl oxidase Ero1 using the light-switchable gene expression system of prokaryotic bacterium, the vector containing the indirect regulation of cI and Ero1 as the reporter gene, Ero1(56-424) gene fragment was amplified from the genome of *Saccharomyces cerevisiae* BY4741 using primers P174 and P175, and was then ligated with pB-colE-cI-$P_{\lambda O12}$-mCherry constructed in this sample by SpeI and EcoRI double digestion to generate the indirect vector pB-colE-cI-$P_{\lambda O12}$-Ero1, the polynucleotide and polypeptide sequences of Ero1(56-424) are SEQ. ID. No:46 and 47.

```
Primers for amplification of Ero1 (56-424) gene
fragment:
Forward primer (P174):
5'-CCCACTAGTATGTTCAATGAATTAAATGC-3'

Reverse primer (P175):
5'-CCCGAATTCTTATAACCTTTTCCCGTAC-3'
```

Example 10 Construction of Single Expression Vector Containing Light-Switchable Transcription Factor and Target Transcription Unit For construction of single expression vector containing both light-switchable transcription factor and target transcription unit. Amp-LV-L0 fragment was amplified from pALV-L0 vector constructed in example 3 using primers P176 and P177 and ligated with pB-colE-mCherry-$P_{\lambda O12}$-mCherry constructed in example 9 by SacI and EcoRI double digestion, the resulting transitional vector was named as pB-colE-mCherry-Amp-LV-L0. pB-colE-mCherry-Amp-LV-L0 was double digested by KpnI and XhoI and ter-colE-mCherry-Amp-LV-L0-ter fragment was recovered, pCDF-Duet1 vector was amplified by PCR using primers P178 and P179, the obtained linearized fragment was ligated with colE-mCherry-Amp-LV-L0 fragment by KpnI and XhoI double digestion, the resulting single vector containing both light-switchable transcription factor and target transcription unit was named as pD-colE-mCherry-Amp-LV, the polynucleotide sequence of ter-colE-mCherry-Amp-LV-ter is SEQ. ID. No: 108.

```
Primers for amplification of Amp-LV-L0 fragment:
Forward primer (P176):
5'-CCCGAGCTCGTGCGCGGAACCCCTATTTG-3'

Reverse primer (P177):
5'-CCCGAATTCTCATTCCGTTTCGCACTGGAA-3'

Primers for amplification of pCDFDuet1 vector:
Forward primer (P178):
5'-CCCCTCGAGCTGCCACCGCTGAGCAATAACT-3'

Reverse primer (P179):
5'-GCCGGTACCGAGCGTCGAGATCCCGGACAC-3'
```

For construction of another single expression vector containing both light-switchable transcription factor and target transcription unit, LacI(1-62,wt)-VVD36(C71V) fragment was amplified from pALaV(wt) vector constructed in example 5 using primers P180 and P181, *Bacillus subtilis* vector pHT01 was amplified using primers P182 and P183, the obtained linearized fragment was ligated with LacI(1-62,wt)-VVD(C71V) fragment by infusion technology, the resulting transitional vector was named as pHT01-LaV(wt). mCherry gene fragment was amplified using primers P184 and P185 and ligated with pHT01-LaV(wt) vector by BamHI and XbaI double digestion, the resulting single vector containing both light-switchable transcription factor and target transcription unit was named as pHT01-LaV(wt)-$P_{grac}$-mCherry, the polynucleotide sequence of LaV(wt)-$P_{grac}$-mCherry is SEQ. ID. No:111.

```
Primers for amplification of LacI-VVD36 (C71V)
fragment:
Forward primer (P180):
5'-AGGGAGACGATTTTGATGAAACCAGTAACGTTA-3'

Reverse primer (P181):
5'-TTAATTGCGTTGCGCTCATTCCGTTTCGCACTGGAA-3'

Primers for amplification of pHT01 vector:
Forward primer (P182):
5'-CAAAATCGTCTCCCTCCGTTTGAATATTTG-3'

Reverse primer (P183):
5'-GCGCAACGCAATTAATGTGAGTTAAGGCC-3'

Primers for amplification of mCherry gene
fragment:
Forward primer (P184):
5'-CCCGGATCCATGGTGAGCAAGGGCGAGGA-3'

Reverse primer (P185):
5'-GGGTCTAGATTACTTGTACAGCTCGTCCAT-3'
```

Example 11 Regulation of Gene Expression by Recombinant Light-Switchable Transcription Factor in *E. coli* Cells The vectors constructed in the samples containing different light-switchable transcription factors and the reporter vector using mCherry as the reporter gene were Co-transformed into the corresponding strains to test light-regulated gene expression by recombinant light-switchable transcription factor.

Figure 13:
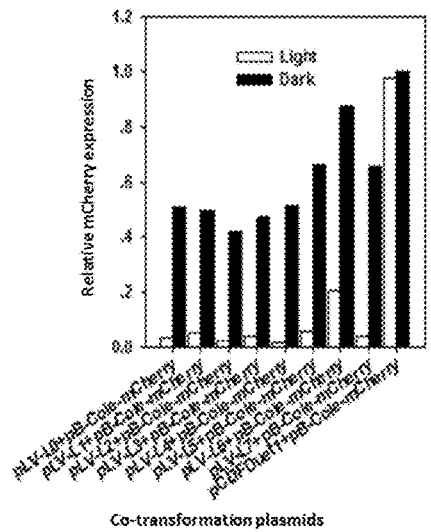
FIG. 13 shows the mCherry expression levels regulated by illuminating JM109(DE3,sulA$^-$,LexA$^-$) cells transformed by the T7 promoter driven expression of light-switchable transcription factors with different linkers. The lateral axis is the names of co-transformed plasmids; the vertical axis is the relative expression of mCherry.

To firstly detect the regulation of gene expression by light-switchable transcription factor containing LexA(1-87)-VVD36 (C71V) with different linkers, pB-colE-mCherry constructed in sample 7 and pLV-Ln (n=0, 1, 2, 3, 4, 5, 6, 7) constructed in sample 2 were co-transformed into JM109 (DE3,sulA⁻,LexA⁻) strains respectively, the difference of mCherry expression levels before and after blue light illumination was determined. Co-transformation of pB-colE-mCherry and pCDFDuet1 containing no light-switchable transcription factor was used as the control to detect the effect of blue light illumination on the bacteria growth and protein expression. High expression levels was observed in the cells containing no light-switchable transcription factor both in the dark and light, indicating that blue light illumination had no effect on bacteria protein expression. The mCherry fluorescence of cells containing light-switchable transcription factor with different linkers significantly decreased after blue light illumination and was much lower than cells in the dark, indicating that these light-switchable transcription factors could be used in controlling gene expression in *E. coli*. In detailed, the gene expression of cells containing pLV-L0 in the light was 13 folds lower than in the dark, the gene expression of cells containing pLV-L4 in the light was 32 folds lower than in the dark, other recombinant light-switchable transcription factors with different linkers also had marked inhibition on mCherry expression upon blue light illumination (FIG. 13).

Figure 14:
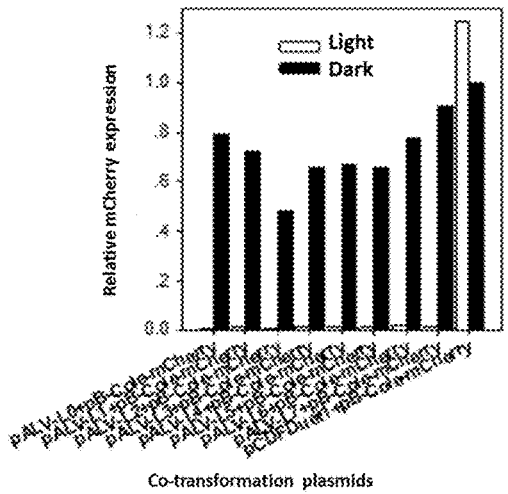
FIG. 14 shows the mCherry expression levels regulated by illuminating JM109(DE3,sulA$^-$,LexA$^-$) cells transformed by the Amp promoter driven expression of light-switchable transcription factors with different linkers. The lateral axis is the names of co-transformed plasmids; the vertical axis is the relative expression of mCherry.

To detect the effect of light-switchable transcription factors when its expression driven by T7 background expression was replaced with Amp promoter, pALV-Ln (n=0, 1, 2, 3, 4, 5, 6, 7) constructed in example 3 and pB-colE-mCherry reporter plasmids were co-transformed into JM109 (DE3, sulA⁻,LexA⁻) strains, the difference of mCherry expression before and after blue light illumination was detected according to the methods described in embodiment 7. Co-transformation of pB-colE-mCherry and pCDFDuet1 containing no light-switchable transcription factor was used as the control to detect the effect of blue light illumination on the bacteria growth and protein expression. The results of the applicants showed that replacement of T7 background expression with Amp promoter had more marked inhibition after blue light illumination. In detailed, the gene expression of cells containing pALV-L0 in the light was 150 folds lower than in the dark, the gene expression of cells containing pALV-L4 in the light was more than 50 folds lower than in the dark (FIG. 14).

Figure 15:
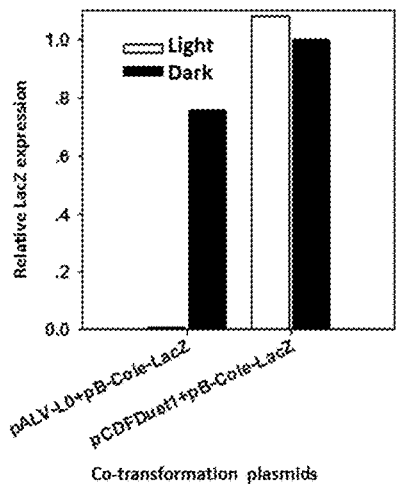
FIG. 15 shows the LacZ expression levels regulated by light-switchable transcription factor LV-L0. The lateral axis is the names of co-transformed plasmids; the vertical axis is the relative expression of LacZ.

To detect the effect of recombinant light-switchable transcription factors on the regulation of LacZ expression, pB-colE-LacZ constructed in example 7 and pALV-L0 constructed in example 3 were con-transformed into constructed in example 7 strains, the difference of LacZ expression before and after blue light illumination was detected according to the methods described in embodiment 8. The results of the applicants showed that the expression level of LacZ in the light was 126 folds lower than in the dark (FIG. 15).

Figure 16:
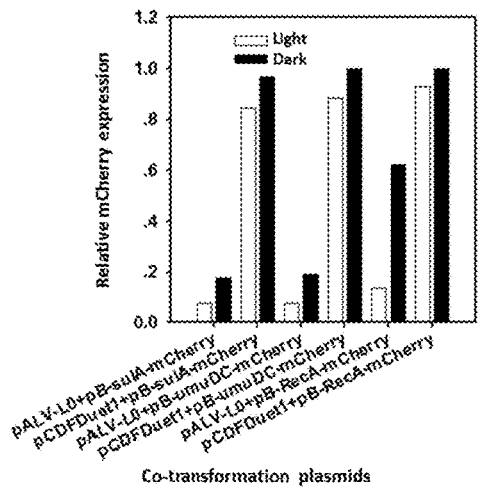
FIG. 16 shows the mCherry expression levels regulated by prokaryotic expression vectors containing light-switchable transcription factor LV-L0 with other three reaction element corresponding to LexA. The lateral axis is the names of co-transformed plasmids; the vertical axis is the relative expression of mCherry.

To detect other three prokaryotic bacteria expression vectors containing LexA reaction unit and mCherry fluorescent protein gene, pB-sulA-mCherry, pB-umuDC-mCherry and pB-RecA-mCherry constructed in example 7 were co-transformed with pALV-L0 into JM109(DE3,sulA⁻,LexA⁻) strains respectively, pCDFDuet1 empty vector was used as the control, the difference of mCherry expression before and after blue light illumination was detected according to the methods described in embodiment 7. The results of the applicants showed that the response of target transcription unit of sulA, umuDC and RecA promoter to light switchable transcription factor was significantly lower than colE promoter, In detailed, the inhibition effect of sulA and umuDC on mCherry expression was less than 3 folds while the RecA had only 5-fold (FIG. 16).

Figure 17:
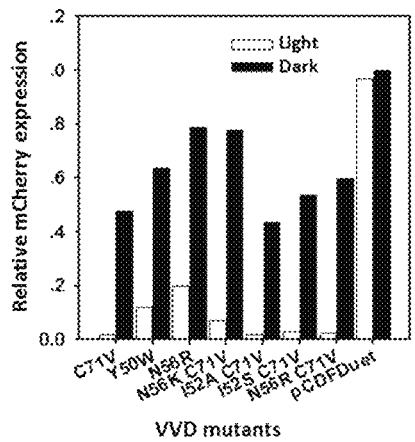
FIG. 17 shows the mCherry expression levels regulated by illuminating JM109(DE3,sulA$^-$,LexA$^-$) cells transformed by the transcription factor expression vectors with several VVD mutants as the second peptide. The lateral axis is the names of co-transformed plasmids; the vertical axis is the relative expression of mCherry.

To detect the regulation of gene expression by light-switchable transcription factor with VVD mutants as the second polypeptide relative to LV-L0, pALV-L0(N56K), pALV-L0(Y50W), pALV-L0(N56K C71V), pALV-L0(I52A C71V), pALV-L0(I52S C71V), pALV-L0(N56R C71V) constructed in example 4 and pALV-L0 were co-transformed with pB-colE-mCherry reporter vector into JM109(DE3, sulA⁻,LexA⁻) strain, the difference of mCherry expression before and after blue light illumination was detected according to the methods described in embodiment 7. The results of the applicants showed that VVD(C71V) and VVD(N56K C71V) had higher inhibition ratios relative to other VVD mutants, due to the lower mCherry expression of VVD (C71V) in the light, VVD(C71V) was chosen as the second peptide of light-switchable transcription factor in following experiments (FIG. 17).

Figure 18:
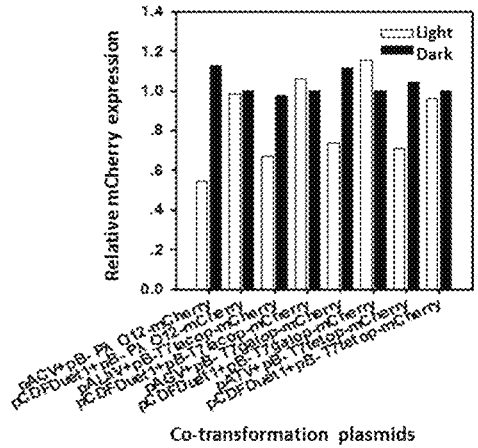
FIG. 18 shows the mCherry expression levels regulated by illuminating JM109(DE3,sulA$^-$,LexA$^-$) cells transformed by the transcription factor expression vectors with cI, LacI, Gal4 or TetR as the first peptide. The lateral axis is the names of co-transformed plasmids; the vertical axis is the relative expression of mCherry.

To detect the regulation of gene expression by light-switchable transcription factor with cI, LacI, Gal4 or TetR as the first polypeptide, pACV, pALaV, pAGV and pATV constructed in example 7 were co-transformed with prokaryotic bacterium expression vectors containing target transcription unit and mCherry fluorescent protein into JM109 (DE3,sulA⁻,LexA⁻) strain, respectively, pCDFDuet1 empty vector was used as the control, the difference of mCherry expression before and after blue light illumination was detected according to the methods described in embodiment 7. The results indicated that the recombinant light-switchable transcription factor CV could result in reduction of mCherry expression in the light to half of that in the dark, mCherry expression in the light was 60%-70% of that in the dark for other three recombinant light-switchable transcription factors LaV, GV and TV, indicating light switchable characteristics of these recombinant light-switchable transcription factors (FIG. 18).

Figure 19:
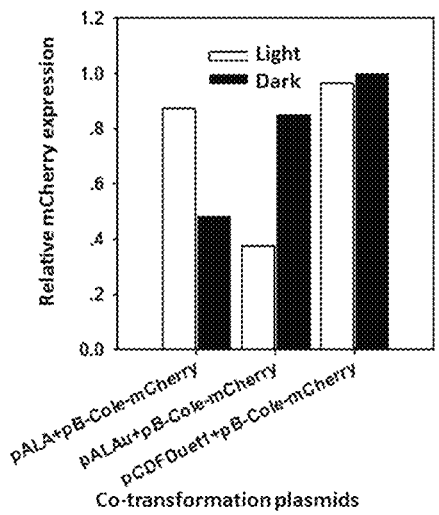
FIG. 19 shows the mCherry expression levels regulated by illuminating JM109(DE3,sulA$^-$,LexA$^-$) cells transformed by the transcription factor expression vectors with AsLOV2 or AuLOV as the second peptide. The lateral axis is the names of co-transformed plasmids; the vertical axis is the relative expression of mCherry.

To detect the regulation of gene expression by light-switchable transcription factor with phot1-LOV2 or LOV domain of aurochrome as the second polypeptide, pALA and pALAu constructed in example 4 were co-transformed with pB-colE-mCherry reporter vector constructed in example 7 into JM109(DE3,sulA⁻,LexA⁻) strain, respectively, the difference of mCherry expression before and after blue light illumination was detected according to the methods described in embodiment 7. The results indicated that the recombinant light-switchable transcription factor with AsLOV2 as the second peptide had greater inhibition in the dark, that the recombinant light-switchable transcription factor with AulOV as the second peptide had higher inhibition ratio of mCherry expression in the light (FIG. 19).

Figure 20:
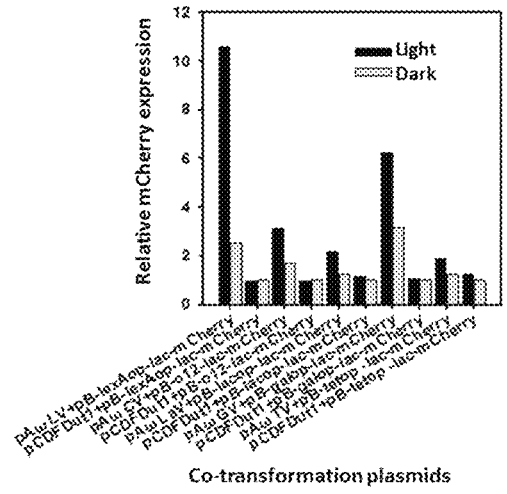
FIG. 20 shows the mCherry expression levels regulated by illuminating JM109(DE3,sulA$^-$,LexA) cells transformed by the transcription factor expression vectors with co as the third peptide. The lateral axis is the names of co-transformed plasmids; the vertical axis is the relative expression of mCherry.

To detect the regulation of gene expression by light-switchable transcription factor with ω as the third polypeptide, pAωLV, pAωCV, pAωLaV, pAωGV and pAωTV constructed in example 8 were co-transformed with prokaryotic bacterium expression vectors containing target transcription unit and mCherry fluorescent protein gene into JM109(DE3, sulA⁻,LexA⁻,ω⁻) strain, the difference of mCherry expression before and after blue light illumination was detected according to the methods described in embodiment 7. 5-fold activation of mCherry expression was observed for the recombinant light-switchable transcription factor ωLV in the light while ωCV and ωGV had 2-fold activation, ωLaV and ωTV also exhibited light-activated characteristics (FIG. 20).

Figure 21:
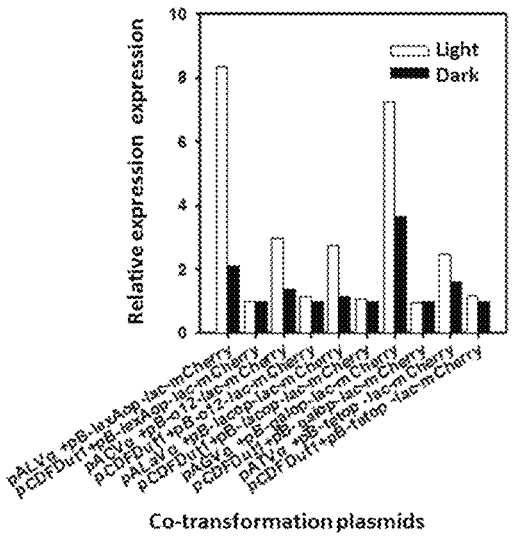
FIG. 21 shows the mCherry expression levels regulated by illuminating JM109(DE3,sulA$^-$,LexA$^-$) cells transformed by the transcription factor expression vectors with a as the third peptide. The lateral axis is the names of co-transformed plasmids; the vertical axis is the relative expression of mCherry.

To detect the regulation of gene expression by light-switchable transcription factor with α as the third polypeptide, pALVα, pACVα, pALaVα, pAGVα and pATVα constructed in example 6 were co-transformed with prokaryotic bacterium expression vectors containing target transcription unit and mCherry fluorescent protein gene into BL21 (sulA$^-$, LexA$^-$,ω$^-$) strain, the difference of mCherry expression before and after blue light illumination was detected according to the methods described in embodiment 7. 4-fold activation of mCherry expression was observed for the recombinant light-switchable transcription factor LVα in the light while CVα, LaVα and GVα had 2-fold activation, TVα also exhibited light-activated characteristics (FIG. 21).

Figure 22:
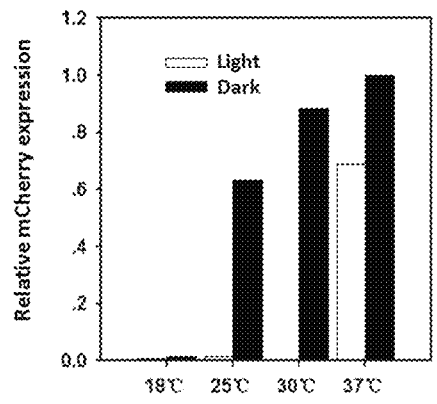
FIG. 22 shows the mCherry expression levels regulated by light-switchable transcription factor LV-L0 at different temperature. The lateral axis is the names of co-transformed plasmids; the vertical axis is the relative expression of mCherry.

To detect the effect of temperature on the regulation of gene expression by light-switchable transcription factor, pALV-L0 constructed in example 3 was co-transformed with pB-colE-mCherry reporter vector constructed in example 7 into JM109(DE3,sulA$^-$,LexA$^-$) strain, the cells were cultured at 18° C., 25° C., 30° C. and 37° C., the difference of mCherry expression before and after blue light illumination was detected. The results showed that the recombinant light-switchable transcription factor LV-L0 had marked inhibition on mCherry expression at 18° C. both in the dark and light, in contrast to 18° C., the recombinant light-switchable transcription factor LV-L0 had little effect on mCherry expression whatever in the dark and light. Therefore, LV-L0 had no light-induced regulation on mCherry expression at these two temperatures. The recombinant light-switchable transcription factor LV-L0 had marked light-induced inhibition on mCherry expression at 25° C. and 30° C., the following measurements were carried out at 30° C. due to the higher growth rate at this temperature (FIG. 22).

Figure 23:
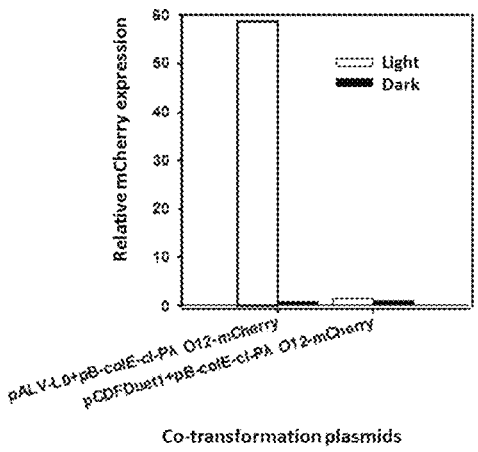
FIG. 23 shows the mCherry expression levels regulated by light-switchable transcription factor LV-L0 using cI repressor for the indirect regulation. The lateral axis is the names of co-transformed plasmids; the vertical axis is the relative expression of mCherry.

To detect the difference of mCherry expression before and after light illumination by light-switchable transcription factor for the prokaryotic bacterium expression vector using cI repressor as the indirect regulation, pB-colE-cI-P$_{\lambda O12}$-mCherry constructed in example 9 was co-transformed with pALV-L0 constructed in example 3 into JM109(DE3,sulA$^-$, LexA$^-$) strain, pCDFDuet1 empty vector was used as the control, the difference of mCherry expression before and after blue light illumination was detected according to the methods described in embodiment 7. More than 50-fold activation of mCherry expression was observed for the recombinant light-switchable transcription factor LV-L0 in the light, demonstrating that such a regulation method using cI as the indirect regulation can be well used to control mCherry expression by light (FIG. 23).

Figure 24:
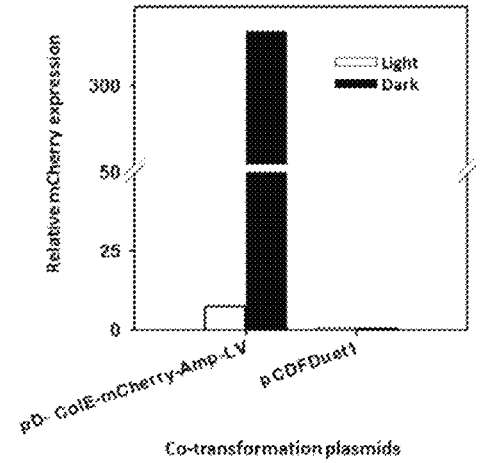
FIG. 24 shows the mCherry expression levels regulated by single plasmid containing both the light-switchable transcription factor LV-L0 and target transcription unit. The lateral axis is the names of co-transformed plasmids; the vertical axis is the relative expression of mCherry.

To detect the difference of mCherry expression before and after light illumination by single expression vector containing both light-switchable transcription factor and target transcription factor, pD-colE-mCherry-Amp-LV constructed in example 10 was transformed into JM109(DE3,sulA$^-$, LexA$^-$) strain, pCDFDuet1 empty vector was used as the control, the difference of mCherry expression before and after blue light illumination was detected according to the methods described in embodiment 7. The result showed that such single expression vector containing both light-switchable transcription factor and target transcription factor could well regulate mCherry expression of the target transcription unit by the recombinant light-switchable transcription factor LV-L0 expressed by itself, which avoids transformation of two vectors and has more important application prospect (FIG. 24).

Figures 25, 26:
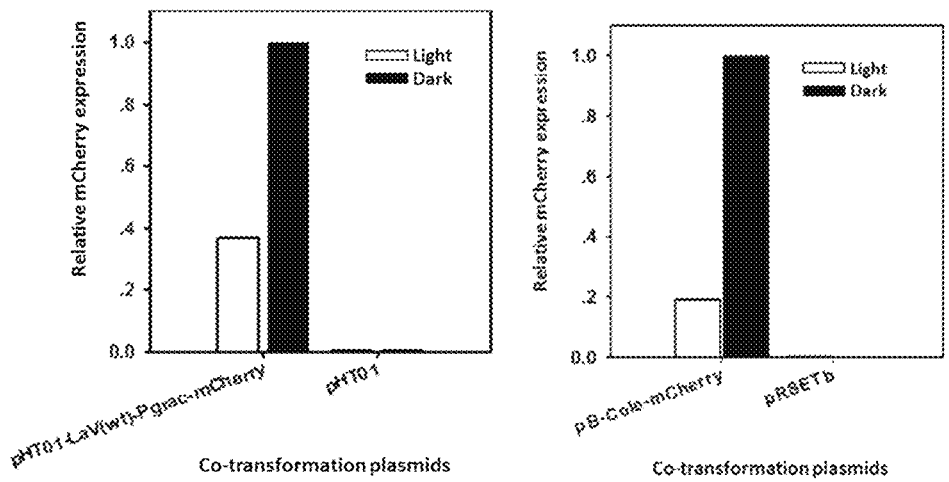
FIG. 25 shows the mCherry expression levels regulated by single plasmid containing both the light-switchable transcription factor LaV(wt) and target transcription unit in *Bacillus subtilis* cells. The lateral axis is the names of co-transformed plasmids; the vertical axis is the relative expression of mCherry.
FIG. 26 shows the mCherry expression levels regulated by the light-switchable transcription factor LV-L0 expressed by JM109(DE3,sulA$^-$, LexA::Amp-LV-L0) itself. The lateral axis is the names of co-transformed plasmids; the vertical axis is the relative expression of mCherry.

To detect the difference of mCherry expression before and after light illumination by *Bacillus subtilis* expression vector containing both light-switchable transcription factor and target transcription factor, pHT01-LaV(wt)-P$_{grac}$-mCherry constructed in example 10 was transformed into *Bacillus subtilis* WB800, pHT01 vector was used as the control. mCherry expression in the dark and light was determined. The result showed that the recombinant light-switchable transcription factor LaV(wt) could well repress mCherry expression in *Bacillus subtilis* cells, the ratio could reach 3 folds (FIG. 25).

To detect the effect of light-switchable transcription factor expressed by JM109(DE3,sulA$^-$, LexA::Amp-LV-L0) strain on mCherry expression, pB-colE-mCherry constructed in example 7 was transformed into JM109(DE3,sulA$^-$, LexA::Amp-LV-L0) strain, pRSETb vector was used as the control, the difference of mCherry expression before and after blue light illumination was detected according to the methods described in embodiment 7. The result showed that mCherry expression could be repressed by the light-switchable transcription factor expressed by the strain itself without introducing exogenous plasmid to express the light-switchable transcription factor, the repression ratio could reach 5 folds (FIG. 26).

Figures 27, 28:
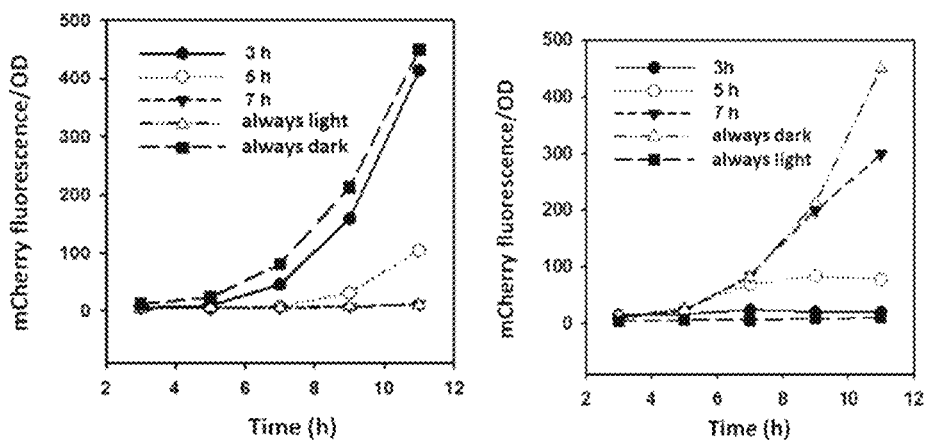
FIG. 27 shows the time course the light-induced gene expression in cells expressing the recombinant light-switchable transcription factor LV-L0. The lateral axis is the time of illumination which represents the time point when the sample is transferred from light to dark; the vertical axis is the relative expression of mCherry.
FIG. 28 shows the reversibility of the light-induced gene expression in cells expressing the recombinant light-switchable transcription factor LV-L0. The lateral axis is the time of illumination which represents the time point when the sample is transferred from light to dark; the vertical axis is the relative expression of mCherry.

Example 12 Characteristics of Gene Expression Regulation Upon Light Illumination Time course and reversibility of light-switchable transcription factor regulated gene expression were tested by co-transformation of pALV-L0 constructed in example 3 and pB-colE-mCherry reporter vector constructed in example 7 into JM109(DE3,sulA$^-$,LexA$^-$) strain, clones were picked into 48-well plate and divided into 6 groups, each group had four wells, all the cells were cultured at 30° C. upon light illumination. The cells were diluted 100 folds into two 48-well plates containing fresh LB, the two plates were labeled as A plate and B plate, respectively. A plate was cultured upon blue light exposure, mCherry expression was determined at 3 h, 5 h, and 7 h time points, after each measurement, one group was transferred from light to dark (residual wells in plate B) until the last time point. B plate was cultured in the dark, mCherry expression was determined at 3 h, 5 h, and 7 h time points, after each measurement, one group was transferred from dark to light (residual wells in plate A) until the last time point. The average of mCherry expression of each time point was plotted. The results showed that mCherry expression was greatly repressed when cells were illuminated by light from the beginning. The repression efficiency gradually weakened and mCherry expression increased when cells were transferred from light to dark, the curve rose slowly shown in the figure (FIG. 27). mCherry expression was not repressed and had high expression level when cells were kept in the dark, mCherry expression was gradually repressed when the cells were transferred to light conditions, the rising rate of the rising curve gradually decreased and the curve tended to horizontal at the last (FIG. 28). These results indicated that the regulation of gene expression by recombinant light-switchable transcription factor is reversible.

Figure 29:
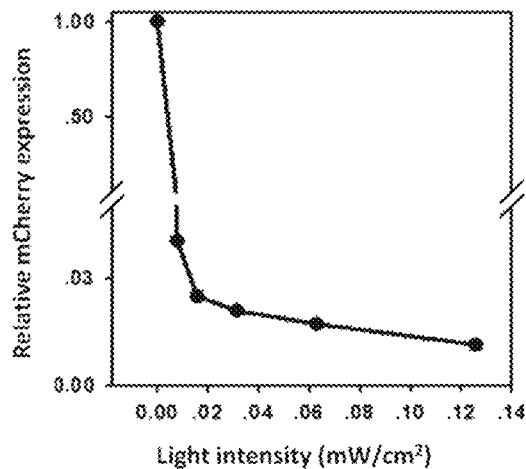
FIG. 29 shows the light dependent light-induced gene expression in cells expressing the recombinant light-switchable transcription factor LV-L0. The lateral axis is the light intensity; the vertical axis is the relative expression of mCherry.

To evaluate the gene expression regulated by light-switchable transcription factor in different light irradiance, mCherry was used as the reporter gene, pALV-L0 constructed in example 3 and pB-colE-mCherry reporter vector constructed in example 7 were co-transformed into JM109 (DE3,sulA$^-$,LexA$^-$) strains. Clones were picked into 48-well plate and divided into 6 groups, each group had four wells, all the cells were cultured at 30° C. upon light illumination. The cells were diluted 100 folds into six 48-well plates containing fresh LB, 5 of the σ plates were cultured upon blue light illumination with the light irradiance 0.125 mW/cm$^2$, 0.063 mW/cm$^2$, 0.031 mW/cm$^2$, 0.016 mW/cm$^2$ and 0.009 mW/cm$^2$ (light intensity determine by a laminator (Sanwa)), the last plate was cultured in the dark.

mCherry expression was measured after 18 h. The result indicated that the gene expression regulated by light-switchable transcription factor is light irradiance dependent; more marked repression of mCherry expression was observed along with increase of light intensity. We also found that the recombinant light-switchable transcription factor LV-L0 functioned well even at extremely weak light (FIG. 29).

Figure 30:
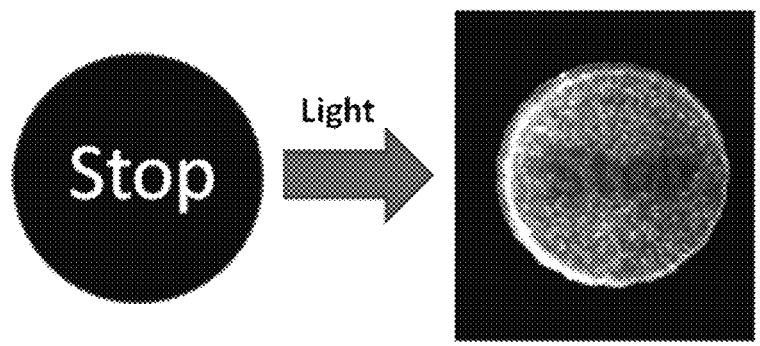
FIG. 30 is the "Stop" pattern obtained from "taking photograph" of the cells expressing the recombinant light-switchable transcription factor LV-L0 using a printed patterns projection film. The left panel is the photograph of culture dish affixed with projection film, and the right panel is the image of fluorescent cells.

To spatially control gene expression by light-switchable transcription factor, mCherry was used as the reporter gene, pALV-L0 constructed in example 3 and pB-colE-mCherry reporter vector constructed in example 7 were co-transformed into JM109(DE3,sulA$^-$,LexA$^-$) strains. Clones were picked into test tubes containing 5 ml fresh LB and cultured upon blue light illumination, the cells were harvested with 4000 rpm centrifugation and resuspended using 200 ul fresh medium the next day, then the OD600 was determined. The solid medium containing 1% agar, 0.5% tryptone, 0.25% yeast extract and 0.5% NaCl was prepared and cooled to 45° C. after autoclave sterilization, the above resuspended cells and antibiotics were added to make sure OD600-0.03, then the mixture was poured onto 90 mm dish. After coagulation, a "Stop" pattern was printed and a gradient slider on laser transparency film using a laser printer was used as photomask, the light intensity of transparent space detected by a luminator was 30 times more than the black space. The printed photomask was pasted on the bottom of the dish. 24 h after illumination, the imaging was conducted using the In-Vivo Multispectral System FX (Kodak) with 600 nm excitation and 670 nm emission filters, image was collected in 4×4 binning for 30 s exposure. Due to LV-L0 induced mCherry expression upon blue light illumination, the result showed that the left panel was the pattern we designed, the circle region of right panel was the fluorescence image of cells, so it could be concluded that the fluorescence image of the cells had the same pattern of the original image used as the mask, we could "take photos" for cells (FIG. 30), indicating that the system could spatially regulate gene expression.

Figure 31:
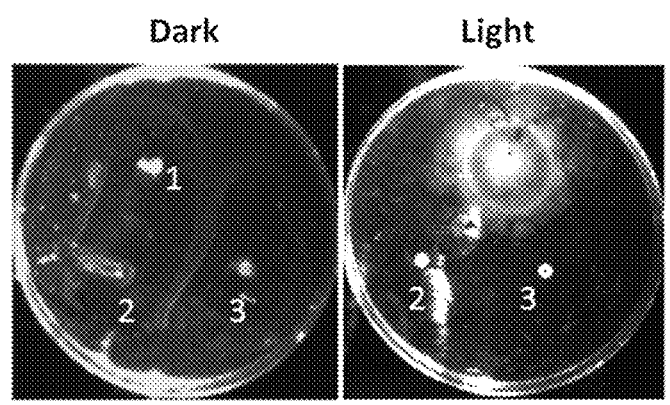
FIG. 31 is the white light imaging result of the regulation on bacteria mobility by the recombinant light-switchable transcription factor LV-L0, the right panel is dark condition, the right panel is light condition, 1, 2,3 represent different plasmids for co-transformation.

Example 13 Regulation of Mobility of *E. coli* Cells by Light-Switchable Transcription Factor Detection of regulation of *E. coli* Swimming by recombinant light-switchable transcription factor was carried out on a special semisolid medium. The semisolid medium containing 1% tryptone, 0.5% NaCl and 0.25 agar was prepared and cooled to 50° C. after autoclave sterilization before addition of antibiotics, then 10 ml of the mixture was poured onto one 90 mm dish and harden at room temperature for 1 h. pALV-L0 constructed in example 3 and pB-colE-cI-P$_{\lambda O12}$-CheZ constructed in example 9 were co-transformed into JM109 (DE3,sulA$^-$,LexA$^-$,CheZ$^-$) strain, clones were picked from the plate into test tubes and cultured overnight in the dark, the cells were diluted 200 folds into fresh medium and cultured in the dark. When the OD600 reached 0.1-0.2, 2 μl of the cultured cells was spotted onto the semisolid medium and cultured at 30° C. in the light. The plates wrapped with foil and kept at the same conditions were used as the control in the dark. The imaging was conducted using the In-Vivo Multispectral System FX (Kodak) after 49 h. The result showed that light-switchable transcription factor LV-L0 could not repress cI expression in dark conditions, resulting in tight repression of CheZ expression by cI, so cells could not spread to form the bacteria ring due to that the bacteria containing no CheZ could not move. In contract to dark conditions, the light-switchable transcription factor LV-L0 could repress cI expression in light conditions, resulting in no effect on P$_{\lambda O12}$ promoter activity, the expression of CheZ protein enabled the mobility of bacteria, so cells could spread around to form the bacteria ring (FIG. 31).

Figure 32:
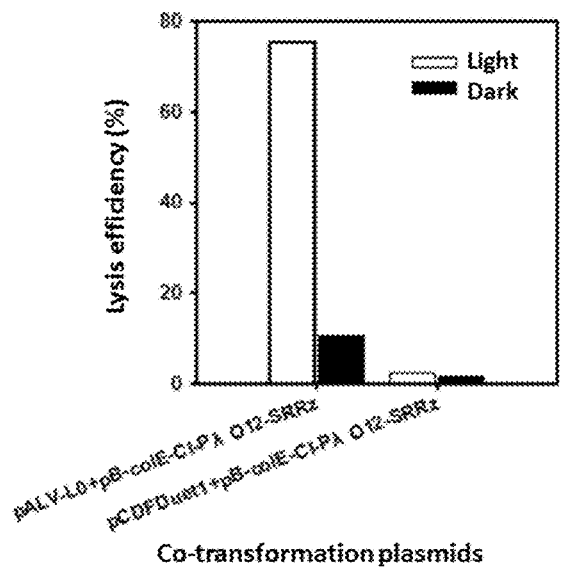
FIG. 32 is the regulation on bacteria cell lysis by the recombinant light-switchable transcription factor LV-L0, the lateral axis is the names of co-transformed plasmids; the vertical axis is the lysis efficency.

Example 14 Regulation of Lysis of *E. coli* Cells by Light-Switchable Transcription Factor To detect the regulation of *E. coli* lysis by light-switchable transcription factor, pALV-L0 constructed in example 3 and pB-colE-cI-P$_{\lambda O12}$-SRRz constructed in example 9 were co-transformed into JM109(DE3,sulA$^-$,LexA$^-$,CheZ$^-$) strain, clones were picked from the plate into test tubes and cultured at 30° C. overnight in the dark, the cells were diluted 100 folds into fresh medium and cultured in the dark. When the OD600 reached 0.4-0.6, 1 mM IPTG was added to induce the expression of LacZ gene in the genome. The cells were transferred to dark conditions to induce the expression of SRRz gene cassette after 1.5 h, the cells were harvested with 4000 rpm centrifugation after σ h, the LacZ activities in the supernatant and precipitate were measured; the percent of LacZ activity in the supernatant to the total LacZ activities in the supernatant and precipitate was calculated. Cells kept in the dark were used as the control and shared the same manipulation with that in light conditions. The results showed that the light-switchable transcription factor LV-L0 could repress cI expression in light conditions, resulting in no effect on P$_{\lambda O12}$ promoter activity, the high expression of S, R and Rz in SRRz gene cassette enabled lysis of 75% of cells, resulting in release of LacZ to the culture. Only 10% of bacteria lysed in the dark (FIG. 32).

Example 15 Large Scale Production of Sulfhydryl Oxidase Ero1 Using the Light-Switchable Gene Expression System of Prokaryotic Bacteria Due to the fast multiplication, low culture costs and the ability of high-level expression of exogenous protein, such a light-switchable gene expression system of prokaryotic bacterium was used for large scale production of sulfhydryl oxidase Ero1 in prokaryotic bacterium cells. pB-colE-mCherry-P$_{\lambda O12}$-Ero1 constructed in example 9 and pALV-L0 constructed in example 3 were co-transformed into JM109(DE3,sulA$^-$,LexA$^-$) strain. The clones were picked into test tube containing 5 ml fresh LB and cultured overnight, the cells were transferred to conical flask containing 100 ml fresh LB and cultured at 37° C. When OD600 reached 0.8, the cells were transferred to conical flask containing 500 ml fresh LB and cultured at 25° C. in dark conditions, there were 9 conical flasks in all. The cells were illuminated with blue light LED when OD600 reached 0.6, cells were harvested with 4000 rpm centrifugation after 18 h and resuspended with Buffer A (0.02 M Na$_3$PO$_4$, 10 mM imidazole, 0.5 M NaCl, PH 7.2). The resuspended cells were broken by sonification, the conditions of the sonification are: P=40%, work for 1 s with 4 s interval, 300 s every cycle, 5 cycles in all. Supernatant was collected after 10,000 rpm centrifugation for 30 min at 4° C. The supernatant was loaded onto GE HisTrap HP (5 mL) column, the progress of loading: GE HisTrap HP→control flow rate at 1 mL/min using peristaltic pump, remove the alcohol in the column using deionized water firstly→equilibrate the column using Buffer A→load the 100 ml supernatant onto the column, control flow rate at 1 mL/min. Gradient elution was carried out using AKTA prime in the following elution procedure (1 mL/min of flow rate):

(1) eluting with 10 ml Buffer A;
(2) gradiently increasing the content of Buffer B (0.02 M Na$_3$PO$_4$, 500 mM imidazole, 0.5 M NaCl, PH 7.2) from 0% to 100% in the following 50 ml elution buffer;

(3) removing all the proteins on the column using 200 ml 100% Buffer B;

(4) gradiently decreasing the content of Buffer B from 100% to 0% in the following 20 ml elution buffer;

(5) eluting the column using 50 ml deionized water; and (6) eluting the column using 20 ml 20% alcohol.

The isoelectric point of Ero1 was 4.8 obtained from ExPASy website, ion-exchange chromatography was carried out using anion-exchange column. Ero1 protein solution after affinity column purification was loaded onto 5 ml Hitrap™ QFF column for ion-exchange chromatography, the experiment precedure: Ero1 protein solution after affinity column purification→dilute into 10 folds using Buffer A (20 mM $Na_3PO_4$, 10 mM NaCl, PH 7.2)→load the solution onto 5 mL Hitrap™ QFF column→elute with 50 ml Buffer A→elute using AKTA purifier. The elution procedure (1 mL/min of flow rate) is as follows:

(1) eluting with 10 ml Buffer A;

(2) gradiently increasing the content of Buffer B (20 mM $Na_3PO_4$, 500 mM NaCl, PH 7.2) from 0% to 100% in the following 25 ml elution buffer;

(3) removing all the proteins on the column using 20 ml 100% Buffer B;

(4) gradiently decreasing the content of Buffer B from 100% to 0% in the following 20 ml elution buffer;

(5) eluting the column using 50 ml deionized water; and (6) eluting the column using 20 ml 20% alcohol.

Figure 33:
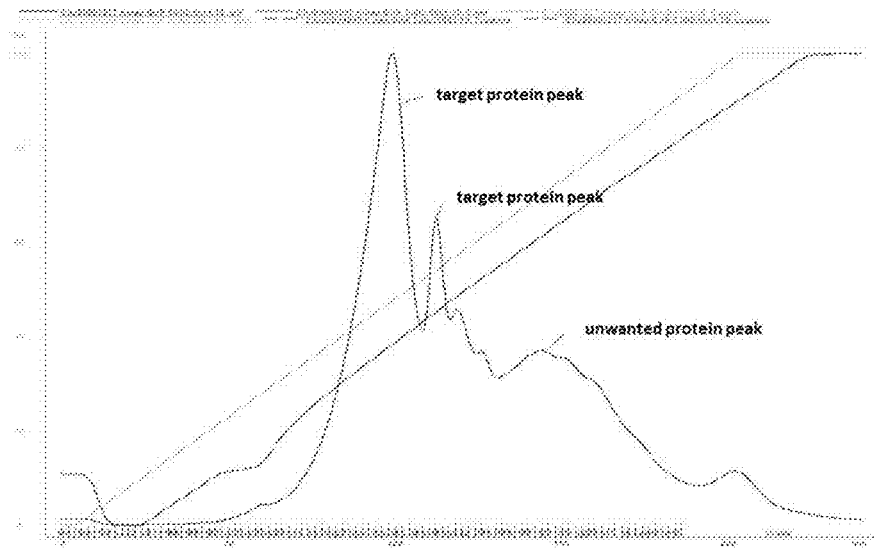
FIG. 33 is the elution result of ion-exchange chromatography using AKTA purifier. The lateral axis is the number of elution tubes; the vertical axis is the value of UV absorption.
Figure 34:
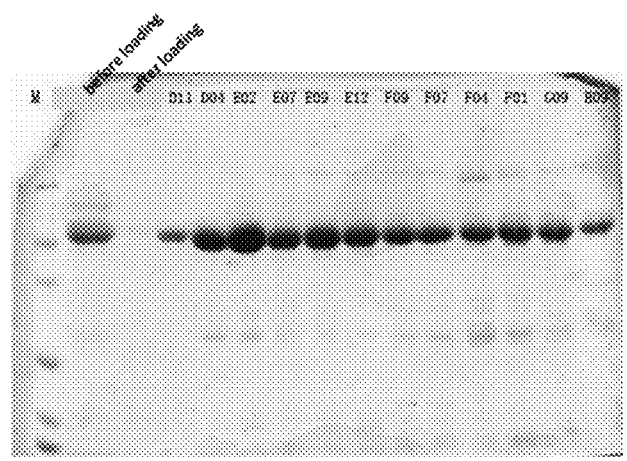
FIG. 34 is the result of 12% SDS PAGE of protein from some tubes after ion-exchange chromatography.
Figure 35:
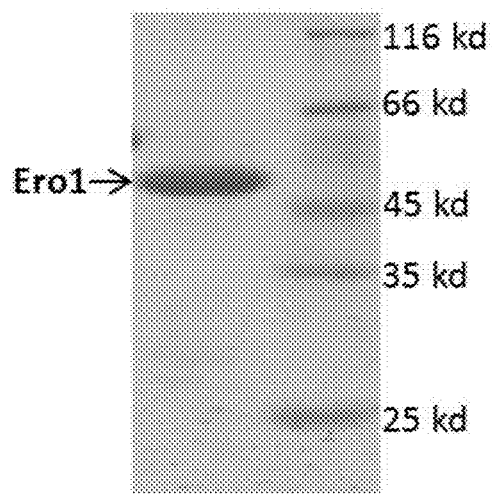
FIG. 35 is the result of 12% SDS PAGE of the obtained protein after merging.

The result of ion-exchange chromatography using AKTA purifier is shown as FIG. 33. Protein solution in part of the collected tubes was loaded onto 12% SDS-PAGE to identify their purity (FIG. 34), the tubes with high purity of protein were collected together. The purity of the lastly obtained protein solution was determined by 12% SDS-PAGE; the result showed that the Ero1 protein had high purity which reached 96% (FIG. 35). The amount of the Ero1 was 25 mg determined by Brandford.

It will be understood that the dosages, reaction conditions, etc., in the examples are approximate values unless noted otherwise, and they can be exactly changed based on the situations to obtain similar results. All of the professional terms used in the Description, except those specially defined, have identical meanings to those known by persons skilled in the art. All the references referred to are incorporated into the application as a whole. The preferable embodiments are only exemplified for the illustration of the invention. Those skilled in the art can adopt similar methods or materials to obtain similar results. All the changes and modifications are within the scope of the attached claims.

REFERENCES

1. Keyes, W. M. and A. A. Mills, *Inducible systems see the light*. Trends Biotechnol, 2003. 21(2): p. 53-5.
2. Levskaya, A., et al., *Synthetic biology: engineering Escherichia coli to see light*. Nature, 2005. 438(7067): p. 441-2.
3. Tabor, J. J., A. Levskaya, and C. A. Voigt, *Multichromatic control of gene expression in Escherichia coli*. J Mol Biol, 2011. 405(2): p. 315-24.
4. Tabor, J. J., et al., *A synthetic genetic edge detection program*. Cell, 2009. 137(7): p. 1272-81.
5. Moglich, A., R. A. Ayers, and K. Moffat, *Design and signaling mechanism of light-regulated histidine kinases*. J Mol Biol, 2009. 385(5): p. 1433-44.
6. Ohlendorf, R., et al., *From dusk till dawn: one plasmid systems for light-regulated gene expression*. J Mol Biol, 2012. 416(4): p. 534-42.
7. Wang, X., X. Chen, and Y. Yang, *Spatiotemporal control of gene expression by a light-switchable transgene system*. Nat Methods, 2012.
8. Yazawa, M., et al., *Induction of protein protein interactions in live cells using light*. Nat Biotechnol, 2009. 27(10): p. 941-5.
9. Kennedy, M. J., et al., *Rapid blue-light-mediated induction of protein interactions in living cells*. Nat Methods, 2010. 7(12): p. 973-5.
10. Pandey, R., et al., *An extended model for the repression of photosynthesis genes by the AppA/PpsR system in Rhodobacter sphaeroides*. FEBS J, 2012.
11. Ye, H., et al., *A synthetic optogenetic transcription device enhances blood-glucose homeostasis in mice*. Science, 2011. 332(6037): p. 1565-8.
12. Schnarr, M., et al., *DNA binding properties of the LexA repressor*. Biochimie, 1991. 73(4): p. 423-31.
13. Little, J. W. and D. W. Mount, *The SOS regulatory system of Escherichia coli*. Cell, 1982. 29(1): p. 11-22.
14. Burz, D. S., et al., *Self-assembly of bacteriophage lambda cI repressor: effects of single-site mutations on the monomer-dimer equilibrium*. Biochemistry, 1994. 33(28): p. 8399-405.
15. Hu, J. C., et al., *Sequence requirements for coiled-coils: analysis with lambda repressor-GCN4 leucine zipper fusions*. Science, 1990. 250(4986): p. 1400-3.
16. Lewis, M., et al., *Crystal structure of the lactose operon repressor and its complexes with DNA and inducer*. Science, 1996. 271(5253): p. 1247-54.
17. Friedman, A. M., T. O. Fischmann, and T. A. Steitz, *Crystal structure of lac repressor core tetramer and its implications for DNA looping*. Science, 1995. 268(5218): p. 1721-7.
18. Kraulis, P. J., et al., *Structure of the DNA-binding domain of zinc GAL4*. Nature, 1992. 356(6368): p. 448-50.
19. Marmorstein, R., et al., *DNA recognition by GAL4: structure of a protein DNA complex*. Nature, 1992. 356 (6368): p. 408-14.
20. Wissmann, A., et al., *Amino acids determining operator binding specificity in the helix-turn-helix motif of Tn10 Tet repressor*. EMBO J, 1991. 10(13): p. 4145-52.
21. Ramos, J. L., et al., *The TetR family of transcriptional repressors*. Microbiol Mol Biol Rev, 2005. 69(2): p. 326-56.
22. Hong, M., et al., *Structural basis for dimerization in DNA recognition by Gal4*. Structure, 2008. 16(7): p. 1019-26.
23. Zoltowski, B. D. and B. R. Crane, *Light activation of the LOV protein vivid generates a rapidly exchanging dimer*. Biochemistry, 2008. 47(27): p. 7012-9.
24. Schwerdtfeger, C. and H. Linden, *VIVID is a flavoprotein and serves as a fungal blue light photoreceptor for photoadaptation*. EMBO J, 2003. 22(18): p. 4846-55.
25. Peter, E., B. Dick, and S. A. Baeurle, *Mechanism of signal transduction of the LOV2-Jalpha photosensor from Avena sativa*. Nat Commun, 2010. 1: p. 122.
26. Halavaty, A. S. and K. Moffat, *N- and C-terminal flanking regions modulate light-induced signal transduction in the LOV2 domain of the blue light sensor phototropin 1 from Avena sativa*. Biochemistry, 2007. 46(49): p. 14001-9.
27. Takahashi, F., et al., *AUREOCHROME, a photoreceptor required for photomorphogenesis in stramenopiles*. Proc Natl Acad Sci USA, 2007. 104(49): p. 19625-30.
28. Dove, S. L. and A. Hochschild, *Conversion of the omega subunit of Escherichia coli RNA polymerase into a transcriptional activator or an activation target*. Genes Dev, 1998. 12(5): p. 745-54.
29. Dove, S. L., J. K. Joung, and A. Hochschild, *Activation of prokaryotic transcription through arbitrary protein protein contacts*. Nature, 1997. 386(6625): p. 627-30.

What is claimed is:

1. A light-switchable gene expression system of prokaryotic bacterium comprising:
a prokaryotic bacterium comprising a gene expression system, the gene expression system comprising:
a) a gene encoding a photosensitive recombinant prokaryotic light-switchable transcription factor, said recombinant light-switchable transcription factor is one fusion protein including the first polypeptide as DNA-binding domain and the second polypeptide as light-switchable domain,
wherein said first polypeptide is selected from helix-turn-helix DNA-binding domain, zinc finger motif or zinc cluster DNA-binding domain, leucine zipper DNA-binding domain, winged helix DNA-binding domain, winged helix-turn-helix DNA-binding domain, helix-loop-helix DNA-binding domain, high mobility family DNA-binding domain and B3 DNA-binding domain,
wherein said second polypeptide is selected from LOV2 domain of *Neurospora crassa* VIVID, AsLOV2 domain of oat phytochrome gene 1, AuLOV domain in aureochrome1 of *Stramenophile algae Vaucheria frigida*, and LOV domain in PpSB1-LOV of *Pseudomonas putida*; and
b) a target transcription unit, including promoter or promoter-reaction element or reaction element promoter containing at least one reaction element recognized/bound by the first polypeptide and a vacancy for the nucleic acid sequence to be transcribed.

2. The light-switchable gene expression system of prokaryotic bacterium according to claim 1, wherein said first polypeptide and second polypeptide are linked each other directly or operatively, and/or wherein said promoter or promoter-reaction element or reaction element-promoter and the nucleic acid sequence to be transcribed in the target transcription unit are linked each other directly or operatively.

3. The light-switchable gene expression system of prokaryotic bacterium according to claim 1, wherein said first polypeptide is selected from DNA binding domain of *E. coli* LexA protein, DNA binding domain of λ phage cI repression protein, DNA binding domain of LacI repression protein, DNA binding domain of yeast Gal4 protein and DNA binding domain of tetracycline repression protein TetR.

4. The light-switchable gene expression system of prokaryotic bacterium according to claim 1, the gene expression system further comprising a third peptide recruiting other components of RNA polymerase, said third polypeptide being linked with the first and the second polypeptides directly or via a linker peptide.

5. The light-switchable gene expression system of prokaryotic bacterium according to claim 4, wherein said third polypeptide is selected from w protein and a protein of *E. coli*.

6. The light-switchable gene expression system of prokaryotic bacterium according to claim 1, wherein said reaction element is a DNA motif which can be specifically recognized and bound by the first polypeptide, wherein said reaction element is selected from LexA binding element, cI binding element, LacI binding element, Gal4 binding element and TetR binding element.

7. A prokaryotic expression vector comprising the gene encoding said recombinant light-switchable transcription factor and/or the target transcription unit of said light-switchable gene expression system according to claim 1.

8. The prokaryotic expression vector according to claim 7, wherein said gene encoding said recombinant light-switchable transcription factor has a nucleotide sequence selected from SEQ. ID. NO: 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 109; said recombinant light-switchable transcription factor has an amino acid sequence selected from SEQ. ID. NO: 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 110.

9. A method for the regulation of gene expression in prokaryotic host cells with a light-switchable gene expression system of prokaryotic bacterium, comprising the steps of:
a) constructing the light-switchable gene expression system according to claim 1 containing a gene to be regulated in prokaryotic expression vectors;
b) introducing the prokaryotic expression vectors into the prokaryotic host cells; and
c) inducing the prokaryotic host cells via illumination to express the gene being regulated.

10. The method for the regulation of gene expression according to claim 9, further comprising the selection of light source and the selection of illumination method, wherein said light source is selected from LED lamp, fluorescent lamp, laser and incandescent lamp; said illumination method is a continuous or discontinuous illumination.

11. The method for the regulation of gene expression according to claim 9, wherein said selection of light source and said selection of illumination method comprises the spatial control of the cellular gene expression level in the different locations by using scan, projection or optical molds.

12. The method for the regulation of gene expression according to claim 9, wherein the illumination method further comprises the spatial control of the cellular gene expression level in the different locations by using a printing projection film or a neutral gray film.

* * * * *